United States Patent
Wang et al.

(10) Patent No.: US 11,235,032 B2
(45) Date of Patent: Feb. 1, 2022

(54) COMBINATION IMMUNOTHERAPY DOSING REGIMEN FOR IMMUNE CHECKPOINT BLOCKADE

(71) Applicant: Massachusetts Institute of Technology, Cambridge, MA (US)

(72) Inventors: Chensu Wang, Allston, MA (US); Karl Dane Wittrup, Boston, MA (US); Darrell J. Irvine, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/692,892

(22) Filed: Nov. 22, 2019

(65) Prior Publication Data
US 2020/0230208 A1    Jul. 23, 2020

Related U.S. Application Data

(60) Provisional application No. 62/796,013, filed on Jan. 23, 2019.

(51) Int. Cl.
| | | |
|---|---|---|
| *A61K 38/20* | (2006.01) | |
| *A61P 35/00* | (2006.01) | |
| *A61K 39/00* | (2006.01) | |
| *A61K 39/39* | (2006.01) | |
| *A61K 39/395* | (2006.01) | |

(52) U.S. Cl.
CPC ...... *A61K 38/2013* (2013.01); *A61K 39/0011* (2013.01); *A61K 39/39* (2013.01); *A61K 39/3955* (2013.01); *A61K 39/39558* (2013.01); *A61P 35/00* (2018.01); *A61K 2039/507* (2013.01); *A61K 2039/545* (2013.01); *A61K 2039/55561* (2013.01)

(58) Field of Classification Search
None
See application file for complete search history.

(56) References Cited

U.S. PATENT DOCUMENTS

| | | |
|---|---|---|
| 7,462,350 B2 | 12/2008 | Gillies et al. |
| 10,888,603 B2 | 1/2021 | Wittrup et al. |
| 2017/0216403 A1 | 8/2017 | Wittrup et al. |
| 2017/0224777 A1 | 8/2017 | Wittrup et al. |
| 2019/0054145 A1 | 2/2019 | Wittrup et al. |

FOREIGN PATENT DOCUMENTS

| | | |
|---|---|---|
| WO | 2004002526 A1 | 1/2004 |
| WO | 2008/003473 A2 | 1/2008 |
| WO | 2008/045252 A2 | 4/2008 |
| WO | 2012/064658 A1 | 5/2012 |
| WO | 2013151771 A1 | 10/2013 |
| WO | 2013/177187 A2 | 11/2013 |
| WO | 2014201378 A1 | 12/2014 |
| WO | 2016/025642 A1 | 2/2016 |
| WO | 2016/025645 A1 | 2/2016 |
| WO | 2016/025647 A1 | 2/2016 |
| WO | 2017/139570 A1 | 8/2017 |
| WO | 2020154032 A1 | 7/2020 |

OTHER PUBLICATIONS

Kimura et al., Engineered cystine knot peptides that bind αvβ3, αvβ5, or α5β1 integrins with low nanomolar affinity. Proteins, 77, 359-369, 2009. (Year: 2009).*
U.S. Appl. No. 15/501,535, filed Feb. 3, 2017, Karl Dane Wittrup.
U.S. Appl. No. 15/501,246, filed Feb. 2, 2017, Karl Dane Wittrup.
U.S. Appl. No. 16/076,597, filed Aug. 8, 2018, Karl Dane Wittrup.
Office Action, U.S. Appl. No. 15/501,535, dated May 29, 2018.
Office Action, U.S. Appl. No. 15/501,535, dated Jan. 29, 2018.
Office Action, U.S. Appl. No. 15/501,246, dated Jun. 27, 2018.
Office Action, U.S. Appl. No. 15/501,246, dated Jan. 17, 2018.
Office Action, U.S. Appl. No. 16/076,597, dated Mar. 17, 2020.
Office Action, U.S. Appl. No. 16/076,597, dated Nov. 6, 2019.
Office Action, U.S. Appl. No. 16/076,597, dated May 30, 2019.
Office Action, U.S. Appl. No. 16/076,597, dated Aug. 25, 2020.
Antony, G.K. et al., "Interleukin 2 in Cancer Therapy," Current Medicinal Chemistry, vol. 17: 3297-3302 (2010).
Becker, J. et al., "An antibody-interleukin 2 fusion protein overcomes tumor heterogeneity by induction of a cellular immune response," Proc. Natl. Acad. Sci., vol. 93: 7826-7831 (1996).
Broucek, J. et al., "Combination immunotherapy with Interleukin-2 and CTLA-4 blockade decreases tumor growth and improves overall survival," J. Immuno Ther. Cancer, 1, Abstract No. P70, Accession No. 0052009444 (2013).
Cho, H. et al., "A Potent Vaccination Strategy that Circumvents Lymphodepletion for Effective Anti-tumor Adoptive T Cell Therapy", Cancer Res., vol. 72(8): 1986-1995 (2012).
Dela Cruz, J.S., et al. "Antibody-cytokine fusion proteins: innovative weapons in the war against cancer," Clin. Exp. Med., vol. 4: 57-64 (2004).
Ellis et al., VEGF-targeted therapy: mechanisms of anti-tumour activity, Nature Reviews Cancer, vol. 8(8):579-589 (2008).
Hornick, J. et al., "Chimeric CLL-1 antibody fusion proteins containing granulocyte-macrophage colony-stimulating factor or interleukin-2 with specificity for B-cell malignancies exhibit enhanced effector functions while retaining tumor targeting properties," Blood, vol. 89:4437-4447(1997).
International Preliminary Report on Patentability, PCT/US2015/044924, dated Feb. 14, 2017, 10 pages.

(Continued)

*Primary Examiner* — Elly-Gerald Stoica
(74) *Attorney, Agent, or Firm* — McDonnell Boehnen Hulbert & Berghoff LLP

(57) ABSTRACT

The present disclosure provides a method of treating cancer with a priming dose of combination immunotherapy comprising IL-2 (e.g., extended-PK IL-2), an immune checkpoint inhibitor, a tumor targeting antibody or integrin-binding polypeptide, and optional cancer vaccine, administered prior to maintenance doses of immune checkpoint inhibitor therapy. The methods of the disclosure can be used to treat a broad range of cancer types.

24 Claims, 27 Drawing Sheets
Specification includes a Sequence Listing.

(56) References Cited

OTHER PUBLICATIONS

International Preliminary Report on Patentability, PCT/US2015/044927, dated Feb. 14, 2017, 10 pages.
International Preliminary Report on Patentability, PCT/US2017/017365, dated Aug. 14, 2018, 9 pages.
International Search Report and Written Opinion, PCT/US2015/044924, dated Dec. 2, 2015, 15 pages.
International Search Report and Written Opinion, PCT/US2015/044927, dated Dec. 2, 2015, 14 pages.
International Search Report and Written Opinion, PCT/US2017/017365, dated May 8, 2017, 13 pages.
Irvine DJ, Engineering amphiphiles that target lymphoid tissues and optimally engage immune cells for more effective vaccines 249th ACS National Meeting & Exposition, Denver, CO, United States, Mar. 22-26, 2015 (2015), POLY-529. (Year: 2015).
Jackaman, C. et al., "Intratumoral interleukin-2/agonist CD40 antibody drives CD4+-independent resolution of treated-tumors and CD4+-dependent systemic and memory responses," Cancer Immunol. Immunother., vol. 61:549-560 (2012).
Kohlhapp, F. et al., "NK cells and CD8+ T cells cooperate to improve therapeutic responses in melanoma treated with CTLA-4 blockade and IL-2 (TUM2P.1039)," J. Immunology, vol. 194(1):Supp. Abstract No. 69.36, Accession No. 0051980006, 2 pages (2015).
Ly, L. V. et al., "Effective Cooperation of Monoclonal Antibody and Peptide Vaccine for the Treatment of Mouse Melanoma," The Journal of Immunology, vol. 190 (1):489-496 (2012).
Moynihan, K. et al., "Eradication of large established tumors in mice by combination immunotherapy that engages innate and adaptive immune responses," Nature Medicine, vol. 22(12):1402-1410 (2016).
Muller, D. "Antibody-cytokine fusion proteins for cancer immunotherapy: an update on recent developments," BioDrugs, vol. 28:123-131 (2014).
Pardoll, D. et al., "The blockade of immune checkpoints in cancer immunotherapy", Nature Reviews Cancer, vol. 12(4): 252-264(2012).
West, E. et al., "PD-L1 blockade synergizes with IL-2 therapy in reinvigorating exhausted T cells," J. Clin. Investig., vol. 123(6):2604-2615 (2013).
Zhu. E. et al., "Synergistic Innate and Adaptive Immune Response to Combination Immunotherapy with Anti-Tumor Antigen Antibodies and Extended Serum Half-Life IL-2," Cancer Cell, vol. 27 (4):489-501 (2015).
International Search Report and Written Opinion, PCT/US2019/062838, dated Jun. 24, 2020, 21 pages.
Liu, H. et al., "Structure-based Programming of Lymph Node Targeting in Molecular Vaccines," Nature, vol. 507(7493): 519-522 (2014).
Kwan, B. et al., "Integrin-targeted cancer immunotherapy elicits protective adaptive immune responses," J Exp Med., vol. 214(6):1679-1690 (2017).

* cited by examiner

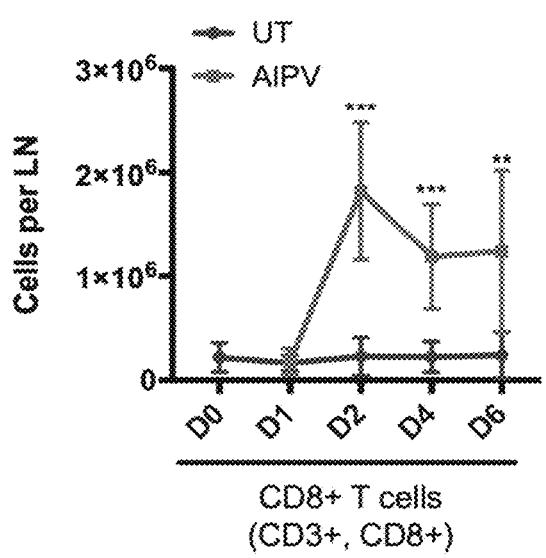
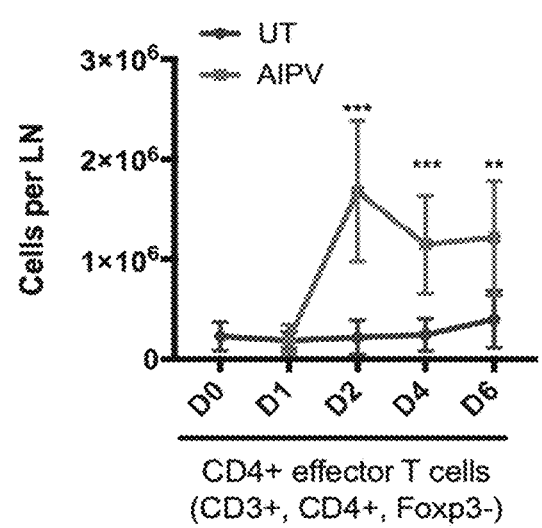
FIG. 1D
FIG. 1E

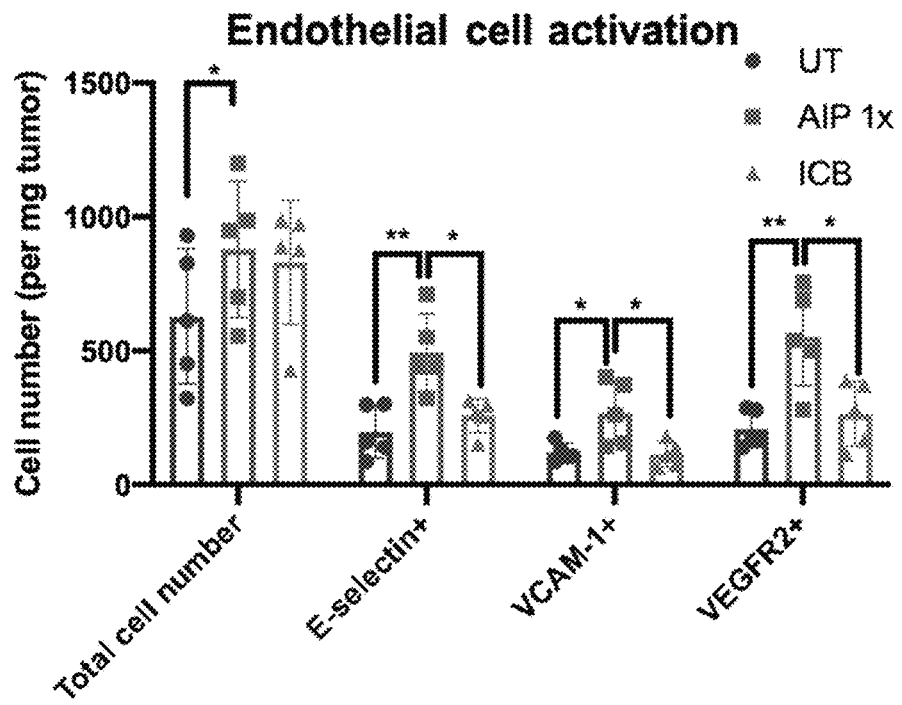
FIG. 24A
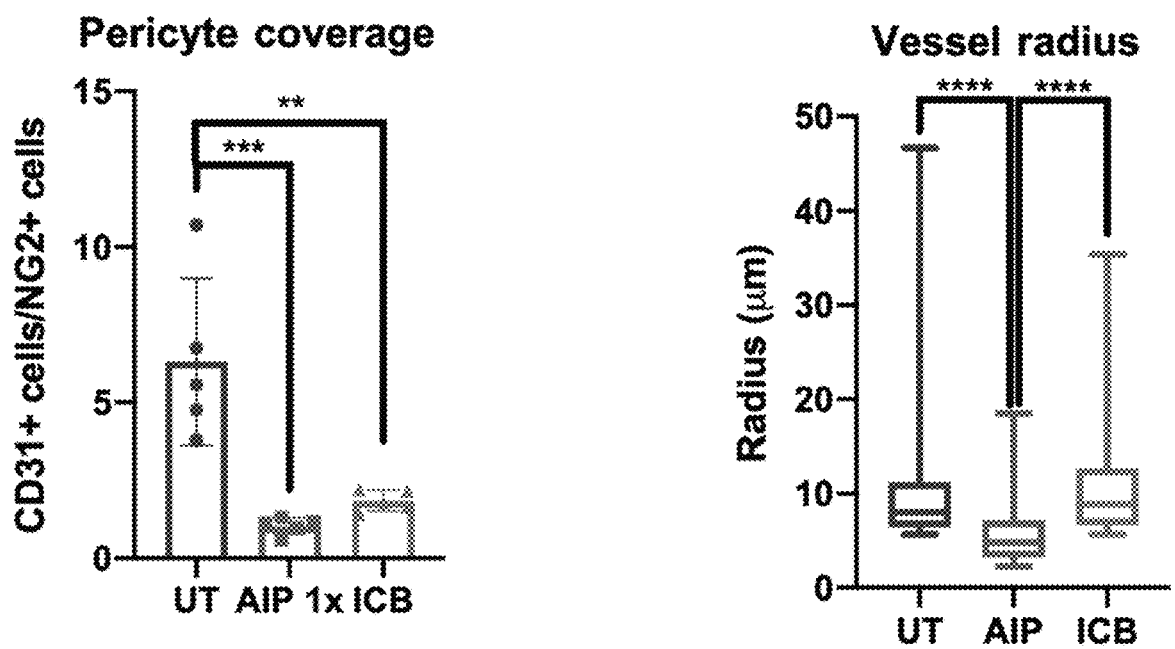
FIG. 24B
FIG. 25

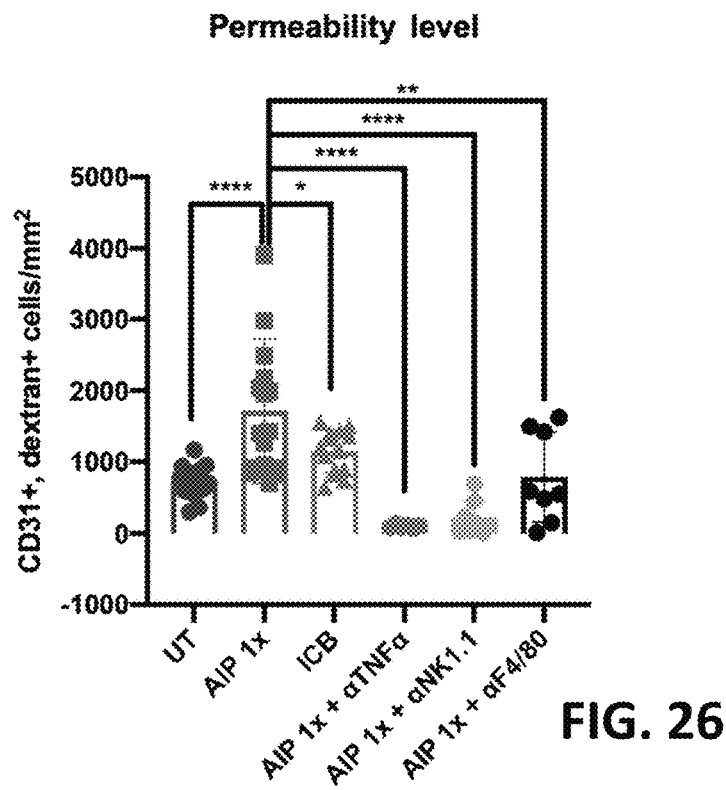
FIG. 26
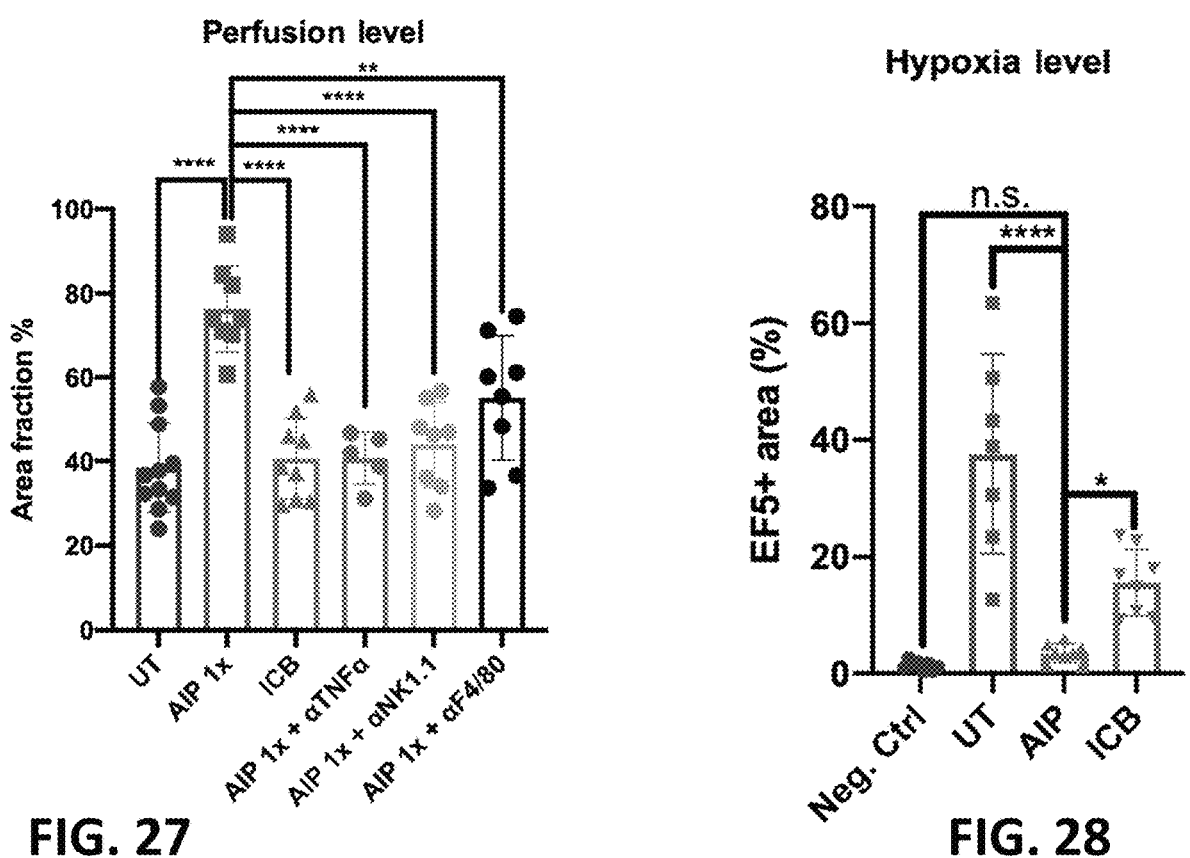
FIG. 27
FIG. 28

COMBINATION IMMUNOTHERAPY DOSING REGIMEN FOR IMMUNE CHECKPOINT BLOCKADE

CROSS-REFERENCE TO RELATED APPLICATIONS

This application claims the benefit of U.S. Provisional Application Ser. No. 62/796,013, filed on Jan. 23, 2019. The entire contents of the above-referenced provisional patent application is incorporated herein by reference.

GOVERNMENT FUNDING

This invention was made with government support under grant number R01 CA174795 awarded by the National Institutes of Health (NIH). The U.S. government has certain rights in this invention.

SEQUENCE LISTING

The instant application contains a Sequence Listing which has been submitted electronically in ASCII format via EFS-Web and is hereby incorporated by reference in its entirety. Said ASCII copy, created Feb. 17, 2020, is named "MITN-051 Sequence-Listing.txt" and is 159080 bytes in size.

BACKGROUND

Immune checkpoint inhibitor therapy using antibodies blocking T cell negative regulatory molecules, such as CTLA-4 and PD-1, has delivered outstanding results in some cancer patients. However, due to the complex network of immunosuppressive pathways present in advanced tumors, only a minority of patients respond to this therapy. Efforts to sensitize tumors to immune checkpoint inhibitor therapy is ongoing.

Novel approaches to convert "cold" tumors into more inflamed and cytotoxic T lymphocyte-infiltrated "hot" ones such that they respond to immune checkpoint inhibitor therapy is needed to combat various cancers.

SUMMARY

The present disclosure is based, in part, on the discovery that administration of a priming dose of combination immunotherapy enhanced the anti-tumor efficacy of immune checkpoint inhibitor therapy. It was demonstrated a single dose of combination immunotherapy (i.e., (i) a tumor targeting antibody or integrin-binding polypeptide, (ii) IL-2, (iii) an immune checkpoint inhibitor, and optionally (iv) a cancer vaccine) was sufficient to induce infiltration of cytotoxic CD8+ T cells, natural killer cells and dendritic cells into tumors and tumor training lymph nodes, along with increasing the ratio of CD8+ T cells to Tregs in tumors. The combination of these individual immunotherapies have different effects on the immune system. For example, tumor-specific antibodies drive antibody-dependent cell-mediated cytotoxicity through neutrophil- and eosinophil-mediated attack, whereas IL-2 activates CD8+ T cells and natural killer cells. Integrin-binding polypeptides have been shown to recruit both innate and adaptive immune responses, while immune checkpoint inhibitors mitigate inhibitory signaling that decreases antitumor T cell responses. Without wishing to be bound by theory, the combination of immunotherapies having distinct mechanisms of action contributes to the enhanced anti-tumor efficacy of immune checkpoint inhibitor therapy administered after a priming dose.

It was also discovered the single dose of combination immunotherapy enhanced expression of various cytokines and chemokines within the tumor just one day after administration. It has been found this single dose of combination immunotherapy enhanced anti-tumor efficacy of immune checkpoint inhibitor therapy (e.g., anti-PD-1 and/or anti-CTLA-4) in various tumor models. Without wishing to be bound by theory, it is believed the single priming dose of combination immunotherapy is sufficient to sensitize tumors to immune checkpoint inhibitor therapy by converting "cold" tumors into more inflamed and cytotoxic T lymphocyte (CTL)-infiltrated "hot" ones, thus allowing for less aggressive treatment with immune checkpoint inhibitors.

Moreover, it was demonstrated an integrin-binding fusion protein provided similar results as a tumor antigen specific antibody when used in the combination immunotherapy priming dose. As integrins are overexpressed in many human tumors, use of an integrin-binding polypeptide broadens the applicability of the combination immunotherapy priming dose and avoids the need to identify specific tumor antigens for treatment.

It was further demonstrated the single priming dose of combination immunotherapy activated natural killer cells, particularly through Fc receptor and IL-2 receptor (IL-2R) engagement. It was shown that NK cells and macrophages activated by the combination immunotherapy priming dose contribute to immunogenic cell death of tumor cells, providing tumor antigen for uptake by dendritic cells. Moreover, the priming dose activates natural killer cells such that they released cytokines (e.g., FLT3L) to expand and maintain cross-presenting dendritic cells within tumors, which led to a skewed antigen uptake towards these professional antigen presentation cells and migration of the same population carrying tumor antigens from the tumor microenvironment to tumor-draining lymph nodes. Without wishing to be bound by theory, it is believed this migration of tumor antigen presenting cells results in the increased infiltration of CTLs in the tumor microenvironment as observed, which subsequently synergizes with the later administered immune checkpoint inhibitor therapy.

Additionally, it was discovered that the priming dose of combination immunotherapy promoted normalization of tumor vaculature, namely by providing tumor blood vessels of more uniform size, with reduced permeability and increased pericyte coverage. Moreover, tumor vasculature normalization induced by the priming dose provided tumors with improved blood perfusion and reduced hypoxia. Without being bound by theory, it is believed that tumor vasculature normalization sensitizes the tumor to subsequent doses of immune checkpoint inhibitor therapy by enabling CTLs to enter and infiltrate the tumor, improving perfusion of the tumor by blood-borne therapeutic molecules (i.e., immune checkpoint inhibitor), and blocking or inhibiting immunosuppressive pathways induced by tumor hypoxia.

Accordingly, in some aspects the disclosure provides a method for treating a cancer in a subject, comprising administering to the subject: (a) a priming dose comprising (i) interleukin (IL)-2, (ii) an immune checkpoint inhibitor polypeptide, and (iii) a tumor targeting antibody or an integrin-binding polypeptide; and (b) at least one maintenance dose comprising an immune checkpoint inhibitor polypeptide, wherein the priming dose is administered prior to the at least one maintenance dose, thereby treating cancer in the subject.

In other aspects, the disclosure provides a method for treating a cancer in a subject, comprising administering to the subject:

(a) a priming dose comprising (i) interleukin (IL)-2, (ii) an immune checkpoint inhibitor polypeptide, and (iii) a tumor targeting antibody or an integrin-binding polypeptide, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In further aspects, the disclosure provides a method for inhibiting or delaying growth of a tumor in a subject, comprising administering to the subject: (a) a priming dose comprising (i) interleukin (IL)-2, (ii) an immune checkpoint inhibitor polypeptide, and (iii) a tumor targeting antibody or an integrin-binding polypeptide; and (b) at least one maintenance dose comprising an immune checkpoint inhibitor polypeptide, wherein the priming dose is administered prior to the at least one maintenance dose, thereby inhibiting or delaying growth of the tumor in the subject.

In other aspects, the disclosure provides a method for inhibiting or delaying growth of a tumor in a subject, comprising administering to the subject:

(a) a priming dose comprising (i) interleukin (IL)-2, (ii) an immune checkpoint inhibitor polypeptide, and (iii) a tumor targeting antibody or an integrin-binding polypeptide, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby inhibiting or delaying growth of the tumor in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, PD-L1, or CTLA-4 and (iii) an integrin-binding-Fc fusion protein; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1 and (iii) an integrin-binding-Fc fusion protein; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1 and (iii) an integrin-binding-Fc fusion protein; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4 and (iii) an integrin-binding-Fc fusion protein; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, PD-L1, or CTLA-4 and (iii) an integrin-binding-Fc fusion protein, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1 and (iii) an integrin-binding-Fc fusion protein, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1 and (iii) an integrin-binding-Fc fusion protein, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4 and (iii) an integrin-binding-Fc fusion protein, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, PD-L1, or CTLA-4 (iii) an integrin-binding-Fc fusion protein, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, (iii) an integrin-binding-Fc fusion protein, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1, (iii) an integrin-binding-Fc fusion protein, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4, (iii) an integrin-binding-Fc fusion protein, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In another aspect, the disclosure provides a method for treating a cancer in a subject, comprising administering to the subject:

(a) a priming dose comprising (i) interleukin (IL)-2, (ii) an antibody or antibody fragment that specifically binds PD-1, PD-L1, or CTLA-4 (iii) an integrin-binding-Fc fusion protein, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, (iii) an integrin-binding-Fc fusion protein, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1, (iii) an integrin-binding-Fc fusion protein, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4, (iii) an integrin-binding-Fc fusion protein, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, PD-L1, or CTLA-4 and (iii) a tumor antigen targeting antibody; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1 and (iii) a tumor antigen targeting antibody; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1 and (iii) a tumor antigen targeting antibody; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4 and (iii) a tumor antigen targeting antibody; and (b) at least one maintenance dose comprising an immune checkpoint inhibitor polypeptide, wherein the priming dose is administered prior to the at least one maintenance dose, thereby treating cancer in the subject.

In yet further aspects, the disclosure provides a method for treating a cancer in a subject, comprising administering to the subject:

(a) a priming dose comprising (i) interleukin (IL)-2, (ii) an antibody or antibody fragment that specifically binds PD-1, PD-L1, or CTLA-4 and (iii) a tumor antigen targeting antibody, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1 and (iii) a tumor antigen targeting antibody, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1 and (iii) a tumor antigen targeting antibody, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4 and (iii) a tumor antigen targeting antibody, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In further aspects, the disclosure provides a method for treating a cancer in a subject, comprising administering to the subject: (a) a priming dose comprising (i) interleukin (IL)-2, (ii) an antibody or antibody fragment that specifically binds PD-1, PD-L1, or CTLA-4 (iii) a tumor antigen targeting antibody, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In further aspects, the disclosure provides a method for treating a cancer in a subject, comprising administering to the subject: (a) a priming dose comprising (i) interleukin (IL)-2, (ii) an antibody or antibody fragment that specifically binds PD-1, (iii) a tumor antigen targeting antibody, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In further aspects, the disclosure provides a method for treating a cancer in a subject, comprising administering to the subject: (a) a priming dose comprising (i) interleukin (IL)-2, (ii) an antibody or antibody fragment that specifically binds PD-L1, (iii) a tumor antigen targeting antibody, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In further aspects, the disclosure provides a method for treating a cancer in a subject, comprising administering to the subject: (a) a priming dose comprising (i) interleukin (IL)-2, (ii) an antibody or antibody fragment that specifically binds CTLA-4, (iii) a tumor antigen targeting antibody, and (iv) a cancer vaccine; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject:

(a) a priming dose comprising (i) interleukin (IL)-2, (ii) an antibody or antibody fragment that specifically binds PD-1, PD-L1, or CTLA-4 (iii) a tumor antigen targeting antibody, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-1, (iii) a tumor antigen targeting antibody, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds PD-L1, (iii) a tumor antigen targeting antibody, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In some aspects, the disclosure provides a method for treating a cancer in a subject, comprising administering to the subject: (a) a priming dose comprising (i) interleukin (IL)-2, (ii) an antibody or antibody fragment that specifically binds CTLA-4, (iii) a tumor antigen targeting antibody, and (iv) a cancer vaccine, wherein the priming dose induces or enhances an anti-tumor immune response in the subject; and (b) at least one maintenance dose comprising an immune checkpoint inhibitor polypeptide, wherein the priming dose is administered prior to the at least one maintenance dose, thereby treating cancer in the subject.

In further aspects, the disclosure provides a priming dose comprising (i) interleukin (IL)-2, (ii) an immune checkpoint inhibitor polypeptide, and (iii) a tumor targeting antibody or an integrin-binding polypeptide, and at least one maintenance dose comprising an immune checkpoint inhibitor polypeptide, for use in a method of treating a cancer in a subject, wherein the priming dose induces or enhances an anti-tumor immune response in the subject, and wherein the priming dose is administered prior to the at least one maintenance dose.

In other aspects, the disclosure provides a priming dose comprising (i) interleukin (IL)-2, (ii) an immune checkpoint inhibitor polypeptide, (iii) a tumor targeting antibody or an integrin-binding polypeptide, and (iv) a cancer vaccine, and at least one maintenance dose comprising an immune checkpoint inhibitor polypeptide, for use in a method of treating cancer in a subject, wherein the priming dose induces or enhances an anti-tumor immune response in the subject, and wherein the priming dose is administered prior to the at least one maintenance dose.

In yet further aspects, the disclosure provides a priming dose comprising (i) interleukin (IL)-2, (ii) an antibody or antibody fragment that specifically binds PD-1, PD-L1 or CTLA-4 and (iii) an integrin-binding-Fc fusion protein; and at least one maintenance dose comprising an immune checkpoint inhibitor polypeptide, for use in a method of treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-1 and (iii) an integrin-binding-Fc fusion protein; and at least one maintenance dose comprising an immune checkpoint inhibitor polypeptide, for use in a method of treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-L1 and (iii) an integrin-binding-Fc fusion protein; and at least one maintenance dose comprising an immune checkpoint inhibitor polypeptide, for use in a method of treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds CTLA-4 and (iii) an integrin-binding-Fc fusion protein; and at least one maintenance dose comprising an immune checkpoint inhibitor polypeptide, for use in a method of treating cancer in a subject, wherein the priming dose induces or enhances an anti-tumor immune response in the subject, and wherein the priming dose is administered prior to the at least one maintenance dose.

In other aspects, the disclosure provides a priming dose comprising (i) interleukin (IL)-2, (ii) an antibody or antibody fragment that specifically binds PD-1, PD-L1, or CTLA-4 (iii) an integrin-binding-Fc fusion protein, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-1, (iii) an integrin-binding-Fc fusion protein, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-L1, (iii) an integrin-binding-Fc fusion protein, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds CTLA-4, (iii) an integrin-binding-Fc fusion protein, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-1, PD-L1, or CTLA-4 and (iii) a tumor antigen targeting antibody; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-1 and (iii) a tumor antigen targeting antibody; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-L1 and (iii) a tumor antigen targeting antibody; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds CTLA-4 and (iii) a tumor antigen targeting antibody; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In additional aspects, the disclosure provides a priming dose comprising (i) interleukin (IL)-2, (ii) an antibody or antibody fragment that specifically binds PD-1, PD-L1, or CTLA-4 (iii) a tumor antigen targeting antibody, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-1, (iii) a tumor antigen targeting antibody, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds PD-L1, (iii) a tumor antigen targeting antibody, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In some aspects, the disclosure provides a priming dose comprising (i) interleukin (IL)-2, (ii) an antibody or antibody fragment that specifically binds CTLA-4, (iii) a tumor antigen targeting antibody, and (iv) a cancer vaccine; and at least one maintenance dose comprising an immune checkpoint inhibitor polypeptide, for use in treating cancer in a subject, wherein the priming dose induces or enhances an anti-tumor immune response in the subject, and wherein the priming dose is administered prior to the at least one maintenance dose.

In other aspects, the disclosure provides a medicament comprising (i) interleukin (IL)-2, (ii) an immune checkpoint inhibitor polypeptide, and (iii) a tumor targeting antibody or an integrin-binding polypeptide, for use in a priming dose to treat cancer in a subject, wherein the priming dose is administered prior to at least one maintenance dose comprising an immune checkpoint inhibitor polypeptide.

In other aspects, the disclosure provides a medicament comprising (i) interleukin (IL)-2, (ii) an immune checkpoint inhibitor polypeptide, (iii) a tumor targeting antibody or an integrin-binding polypeptide, and (iv) a cancer vaccine, for use in a priming dose to treat cancer in a subject, wherein the priming dose is administered prior to at least one maintenance dose comprising an immune checkpoint inhibitor polypeptide.

In further aspects, the disclosure provides a medicament comprising (i) interleukin (IL)-2, (ii) an antibody or antibody fragment that specifically binds PD-1, PD-L1, or CTLA-4 and (iii) an integrin-binding-Fc fusion protein, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-1, and (iii) an integrin-binding-Fc fusion protein, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-L1, and (iii) an integrin-binding-Fc fusion protein, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds CTLA-4, and (iii) an integrin-binding-Fc fusion protein, for use in a priming dose to treat cancer in a subject, wherein the priming dose is administered prior to at least one maintenance dose comprising an immune checkpoint inhibitor polypeptide.

In further aspects, the disclosure provides a medicament comprising (i) interleukin (IL)-2, (ii) an antibody or antibody fragment that specifically binds PD-1, PD-L1 or CTLA-4 (iii) an integrin-binding-Fc fusion protein, and (iv) a cancer vaccine, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-1 (iii) an integrin-binding-Fc fusion protein, and (iv) a cancer vaccine, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-L1 (iii) an integrin-binding-Fc fusion protein, and (iv) a cancer vaccine, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds CTLA-4 (iii) an integrin-binding-Fc fusion protein, and (iv) a cancer vaccine, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-1, PD-L1 or CTLA-4 and (iii) a tumor antigen targeting antibody, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-1, and (iii) a tumor antigen targeting antibody, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-L1, and (iii) a tumor antigen targeting antibody, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds CTLA-4, and (iii) a tumor antigen targeting antibody, for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-1, PD-L1, or CTLA-4 (iii) a tumor antigen targeting antibody, and (iv) a cancer vaccine for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-1, (iii) a tumor antigen targeting antibody, and (iv) a cancer vaccine for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds PD-L1, (iii) a tumor antigen targeting antibody, and (iv) a cancer vaccine for use in a priming dose to treat cancer in a subject, wherein the priming dose is administered prior to at least one maintenance dose comprising an immune checkpoint inhibitor polypeptide.

In some aspects, the disclosure provides a medicament comprising (i) interleukin (IL)-2, (ii) an antibody or antibody fragment that specifically binds CTLA-4, (iii) a tumor antigen targeting antibody, and (iv) a cancer vaccine for use in a priming dose to treat cancer in a subject, wherein the priming dose is administered prior to at least one maintenance dose comprising an immune checkpoint inhibitor polypeptide.

In further aspects, the disclosure provides use of (i) interleukin (IL)-2, (ii) an immune checkpoint inhibitor polypeptide, and (iii) a tumor targeting antibody or an integrin-binding polypeptide, for the manufacture of a medicament for use in a priming dose to treat cancer in a subject, wherein the priming dose is administered prior to at least one maintenance dose comprising an immune checkpoint inhibitor polypeptide.

In further aspects, the disclosure provides use of (i) interleukin (IL)-2, (ii) an immune checkpoint inhibitor polypeptide, (iii) a tumor targeting antibody or an integrin-binding polypeptide, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In other aspects, the disclosure provides use of (i) interleukin (IL)-2, (ii) an antibody or antibody fragment that specifically binds PD-1, PD-L1, or CTLA-4 and (iii) an integrin-binding-Fc-fusion protein, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-1, and (iii) an integrin-binding-Fc-fusion protein, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-L1, and (iii) an integrin-binding-Fc-fusion protein, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds CTLA-4, and (iii) an integrin-binding-Fc-fusion protein, for the manufacture of a medicament for use in a priming dose to treat cancer in a subject, wherein the priming dose is administered prior to at least one maintenance dose comprising an immune checkpoint inhibitor polypeptide.

In other aspects, the disclosure provides use of (i) interleukin (IL)-2, (ii) an antibody or antibody fragment that specifically binds PD-1, PD-L1, or CTLA-4 (iii) an integrin-binding-Fc-fusion protein, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-1, (iii) an integrin-binding-Fc-fusion protein, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-L1, (iii) an integrin-binding-Fc-fusion protein, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds CTLA-4, (iii) an integrin-binding-Fc-fusion protein, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-1, PD-L1, or CTLA-4 and (iii) a tumor antigen targeting antibody, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-1, and (iii) a tumor antigen targeting antibody, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-L1, and (iii) a tumor antigen targeting antibody, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds CTLA-4, and (iii) a tumor antigen targeting antibody, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-1, PD-L1, or CTLA-4 (iii) a tumor antigen targeting antibody, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-1, (iii) a tumor antigen targeting antibody, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds PD-L1, (iii) a tumor antigen targeting antibody, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In some aspects, the disclosure provides use of (i) interleukin (IL)-2, (ii) an antibody or antibody fragment that specifically binds CTLA-4, (iii) a tumor antigen targeting antibody, and (iv) a cancer vaccine, for the manufacture of a medicament for use in a priming dose to treat cancer in a subject, wherein the priming dose is administered prior to at least one maintenance dose comprising an immune checkpoint inhibitor polypeptide.

In other aspects, the disclosure provides a kit comprising a container comprising IL-2 and a package insert comprising instructions for administration of IL-2 in a priming dose comprising an immune checkpoint inhibitor polypeptide and a tumor targeting antibody or an integrin-binding polypeptide, wherein the priming dose is administered prior to administration of at least one maintenance dose comprising an immune checkpoint inhibitor polypeptide for treating or delaying progression of cancer or reducing or inhibiting tumor growth in a subject in need thereof.

In some aspects, the disclosure provides a kit comprising a container comprising a tumor targeting antibody and a package insert comprising instructions for administration of the tumor targeting antibody in a priming dose comprising an immune checkpoint inhibitor polypeptide and IL-2, wherein the priming dose is administered prior to administration of at least one maintenance dose comprising an immune checkpoint inhibitor polypeptide for treating or delaying progression of cancer or reducing or inhibiting tumor growth in a subject in need thereof.

In further aspects, the disclosure provides a kit comprising a container comprising an integrin-binding polypeptide and a package insert comprising instructions for administration of the integrin-binding polypeptide in a priming dose comprising an immune checkpoint inhibitor polypeptide and IL-2, wherein the priming dose is administered prior to administration of at least one maintenance dose comprising an immune checkpoint inhibitor polypeptide for treating or delaying progression of cancer or reducing or inhibiting tumor growth in a subject in need thereof.

In yet other aspects, the disclosure provides a kit comprising a container comprising an immune checkpoint inhibitor polypeptide and a package insert comprising instructions for administration of the immune checkpoint inhibitor polypeptide in a priming dose comprising IL-2 and a tumor targeting antibody or an integrin-binding polypeptide, wherein the priming dose is administered prior to administration of at least one maintenance dose comprising an immune checkpoint inhibitor polypeptide for treating or delaying progression of cancer or reducing or inhibiting tumor growth in a subject in need thereof.

In further aspects, the disclosure provides a kit comprising (a) a priming dose comprising (i) interleukin (IL)-2, (ii) an immune checkpoint inhibitor polypeptide, and (iii) a tumor targeting antibody or an integrin-binding polypeptide and (b) a package insert comprising instructions for administration of the priming dose prior to administration of at least one maintenance dose comprising an immune checkpoint inhibitor polypeptide for treating or delaying progression of cancer or reducing or inhibiting tumor growth in a subject in need thereof.

In further aspects, the disclosure provides a kit comprising (a) a priming dose comprising (i) interleukin (IL)-2, (ii) an immune checkpoint inhibitor polypeptide, (iii) a tumor targeting antibody or an integrin-binding polypeptide, and (iv) a cancer vaccine and (b) a package insert comprising instructions for administration of the priming dose prior to administration of at least one maintenance dose comprising an immune checkpoint inhibitor polypeptide for treating or delaying progression of cancer or reducing or inhibiting tumor growth in a subject in need thereof.

In any of the foregoing or related aspects, IL-2 is Proleukin. In some aspects, IL-2 is administered at a dose of less than 14 MIU/m$^2$, less than 12 MIU/m$^2$, less than 10 MIU/m$^2$, less than 8 MIU/m$^2$, less than 6 MIU/m$^2$, less than 4 MIU/m$^2$, or less than 2 MIU/m$^2$.

In any of the foregoing or related aspects, wherein IL-2 is an extended pharmacokinetic (PK) IL-2. In some aspects, the extended-PK IL-2 comprises a fusion protein. In some aspects, the fusion protein comprises an IL-2 moiety and a moiety selected from the group consisting of an immunoglobulin fragment, human serum albumin, and Fn3. In some aspects, the fusion protein comprises an IL-2 moiety operably linked to an immunoglobulin Fc domain. In other aspects, the fusion protein comprises an IL-2 moiety operably linked to human serum albumin. In yet other aspects, the extended-PK IL-2 comprises an IL-2 moiety conjugated to a non-protein polymer. In some aspects, the non-protein polymer is a polyethylene glycol.

In any of the foregoing or related aspects, the immune checkpoint inhibitor polypeptide of the priming dose is an antibody or antibody fragment targeting PD-1, PD-L1, CTLA-4, LAG3, TIM3, or a member of the B7 ligand family. In some aspects, the immune checkpoint inhibitor polypeptide is an antibody or antibody fragment targeting PD-1. In some aspects, the antibody or antibody fragment targeting PD-1 is selected from the group consisting of: nivolumab and pembrolizumab. In other aspects, the immune checkpoint inhibitor polypeptide is an antibody or antibody fragment targeting PD-L1. In some aspects, the antibody or antibody fragment targeting PD-L1 is selected from the group consisting of: atezolizumab, avelumab, and durvalumab. In yet other aspects, the immune checkpoint inhibitor polypeptide is an antibody or antibody fragment targeting CTLA-4. In some aspects, the antibody or antibody fragment targeting CTLA-4 is selected from the group consisting of: tremelimumab and ipilimumab.

In any of the foregoing or related aspects, the tumor targeting antibody specifically binds to a tumor associated antigen.

In any of the foregoing or related aspects, the integrin-binding polypeptide comprises an integrin-binding loop and a knottin polypeptide scaffold. In some aspects, the integrin-binding polypeptide binds to a tumor-associated integrin selected from the group consisting of $\alpha_v\beta_3$, $\alpha_v\beta_5$, $\alpha_5\beta_1$, or combination thereof. In some aspects, the integrin-binding polypeptide binds to $\alpha_v\beta_3$, $\alpha_v\beta_5$ and $\alpha_5\beta_1$. In some aspects, the knottin polypeptide scaffold comprises at least three cysteine disulfide linkages or crosslinked cysteine residues, and wherein the integrin-binding loop is adjacent to cysteine residues of the knottin polypeptide scaffold. In some aspects, the integrin-binding loop comprises an RGD peptide sequence. In other aspects, the knottin polypeptide scaffold is derived from a knottin protein selected from the group consisting of EETI-II, AgRP, and agatoxin. In some aspects, the knottin protein is EETI-II. In some aspects, the integrin-binding loop comprises an RGD peptide sequence and the knottin polypeptide scaffold is derived from EETI-II. In some aspects, the knottin polypeptide scaffold is derived from EETI-II and the integrin-binding loop comprises the sequence $X_1X_2X_3RGDX_7X_8X_9X_{10}X_{11}$ (SEQ ID NO: 136), wherein each X represents any amino acid, wherein the loop is inserted between 2 cysteine residues in the EETI-II sequence and replaces the native EETI-II sequence. In some aspects, the integrin-binding loop is inserted after the first cysteine in the native EETI-II sequence.

In any of the foregoing or related aspects, the integrin-binding polypeptide comprises the amino acid sequence set forth SEQ ID NO: 42 or 43, wherein $X_1$ is selected from the group consisting of A, V, L, P, F, Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E. In other aspects, the integrin-binding polypeptide comprises an amino acid sequence selected from the group consisting of SEQ ID NOs: 59-125. In some aspects, the integrin-binding polypeptide comprises the amino acid sequence of SEQ ID NO: 86 or 88.

In any of the foregoing or related aspects, the integrin-binding polypeptide is operably linked to an immunoglobulin Fc domain. In some aspects, the Fc domain is a human IgG1 Fc domain. In some aspects, the integrin-binding polypeptide is operably linked with or without a linker to the Fc domain. In some aspects, the integrin-binding polypeptide is operably linked to the N-terminus of the Fc domain or the C-terminus of the Fc domain. In some aspects, the integrin-binding polypeptide operably linked to an immunoglobulin Fc domain comprises the amino acid sequence of SEQ ID NO: 48, 49, 50, or 51.

In any of the foregoing or related aspects, the priming dose comprises a cancer vaccine. In some aspects, the cancer vaccine is a population of cells immunized in vitro with a tumor antigen and administered to the subject. In other aspects, the cancer vaccine is an amphiphilic peptide conjugate comprising a tumor-associated antigen, and a lipid component, and optionally a linker, wherein the amphiphilic peptide conjugate binds albumin under physiological conditions. In some aspects, the tumor-associated antigen is conjugated to a lipid via a linker. In some aspects, the linker is selected from the group consisting of hydrophilic polymers, a string of hydrophilic amino acids, polysaccharides or a combination thereof. In some aspects, the linker comprises "N" consecutive polyethylene glycol units, wherein N is between 25-50. In some aspects, the lipid is a diacyl lipid.

In any of the foregoing or related aspects; the cancer vaccine further comprises an adjuvant. In some aspects, the adjuvant is an amphiphilic oligonucleotide conjugate comprising an immunostimulatory oligonucleotide conjugated to a lipid with or without a linker, and optionally a polar compound, wherein the conjugate binds albumin under physiological conditions. In some aspects, the adjuvant is an immunostimulatory oligonucleotide that can bind a pattern recognition receptor. In some aspects, the immunostimulatory oligonucleotide comprises CpG. In some aspects, the immunostimulatory oligonucleotide is a ligand for a toll-like receptor. In some aspects, the linker is an oligonucleotide linker. In some aspects, the oligonucleotide linker comprises "N" consecutive guanines, wherein N is between 0-2. In some aspects, the lipid is a diacyl lipid.

In any of the foregoing or related aspects, the immune checkpoint inhibitor polypeptide of the maintenance dose is an antibody or antibody fragment targeting PD-1, PD-L1, CTLA-4, LAG3, TIM3, or a member of the B7 ligand family. In some aspects, the immune checkpoint inhibitor polypeptide is an antibody or antibody fragment targeting PD-1. In some aspects, the antibody or antibody fragment targeting PD-1 is selected from the group consisting of: nivolumab and pembrolizumab. In other aspects, the immune checkpoint inhibitor polypeptide is an antibody or antibody fragment targeting PD-L1. In some aspects, the antibody or antibody fragment targeting PD-L1 is selected from the group consisting of: atezolizumab, avelumab, and durvalumab. In yet other aspects, the immune checkpoint inhibitor polypeptide is an antibody or antibody fragment targeting CTLA-4. In some aspects, the antibody or antibody fragment targeting CTLA-4 is selected from the group consisting of: tremelimumab and ipilimumab.

In any of the foregoing or related aspects, the maintenance dose comprises a second different immune checkpoint inhibitor polypeptide. In some aspects, the second different immune checkpoint inhibitor polypeptide is an antibody or antibody fragment targeting PD-1, PD-L1, CTLA-4, LAG3, TIM3, or a member of the B7 ligand family. In some aspects, the maintenance dose comprises an antibody or antibody fragment targeting PD-1 and an antibody or antibody fragment targeting CTLA-4.

In any of the foregoing or related aspects, the priming dose induces infiltration of immune cells in a tumor. In some aspects, the immune cells are CD8+ T cells, natural killer cells, dendritic cells, or any combination thereof. In some aspects, the immune cells are cytotoxic T lymphocytes (CTLs).

In any of the foregoing or related aspects, the priming dose induces or promotes tumor cell apoptosis. In some embodiments, tumor cell apoptosis is determined by positive staining with annexin V, propidium iodide, or both. In some embodiments, positive staining of tumor cells is determined by flow cytometry.

In any of the foregoing or related aspects, the priming dose induces or promotes tumor cell immunogenic cell death. In some aspects, immunogenic cell death is characterized by surface exposure of one or more markers selected from: heat-shock protein, calreticulin, and phosphatidylserine. In some aspects, immunogenic cell death is characterized by release of one or more markers selected from: ATP and HMGB1.

In any of the foregoing or related aspects, the priming dose induces migration of dendritic cells to tumor draining lymph nodes.

In any of the foregoing or related aspects, the priming dose induces tumor antigen uptake by dendritic cells in the tumor, tumor draining lymph nodes, or both.

In any of the foregoing or related aspects, the priming dose induces expression of at least one cytokine or chemokine. In some aspects, the at least one cytokine or chemokine is selected from the group consisting of: IFN-γ, IL-1β, MIP-1α, G-CSF, Eotaxin, IP-10, MIG, M-CSF, MCP-1, RANTES, IL-12, GM-CSF, MIP-2, TNFα, IL-5, MIP-1β and any combination thereof.

In any of the foregoing or related aspects, the priming dose induces expression of FLT3L and XCL1 in a tumor.

In any of the foregoing or related aspects, the priming dose induces or promotes normalization of vasculature within the tumor. In some aspects, normalization of vasculature comprises (i) reduction of average blood vessel radius, (ii) increased pericyte to epithelial cell ratio, (iii) increased blood perfusion, (iv) reduced blood vessel leakiness, (v) decreased tumor hypoxia, or (vi) any combination of (i)-(v).

In any of the foregoing or related aspects, the priming dose is administered one day, two days, three days, four days, five days, six days or seven days before the at least one maintenance dose.

In any of the foregoing or related aspects, (i), (ii) and (iii) of the priming dose are formulated in the same composition. In some aspects the priming dose comprises (iv) a cancer vaccine, wherein the cancer vaccine is formulated in the same composition as (i), (ii) and (iii).

In any of the foregoing or related aspects, (i), (ii) and (iii) of the priming dose are formulated in different compositions. In some aspects the priming dose comprises (iv) a cancer vaccine, wherein the cancer vaccine is formulated in a separate composition.

In any of the foregoing or related aspects, (i), (ii) and (iii) of the priming dose are administered simultaneously or sequentially. In some aspects, the priming dose comprises (iv) a cancer vaccine, wherein the cancer vaccine is administered simultaneously or sequentially with (i), (ii) and (iii). In some aspects, the compositions are administered by the same route of administration. In some aspects, the route of administration is intravenous or intratumoral. In some aspects, the compositions are administered by different routes of administration.

In any of the foregoing or related aspects, the priming dose and at least one maintenance dose are administered by the same route of administration. In other aspects, the priming dose and at least one maintenance dose are administered by different routes of administration. In some aspects, the route of administration is intravenous or intratumoral.

In any of the foregoing or related aspects, the cancer is selected from a group consisting of melanoma, leukemia, lymphoma, lung cancer, breast cancer, prostate cancer, ovarian cancer, colon cancer, mesothelioma, renal cell carcinoma, and brain cancer. In some aspects, the cancer comprises a tumor with low infiltration of lymphocytes. In some aspects, the cancer comprises a tumor with low infiltration of CD8+ T cells. In some embodiments, tumor infiltration is measured by histological analysis.

BRIEF DESCRIPTION OF THE DRAWINGS

FIGS. 1A-1E provide graphs showing analysis of immune cells over time in mice having B16F10 tumors that received AIPV (combination of TA99 (anti-TRP1 antibody) (A), MSA-IL-2 (I), anti-PD-1 (P), and a cancer vaccine comprising amphiphilic Trp-2+amphiphilic CpG (V)) compared to untreated mice (UT). FIG. 1A shows the number of tumor infiltrating CD8+ T cells; FIG. 1B shows the number of CD4+ effector T cells in the tumor; FIG. 1C shows the ratio of CD8+ T cells to Treg cells in the tumor; FIG. 1D shows the number of CD8+ T cells in tumor draining lymph nodes; and FIG. 1E shows the number of CD4+ effector cells in tumor draining lymph nodes.

FIG. 6A shows the total number of infiltrating CD8+ T cells and the number of activated tumor infiltrating CD8+ T cells. FIG. 6B shows the ratio of CD8+ T cells to Treg cells. A=integrin binding 2.5F-Fc; I=MSA-IL-2; P=anti-PD-1. *P<0.05; P<0.01; *P<0.001; ****P<0.0001 by two-way ANOVA.

FIGS. 24A-24B provide graphs showing quantification by flow cytometry of intratumoral endothelial cells expressing E-selectin, VCAM-1, or VEGFR2 (FIG. 24A) and the ratio of endothelial cells (CD31+ cells) to pericytes (NG2+ cells) (FIG. 24B) in B16F10 tumors obtained from untreated mice (UT) or from mice 3 days following a single priming dose of AIP or ICB (anti-PD-1+anti-CTLA-4). A=integrin binding 2.5F-Fc; I=MSA-IL-2; P=anti-PD-1.

FIG. 25 provides a graph showing quantification of tumor vessel radius as measured from immunofluorescent images of B16F10 tumor slices, with tumors isolated from untreated mice (UT) or isolated from mice 3 days following a single priming dose of AIP or ICB (anti-PD-1+anti-CTLA-4). A=integrin binding 2.5F-Fc; I=MSA-IL-2; P=anti-PD-1.

FIG. 26 provides a bar graph showing tumor permeability based upon measurement of blood vessel endothelial cells labeled with dextran (CD31+, dextran+ cells) in confocal images of B16F10 tumor slices, with tumors isolated from mice following no treatment or at 3 days following a single priming dose of AIP or ICB (anti-PD-1+anti-CTLA-4). Mice receiving AIP were administered depleting antibody against NK cells (anti-NK1.1), macrophages (anti-F4/80), or TNFα (anti-TNFα) 1 day prior to AIP. A=integrin binding 2.5F-Fc; I=MSA-IL-2; P=anti-PD-1. Mice were intravenously injected with fluorescent 70 kDa dextran prior to tumor isolation.

FIG. 27 provides a bar graph showing quantification of tumor perfusion based upon measurement of tumor area labeled with Hoechst dye in confocal images of B16F10 tumor slices, with tumors isolated from mice treated as described in FIG. 26. Mice were intravenously injected with Hoeschst dye prior to tumor isolation.

FIG. 28 provides a bar graph quantifying tumor area labeled with the hypoxia-detecting agent EF5 in confocal images of B16F10 tumor slices, with the tumors isolated from untreated mice (UT) or from mice 3 days following a single priming dose of AIP or ICB (anti-PD-1+anti-CTLA-4). A=integrin binding 2.5F-Fc; I=MSA-IL-2; P=anti-PD-1. Mice were intravenously injected with EF5 prior to tumor isolation.

DETAILED DESCRIPTION

Overview

Figure 1A:
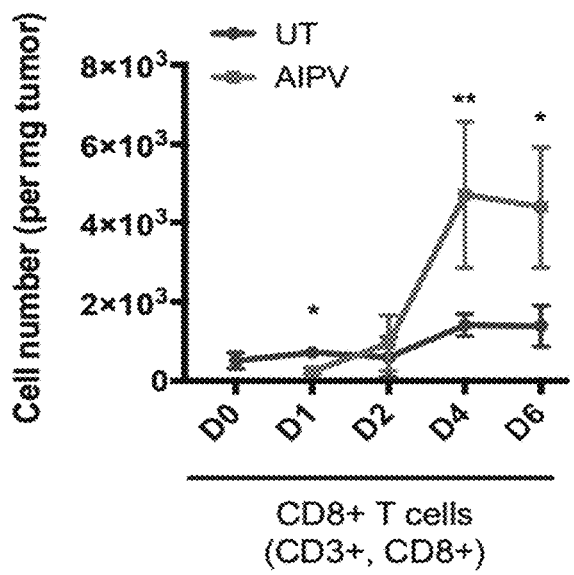

Various diseases are characterized by the development of progressive immunosuppression in a patient. The presence of an impaired immune response in patients with malignancies has been particularly well documented. Cancer patients and tumor-bearing mice exhibit a variety of altered immune functions such as a decrease in delayed type hypersensitivity, a decrease in lytic function and proliferative response of lymphocytes. Augmenting immune functions in cancer patients could have beneficial effects for tumor control.

In one aspect, the present disclosure relates to a method of treating cancer comprising administering to a subject: (a) a priming dose comprising (i) interleukin (IL)-2, (ii) an immune checkpoint inhibitor polypeptide, (iii) a tumor targeting antibody or an integrin-binding polypeptide, optionally with (iv) a cancer vaccine, and (b) at least one maintenance dose comprising an immune checkpoint inhibitor polypeptide, wherein the priming dose is administered prior to the maintenance dose. In some embodiments, the priming dose induces or enhances an anti-tumor immune response.

In some embodiments, the methods of the present disclosure prolong survival of subjects with cancer. In yet other embodiments, the methods of the present disclosure inhibit metastases. In some embodiments, the methods of the present disclosure reduce tumor size. In some embodiments, the methods of the present disclosure inhibit or delay the growth of tumor cells.

Methods of Use and Dosing Regimens

In some embodiments, the present disclosure provides methods of administering a priming dose of combination immunotherapy followed by subsequent maintenance doses of an immune checkpoint inhibitor polypeptide.

Immune cells and the cytokine milieu in the tumor microenvironment mediate the balance between immune tolerance and anti-tumor immunity. See e.g., Fu, C and Jiang, A, Front. Immunol. 9, 3059 (2018); Tormoen et al., Adv. Rad. Oncol. 3:52-526 (2018). In some embodiments, the combination immunotherapy priming dose described herein induces an anti-tumor response. In some embodiments, the combination immunotherapy priming dose overcomes the immunosuppressive pathway in the tumor microenvironment which is maintained by immune checkpoint inhibitor therapy.

In some embodiments, the combination immunotherapy priming dose primes an anti-tumor immune response that is sustained or promoted by one or more subsequent doses of immune checkpoint inhibitor therapy. In some embodiments, the combination immunotherapy priming dose reverses or overcomes immunosuppressive pathways in the tumor microenvironment, thereby priming an anti-tumor response that is sustained or promoted by one or more subsequent doses of immune checkpoint inhibitor therapy.

In some embodiments, the methods described herein comprise administering to a subject a priming dose comprising (i) IL-2; (ii) a tumor targeting antibody or integrin-binding polypeptide; (iii) an immune checkpoint inhibitor polypeptide; and optionally (iv) a cancer vaccine, and at least one maintenance dose of an immune checkpoint inhibitor polypeptide, wherein the priming dose is administered prior to the maintenance dose. In some embodiments, the priming dose induces an anti-tumor immune response. In some embodiments, the maintenance dose sustains or promotes the anti-tumor immune response induced by the priming dose.

Compositions of the disclosure are administered to a subject in an effective amount. In general, an effective amount of the compositions induce an anti-tumor immune response and subsequently maintain the immune response.

The methods of the disclosure for treating cancer are used in a variety of clinical or therapeutic applications. For example, the methods are used to stimulate anti-tumor immune responses in a subject with cancer. The compositions of the present disclosure are useful in methods for treating or delaying progression of solid tumor malignancy or lymphoma in a subject, e.g., a human patient by injection. The injection can be in a single injection at a single site or multiple injections at one or more sites (one or more tumors). The injection can be a bolus injection or a continuous infusion.

Suitable priming combination immunotherapy composition according to the present disclosure includes combinations and sub-combinations selected from a group comprising a tumor targeting antibody or an integrin-binding polypeptide, a cancer vaccine, interleukin (IL)-2 (e.g., half-life extended IL-2) and an immune checkpoint inhibitor polypeptide. In some embodiments, the antibody is a tumor specific antigen (TSA) targeting antibody. In some embodiments, the antibody is a tumor associated antigen (TAA) targeting antibody. In some embodiments, the integrin-binding polypeptide is a knottin protein. See e.g., Kwan, B.

H., et al., J Exp. Med. 214:1679-1690 (2017); US 2017/0368138, each of which is incorporated herein by reference.

In some embodiments, the dosing method described herein primes native and adaptive immune responses with a priming dose of combination immunotherapy, followed by maintenance doses of immune checkpoint inhibitor polypeptide to overcome the immunosuppressive mechanisms in the tumor microenvironment. In some embodiments, the immune checkpoint inhibitor polypeptide suitable for use in the priming dose and the maintenance dose targets PD-1, PD-L1, CTLA-4, LAG3, B7-H3, B7-H4 and TIM. In some embodiments, the immune checkpoint inhibitor polypeptide is an antibody selected from a group comprising anti-CTLA4 and anti-PD-1. In some embodiments, the immune checkpoint inhibitor polypeptide is an antibody selected from a group comprising anti-CTLA-4, anti-PD-L1, and anti-PD-1. In some embodiments, the priming dose comprises a combination of anti-CTLA-4 and anti-PD-1 antibodies. In some embodiments, the priming dose comprises a combination of anti-CTLA-4 and anti-PD-L1 antibodies. In some embodiments, the maintenance dose comprises a combination of anti-CTLA4 and anti-PD-1 antibodies. In some embodiments, the maintenance dose comprises a combination of anti-CTLA4 and anti-PD-L1 antibodies.

In some embodiments, the disclosure provides a method for treating a cancer, comprising administering (a) a priming dose comprising (i) interleukin (IL)-2, (ii) an immune checkpoint inhibitor polypeptide, and (iii) a tumor targeting antibody or an integrin-binding polypeptide, optionally with (iv) a cancer vaccine, wherein the priming dose induces or enhances an anti-tumor immune response in the subject; and (b) at least one maintenance dose comprising an immune checkpoint inhibitor polypeptide, and wherein the priming dose is administered prior to the maintenance dose.

In some embodiments, the priming dose is administered one day, two days, three days, four days, five days, six days or seven days before the maintenance dose. In some embodiments, the priming dose is administered at least one day, at least two days, at least three days, at least four days, at least five days, at least six days, at least seven days, at least two weeks, or at least three weeks before the maintenance dose.

Effects of Priming Dose

In some embodiments, a priming dose of combination immunotherapy induces the release of chemokines and cytokines in the tumor microenvironment. In some embodiments, a priming dose of combination immunotherapy induces the release of IFN-γ, IL-1β, MIP-1α, G-CSF, Eotaxin, IP-10, MIG, M-CSF, MCP-1, RANTES, IL-12, GM-CSF, MIP-2, TNFα, IL-5, MIP-1β, or any combination thereof. In some embodiments, a priming dose of combination immunotherapy induces expression of FLT3L, XCL1, or both in the tumor microenvironment. In some embodiments, a priming dose of combination immunotherapy induces expression of FLT3L by NK cells, CD8+ T cells, or both in the tumor microenvironment. In some embodiments, a priming dose of combination immunotherapy induces expression of XCL1 by NK cells, CD8+ T cells, or both in the tumor microenvironment.

In some embodiments, a priming dose of combination immunotherapy promotes tumor immunity by release of cytokines that recruit immune cells such as dendritic cells. The role of dendritic cells in cancer immunity is reviewed in Gardner, A. and Ruffell, B., Trends. Immunol. 37, 855-865 (2016), herein incorporated by this reference. In some embodiments, the administration of a priming dose of combination immunotherapy induces the recruitment of infiltrating NK and CD8+ T cells, resulting in the secretion of FLT3L, which in turn affects the accumulation of dendritic cells in the tumor microenvironment. In some embodiments, the uptake and presentation of tumor antigens by antigen-presenting cells such as DCs activates and maintain efficacious anti-tumor response.

Stimulation of cross-presenting dendritic cells in particular contributes to activation of anti-tumor immune responses. For example, anti-tumor immune responses in mice require intratumoral cross-presenting dendritic cells or type 1 conventional denritic cells (cDC1s) characterized by CD103 expression, wherein the anti-tumor immune response is facilitated by functions of the cross-presenting dendritic cells that comprise (i) tumor antigen uptake and cross-presentation, (ii) migration to tumor draining lymphatic tissues or lymph nodes, and (iii) priming of tumor antigen-specific cytotoxic T cells (see, e.g., Fu, C. et al (2018) *Front. Immunol.* 9:1). In humans, intratumoral cross-presenting cDC1s important for anti-tumor immune response are characterized by expression of BDCA3 (also known as CD141) (see, e.g., Broz, M. et al (2014) *Cancer Cell* 26:638-652). The release of certain chemokines and cytokines in the tumor microenvironment is known to recruit and activate cross-presenting dendritic cells in both human and mouse tumors (see, e.g., Barry, et al. (2018) *Nat. Med.* 24:1178). For example, FLT3L in the tumor is known to promote expansion of dendritic cells and is predominantly produced by lymphocytes, notably natural killer cells (see, e.g., Barry, K. et al (2018) *Nat. Med.* 24:1178-1191).

In some embodiments, a priming dose of combination immunotherapy induces accumulation of cross-presenting DCs in the tumor, the tumor draining lymph nodes, or both. In some embodiments, a priming dose of combination immunotherapy induces activation and FLT3L production by lymphocytes (e.g., natural killer cells, cytotoxic T cells), thereby promoting accumulation and activation of cross-presenting DCs in the tumor, tumor draining lymph nodes, or both. In some embodiments, tumor antigen uptake and presentation by cross-presenting dendritic cells promotes priming of tumor-specific cytotoxic T cells (e.g., activation of tumor-specific cytotoxic T cells). In some embodiments, priming of tumor-specific cytotoxic T cells by cross-presenting dendritic cells promotes an efficacious anti-tumor immune response.

In some embodiments, a priming dose of combination immunotherapy induces or increases tumor cell death. Tumor cell death can occur through cellular processes initiated by one or more signal transduction pathways in response to stimuli in the intracellular or extraceullar microenvironment, such as by apoptosis (see e.g., Galluzzi, et al. (2018) *Cell Death & Differentiation* 25:486-541). In some embodiments, a priming dose of combination immunotherapy promotes cell death of tumor cells. In some embodiments, a priming dose of combination immunotherapy promotes tumor cell apoptosis. In some embodiments, a priming dose of combination immunotherapy promotes cell death of tumor cells, thereby providing tumor antigens for uptake and cross presentation by dendritic cells.

A particular form of cell death that is pro-inflammatory and sufficient to activate an adaptive immune response in an immunocompetent host is referred to as immunogenic cell death (ICD). ICD is characterized by exposure or release of damage-associated molecular patterns (DAMPs) that provide immunostimulatory signals for promoting recruitment, activation, and antigen uptake by immune cells (see, e.g., Zhou, J. (2019) *J Cell Mol Med.* 23:4854-4865). DAMPs associated with immunogenic cell death include surface exposure of calreticulin and heat shock proteins (HSPs), release of high mobility group B1 (HMGB1) from the nucleus, production of type I interferons (Type I IFN), and extracellular secretion of adenosine triphosphate (ATP).

Release or exposure of DAMPs by dying tumor cells is thought to promote recruitment of immune cells to the tumor microenvironment, as well as promoting activation, tumor antigen uptake and cross presentation by dendritic cells (Galluzzi, et al. (2018) *Cell Death & Differentiation* 25:486-541). For example, exposure of calreticulin by dying tumor cells is thought to provide a signal to promote phagocytosis by antigen presenting cells (see, e.g., Obeid et al (2007) *Nat Med* 13:54 and Obeid et al (2007) 67:7941-7944); secretion of ATP by dying tumor cells is thought to provide a chemoattractant signal to recruit immune cells to the tumor microenvironemnt (see, e.g., Michaud, et al (2011) *Science* 334:1573-1577; Elliott et al (2009) *Nature* 461:282-6); and exposure or release of HMGB1, HSPs, type I IFNs by dying tumor cells is thought to activate dendritic cells and promote cross-presentation of tumor antigens (see, e.g., Apetoh, et al (2007) *Nat Med* 13:1050-1059; Scaffidi (2002) *Nature* 418-191-195; Garg et al (2012) *Cancer Immunol Immunother* (2012) 61:215-221; Sistigu et al (2014) *Nat Med* 20:1301-1309).

In some embodiments, a priming dose of combination immunotherapy induces immunogenic cell death. In some embodiments, a priming dose of combination immunotherapy promotes exposure or release of DAMPs in the tumor microenvironment by inducing immunogenic cell death of tumor cells. For example, in some embodiments, the exposure or release of DAMPs in the tumor microenvironment induced by the priming dose comprises (i) surface exposure of calreticulin, (ii) surface exposure of heat shock proteins, (iii) surface exposure of phosphatidylserine, (iv) release of HMGB1, (v) release of ATP, (vi) release of type I IFNs or (vii) any combination of (i)-(vi). In some embodiments, the exposure or release of DAMPs induced by the priming dose promotes the recruitment, activation and cross presentation of tumor antigens by dendritic cells, thereby promoting an anti-tumor immune response.

In some embodiments, the present disclosure provides a method for treating cancer by sensitizing a tumor to immune checkpoint inhibitor polypeptide therapy by inducing migration of tumor-specific cells and creating an inflamed T cell-infiltrate tumor microenvironment (TME). More specifically, the compositions and methods of the present disclosure aid in sensitizing the anti-cancer response and overcoming immune suppression by inducing the infiltration of NK, DC and effector T cells into the tumor microenvironment.

In some embodiments, the disclosure provides a method of treating cancer by administering a priming dose of a combination immunotherapy, wherein the priming dose promotes normalization of tumor vasculature. Solid tumors are often characterized by abnormal vasculature, wherein the abnormal tumor vasculature results in hypoxia, acidity, and elevated interstitual fluid pressure in the tumor microenvironment that contributes to tumor progression and metastasis, resistance to cancer therapy, and immunosuppression (see, e.g., Martin, J. et al (2019) *Ann Rev Physiol* 81:505-534). Hallmarks of abnormal tumor vessels comprise enlarged blood vessels, disorganized vasculature, permeable or leaky blood vessels, and blood vessels with detached pericytes and/or large gaps between endothelial cells (see, e.g., Jain, R. (2013) *J. Clin. Oncol.* 31:2205-2218).

Normalized tumor vessels comprise a number of characteristics. Non-limiting examples include reduced tumor vessel size; increased pericyte coverage of blood vessels; improved blood vessel perfusion; reduced leakiness of blood vessels; increased expression of adhesion factors by blood vessel endothelial cells. As a result of vessel normalization, the tumor has decreased interstitutal fluid pressure, increased blood perfusion, reduced hypoxia, and increased lymphocyte infiltration (see, e.g., Schaaf, M. et al (2018) *Cell Death & Disease* 9:115; Tian, L. et al (2017) *Nature* 544:250-254; Huang, Y. et al (2012) *PNAS* 109:17561-17566). Such features contribute to restoration of tumor immune surveillance by mitigating immune suppression caused by a hypoxic tumor microenvironment (see, e.g., Chouaib, et al (2017) *Oncogene* 36:439-445) and enabling increased infiltration of anti-tumor cytotoxic T cells. Additionally, improved blood perfusion in the tumor allows increased transport of blood-borne molecules (e.g., immune checkpoint inhibitor polypeptide) throughout the tumor microenvironment, thereby enabling therapeutic molecules to effectively engage targets within the tumor.

In some embodiments, a priming dose of combination immunotherapy promotes normalization of tumor vasculature. In some embodiments, normalization of tumor vasculature comprises (i) reduction of average blood vessel radius, (ii) reduced variability of blood vessel radius, (iii) increased pericyte to epithelial cell ratio, (iv) increased pericyte coverage of tumor blood vessels, (v) increased expression of adhesion molecules by endothelial cells, (vi) increased blood perfusion of the tumor, (vii) reduced blood vessel leakiness, (viii) decreased tumor hypoxia, or (ix) any combination of (i)-(viii).

In some embodiments, a priming dose of combination immunotherapy promotes increased blood perfusion of the tumor. In some embodiments, increased blood perfusion of the tumor following the priming dose reduces tumor hypoxia, thereby overcoming or mitigating immunesuppressive mechanisms in the tumor microenvironment. In some embodiments, increased blood perfusion of the tumor following the priming dose promotes transport of blood-borne molecules (e.g., immune checkpoint inhibitor polypeptide) throughout the tumor microenvironment, thereby sensitizing the tumor to a subsequent maintenance dose.

In some embodiments, a priming dose of combination immunotherapy promotes increased expression of adhesion molecules by endothelial cells. In some embodiments, increased expression of adhesion molecules promotes infiltration of cytotoxic T cells into the tumor microenvironment, thereby promotin an anti-tumor immune response.

The presence of immune cells and cytokines in a tumor microenvironment can be measured by methods known in the art. In some embodiments, the accumulation of dendritic and other effector immune cells in the tumor environment results in the uptake and presentation of tumor antigen in antigen-presenting cells such as DCs. The tumor antigen-laden dendritic cells subsequently migrate to tumor draining lymph nodes (TDLNs), where the DC continues to present the tumor antigen, thus inducing effector T cell activation, proliferation and development. In another embodiment, the priming dose of combination immunotherapy induces recruitment of natural killer (NK) cells, DC and dendritic cells into TDLNs.

Methods of Measuring Effects of Priming Dose

In some embodiments, sufficient priming is determined by measuring intratumoral immune cell infiltration. For example, in some embodiments priming of a tumor results in increased CD8+ T cell infiltration, natural killer cell infiltration and/or dendritic cell infiltration into a tumor, relative to non-primed tumors. Methods for determining immune cell infiltration are known to those of skill in the art, and include but are not limited to flow cytometry, immunohistochemistry, and tissue microarray. In some embodiments, immune cell infiltration is increased by 5%, 10%, 15%, 20%, 25%, 30%, 35%, 40%, 45%, 50% or more than 50% relative to tumors that did not receive a priming dose (e.g., tumor sample obtained prior to priming dose).

In some embodiments, sufficient priming is determined by measuring cytokine and/or chemokine expression levels within a tumor. Methods for measuring intratumoral protein levels are known to those of skill in the art and include, but are not limited to, Luminex, ELISA and western blotting. In some embodiments, chemokine or cytokine expression is increased by 5%, 10%, 15%, 20%, 25%, 30%, 35%, 40%, 45%, 50% or more than 50% relative to tumors that did not receive a priming dose (e.g., tumor sample obtained prior to administration of priming dose).

In some embodiments, sufficient priming is determined by measuring normalization of tumor vasculature. Methods of assessing and measuring tumor vasculature are known in the art, for example, by noninvasive techniques such as magnetic resonance imaging (MRI) or by immunohistochemical analysis of excised tumors or tumor biopsy histology samples. In some embodiments, normalization of tumor vasculature is assessed by measuring vasculature morphology parameters, wherein vessels of tumor samples are visualized using a marker such as von Willebrand factor, CD34, or CD31 and the microvascular density (MVD), the relative vascular volume (RVV), or the mean vessel diameter or radius are determined as described by Weidner, N. et al (1991) *N Engl J Med.* 324:1-8; Weidner, N. (1998) *J. Pathol.* 184:119-122; Fox, S. (1997) *Histopathology* 30:294-301; and Forster, J. et al (2017) *Hypoxia* 5:21-32. In some embodiments, MVD in tumors receiving a priming dose is substantially equivalent to MVD in corresponding normal tissue (e.g., approximately 80%, 85%, 90%, 95%, 96%, 97%, 98%, 99%, 100%, 105%, 110%, 115%, 120%, or between 80% and 120% of MVD in corresponding normal tissue). In some embodiments, mean vessel diameter in tumors receiving a priming dose is substantially equivalent to mean vessel diameter in corresponding normal tissue (e.g., approximately 80%, 85%, 90%, 95%, 96%, 97%, 98%, 99%, 100%, 105%, 110%, 115%, 120%, or between 80% and 120% of mean vessel diameter in corresponding normal tissue). It is understood that corresponding normal tissue refers to a corresponding healthy tissue lacking malignant cells (e.g., lung carcinoma as compared to lung tissue, mammary carcinoma as compared to mammary tissue, renal cell carcinoma as compared to kidney tissue, prostate carcinoma as compared to prostate tissue, glioblastoma as compared to brain tissue, etc.).

In some embodiments, normalization of tumor vasculature is assessed by measuring tumor hypoxia. Methods of measuring hypoxia in tumors are known in the art. For example, by staining tumor sections with markers for blood vessels and hypoxia (see, e.g., Wijffels, et al (2000) *Br J Cancer* 83:674-683, Chou, S. et al (2004) *Br J Cancer* 90:728-735, and Le, Q. et al (2008) *Cancer Metastasis Rev* 27:351-362). Non-limiting examples of hypoxic markers include pimonidazole and EFS. In some embodiments, the hypoxic fraction is determined, wherein the hypoxic fraction is defined as the proportion of tumor area stained with a hypoxic marker. In some embodiments, hypoxic fraction in tumors receiving a priming dose is reduced by 5%, 10%, 15%, 20%, 25%, 30%, 35%, 40%, 45%, 50% or more than 50% relative to tumors that did not receive a priming dose (e.g., tumor sample obtained prior to administration of priming dose). In some embodiments, hypoxic fraction in tumors receiving a priming dose is substantially equivalent to the hypoxic fraction in corresponding normal tissue (e.g., not more than 1.1-fold, 1.2-fold, 1.3-fold, 1.4-fold, 1.5-fold, 1.6-fold, 1.7-fold, 1.8-fold, 1.9-fold, or 2-fold higher). In some embodiments, no staining of tumors receiving a priming dose is detectable using a hypoxic marker (e.g., EFS) when compared to background (e.g., an unstained tumor sample).

Dosing Regimen

In some embodiments, the methods described herein comprise administering to a subject a priming dose comprising (i) a tumor targeting antibody or an integrin-binding polypeptide; (ii) interleukin (IL)-2 (e.g., half-life extended IL-2); (iii) an immune checkpoint inhibitor polypeptide; and optionally (iv) a cancer vaccine, and at least one maintenance dose of an immune checkpoint inhibitor polypeptide. In some embodiments, the priming dose and the maintenance dose comprise a combination of immune checkpoint inhibitor polypeptides (e.g., anti-PD-1 and anti-CTLA-4).

In some embodiments, the priming dose and the maintenance dose comprise an immune checkpoint inhibitor polypeptide or combination of immune checkpoint inhibitor polypeptides that are the same. For example, in some embodiments, both the priming dose and the maintenance dose are selected from: anti-PD-1 alone, anti-CTLA-4 alone, or anti-PD-1 and anti-CTLA-4 in combination. In some embodiments, the priming dose and the maintenance dose comprise an immune checkpoint inhibitor polypeptide that are the different. For example, in some embodiments the priming dose comprises anti-PD-1 alone and the maintenance dose comprises anti-CTLA-4 alone. In some embodiments, the priming dose and the maintenance dose comprises one or more immune checkpoint inhibitor polypeptides with at least one inhibitor in common. For example, in some embodiments, the priming dose comprises anti-PD-1 and anti-CTLA-4 in combination and the maintenance dose is selected from anti-PD-1 or anti-CTLA-4.

In some embodiments, the methods of the disclosure comprise administering a priming dose and a maintenance dose comprising an immune checkpoint inhibitor polypeptide, wherein the same amount of the immune checkpoint inhibitor polypeptide is administered in both the priming dose and the maintenance dose. While, in some embodiments, a different amount of the immune checkpoint inhibitor polypeptide is administered in the priming dose and the maintenance dose (i.e., the maintenance dose comprises an amount of the immune checkpoint inhibitor polypeptide that is more or less than the amount administered in the priming dose).

In some embodiments, the components of the priming dose of combination immunotherapy are administered to a subject in the same pharmaceutical composition. In some embodiments, the components of the priming dose of combination immunotherapy are administered to a subject in separate pharmaceutical compositions. In some embodiments, the separate pharmaceutical compositions are administered simultaneously or sequentially. In some embodiments, the separate pharmaceutical compositions are administered by the same route of administration. In some embodiments, the separate pharmaceutical compositions are administered by different routes of administration. In embodiments wherein the maintenance dose comprises more than one immune checkpoint inhibitor polypeptide, the immune checkpoint inhibitor polypeptides are administered in the same pharmaceutical composition. In some embodiments, the more than one immune checkpoint inhibitor polypeptides are administered in separate pharmaceutical compositions, wherein the separate pharmaceutical compositions are administered simultaneously or sequentially. In some embodiments, the separate pharmaceutical compositions are administered by the same route of administration or different routes of administration.

In some embodiments, combination immunotherapy or maintenance dose can therefore be administered as a single dose or as two or more doses (which may or may not contain the same amount of the desired composition) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In some embodiments, the dosing regimen is determined by the pharmacodynamics effects of the combination immunotherapy. In some embodiments, the pharmacodynamics effects include an increase in T cells within tumors after administration. In some embodiments, the increase in T cells is maintained over a specified period of time (e.g., one week, two weeks, three weeks).

In some embodiments, after administration of the priming dose the maintenance doses of an immune checkpoint inhibitor polypeptide are administered to a subject about every 7-42 days for a specified time period. In some embodiments, after administration of the priming dose the maintenance doses of an immune checkpoint inhibitor polypeptide are administered to a subject about every 7-21 days for a specified time period. In some embodiments, after administration of the priming dose the maintenance doses of an immune checkpoint inhibitor polypeptide are administered to a subject about every 14-21 days for a specified time period. In some embodiments, after administration of the priming dose the maintenance doses of an immune checkpoint inhibitor polypeptide are administered to a subject about every 14-28 days for a specified time period. In some embodiments, after administration of the priming dose the maintenance doses of an immune checkpoint inhibitor polypeptide are administered to a subject about every 21-28 days for a specified time period. In some embodiments, after administration of the priming dose the maintenance doses of an immune checkpoint inhibitor polypeptide are administered to a subject about every 21-35 days for a specified time period. In some embodiments, after administration of the priming dose the maintenance doses of an immune checkpoint inhibitor polypeptide are administered to a subject about every 28-42 days for a specified time period.

In some embodiments, the specified time period is determined by a clinician. In some embodiments, dosing occurs until a positive therapeutic outcome is achieved. For example, in some embodiments, dosing occurs until growth of cancer cells, tumor cells or tumors is inhibited. In some embodiments, dosing occurs until growth of cancer cells, tumor cells or tumors is reduced. In some embodiments, dosing occurs until there is no detection of cancer cells, tumor cells or tumors in a biological sample. In some embodiments, dosing occurs until progression of a cancer is delayed. In some embodiments, dosing occurs until progression of a cancer is inhibited. In some embodiments, the specified time period is determined once a positive therapeutic outcome is achieved.

In some embodiments, a positive therapeutic outcome is determined by analyzing a biological sample (e.g., biopsy, blood sample) shortly following administration of a priming or maintenance dose (e.g., within 6 weeks, 5 weeks, 4 weeks, 3 weeks, 2 weeks, or 1 week of administration). In some embodiments, a positive therapeutic outcome is determined by analyzing a biological sample (e.g., biopsy, blood sample) at regular intervals between a priming dose and a maintenance dose or between maintenance doses. In some embodiments, maintenance of a positive therapeutic outcome is determined by analyzing a biological sample (e.g., biopsy, blood sample) prior to administration of a subsequent maintenance dose.

In some embodiments, dosing of an immune checkpoint inhibitor polypeptide will occur indefinitely, or until a positive therapeutic outcome is achieved. In some embodiments, the dosing interval remains consistent. In some embodiments, the dosing interval changes as needed based on a clinician's assessment. In some embodiments, dosing occurs indefinitely to maintain remission of a cancer.

Composition for Prime and Maintenance Dosing

A. IL-2 and Extended-PK IL-2

In some embodiments, the priming dose of combination immunotherapy comprises interleukin-2 (IL-2). IL-2 has been approved as an anti-cancer treatment, but the application of IL-2 is limited by its pleiotropic effect on both effector and regulatory T cells, and by the systemic toxicity associated with IL-2 therapy. Jiang, T., et al., Oncoimmunology 5, e1163462 (2016); Choudhry, H. et al., BioMed. Res. Int. 9056173 (2018); Pachella, J. A., et al., J. Adv. Pract. Oncol. 6, 212-221 (2015). In some embodiments, the methods of the present disclosure maximize the induction of soluble and cellular anti-tumor immunity while concurrently minimizing systemic toxic effect of IL-2 therapy with a single priming dose using combination immunotherapy comprising a tumor targeting antibody or an integrin-binding polypeptide, IL-2, and an immune checkpoint inhibitor polypeptide. In some embodiments, the combination immunotherapy comprises a cancer vaccine.

IL-2 is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Rα, the alpha subunit, also known as CD25 in humans), p75 (IL-2Rβ, the beta subunit, also known as CD 122 in humans) and p64 (IL-2Rγ, the gamma subunit, also known as CD 132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2:IL-2R complex is internalized upon ligand binding and the different components undergo differential sorting. IL-2Rα is recycled to the cell surface, while IL-2 associated with the IL-2:IL-2Rβγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with high-dose IL-2 treatment is largely attributable to the activity of natural killer (NK) cells. NK cells express the intermediate-affinity receptor, IL-2RPγ$_c$, and thus are stimulated at nanomolar concentrations of IL-2, which do in fact result in patient sera during high-dose IL-2 therapy. Attempts to reduce serum concentration, and hence selectively stimulate IL-2RaPγ$_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

It was recently discovered that the ability of IL-2 to control tumors in various cancer models could be substantially increased by attaching IL-2 to a pharmacokinetic modifying group. The resulting molecule, hereafter referred to as "extended-pharmacokinetic (PK) IL-2," has a prolonged circulation half-life relative to free IL-2. The prolonged circulation half-life of extended-PK IL-2 permits in vivo serum IL-2 concentrations to be maintained within a therapeutic range, leading to the enhanced activation of many types of immune cells, including T cells. Because of its favorable pharmacokinetic profile, extended-PK IL-2 can be dosed less frequently and for longer periods of time when compared with unmodified IL-2. Extended-PK IL-2 is described in detail in International Patent Application NO. PCT/US2013/042057, filed May 21, 2013, and claiming the benefit of priority to U.S. Provisional Patent Application No. 61/650,277, filed May 22, 2012. The entire contents of the foregoing applications are incorporated by reference herein.

1. IL-2 and Mutants Thereof

In certain embodiments, an effective amount of human IL-2 is administered systemically. In some embodiments, an effective amount of an extended-PK IL-2 is administered systemically. In one embodiment, the IL-2 is a human recombinant IL-2 such as Proleukin® (aldesleukin). Proleukin® is a human recombinant interleukin-2 product produced in E. coli. Proleukin® differs from the native interleukin-2 in the following ways: a) it is not glycosylated; b) it has no N-terminal alanine; and c) it has serine substituted for cysteine at amino acid positions 125. Proleukin® exists as biologically active, non-covalently bound microaggregates with an average size of 27 recombinant interleukin-2 molecules. Proleukin® (aldesleukin) is administered by intravenous infusion. In some aspects, the IL-2 portion of the extended-PK IL-2 is wild-type IL-2 (e.g., human IL-2 in its precursor form (SEQ ID NO: 33) or mature IL-2 (SEQ ID NO: 35)).

In certain embodiments, the extended-PK IL-2 is mutated such that it has an altered affinity (e.g., a higher affinity) for the IL-2R alpha receptor compared with unmodified IL-2.

Site-directed mutagenesis can be used to isolate IL-2 mutants that exhibit high affinity binding to CD25, i.e., IL-2Rα, as compared to wild-type IL-2. Increasing the affinity of IL-2 for IL-2Rα at the cell surface will increase receptor occupancy within a limited range of IL-2 concentration, as well as raise the local concentration of IL-2 at the cell surface.

In certain embodiments, the disclosure features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants which are high affinity binders include those described in WO2013/177187A2 (herein incorporated by reference in its entirety), such as those with amino acid sequences set forth in SEQ ID NOs: 7, 23, 25, 27, 29, and 31. Further exemplary IL-2 mutants with increased affinity for CD25 are disclosed in U.S. Pat. No. 7,569,215, the contents of which are incorporated herein by reference. In one embodiment, the IL-2 mutant does not bind to CD25, e.g., those with amino acid sequences set forth in SEQ ID NOs: 9 and 11.

IL-2 mutants include an amino acid sequence that is at least 80% identical to SEQ ID NO: 33 that bind CD25. For example, an IL-2 mutant can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586) of SEQ ID NO: 32; amino acid sequence (accession: P60568) of SEQ ID NO: 33) or human IL-2 without the signal peptide (nucleic acid sequence of SEQ ID NO: 34; amino acid sequence of SEQ ID NO: 35). Accordingly, in certain embodiments, the IL-2 moiety of the extended-PK IL-2 is human IL-2. In other embodiments, the IL-2 moiety of the extended-PK IL-2 is a mutant human IL-2.

IL-2 mutants can be at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical in amino acid sequence to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO: 33 is a polypeptide that includes a sequence that is identical to the reference sequence except for the inclusion of up to five alterations of the reference amino acid of SEQ ID NO: 33. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N–) or carboxy (C–) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact IL-2Rα.

In general, the polypeptides suitable for use in the methods disclosed herein will be synthetic, or produced by expression of a recombinant nucleic acid molecule. In the event the polypeptide is an extended-PK IL-2 (e.g., a fusion protein containing at least IL-2 and a heterologous polypeptide, such as a hexa-histidine tag or hemagglutinin tag or an Fc region or human serum albumin), it can be encoded by a hybrid nucleic acid molecule containing one sequence that encodes IL-2 and a second sequence that encodes all or part of the heterologous polypeptide.

The techniques that are required to make IL-2 mutants are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of IL-2 mutants). Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating IL-2 mutants via expression of nucleic acid molecules that have been altered by recombinant molecular biological techniques, IL-2 mutants can be chemically synthesized. Chemically synthesized polypeptides are routinely generated by those of skill in the art.

As noted above, IL-2 can also be prepared as fusion or chimeric polypeptides that include IL-2 and a heterologous polypeptide (i.e., a polypeptide that is not IL-2). The heterologous polypeptide can increase the circulating half-life of the chimeric polypeptide in vivo, and may, therefore, further enhance the properties of IL-2. As discussed in further detail infra, the polypeptide that increases the circulating half-life may be serum albumin, such as human or mouse serum albumin.

In certain embodiments, the chimeric polypeptide can include IL-2 and a polypeptide that functions as an antigenic tag, such as a FLAG sequence. FLAG sequences are recognized by biotinylated, highly specific, anti-FLAG antibodies, as described herein (see also Blanar et al., Science 256: 1014, 1992; LeClair et al., Proc. Natl. Acad. Sci. USA 89:8145, 1992). In certain embodiments, the chimeric polypeptide further comprises a C-terminal c-myc epitope tag.

Chimeric polypeptides can be constructed using no more than conventional molecular biological techniques, which are well within the ability of those of ordinary skill in the art to perform.

a. Nucleic Acid Molecules Encoding IL-2

IL-2, either alone or as a part of a chimeric polypeptide, such as those described herein, can be obtained by expression of a nucleic acid molecule. Thus, nucleic acid molecules encoding polypeptides containing IL-2 or an IL-2 mutant are considered within the scope of the disclosure, such as those with nucleic acid sequences set forth in SEQ ID Nos: 4, 6, 8, 10, 12, 14, 16, 18, 20, 22, 24, 26, 28, 30, 32, and 34. Just as IL-2 mutants can be described in terms of their identity with wild-type IL-2, the nucleic acid molecules encoding them will necessarily have a certain identity with those that encode wild-type IL-2. For example, the nucleic acid molecule encoding an IL-2 mutant can be at least 50%, at least 65%, preferably at least 75%, more preferably at least 85%, and most preferably at least 95% (e.g., 99%) identical to the nucleic acid encoding full length wild-type IL-2 (e.g., SEQ ID NO: 32) or wild-type IL-2 without the signal peptide (e.g., SEQ ID NO: 34).

The nucleic acid molecules suitable for use in the methods disclosed herein contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules can include fragments not found as such in the natural state. Thus, the disclosure encompasses use of recombinant molecules, such as those in which a nucleic acid sequence (for example, a sequence encoding an IL-2 mutant) is incorporated into a vector (e.g., a plasmid or viral vector) or into the genome of a heterologous cell (or the genome of a homologous cell, at a position other than the natural chromosomal location).

As described above, IL-2 mutants suitable for use in the methods disclosed herein may exist as a part of a chimeric polypeptide. In addition to, or in place of, the heterologous polypeptides described above, a nucleic acid molecule suitable for use in the methods disclosed herein can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hospho-transferase (HPH), thymidine kinase (TK), lacz (encoding β-galactosidase), and xanthine guanine phosphoribosyl transferase (XGPRT). Skilled artisans will be aware of additional useful reagents, for example, of additional sequences that can serve the function of a marker or reporter.

The nucleic acid molecules suitable for use in the methods disclosed herein can be obtained by introducing a mutation into IL-2-encoding DNA obtained from any biological cell, such as the cell of a mammal. Thus, the nucleic acids (and the polypeptides they encode) can be those of a mouse, rat, guinea pig, cow, sheep, horse, pig, rabbit, monkey, baboon, dog, or cat. Typically, the nucleic acid molecules will be those of a human.

2. Extended-PK Groups

As described supra, in some embodiments IL-2 or mutant IL-2 is fused to an extended-PK group, which increases circulation half-life. Non-limiting examples of extended-PK groups are described infra. It should be understood that other PK groups that increase the circulation half-life of IL-2, or variants thereof, are also applicable to the present disclosure. In certain embodiments, the extended-PK group is a serum albumin domain (e.g., mouse serum albumin, human serum albumin).

In certain embodiments, the serum half-life of extended-PK IL-2 is increased relative to IL-2 alone (i.e., IL-2 not fused to an extended-PK group). In certain embodiments, the serum half-life of extended-PK IL-2 is at least 20, 40, 60, 80, 100, 120, 150, 180, 200, 400, 600, 800, or 1000% longer relative to the serum half-life of IL-2 alone. In certain embodiments, the serum half-life of the extended-PK IL-2 is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of IL-2 alone. In certain embodiments, the serum half-life of the extended-PK IL-2 is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

a. Serum Albumin and Serum Albumin Binding Proteins

In certain embodiments, the extended-PK group is a serum albumin, or fragments thereof. Methods of fusing serum albumin to proteins are disclosed in, e.g., US2010/0144599, US2007/0048282, and US2011/0020345, which are herein incorporated by reference in their entirety. In certain embodiments, the extended-PK group is human serum albumin (HSA), or variants or fragments thereof, such as those disclosed in U.S. Pat. No. 5,876,969, WO 2011/124718, WO 2013/075066, and WO 2011/0514789. In some embodiments, the extended-PK group is HSA, or variants or fragments thereof, wherein the amino acid sequence of HSA comprising a signal peptide is set forth by SEQ ID NO: 36 and the amino acid sequence of mature HSA is set forth by SEQ ID NO: 37.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety.

b. PEGylation

In certain embodiments, an extended-PK IL-2 suitable for use in the methods disclosed herein includes a polyethylene glycol (PEG) domain. PEGylation is well known in the art to confer increased circulation half-life to proteins. Methods of PEGylation are well known and disclosed in, e.g., U.S. Pat. Nos. 7,610,156, 7,847,062, all of which are hereby incorporated by reference.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_{n-1}CH_2CH_2OH$, where n is 20 to 2300 and X is H or a terminal modification, e.g., a $C_{1-4}$ alkyl. In certain embodiments, the PEG suitable for use in the methods disclosed herein terminates on one end with hydroxy or methoxy, i.e., X is H or $CH_3$ ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462, both of which are hereby incorporated by reference. One form of PEGs includes two PEG side-chains (PEG2) linked via the primary amino groups of a lysine (Monfardini et al., Bioconjugate Chem 1995; 6:62-9).

In certain embodiments, pegylated IL-2 is produced by site-directed pegylation, particularly by conjugation of PEG to a cysteine moiety at the N- or C-terminus. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., JBC 1977; 252:3571 and JBC 1977; 252:3582, and Harris et. al., in: Poly(ethylene glycol) Chemistry: Biotechnical and Biomedical Applications; (J. M. Harris ed.) Plenum Press: New York, 1992; Chap. 21 and 22).

A variety of molecular mass forms of PEG can be selected, e.g., from about 1,000 Daltons (Da) to 100,000 Da (n is 20 to 2300), for conjugating to IL-2. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

One skilled in the art can select a suitable molecular mass for PEG, e.g., based on how the pegylated IL-2 will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 1993; 10:91-114.

In certain embodiments, PEG molecules may be activated to react with amino groups on IL-2 such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In certain embodiments, carbonate esters of PEG are used to form the PEG-IL-2 conjugates. N,N'-disuccinimidylcarbonate (DSC) may be used in the reaction with PEG to form active mixed PEG-succinimidyl carbonate that may be subsequently reacted with a nucleophilic group of a linker or an amino group of IL-2 (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively. Pegylation of IL-2 can be performed according to the methods of the state of the art, for example by reaction of IL-2 with electrophilically active PEGs (Shearwater Corp., USA, www.shearwatercorp.com). Preferred PEG reagents suitable for use in the methods disclosed herein are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C, et al., Bioconjugate Chem. 6 (1995) 62-69).

In certain embodiments, PEG molecules may be coupled to sulfhydryl groups on IL-2 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describe exemplary reactive PEG species that may be coupled to sulfhydryl groups.

In certain embodiments where PEG molecules are conjugated to cysteine residues on IL-2 the cysteine residues are native to IL-2 whereas in certain embodiments, one or more cysteine residues are engineered into IL-2. Mutations may be introduced into the coding sequence of IL-2 to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

In certain embodiments, pegylated IL-2 comprise one or more PEG molecules covalently attached to a linker.

In certain embodiments, IL-2 is pegylated at the C-terminus. In certain embodiments, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5): 1005-1009.

Monopegylation of IL-2 can also be achieved according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of IL-2 to activated PEG in the conjugation reaction can be from about 1:0.5 to 1:50, between from about 1:1 to 1:30, or from about 1:5 to 1:15. Various aqueous buffers can be used to catalyze the covalent addition of PEG to IL-2, or variants thereof. In certain embodiments, the pH of a buffer used is from about 7.0 to 9.0. In certain embodiments, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated IL-2, such as size exclusion (e.g. gel filtration) and ion exchange chromatography. Products may also be separated using SDS-PAGE. Products that may be separated include mono-, di-, tri- poly- and un-pegylated IL-2 as well as free PEG. The percentage of mono-PEG conjugates can be controlled by pooling broader fractions around the elution peak to increase the percentage of mono-PEG in the composition.

In certain embodiments, PEGylated IL-2 suitable for use in the methods disclosed herein contains one, two or more PEG moieties. In certain embodiments, the PEG moiety(ies) are bound to an amino acid residue which is on the surface of the protein and/or away from the surface that contacts CD25. In certain embodiments, the combined or total molecular mass of PEG in PEG-IL-2 is from about 3,000 Da to 60,000 Da, optionally from about 10,000 Da to 36,000 Da. In certain embodiments, PEG in pegylated IL-2 is a substantially linear, straight-chain PEG.

In certain embodiments, pegylated IL-2 suitable for use in the methods disclosed herein will preferably retain at least 25%, 50%, 60%, 70%, 80%, 85%, 90%, 95% or 100% of the biological activity associated with the unmodified protein. In certain embodiments, biological activity refers to the ability to bind CD25. The serum clearance rate of PEG-modified IL-2 may be decreased by about 10%, 20%, 30%, 40%, 50%, 60%, 70%, 80%, or even 90%, relative to the clearance rate of the unmodified IL-2. PEG-modified IL-2 may have a circulation half-life ($t^½$) which is enhanced relative to the half-life of unmodified IL-2. The half-life of PEG-IL-2, or variants thereof, may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of unmodified IL-2. In certain embodiments, the protein half-life is determined in vitro, such as in a buffered saline solution or in serum. In certain embodiments, the protein half-life is an in vivo circulation half-life, such as the half-life of the protein in the serum or other bodily fluid of an animal.

c. Other Extended-PK Groups

In certain embodiments, the extended-PK group is transferrin, as disclosed in U.S. Pat. Nos. 7,176,278 and 8,158,579, which are herein incorporated by reference in their entirety.

In certain embodiments, the extended-PK group is a serum immunoglobulin binding protein such as those disclosed in US2007/0178082, which is herein incorporated by reference in its entirety.

In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

d. Fc Domains

In certain embodiments, an extended-PK IL-2 includes an Fc domain, as described in WO2013177187. The Fc domain does not contain a variable region that binds to antigen. Fc domains useful for producing the extended-PK IL-2 described herein may be obtained from a number of different sources. In certain embodiments, an Fc domain of the extended-PK IL-2 is derived from a human immunoglobulin. In a certain embodiment, the Fc domain is from a human IgG1 constant region (SEQ ID NO: 1). The Fc domain of human IgG1 is set forth in SEQ ID NO: 2. In certain embodiments, the Fc domain of human IgG1 does not have the upper hinge region (SEQ ID NO: 3). It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some aspects, an extended-PK IL-2 includes a mutant Fc domain. In some aspects, an extended-PK IL-2 includes a mutant, IgG1 Fc domain. In some aspects, a mutant Fc domain comprises one or more mutations in the hinge, CH2, and/or CH3 domains. In some aspects, a mutant Fc domain includes a D265A mutation.

In one embodiment, the extended-PK IL-2 of the disclosure lacks one or more constant region domains of a complete Fc region, i.e., they are partially or entirely deleted. In certain embodiments, the extended-PK IL-2 of the disclosure will lack an entire CH2 domain. In certain embodiments, the extended-PK IL-2 of the disclosure comprise CH2 domain-deleted Fc regions derived from a vector (e.g., from IDEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

e. Linkers

In certain embodiments, the extended-PK group is optionally fused to IL-2 via a linker. In certain embodiments, an integrin-binding polypeptide is fused to an Fc fragment via a linker. Suitable linkers are well known in the art, such as those disclosed in, e.g., US2010/0210511 US2010/0179094, and US2012/0094909, which are herein incorporated by reference in its entirety. Exemplary linkers include gly-ser polypeptide linkers, glycine-proline polypeptide linkers, and proline-alanine polypeptide linkers. In a certain embodiment, the linker is a gly-ser polypeptide linker, i.e., a peptide that consists of glycine and serine residues.

Exemplary gly-ser polypeptide linkers comprise the amino acid sequence Ser(Gly$_4$Ser)n (SEQ ID NO: 126). In one embodiment, n=1. In one embodiment, n=2. In another embodiment, n=3, i.e., Ser(Gly$_4$Ser)3 (SEQ ID NO: 127). In another embodiment, n=4, i.e., Ser(Gly$_4$Ser)4 (SEQ ID NO: 137). In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises (Gly$_4$Ser)n (SEQ ID NO: 128). In one embodiment, n=1. In one embodiment, n=2. In a certain embodiment, n=3. In another embodiment, n=4. In another embodiment, n=5. In yet another embodiment, n=6. Another exemplary gly-ser polypeptide linker comprises (Gly$_3$Ser)n (SEQ ID NO: 129). In one embodiment, n=1. In one embodiment, n=2. In a certain embodiment, n=3. In another embodiment, n=4. In another embodiment, n=5. In yet another embodiment, n=6.

B. Integrin-Binding Polypeptides and Tumor Targeting Antibodies

Integrin-Binding Polypeptide

In some embodiments, the priming dose of combination immunotherapy comprises an integrin-binding polypeptide. Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$.

Integrin-binding polypeptides suitable for use in the methods disclosed herein are administered in a priming dose with IL-2 (e.g., extended-PK IL-2), an immune checkpoint blocker (e.g., anti PD-1 antibody), and optionally, a cancer vaccine.

In some embodiments, the integrin-binding polypeptide-Fc fusions bind to one more integrins selected from $\alpha_v\beta_1$, $\alpha_v\beta_3$, $\alpha_v\beta_5$, $\alpha_v\beta_6$, and $\alpha_5\beta_1$ with high affinity. In some embodiments, the integrin-binding polypeptide-Fc fusions bind to two integrins selected from $\alpha_v\beta_1$, $\alpha_v\beta_3$, $\alpha_v\beta_5$, $\alpha_v\beta_6$, and $\alpha_5\beta_1$ with high affinity. In some embodiments, the integrin-binding polypeptide-Fc fusions bind to three integrins selected from $\alpha_v\beta_1$, $\alpha_v\beta_3$, $\alpha_v\beta_5$, $\alpha_v\beta_6$, and $\alpha_5\beta_1$ with high affinity. In some embodiments, the binding affinity is less than about 100 nM, less than about 50 nM, less than about 40 nM, less than about 30 nM, less than about 20 nM, less thank about 20 nM, less than about 10 nM, less than about 5 nM, less than about 4 nM, less than about 3 nM, less than about 2 nM, or less than about 1 nM. In some embodiments, the binding affinity is less than 5 nM. In some embodiments, the binding affinity is less than about 4 nM. In some embodiments, the binding affinity is less than about 3 nM. In some embodiments, the binding affinity is less than about 2 nM. In some embodiments, the binding affinity is less than about 1 nM. In some embodiments, the binding affinity is about 1.6 nM. In some embodiments, the binding affinity is about 1.5 nM. In some embodiments, the binding affinity is about 1 nM. In some embodiments, the binding affinity is about 0.7 nM.

Knottin proteins are small compact peptides that have high thermal and proteolytic stability and are tolerant to mutagenesis, making them good molecular scaffolds. These peptides contain at least 3 disulfide bonds that form a "knot" core. They also contain several loops exposed to the surface, allowing these loops to bind targets. These loops can be engineered to bind specific targets with high affinity, making them a useful tool for therapy.

In some embodiments, the methods and compositions of the present disclosure utilize a knottin polypeptide scaffold engineered with an RGD sequence capable of binding integrins, fused to an Fc donor, which confers a therapeutic benefit (also referred to as "knottin-Fc"). As described supra, Fc fragments have been added to proteins and/or therapeutics to extend half-life. In the context of knottin-Fc as used herein, the effector function of Fc contributes to the treatment of a variety of cancers when used in conjunction with systemic IL-2, such as extended-PK IL-2. In certain embodiments, a knottin-Fc that binds two integrins simultaneously is used (2.5D, SEQ ID NO: 85 or 87). In certain embodiments, a knottin-Fc that binds three integrins simultaneously is used (2.5F, SEQ ID NO: 86 or 88).

1. Methods of Engineering Knottin Polypeptide Scaffolds

Knottin polypeptide scaffolds are used to insert an integrin-binding sequence, preferably in the form of a loop, to confer specific integrin binding. Integrin-binding is preferably engineered into a knottin polypeptide scaffold by inserting an integrin-binding peptide sequence, such as an RGD peptide. In some embodiments, insertion of an integrin-binding peptide sequence results in replacement of portion of the native knottin protein. For example, in one embodiment an RGD peptide sequence is inserted into a native solvent exposed loop by replacing all or a portion of the loop with an RGD-containing peptide sequence (e.g., 5-12 amino acid sequence) that has been selected for binding to one or more integrins. The solvent-exposed loop (i.e., on the surface) will generally be anchored by disulfide-linked cysteine residues in the native knottin protein sequence. The integrin-binding replacement amino acid sequence can be obtained by randomizing codons in the loop portion, expressing the engineered peptide, and selecting the mutants with the highest binding to the predetermined ligand. This selection step may be repeated several times, taking the tightest binding proteins from the previous step and re-randomizing the loops.

Integrin-binding polypeptides may be modified in a number of ways. For example, the polypeptide may be further cross-linked internally, or may be cross-linked to each other, or the RGD loops may be grafted onto other cross linked molecular scaffolds. There are a number of commercially available crosslinking reagents for preparing protein or peptide bioconjugates. Many of these crosslinkers allow dimeric homo- or heteroconjugation of biological molecules through free amine or sulfhydryl groups in protein side chains. More recently, other crosslinking methods involving coupling through carbohydrate groups with hydrazide moieties have been developed. These reagents have offered convenient, facile, crosslinking strategies for researchers with little or no chemistry experience in preparing bioconjugates.

The EETI-11 knottin protein (SEQ ID NO: 39) contains a disulfide knotted topology and possesses multiple solvent-exposed loops that are amenable to mutagenesis. Preferred embodiments use EETI-II as the molecular scaffold.

Another example of a knottin protein which can be used as a molecular scaffold is AgRP or agatoxin. The amino acid sequences of AgRP (SEQ ID NO: 40) and agatoxin (SEQ ID NO: 41) differ but their structure is identical. Exemplary AgRP knottins are found in Table 1.

Additional AgRP engineered knottins can be made as described in the above-referenced US 2009/0257952 to Cochran et al. (the contents of which are incorporated herein by reference). AgRP knottin fusions can be prepared using AgRP loops 1, 2 and 3, as well as loop 4 as exemplified above.

The present polypeptides may be produced by recombinant DNA or may be synthesized in solid phase using a peptide synthesizer, which has been done for the peptides of all three scaffolds described herein. They may further be capped at their N-termini by reaction with fluorescein isothiocyanate (FITC) or other labels, and, still further, may be synthesized with amino acid residues selected for additional crosslinking reactions. TentaGel S RAM Fmoc resin (Advanced ChemTech) may be used to give a C-terminal amide upon cleavage. B-alanine is used as the N-terminal amino acid to prevent thiazolidone formation and release of fluorescein during peptide deprotection (Hermanson, 1996). Peptides are cleaved from the resin and side-chains are deprotected with 8% trifluoroacetic acid, 2% triisopropylsilane, 5% dithiothreitol, and the final product is recovered by ether precipitation. Peptides are purified by reverse phase HPLC using an acetonitrile gradient in 0.1% trifluoroacetic acid and a C4 or C18 column (Vydac) and verified using matrix-assisted laser desorption/ionization time-of-flight mass spectrometry (MALDI-TOF) or electrospray ionization-mass spectrometry (ESI-MS).

When the present peptides are produced by recombinant DNA, expression vectors encoding the selected peptide are transformed into a suitable host. The host should be selected to ensure proper peptide folding and disulfide bond formation as described above. Certain peptides, such as EETI-II, can fold properly when expressed in prokaryotic hosts such as bacteria.

Dimeric, trimeric, and tetrameric complexes of the present peptides can be formed through genetic engineering of the above sequences or by reaction of the synthetic cross-linkers with engineered peptides carrying an introduced cysteine residue, for example on the C-terminus of the peptide. These oligomeric peptide complexes can be purified by gel filtration. Oligomers of the present peptides can be prepared by preparing vectors encoding multiple peptide sequences end-to-end. Also, multimers may be prepared by complexing the peptides, such as, e.g., described in U.S. Pat. No. 6,265,539. There, an active HIV peptide is prepared in multimer form by altering the amino-terminal residue of the peptide so that it is peptide-bonded to a spacer peptide that contains an amino-terminal lysyl residue and one to about five amino acid residues such as glycyl residues to form a composite polypeptide. Alternatively, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimer. Multimers may also be prepared by solid phase peptide synthesis utilizing a lysine core matrix. The present peptides may also be prepared as nanoparticles. See, "Multivalent Effects of RGD Peptides Obtained by Nanoparticle Display," Montet, et al., J. Med. Chem.; 2006; 49(20) pp 6087-6093. EETI dimerization may be carried out with the present EETI-II peptides according to the EETI-II dimerization paper: "Grafting of thrombopoietin-mimetic peptides into cystine knot miniproteins yields high-affinity thrombopoietin antagonist and agonists," Krause, et al., FEBS Journal; 2006; 274 pp 86-95. This is further described in PCT application No. PCT/US2013/065610, herein incorporated by reference.

Synergistic sites on fibronectin and other adhesion proteins have been identified for enhanced integrin binding (Ruoslahti, 1996; Koivunen et al., 1994; Aota et al., 1994; Healy et al., 1995). The ability to incorporate different integrin-specific motifs into one soluble molecule would have an important impact on therapeutic development. Crosslinkers with heterofunctional specificity may be used for creating integrin-binding proteins with synergistic binding effects. In addition, these same crosslinkers could easily be used to create bispecific targeting molecules, or as vehicles for delivery of radionuclides or toxic agents for therapeutic applications.

a. Integrin-Binding Peptides

In some embodiments the integrin-binding polypeptides for use in Fc fusions include an integrin-binding loop (e.g., RGD peptide sequence) and a knottin polypeptide scaffold. Such integrin-binding polypeptides are described in U.S. Pat. No. 8,536,301, the contents of which are incorporated herein by reference. As described in U.S. Pat. No. 8,536,301, integrin-binding polypeptides may be varied in the non-RGD residues to a certain degree without affecting binding specificity and potency. For example, if three of the eleven residues were varied, one would have about 70% identity to 2.5D. Table 1 shows exemplary integrin-binding polypeptides within the scope of the disclosure, and their specific knottin polypeptide scaffold (e.g., EETI-II or AgRP). Preferred integrin-binding polypeptides for use in Fc fusions are peptides 2.5D and 2.5F.

In certain embodiments, the integrin-binding polypeptide binds to $\alpha_v\beta_3$, $\alpha_v\beta_5$, or $\alpha_5\beta_1$ separately. In certain embodiments, the integrin-binding polypeptide binds to $\alpha_v\beta_3$ and $\alpha_v\beta_5$ simultaneously. In certain embodiments, the integrin-binding polypeptide binds to $\alpha_v\beta_3$, $\alpha_v\beta_5$, and $\alpha_5\beta_1$ simultaneously.

In certain embodiments, the integrin-binding loop is within an engineered EETI-II scaffold. In certain embodiments, the lysine in position 15 of the EETI-II scaffold is replaced with a serine. In certain embodiments, the integrin-binding polypeptide comprises the amino acid sequence set forth in SEQ ID NO: 42 or 43, wherein $X_1$ is selected from the group consisting of A, V, L, P, F. Y, S, H, D, and N; $X_2$ is selected from the group consisting of G, V, L, P, R, E, and Q; $X_3$ is selected from the group consisting of G, A, and P; $X_7$ is selected from the group consisting of W and N; $X_8$ is selected from the group consisting of A, P, and S; $X_9$ is selected from the group consisting of P and R; $X_{10}$ is selected from the group consisting of A, V, L, P, S, T, and E; and $X_{11}$ is selected from the group consisting of G, A, W, S, T, K, and E. In a further embodiment, the integrin-binding-Fc fusion comprises an integrin-binding polypeptide, as set forth in SEQ ID Nos: 42 or 43, operably linked to a human IgG Fc domain, as set forth in SEQ ID Nos: 2 or 3.

In certain embodiments, the integrin-binding loop is within an engineered AgRP or agatoxin scaffold.

In certain embodiments, the integrin-binding polypeptide is 2.5D and 2.5F, disclosed in Table 1. Any of the integrin-binding polypeptides in Table 1 can be used in Fc fusion as described herein.

TABLE 1

Integrin Binding Knottin Sequences

| SEQ ID NO | Peptide Identifier | Scaffold | Sequence (RGD motif is underlined with flanking residues) |
|---|---|---|---|
| 59 | 1.4A | EETI-II | GCAEPRGDMPWTWCKQDSDCLAGCVCGPNGFCG |
| 60 | 1.4B | EETI-II | GCVGGRGDWSPKWCKQDSDCPAGCVCGPNGFCG |
| 61 | 1.4C | EETI-II | GC AELRGDRSYPECKQDSDCLAGCVCGPNGFCG |
| 62 | 1.4E | EETI-II | GC RLPRGDVPRPHCKQDSDCQAGCVCGPNGFCG |
| 63 | 1.4H | EETI-II | GC YPLRGDNPYAACKQDSDCRAGCVCGPNGFCG |
| 64 | 1.5B | EETI-II | GC TIGRGDWAPSECKQDSDCLAGCVCGPNGFCG |
| 65 | 1.5F | EETI-II | GC HPPRGDNPPVTCKQDSDCLAGCVCGPNGFCG |
| 66 | 2.3A | EETI-II | GC PEPRGDNPPPSCKQDSDCRAGCVCGPNGFCG |
| 67 | 2.3B | EETI-II | GC LPPRGDNPPPSCKQDSDCQAGCVCGPNGFCG |
| 68 | 2.3C | EETI-II | GCHLGRGDWAPVGCKQDSDCPAGCVCGPNGFCG |
| 69 | 2.3D | EETI-II | GC NVGRGDWAPSECKQDSDCPAGCVCGPNGFCG |
| 70 | 2.3E | EETI-II | GC FPGRGDWAPSSCKQDSDCRAGCVCGPNGFCG |
| 71 | 2.3F | EETI-II | GC PLPRGDNPPTECKQDSDCQAGCVCGPNGFCG |
| 72 | 2.3G | EETI-II | GC SEARGDNPRLSCKQDSDCRAGCVCGPNGFCG |
| 73 | 2.3H | EETI-II | GC LLGRGDWAPEACKQDSDCRAGCVCPNGFCG |
| 74 | 2.3I | EETI-II | GCHVGRGDWAPLKCKQDSDCQAGCVCGPNGFCG |
| 75 | 2.3J | EETI-II | GC VRGRGDWAPPSCKQDSDCPAGCVCGPNGFCG |
| 76 | 2.4A | EETI-II | GC LGGRGDWAPPACKQDSDCRAGCVCGPNGFCG |
| 77 | 2.4C | EETI-II | GC FVGRGDWAPLTCKQDSDCQAGCVCGPNGFCG |
| 78 | 2.4D | EETI-II | GC PVGRGDWSPASCKQDSDCRAGCVCGPNGFCG |
| 79 | 2.4E | EETI-II | GC PRPRGDNPPLTCKQDSDCLAGCVCGPNGFCG |
| 80 | 2.4F | EETI-II | GC YQGRGDWSPSSCKQDSDCPAGCVCGPNGFCG |
| 81 | 2.4G | EETI-II | GC APGRGDWAPSECKQDSDCQAGCVCGPNGFCG |
| 82 | 2.4J | EETI-II | GC VQGRGDWSPPSCKQDSDCPAGCVCGPNGFCG |
| 83 | 2.5A | EETI-II | GC HVGRGDWAPEECKQDSDCQAGCVCGPNGFCG |

TABLE 1-continued

Integrin Binding Knottin Sequences

| SEQ ID NO | Peptide Identifier | Scaffold | Sequence (RGD motif is underlined with flanking residues) |
|---|---|---|---|
| 84 | 2.5C | EETI-II | GC DGGRGDWAPPACKQDSDCRAGCVCGPNGFCG |
| 85 | 2.5D | EETI-II | GC PQGRGDWAPTSCKQDSDCRAGCVCGPNGFCG |
| 86 | 2.5F | EETI-II | GC PRPRGDNPPLTCKQDSDCLAGCVCGPNGFCG |
| 87 | 2.5D K15S Mutant | EETI-II | GCPQGRGDWAPTSCSQDSDCLAGCVCGPNGFCG |
| 88 | 2.5F K15S Mutant | EETI-II | GCPRPRGDNPPLTCSQDSDCLAGCVCGPNGFCG |
| 89 | 2.5H | EETI-II | GCPQGRGDWAPEWCKQDSDCPAGCVCGPNGFCG |
| 90 | 2.5J | EETI-II | GCPRGRGDWSPPACKQDSDCQAGCVCGPNGFCG |
| 91 | 3A | AgRp | GCVRLHESCLGQQVPCCDPAATCYCVVRGDWRKRCYCR |
| 92 | 3B | AgRp | GCVRLHESCLGQQVPCCDPAATCYCEERGDMLEKCYCR |
| 93 | 3C | AgRp | GCVRLHESCLGQQVPCCDPAATCYCETRGDKEKCYCR |
| 94 | 3D | AgRp | GCVRLHESCLGQQVPCCDPAATCYCQWRGDGDVKCYCR |
| 95 | 3E | AgRp | GCVRLHESCLGQQVPCCDPAATCYCSRRGDMRERCYCR |
| 96 | 3F | AgRp | GCVRLHESCLGQQVPCCDPAATCYCQYRGDGMKHCYCR |
| 97 | 3G | AgRp | GCVRLHESCLGQQVPCCDPAATCYCTGRGDTKVLCYCR |
| 98 | 3H | AgRp | GCVRLHESCLGQQVPCCDPAATCYCVERGDMKRRCYCR |
| 99 | 3I | AgRp | GCVRLHESCLGQQVPCCDPAATCYCTGRGDVRMNCYCR |
| 100 | 3J | AgRp | GCVRLHESCLGQQVPCCDPAATCYCVERGDGMSKCYCR |
| 101 | 4A | AgRp | GCVRLHESCLGQQVPCCDPAATCYCRGRGDMRRECYCR |
| 102 | 4B | AgRp | GCVRLHESCLGQQVPCCDPAATCYCEGRGDVKVNCYCR |
| 103 | 4C | AgRp | GCVRLHESCLGQQVPCCDPAATCYCVGRGDEKMSCYCR |
| 104 | 4D | AgRp | GCVRLHESCLGQQVPCCDPAATCYCVSRGDMRKRCYCR |
| 105 | 4E | AgRp | GCVRLHESCLGQQVPCCDPAATCYCERRGDSVKKCYCR |
| 106 | 4F | AgRp | GCVRLHESCLGQQVPCCDPAATCYCEGRGDTRRRCYCR |
| 107 | 4G | AgRp | GCVRLHESCLGQQVPCCDPAATCYCEGRGDVVRRCYCR |
| 108 | 4H | AgRp | GCVRLHESCLGQQVPCCDPAATCYCKGRGDNKRKCYCR |
| 109 | 4I | AgRp | GCVRLHESCLGQQVPCCDPAXTCYCKGRGDVRRVCYCR |
| 110 | 4J | AgRp | GCVRLHESCLGQQVPCCDPAATCYCVGRGDNKVKCYCR |
| 111 | 5A | AgRp | GCVRLHESCLGQQVPCCDPAATCYCVGRGDNRLKCYCR |
| 112 | 5B | AgRp | GCVRLHESCLGQQVPCCDPAATCYCVERGDGMKKCYCR |
| 113 | 5C | AgRp | GCVRLHESCLGQQVPCCDPAATCYCEGRGDMRRRCYCR |
| 114 | 5D | AgRp | GCVRLHESCLGQQVPCCDPAATCYCQGRGDGDVKCYCR |
| 115 | 5E | AgRp | GCVRLHESCLGQQVPCCDPAATCYCSGRGDNDLVCYCR |
| 116 | 5F | AgRp | GCVRLHESCLGQQVPCCDPAATCYCVERGDGMIRCYCR |
| 117 | 5G | AgRp | GCVRLHESCLGQQVPCCDPAATCYCSGRGDNDLVCYCR |
| 118 | 5H | AgRp | GCVRLHESCLGQQVPCCDPAATCYCEGRGDMKMKCYCR |

TABLE 1-continued

Integrin Binding Knottin Sequences

| SEQ ID NO | Peptide Identifier | Scaffold | Sequence (RGD motif is underlined with flanking residues) |
|---|---|---|---|
| 119 | 5I | AgRp | GCVRLHESCLGQQVPCCDPAATCYCIGRGDVRRRCYCR |
| 120 | 5J | AgRp | GCVRLHESCLGQQVPCCDPAATCYCEERGDGRKKCYCR |
| 121 | 6B | AgRp | GCVRLHESCLGQQVPCCDPAATCYCEGRGDRDMKCYCR |
| 122 | 6C | AgRp | GCVRLHESCLGQQVPCCDPAATCYCTGRGDEKLRCYCR |
| 123 | 6E | AgRp | GCVRLHESCLGQQVPCCDPAATCYCVERGDGNRRCYCR |
| 124 | 6F | AgRp | GCVRLHESCLGQQVPCCDPAATCYCESRGDVVRKCYCR |
| 125 | 7C | AgRp | GCVRLHESCLGQQVPCCDPAATCYCYGRGDNDLRCYCR |

The present polypeptides target $\alpha_v\beta_3$, $\alpha_v\beta_5$, and in some cases $\alpha_5\beta_1$ integrin receptors. They do not bind to other integrins tested, such as $\alpha_{IIb}\beta_3$, where there was little to no affinity. Thus, these engineered integrin-binding polypeptides have broad diagnostic and therapeutic applications in a variety of human cancers that specifically overexpress the above named integrins. As described below, these polypeptides bind with high affinity to both detergent-solubilized and tumor cell surface integrin receptors.

The $\alpha_v\beta_3$ (and $\alpha_v\beta_5$) integrins are also highly expressed on many tumor cells including osteosarcomas, neuroblastomas, carcinomas of the lung, breast, prostate, and bladder, glioblastomas, and invasive melanomas The $\alpha_v\beta_3$ integrin has been shown to be expressed on tumor cells and/or the vasculature of breast, ovarian, prostate, and colon carcinomas, but not on normal adult tissues or blood vessels. Also, the $\alpha_v\beta_3$ integrin has been shown to be expressed on tumor cells and/or the vasculature of breast, ovarian, prostate, and colon carcinomas, but not on normal adult tissue or blood vessels. The present, small, conformationally-constrained polypeptides (about 33 amino acids) are so constrained by intramolecular bonds. For example, EETI-II has three disulfide linkages. This will make it more stable in vivo. These peptides target $\alpha_v$ integrins alone, or both $\alpha_v$ and $\alpha_5\beta_1$ integrins. Until now, it is believed that the development of a single agent that can bind $\alpha_v\beta_3$, $\alpha_v\beta_5$, and $\alpha_5\beta_1$ integrins with high affinity and specificity has not been achieved. Since all three of these integrins are expressed on tumors and are involved in mediating angiogenesis and metastasis, a broad spectrum targeting agent (i.e., $\alpha_v\beta_3$, $\alpha_v\beta_5$, and $\alpha_5\beta_1$) will likely be more effective for diagnostic and therapeutic applications.

The present engineered knottin-Fc fusions have several advantages over previously identified integrin-targeting compounds. They possess a compact, disulfide-bonded core that confers proteolytic resistance and exceptional in vivo stability.

Our studies indicate the half-life of integrin-binding-Fc fusion protein in mouse serum to be greater than 90 hours. Their larger size (~3-4 kDa) and enhanced affinity compared to RGD-based cyclic peptides confer enhanced pharmacokinetics and biodistribution for molecular imaging and therapeutic applications. These knottin-Fc proteins are small enough to allow for chemical synthesis and site-specific conjugation of imaging probes, radioisotopes, or chemotherapeutic agents. Furthermore, they can easily be chemically modified to further improve in vivo properties if necessary.

2. Knottin-Fc Fusion

In some embodiments, the priming dose of combination immunotherapy comprises a knottin-Fc fusion (i.e., an integrin-binding polypeptide). The knottin-Fc fusions described herein and in U.S. Patent Application No. 2014/0073518, herein incorporated by reference in its entirety, combine an engineered integrin-binding polypeptide (within a knottin scaffold) and an Fc domain or antibody like construct capable of binding FcγR and inducing ADCC.

The Fc portion of an antibody is formed by the two carboxy terminal domains of the two heavy chains that make up an immunoglobin molecule. The IgG molecule contains 2 heavy chains (~50 kDa each) and 2 light chains (~25 kDa each). The general structure of all antibodies is very similar, a small region at the tip of the protein is extremely variable, allowing millions of antibodies with slightly different tip structures to exist. This region is known as the hypervariable region (Fab). The other fragment contains no antigen-binding activity but was originally observed to crystallize readily, and for this reason was named the Fc fragment, for Fragment crystallizable. This fragment corresponds to the paired CH2 and CH3 domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge. This has been demonstrated by electron microscopy of antibodies bound to haptens. Thus the present fusion proteins can be made to contain two knottin peptides, one on each arm of the antibody fragment.

The Fc portion varies between antibody classes (and subclasses) but is identical within that class. The C-terminal end of the heavy chain forms the Fc region. The Fc region plays an important role as a receptor binding portion. The Fc portion of antibodies will bind to Fc receptors in two different ways. For example, after IgG and IgM bind to a pathogen by their Fab portion their Fc portions can bind to receptors on phagocytic cells (like macrophages) inducing phagocytosis.

The present knottin-Fc fusions can be implemented such that the Fc portion is used to provide dual binding capability, and/or for half-life extension, for improving expression levels, etc. The Fc fragment in the knottin-Fc can be, for example, from murine IgG2a or human IgG1 (e.g., SEQ ID NO: 1). Linkers can be optionally used to connect the knottin to the Fc portion. Preferably, the linkers do not affect the binding affinity of the knottin-Fc to integrins or Fc receptors. A variety of Fc domain gene sequences (e.g., mouse and human constant region gene sequences) are available in the form of publicly accessible deposits.

a. Fc-Domains

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g., hinge, CH2, and/or CH3 sequences, or portions thereof) can be derived from these sequences using art recognized techniques. The genetic material obtained using any of the foregoing methods may then be altered or synthesized to obtain polypeptides used herein. It will further be appreciated that alleles, variants and mutations of constant region DNA sequences are suitable for use in the methods disclosed herein.

Knottin-Fc suitable for use in the methods disclosed herein may comprise one or more Fc domains (e.g., 2, 3, 4, 5, 6, 7, 8, 9, 10, or more Fc domains). In one embodiment, the Fc domains may be of different types. In one embodiment, at least one Fc domain present in a knottin-Fc comprises a hinge domain or portion thereof. In another embodiment, a knottin-Fc comprises at least one Fc domain which comprises at least one CH2 domain or portion thereof. In another embodiment, a knottin-Fc comprises at least one Fc domain which comprises at least one CH3 domain or portion thereof. In another embodiment, a knottin-Fc comprises at least one Fc domain which comprises at least one CH4 domain or portion thereof. In another embodiment, a knottin-Fc comprises at least one Fc domain which comprises at least one hinge domain or portion thereof and at least one CH2 domain or portion thereof (e.g, in the hinge-CH2 orientation). In another embodiment, a knottin-Fc comprises at least one Fc domain which comprises at least one CH2 domain or portion thereof and at least one CH3 domain or portion thereof (e.g, in the CH2-CH3 orientation). In another embodiment, a knottin-Fc comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, a knottin-Fc comprises at least one complete Fc region derived from one or more immunoglobulin heavy chains (e.g., an Fc domain including hinge, CH2, and CH3 domains, although these need not be derived from the same antibody). In other embodiments a knottin-Fc comprises at least two complete Fc domains derived from one or more immunoglobulin heavy chains. In certain embodiments, the complete Fc domain is derived from a human IgG immunoglobulin heavy chain (e.g., human IgG1).

In another embodiment, a knottin-Fc comprises at least one Fc domain comprising a complete CH3 domain. In another embodiment, a knottin-Fc comprises at least one Fc domain comprising a complete CH2 domain. In another embodiment, a knottin-Fc comprises at least one Fc domain comprising at least a CH3 domain, and at least one of a hinge region, and a CH2 domain. In one embodiment, a knottin-Fc comprises at least one Fc domain comprising a hinge and a CH3 domain. In another embodiment, a knottin-Fc comprises at least one Fc domain comprising a hinge, a CH2, and a CH3 domain. In certain embodiments, the Fc domain is derived from a human IgG immunoglobulin heavy chain (e.g., human IgG1). In certain embodiments, a human IgG1 Fc domain is used with a hinge region mutation, substitution, or deletion to remove or substitute one or more hinge region cysteine residues.

The constant region domains or portions thereof making up an Fc domain of a knottin-Fc may be derived from different immunoglobulin molecules. For example, a polypeptide used in the disclosure may comprise a CH2 domain or portion thereof derived from an IgG1 molecule and a CH3 region or portion thereof derived from an IgG3 molecule. In another example, a knottin-Fc can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant disclosure will be relatively non-immunogenic and not prevent proper folding of the Fc.

b. Changes to Fc Amino Acids

In certain embodiments, an Fc domain is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In certain embodiments, the hinge region of human IgG1 Fc domain is altered by an amino acid substitution or deletion to mutate or remove one or more of three hinge region cysteine residues (located at residues 220, 226, and 229 by EU numbering). In some aspects, the upper hinge region is deleted to remove a cysteine that pairs with the light chain. For example, amino acids "EPKSC" (SEQ ID NO: 135) in the upper hinge region are deleted, as set forth in SEQ ID NO: 3. In other aspects, one or more of three hinge region cysteines is mutated (e.g., to serine). In certain embodiments, cysteine 220 is mutated to serine.

In certain embodiments, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

In certain embodiments, a knottin-Fc fusion comprises an Fc variant comprising more than one amino acid substitution. The knottin-Fc fusion used in the methods described herein may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, a knottin-Fc fusion comprises an amino acid substitution to an Fc domain which alters the antigen-independent effector functions of the polypeptide, in particular the circulating half-life of the polypeptide.

In one embodiment, the knottin-Fc exhibits enhanced binding to an activating FcγR (e.g. Fcγ1, Fcγ1a, or FcγRIIIa). Exemplary amino acid substitutions which altered FcR or complement binding activity are disclosed in International PCT Publication No. WO 2005/063815 which is incorporated by reference herein. In certain embodiments the Fc region contains at least one of the following mutations: S239D, S239E, L261A, H268D, S298A, A330H, A330L, I332D, I332E, I332Q, K334V, A378F, A378K, A378W, A378Y, H435S, or H435G. In certain embodiments, the Fc region contains at least one of the following mutations: S239D, S239E, I332D or I332E or H268D. In certain embodiments, the Fc region contains at least one of the following mutations: I332D or I332E or H268D.

The knottin-Fc used herein may also comprise an amino acid substitution which alters the glycosylation of the knottin-Fc. For example, the Fc domain of the knottin-Fc may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the knottin-Fc has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, which are incorporated by reference herein. In other embodiments, the knottin-Fc used herein comprises at least one Fc domain having engineered cysteine residue or analog thereof which is located at the solvent-exposed surface. In certain embodiments, the knottin-Fc used herein comprises an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the knottin-Fc used herein may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the knottin-Fc used herein comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc domains of the knottin-Fc used herein may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Tumor Targeting Antibodies

In some embodiments, the priming dose combination immunotherapy comprises a tumor targeting antibody. Therapeutic monoclonal antibodies have been conceived as a class of pharmaceutically active agents which should allow tumor selective treatment by targeting tumor selective antigens or epitopes.

Tumor targeting antibodies suitable for use in the methods disclosed herein are administered in a priming dose with IL-2 (e.g., extended-PK IL-2), an immune checkpoint blocker (e.g., anti PD-1 antibody), and optionally, a cancer vaccine.

Methods of producing antibodies, and antigen-binding fragments thereof, are well known in the art and are disclosed in, e.g., U.S. Pat. Nos. 7,247,301, 7,923,221, and U.S. Patent Application 2008/0138336, all of which are herein incorporated by reference in their entirety.

Therapeutic antibodies that can be used in the methods of the present disclosure include, but are not limited to, any of the art-recognized anti-cancer antibodies that are approved for use, in clinical trials, or in development for clinical use. In certain embodiments, more than one anti-cancer antibody can be included in the combination therapy of the present disclosure.

Non-limiting examples of anti-cancer antibodies include the following, without limitation: trastuzumab (HERCEPTIN™. by Genentech, South San Francisco, Calif.), which is used to treat HER-2/neu positive breast cancer or metastatic breast cancer; bevacizumab (AVASTIN™ by Genentech), which are used to treat colorectal cancer, metastatic colorectal cancer, breast cancer, metastatic breast cancer, non-small cell lung cancer, or renal cell carcinoma; rituximab (RITUXAN™ by Genentech), which is used to treat non-Hodgkin's lymphoma or chronic lymphocytic leukemia; pertuzumab (OMNITARG™ by Genentech), which is used to treat breast cancer, prostate cancer, non-small cell lung cancer, or ovarian cancer; cetuximab (ERBITUX™ by ImClone Systems Incorporated, New York, N.Y.), which can be used to treat colorectal cancer, metastatic colorectal cancer, lung cancer, head and neck cancer, colon cancer, breast cancer, prostate cancer, gastric cancer, ovarian cancer, brain cancer, pancreatic cancer, esophageal cancer, renal cell cancer, prostate cancer, cervical cancer, or bladder cancer; IMC-1C11 (ImClone Systems Incorporated), which is used to treat colorectal cancer, head and neck cancer, as well as other potential cancer targets; tositumomab and tositumomab and iodine I 131 (BEXXAR XM by Corixa Corporation, Seattle, Wash.), which is used to treat non-Hodgkin's lymphoma, which can be CD20 positive, follicular, non-Hodgkin's lymphoma, with and without transformation, whose disease is refractory to Rituximab and has relapsed following chemotherapy; $In^{111}$ ibirtumomab tiuxetan; $Y^{90}$ ibirtumomab tiuxetan; $In^{111}$ ibirtumomab tiuxetan and $Y^{90}$ ibirtumomab tiuxetan (ZEVALIN™ by Biogen Idee, Cambridge, Mass.), which is used to treat lymphoma or non-Hodgkin's lymphoma, which can include relapsed follicular lymphoma; relapsed or refractory, low grade or follicular non-Hodgkin's lymphoma; or transformed B-cell non- Hodgkin's lymphoma; EMD 7200 (EMD Pharmaceuticals, Durham, N.C.), which is used for treating non-small cell lung cancer or cervical cancer; SGN-30 (a genetically engineered monoclonal antibody targeted to CD30 antigen by Seattle Genetics, Bothell, Wash.), which is used for treating Hodgkin's lymphoma or non-Hodgkin's lymphoma; SGN-15 (a genetically engineered monoclonal antibody targeted to a Lewisy-related antigen that is conjugated to doxorubicin by Seattle Genetics), which is used for treating non-small cell lung cancer; SGN-33 (a humanized antibody targeted to CD33 antigen by Seattle Genetics), which is used for treating acute myeloid leukemia (AML) and myelodysplasia syndromes (MDS); SGN-40 (a humanized monoclonal antibody targeted to CD40 antigen by Seattle Genetics), which is used for treating multiple myeloma or non-Hodgkin's lymphoma; SGN-35 (a genetically engineered monoclonal antibody targeted to a CD30 antigen that is conjugated to auristatin E by Seattle Genetics), which is used for treating non-Hodgkin's lymphoma; SGN-70 (a humanized antibody targeted to CD70 antigen by Seattle Genetics), which is used for treating renal cancer and nasopharyngeal carcinoma; SGN-75 (a conjugate comprised of the SGN70 antibody and an Auristatin derivative by Seattle Genetics); and SGN-17/19 (a fusion protein containing antibody and enzyme conjugated to melphalan prodrug by Seattle Genetics), which is used for treating melanoma or metastatic melanoma.

It should be understood that the therapeutic antibodies to be used in the methods of the present disclosure are not limited to those described supra. For example, the following approved therapeutic antibodies can also be used in the methods of the disclosure: brentuximab vedotin (ADCETRIS™) for anaplastic large cell lymphoma and Hodgkin lymphoma, ipilimumab (MDX-101; YERVOY™) for melanoma, ofatumumab (ARZERRA™) for chromic lymphocytic leukemia, panitumumab (VECTIBIX™) for colorectal cancer, alemtuzumab (CAMPATH™) for chronic lymphocytic leukemia, ofatumumab (ARZERRA™) for chronic lymphocytic leukemia, gemtuzumab ozogamicin (MYLOTARG™) for acute myelogenous leukemia.

Antibodies suitable for use in the methods disclosed herein can also target molecules expressed by immune cells, such as, but not limited to, $0X_{86}$ which targets OX40 and increases antigen-specific CD8+ T cells at tumor sites and enhances tumor rejection; BMS-663513 which targets CD137 and causes regression of established tumors, as well as the expansion and maintenance of CD8+ T cells, and daclizumab (ZENAPAX™) which targets CD25 and causes transient depletion of CD4+CD25+FOXP3+Tregs and enhances tumor regression and increases the number of effector T cells. A more detailed discussion of these antibodies can be found in, e.g., Weiner et al., Nature Rev. Immunol 2010; 10:317-27.

Other therapeutic antibodies can be identified that target tumor antigens (e.g., tumor antigens associated with different types of cancers, such as carcinomas, sarcomas, myelomas, leukemias, lymphomas, and combinations thereof). For example, the following tumor antigens can be targeted by therapeutic antibodies in the methods disclosed herein.

The tumor antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. In certain embodiments, the tumor antigen is a lymphoma antigen (e.g., non-Hodgkin's lymphoma or Hodgkin's lymphoma), a B-cell lymphoma cancer antigen, a leukemia antigen, a myeloma (e.g., multiple myeloma or plasma cell myeloma) antigen, an acute lymphoblastic leukemia antigen, a chronic myeloid leukemia antigen, or an acute myelogenous leukemia antigen. It should be understood that the described tumor antigens are only exemplary and that any tumor antigen can be targeted for use in the methods disclosed herein.

In certain embodiments, the tumor antigen is a mucin-1 protein or peptide (MUC-1) that is found on most or all human adenocarcinomas: pancreas, colon, breast, ovarian, lung, prostate, head and neck, including multiple myelomas and some B cell lymphomas. Patients with inflammatory bowel disease, either Crohn's disease or ulcerative colitis, are at an increased risk for developing colorectal carcinoma. MUC-1 is a type I transmembrane glycoprotein. The major extracellular portion of MUC-1 has a large number of tandem repeats consisting of 20 amino acids which comprise immunogenic epitopes. In some cancers it is exposed in an unglycosylated form that is recognized by the immune system (Gendler et al., *J Biol Chem* 1990; 265:15286-15293).

In certain embodiments, the tumor antigen is a mutated B-Raf antigen, which is associated with melanoma and colon cancer. The vast majority of these mutations represent a single nucleotide change of T-A at nucleotide 1796 resulting in a valine to glutamic acid change at residue 599 within the activation segment of B-Raf. Raf proteins are also indirectly associated with cancer as effectors of activated Ras proteins, oncogenic forms of which are present in approximately one-third of all human cancers. Normal non-mutated B-Raf is involved in cell signaling, relaying signals from the cell membrane to the nucleus. The protein is usually only active when needed to relay signals. In contrast, mutant B-Raf has been reported to be constantly active, disrupting the signaling relay (Mercer and Pritchard, Biochim Biophys Acta (2003) 1653(1):25-40; Sharkey et al., Cancer Res. (2004) 64(5):1595-1599).

In certain embodiments, the tumor antigen is a human epidermal growth factor receptor-2 (HER-2/neu) antigen. Cancers that have cells that overexpress HER-2/neu are referred to as HER-2/nee cancers. Exemplary HER-2/nee cancers include prostate cancer, lung cancer, breast cancer, ovarian cancer, pancreatic cancer, skin cancer, liver cancer (e.g., hepatocellular adenocarcinoma), intestinal cancer, and bladder cancer.

HER-2/neu has an extracellular binding domain (ECD) of approximately 645 aa, with 40% homology to epidermal growth factor receptor (EGFR), a highly hydrophobic transmembrane anchor domain (TMD), and a carboxyterminal intracellular domain (ICD) of approximately 580 aa with 80% homology to EGFR. The nucleotide sequence of HER-2/neu is available at GENBANK™. Accession Nos. AH002823 (human HER-2 gene, promoter region and exon 1); M16792 (human HER-2 gene, exon 4): M16791 (human HER-2 gene, exon 3); M16790 (human HER-2 gene, exon 2); and M16789 (human HER-2 gene, promoter region and exon 1). The amino acid sequence for the HER-2/neu protein is available at GENBANK™ Accession No. AAA58637. Based on these sequences, one skilled in the art could develop HER-2/neu antigens using known assays to find appropriate epitopes that generate an effective immune response. Exemplary HER-2/neu antigens include p369-377 (a HER-2/neu derived HLA-A2 peptide); dHER2 (Corixa Corporation); li-Key MHC class II epitope hybrid (Generex Biotechnology Corporation); peptide P4 (amino acids 378-398); peptide P7 (amino acids 610-623); mixture of peptides P6 (amino acids 544-560) and P7; mixture of peptides P4, P6 and P7; HER2 [$9_{754}$]; and the like.

In certain embodiments, the tumor antigen is an epidermal growth factor receptor (EGFR) antigen. The EGFR antigen can be an EGFR variant 1 antigen, an EGFR variant 2 antigen, an EGFR variant 3 antigen and/or an EGFR variant 4 antigen. Cancers with cells that overexpress EGFR are referred to as EGFR$^+$ cancers. Exemplary EGFR cancers include lung cancer, head and neck cancer, colon cancer, colorectal cancer, breast cancer, prostate cancer, gastric cancer, ovarian cancer, brain cancer and bladder cancer.

In certain embodiments, the tumor antigen is a vascular endothelial growth factor receptor (VEGFR) antigen. VEGFR is considered to be a regulator of cancer-induced angiogenesis. Cancers with cells that overexpress VEGFR are called VEGFR$^+$ cancers. Exemplary VEGFR$^+$ cancers include breast cancer, lung cancer, small cell lung cancer, colon cancer, colorectal cancer, renal cancer, leukemia, and lymphocytic leukemia.

In certain embodiments, the tumor antigen is prostate-specific antigen (PSA) and/or prostate-specific membrane antigen (PSMA) that are prevalently expressed in androgen-independent prostate cancers.

In certain embodiments, the tumor antigen is Glycoprotein 100 (gp 100), a tumor-specific antigen associated with melanoma.

In certain embodiments, the tumor antigen is a carcinoembryonic (CEA) antigen. Cancers with cells that overexpress CEA are referred to as CEA$^+$ cancers. Exemplary CEA$^+$ cancers include colorectal cancer, gastric cancer and pancreatic cancer. Exemplary CEA antigens include CAP-1 (i.e., CEA aa 571-579), CAP1-6D, CAP-2 (i.e., CEA aa 555-579), CAP-3 (i.e., CEA aa 87-89), CAP-4 (CEA aa 1-11), CAP-5 (i.e., CEA aa 345-354), CAP-6 (i.e., CEA aa 19-28) and CAP-7.

In certain embodiments, the tumor antigen is carbohydrate antigen 10.9 (CA 19.9). CA 19.9 is an oligosaccharide related to the Lewis A blood group substance and is associated with colorectal cancers.

In certain embodiments, the tumor antigen is a melanoma cancer antigen. Melanoma cancer antigens are useful for treating melanoma. Exemplary melanoma cancer antigens include MART-1 (e.g., MART-1 26-35 peptide, MART-1 27-35 peptide); MART-1/Melan A; pMel17; pMel17/gp100; gp100 (e.g., gp 100 peptide 280-288, gp 100 peptide 154-162, gp 100 peptide 457-467); TRP-1; TRP-2; NY-ESO-1; p16; beta-catenin; mum-1; and the like.

In certain embodiments, the tumor antigen is a mutant or wild type ras peptide. The mutant ras peptide can be a mutant K-ras peptide, a mutant N-ras peptide and/or a mutant H-ras peptide. Mutations in the ras protein typically occur at positions 12 (e.g., arginine or valine substituted for glycine), 13 (e.g., asparagine for glycine), 61 (e.g., glutamine to leucine) and/or 59. Mutant ras peptides can be useful as lung cancer antigens, gastrointestinal cancer antigens, hepatoma antigens, myeloid cancer antigens (e.g., acute leukemia, myelodysplasia), skin cancer antigens (e.g., melanoma, basal cell, squamous cell), bladder cancer antigens, colon cancer antigens, colorectal cancer antigens, and renal cell cancer antigens.

In certain embodiments, the tumor antigen is a mutant and/or wildtype p53 peptide. The p53 peptide can be used as colon cancer antigens, lung cancer antigens, breast cancer antigens, hepatocellular carcinoma cancer antigens, lymphoma cancer antigens, prostate cancer antigens, thyroid cancer antigens, bladder cancer antigens, pancreatic cancer antigens and ovarian cancer antigens.

Further tumor antigens are well known in the art and include, for example, a glioma-associated antigen, carcinoembryonic antigen (CEA), β-human chorionic gonadotropin, alphafetoprotein (AFP), lectin-reactive AFP, thyroglobulm, RAGE-1, MN-CA IX, human telomerase reverse transcriptase, RU1, RU2 (AS), intestinal carboxy esterase, mut hsp70-2, M-CSF, prostase, prostate-specific antigen (PSA), PAP, NY-ESO-1, LAGE-1a, p53, tyrosinase, prostein, PSMA, ras, Her2/neu, TRP-1, TRP-2, TAG-72, KSA, CA-125, PSA, BRCI, BRC-II, bcr-abl, pax3-fkhr, ews-fli-1, survivin and telomerase, prostate-carcinoma tumor antigen-1 (PCTA-1), MAGE, GAGE, GP-100, MUC-1, MUC-2, ELF2M, neutrophil elastase, ephrinB2, CD22, insulin growth factor (IGF)-I, IGF-II, IGF-I receptor, and mesothelin, In certain embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The tumor antigen may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-1), Pmel 17, tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations such as BCR-ABL, E2A-PRL, H4-RET, 1GH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4(791Tgp72} alpha-fetoprotem, beta-HCG, BCA225, BTAA, CA 125, CA 15-3\CA 27.29\BCAA, CA 195, CA 242, CA-50, CAM43, CD68\I, CO-029, FGF-5, G250, Ga733VEpCAM, HTgp-175, M344, MA-50, MG7-Ag, MOV 18, NB/70K, NY-CO-1, RCAS 1, SDCCAG16, TA-90\Mac-2 binding protein, Acyclophilin C-associated protein, TAAL6, TAG72, TLP, and TPS.

In certain embodiments, the tumor-associated antigen is determined by sequencing a patient's tumor cells and identifying mutated proteins only found in the tumor. These antigens are referred to as "neoantigens." Once a neoantigen has been identified, therapeutic antibodies can be produced against it and used in the methods described herein.

The therapeutic antibody can be a fragment of an antibody; a complex comprising an antibody; or a conjugate comprising an antibody. The antibody can optionally be chimeric or humanized or fully human.

C. Cancer Vaccine

1. Overview

In some embodiments, cancer vaccines are used in a priming dose combination immunotherapy described herein (e.g., extended-PK IL-2, an immune checkpoint inhibitor, and a tumor targeting antibody or an integrin-binding polypeptide). In certain embodiments, the cancer vaccine stimulates a specific immune response against a specific target, such as a tumor-associated antigen.

In certain embodiments, the cancer vaccine will include viral, bacterial or yeast vectors to deliver recombinant genes to antigen presenting cells (APCs). In certain embodiments the cancer vaccine uses autologous or allogeneic tumor cells. In certain embodiments, these tumor cells may be modified for expression of MHC, costimulatory molecules, or cytokines.

In certain embodiments, the tumor-associated antigen is determined by sequencing a patient's tumor cells and identifying mutated proteins only found in the tumor. These antigens are referred to as "neoantigens." Once a neoantigen has been identified, it can be used as the antigen for a vaccine or for developing monoclonal antibodies specifically reactive with the neoantigen.

In certain embodiments, the vaccine includes irradiated tumor cells transduced with cytokines such as GM-CSF or loaded with adjuvant compounds, such as the GM-CSF-secreting tumor cell vaccine GVAX (*Immunological Reviews*, 222(1): 287-298, 2008). In certain embodiments the vaccine includes one or more tumor-associated antigens in the form of an immunogenic composition, optionally in combination with an adjuvant. For example, vaccination against HPV-16 oncoproteins resulted in positive clinical outcomes for vulvar intraepithelial neoplasia (*The New England Journal of Medicine*, 361(19), 1838-1847. 2012). Also, multipeptide immune response to cancer vaccine IMA901 after single-dose cyclophosphamide associates with longer patient survival (*Nature Medicine.*, 18(8): 1254-61, 2012). Alternatively, a DNA based approach can be used to immunize a patient with one or more tumor-associated antigens. Improved tumor immunity is observed using a DNA vaccine in combination with an anti-tyrosinase related protein-1 monoclonal antibody in murine melanoma (*Cancer Research*, 68(23), 9884-9891, 2008).

Other vaccine approaches utilize patient immune cells, such as dendritic cells which can be cultured with a tumor-associated antigen to produce antigen presenting cells that will stimulate the immune system and target the antigen of interest. A current FDA approved cancer treatment vaccine using this approach is Provenge® (Dendreon), approved for use in some men with metastatic prostate cancer. This vaccine stimulates an immune response to prostatic acid phosphatase (PAP), an antigen found on most prostate cancer cells. The vaccine is created by isolating a specific patient's immune cells and culturing dendritic cells with PAP to produce antigen presenting cells that will stimulate the immune system and target PAP. These and other cancer vaccines can be used in combination with other treatments as described herein.

2. Amphiphile Vaccines

In certain embodiments, an amphiphile vaccine, as described in US 2013/0295129, herein incorporated by reference, is used in the methods disclosed herein. An amphiphile vaccine combines an albumin-binding lipid and a peptide antigen or molecular adjuvant to efficiently target the peptide or adjuvant to lymph nodes in vivo. Lipid conjugates bind to endogenous albumin, which targets them to lymphatics and draining lymph nodes where they accumulate due to the filtering of albumin by antigen presenting cells. When the lipid conjugate includes an antigenic peptide or molecular adjuvant, the conjugates induce or enhance a robust immune response.

Lymph node-targeting conjugates typically include three domains: a highly lipophilic, albumin-binding domain (e.g., an albumin-binding lipid), a cargo such as a molecular adjuvant or a peptide antigen, and a polar block linker, which promotes solubility of the conjugate and reduces the ability of the lipid to insert into cellular plasma membranes. Accordingly, in certain embodiments, the general structure of the conjugate is L-P-C, where "L" is an albumin-binding lipid, "P" is a polar block, and "C" is a cargo such as a molecular adjuvant or a polypeptide. In some embodiments, the cargo itself can also serve as the polar block domain, and a separate polar block domain is not required. Therefore, in certain embodiments the conjugate has only two domains: an albumin-binding lipid and a cargo.

The cargo of the conjugates suitable for use in the methods disclosed herein is typically a molecular adjuvant such as an immunostimulatory oligonucleotide, or a peptide antigen. However, the cargo can also be other oligonucleotides, peptides, Toll-like receptor agonists or other immunomodulatory compounds, dyes, MRI contrast agents, fluorophores or small molecule drugs that require efficient trafficking to the lymph nodes.

In certain embodiments, a lipid-oligonucleotide conjugates includes an immunostimulatory oligonucleotide which is conjugated directly to a lipid, or is linked to a linker which is conjugated to a lipid. A schematic representation of an exemplary lipid-oligonucleotide conjugate is shown below:

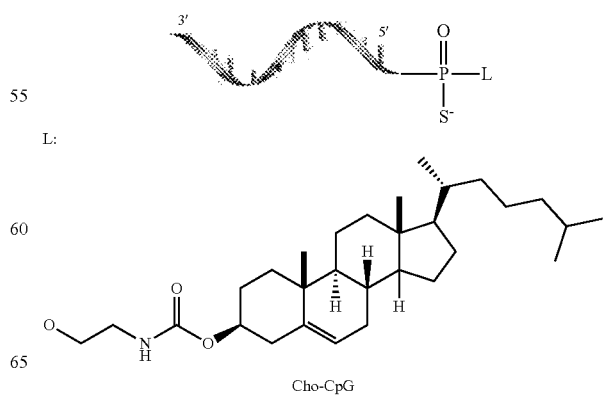

Cho-CpG

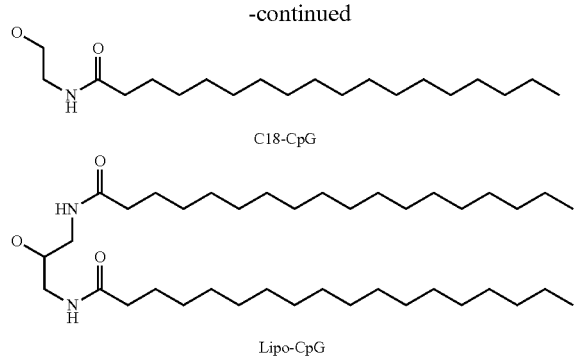

C18-CpG

Lipo-CpG

Other embodiments are directed to lipid-peptide conjugates which include an antigenic peptide conjugated directly to a lipid, or is linked to a linker which is conjugated to a lipid. A schematic representation of an exemplary lipid-peptide conjugate is shown below:

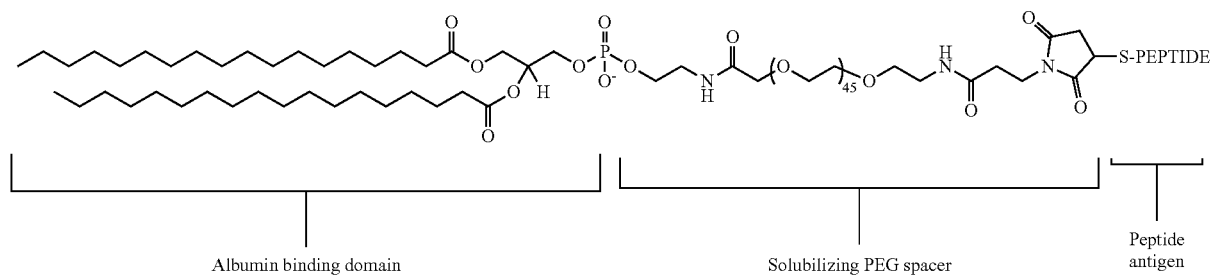

limited to, linear unsaturated and saturated fatty acids, branched saturated and unsaturated fatty acids, and fatty acids derivatives, such as fatty acid esters, fatty acid amides, and fatty acid thioesters, diacyl lipids, cholesterol, cholesterol derivatives, and steroid acids such as bile acids; Lipid A or combinations thereof.

In certain embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, or combinations thereof. In a particular embodiment, the diacyl lipids are phosphate lipids, glycolipids, sphingolipids, or combinations thereof.

Preferably, lymph node-targeting conjugates include a lipid that is 8 or more carbon units in length. It is believed that increasing the number of lipid units can reduce insertion of the lipid into plasma membrane of cells, allowing the lipid conjugate to remain free to bind albumin and traffic to the lymph node.

a. Lipids

The lipid conjugates typically include a hydrophobic lipid. The lipid can be linear, branched, or cyclic. The lipid is preferably at least 17 to 18 carbons in length, but may be shorter if it shows good albumin binding and adequate targeting to the lymph nodes. Lymph node-targeting conjugates include lipid-oligonucleotide conjugates and lipid-peptide conjugates that can be trafficked from the site of delivery through the lymph to the lymph node. In certain embodiments, the activity relies, in-part, on the ability of the conjugate to associate with albumin in the blood of the subject. Therefore, lymph node-targeted conjugates typically include a lipid that can bind to albumin under physiological conditions. Lipids suitable for targeting the lymph node can be selected based on the ability of the lipid or a lipid conjugate including the lipid to bind to albumin. Suitable methods for testing the ability of the lipid or lipid conjugate to bind to albumin are known in the art.

For example, in certain embodiments, a plurality of lipid conjugates is allowed to spontaneously form micelles in aqueous solution. The micelles are incubated with albumin, or a solution including albumin such as Fetal Bovine Serum (FBS). Samples can be analyzed, for example, by ELISA, size exclusion chromatography or other methods to determine if binding has occurred. Lipid conjugates can be selected as lymph node-targeting conjugates if in the presence of albumin, or a solution including albumin such as Fetal Bovine Serum (FBS), the micelles dissociate and the lipid conjugates bind to albumin as discussed above.

Examples of preferred lipids for use in lymph node targeting lipid conjugates include, but are not limited to fatty acids with aliphatic tails of 8-30 carbons including, but not For example, the lipid can be a diacyl lipid composed of two C18 hydrocarbon tails.

In certain embodiments, the lipid for use in preparing lymph node targeting lipid conjugates is not a single chain hydrocarbon (e.g., C18), or cholesterol. Cholesterol conjugation has been explored to enhance the immunomodulation of molecular adjuvants such as CpG and immunogenicity of peptides, but cholesterol conjugates, which associate well with lipoproteins but poorly with albumin, show poor lymph node targeting and low immunogenicity in vaccines compared to optimal albumin-binding conjugates.

b. Molecular Adjuvants

In certain embodiments, lipid-oligonucleotide conjugates are used in the vaccine. The oligonucleotide conjugates typically contain an immunostimulatory oligonucleotide.

In certain embodiments, the immunostimulatory oligonucleotide can serve as a ligand for pattern recognition receptors (PRRs). Examples of PRRs include the Toll-like family of signaling molecules that play a role in the initiation of innate immune responses and also influence the later and more antigen specific adaptive immune responses. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone. In certain embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, *Advanced drug delivery reviews* 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, PNAS USA 94(20): 10833-7 (1997); Dalpke, A H, Immunology 106(1): 102-12 (2002); Hartmann, G, J of Immun. 164(3): 1617-2 (2000), each of which is incorporated herein by reference).

According to some embodiments, a lipophilic-CpG oligonucleotide conjugate is used to enhance an immune response to a peptide antigen. The lipophilic-CpG oligonucleotide is represented by the following, wherein "L" is a lipophilic compound, such as diacyl lipid, "Ga" is a guanine repeat linker and "n" represents 1, 2, 3, 4, or 5.

(SEQ ID NO: 130)
5'-L-G$_n$TCCATGACGTTCCTGACGTT-3'

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol. Therefore, in certain embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. *Recent Pat Inflamm Allergy Drug Discov.* 5(1):87-93 (2011), incorporated herein by reference.

In certain embodiments, the oligonucleotide cargo includes two or more immunostimulatory sequences.

The oligonucleotide can be between 2-100 nucleotide bases in length, including for example, 5 nucleotide bases in length, 10 nucleotide bases in length, 15 nucleotide bases in length, 20 nucleotide bases in length, 25 nucleotide bases in length, 30 nucleotide bases in length, 35 nucleotide bases in length, 40 nucleotide bases in length, 45 nucleotide bases in length, 50 nucleotide bases in length, 60 nucleotide bases in length, 70 nucleotide bases in length, 80 nucleotide bases in length, 90 nucleotide bases in length, 95 nucleotide bases in length, 98 nucleotide bases in length, 100 nucleotide bases in length or more.

The 3' end or the 5' end of the oligonucleotides can be conjugated to the polar block or the lipid. In certain embodiments the 5' end of the oligonucleotide is linked to the polar block or the lipid.

The oligonucleotides can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds. In certain embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In certain embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In certain embodiments, the analogs have a substantially uncharged, phosphorus containing backbone.

c. Peptide Antigens

The peptide conjugates suitable for use in the methods disclosed herein typically include an antigenic protein or polypeptide, such as a tumor-associated antigen or portion thereof.

The peptide can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids. In some embodiments, a peptide can be greater than 50 amino acids. In some embodiments, the peptide can be >100 amino acids. A protein/peptide can be linear, branched or cyclic. The peptide can include D amino acids, L amino acids, or a combination thereof. The peptide or protein can be conjugated to the polar block or lipid at the N-terminus or the C-terminus of the peptide or protein.

The protein or polypeptide can be any protein or peptide that can induce or increase the ability of the immune system to develop antibodies and T-cell responses to the protein or peptide. A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be, but is not limited to, TRP-1, TRP-2, MART-1/Melan-A, gp100, adenosine deaminase-binding protein (ADAbp), FAP, cyclophilin b, colorectal associated antigen (CRC)-0017-1A/ GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2. Additional cancer antigens include the tumor antigens described herein.

Suitable antigens are known in the art and are available from commercial government and scientific sources. In certain embodiments, the antigens are whole inactivated or irradiated tumor cells. The antigens may be purified or partially purified polypeptides derived from tumors. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

In certain embodiments, antigens may be provided as single antigens or may be provided in combination. Antigens may also be provided as complex mixtures of polypeptides or nucleic acids.

d. Polar Block/Linker

For the conjugate to be trafficked efficiently to the lymph node, the conjugate should remain soluble. Therefore, a polar block linker can be included between the cargo and the lipid to increase solubility of the conjugate. The polar block reduces or prevents the ability of the lipid to insert into the plasma membrane of cells, such as cells in the tissue adjacent to the injection site. The polar block can also reduce or prevent the ability of cargo, such as synthetic oligonucleotides containing a PS backbone, from non-specifically associating with extracellular matrix proteins at the site of administration. The polar block increases the solubility of the conjugate without preventing its ability to bind to albumin. It is believed that this combination of characteristics allows the conjugate to bind to albumin present in the serum or interstitial fluid, and remain in circulation until the albumin is trafficked to, and retained in a lymph node. The length and composition of the polar block can be adjusted based on the lipid and cargo selected. For example, for oligonucleotide conjugates, the oligonucleotide itself may be polar enough to insure solubility of the conjugate, for example, oligonucleotides that are 10, 15, 20 or more nucleotides in length. Therefore, in certain embodiments, no additional polar block linker is required. However, depending on the amino acid sequence, some lipidated peptides can be essentially insoluble. In these cases, it can be desirable to include a polar block that mimics the effect of a polar oligonucleotide.

A polar block can be used as part of any of lipid conjugates suitable for use in the methods disclosed herein, for example, lipid-oligonucleotide conjugates and lipid-peptide conjugates, which reduce cell membrane insertion/preferential portioning ont albumin. Suitable polar blocks include, but are not limited to, oligonucleotides such as those discussed above, a hydrophilic polymer including but not limited to poly(ethylene glycol) (MW: 500 Da to 20,000 Da), polyacrylamide (MW: 500 Da to 20,000 Da), polyacrylic acid; a string of hydrophilic amino acids such as serine, threonine, cysteine, tyrosine, asparagine, glutamine, aspartic acid, glutamic acid, lysine, arginine, histidine, or combinations thereof polysaccharides, including but not limited to, dextran (MW: 1,000 Da to 2,000,000 Da), or combinations thereof.

The hydrophobic lipid and the linker/cargo are covalently linked. The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage.

i. Ethylene Glycol Linkers

In certain embodiments, the polar block is one or more ethylene glycol (EG) units, more preferably two or more EG units (i.e., polyethylene glycol (PEG)). For example, in certain embodiments, a peptide conjugate includes a protein or peptide (e.g., peptide antigen) and a hydrophobic lipid linked by a polyethylene glycol (PEG) molecule or a derivative or analog thereof.

In certain embodiments, protein conjugates suitable for use in the methods disclosed herein contain protein antigen linked to PEG which is in turn linked to a hydrophobic lipid, or lipid-Gn-ON conjugates, either covalently or via formation of protein-oligo conjugates that hybridize to oligo micelles. The precise number of EG units depends on the lipid and the cargo, however, typically, a polar block can have between about 1 and about 100, between about 20 and about 80, between about 30 and about 70, or between about 40 and about 60 EG units. In certain embodiments, the polar block has between about 45 and 55 EG, units. For example, in certain embodiments, the polar block has 48 EG units.

ii. Oligonucleotide Linkers

As discussed above, in certain embodiments, the polar block is an oligonucleotide. The polar block linker can have any sequence, for example, the sequence of the oligonucleotide can be a random sequence, or a sequence specifically chosen for its molecular or biochemical properties (e.g., highly polar). In certain embodiments, the polar block linker includes one or more series of consecutive adenine (A), cytosine (C), guanine (G), thymine (T), uracil (U), or analog thereof. In certain embodiments, the polar block linker consists of a series of consecutive adenine (A), cytosine (C), guanine (G), thymine (T), uracil (U), or analog thereof.

In certain embodiments, the linker is one or more guanines, for example between 1-10 guanines. It has been discovered that altering the number of guanines between a cargo such as a CpG oligonucleotide, and a lipid tail controls micelle stability in the presence of serum proteins. Therefore, the number of guanines in the linker can be selected based on the desired affinity of the conjugate for serum proteins such as albumin. When the cargo is a CpG immunostimulatory oligonucleotide and the lipid tail is a diacyl lipid, the number of guanines affects the ability of micelles formed in aqueous solution to dissociate in the presence of serum: 20% of the non-stabilized micelles (lipo-$G_0T_{10}$-CG) were intact, while the remaining 80% were disrupted and bonded with FBS components. In the presence of guanines, the percentage of intact micelles increased from 36% (lipo-$G_2T_8$-CG) to 73% (lipo-$G_4T_6$-CG), and finally reached 90% (lipo-$G_6T_4$-CG) (SEQ ID NO: 138). Increasing the number of guanines to eight (lipo-$G_8T_2$-CG) and ten (lipo-$G_{10}T_0$-CG) did not further enhance micelle stability.

Therefore, in certain embodiments, the linker in a lymph node-targeting conjugate suitable for use in the methods disclosed herein can include 0, 1, or 2 guanines. As discussed in more detail below, linkers that include 3 or more consecutive guanines can be used to form micelle-stabilizing conjugates with properties that are suitable for use in the methods disclosed herein.

3. Immunogenic Compositions

The conjugates suitable for use in the methods disclosed herein can be used in immunogenic compositions or as components in vaccines. Typically, immunogenic compositions disclosed herein include an adjuvant, an antigen, or a combination thereof. The combination of an adjuvant and an antigen can be referred to as a vaccine. When administered to a subject in combination, the adjuvant and antigen can be administered in separate pharmaceutical compositions, or they can be administered together in the same pharmaceutical composition. When administered in combination, the adjuvant can be a lipid conjugate, the antigen can be a lipid conjugate, or the adjuvant and the antigen can both be lipid conjugates.

An immunogenic composition suitable for use in the methods disclosed herein can include a lipid conjugate that is an antigen such as an antigenic polypeptide-lipid conjugate, administered alone, or in combination with an adjuvant. The adjuvant may be without limitation alum (e.g., aluminum hydroxide, aluminum phosphate); saponins purified from the bark of the Q. saponaria tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed above. Adjuvants that act through TLR3 include, without limitation, double-stranded RNA. Adjuvants that act through TLR4 include, without limitation, derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include, without limitation, flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

D. Immune Checkpoint Inhibitors

In certain embodiments, immune checkpoint inhibitors are used in a priming dose combination immunotherapy with other therapeutic agents described herein (e.g., extended-PK IL-2, integrin-binding polypeptide or tumor targeting antibody, and optionally a cancer vaccine) as priming therapy. In certain embodiments, at least one maintenance dose comprising an immune checkpoint inhibitors is administered after the priming dose.

T cell activation and effector functions are balanced by co-stimulatory and inhibitory signals, referred to as "immune checkpoints." Inhibitory ligands and receptors that regulate T cell effector functions are overexpressed on tumor cells. Subsequently, agonists of co-stimulatory receptors or antagonists of inhibitory signals, result in the amplification of antigen-specific T cell responses. In contrast to therapeutic antibodies which target tumor cells directly, immune checkpoint inhibitor enhances endogenous anti-tumor activity. In certain embodiments, an immune checkpoint inhibitors suitable for use in the methods disclosed herein, is an antagonist of inhibitory signals, e.g., an antibody which targets, for example, PD-1, PD-L1, CTLA-4, LAG3, B7-H3, B7-H4, or TIM3. These ligands and receptors are reviewed in Pardoll, D., Nature. 12: 252-264, 2012.

Disclosed herein are methods for treating a subject afflicted with diseases such as cancer, which methods comprise administering to the subject a priming dose comprising an immune checkpoint inhibitor, IL-2 (e.g., extended-PK IL-2), a tumor targeting antibody or an integrin-binding polypeptide, and optionally a cancer vaccine, prior to a maintenance dose comprising an immune checkpoint inhibitor. In certain embodiments, the immune checkpoint inhibitor is an antibody or an antigen-binding portion thereof, that disrupts or inhibits signaling from an inhibitory immunoregulator. In certain embodiments, the immune checkpoint inhibitor is a small molecule that disrupts or inhibits signaling from an inhibitory immunoregulator.

In certain embodiments, the inhibitory immunoregulator (immune checkpoint inhibitor) is a component of the PD-1/PD-L1 signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that disrupts the interaction between the PD-1 receptor and its ligand, PD-L1. Antibodies known in the art which bind to PD-1 and disrupt the interaction between the PD-1 and its ligand, PD-L1, and stimulates an anti-tumor immune response, are suitable for use in the methods disclosed herein. In certain embodiments, the antibody or antigen-binding portion thereof binds specifically to PD-1. For example, antibodies that target PD-1 and are in clinical trials include, e.g., nivolumab (BMS-936558, Bristol-Myers Squibb) and pembrolizumab (lambrolizumab, MK03475, Merck). Other suitable antibodies for use in the methods disclosed herein are anti-PD-1 antibodies disclosed in U.S. Pat. No. 8,008,449, herein incorporated by reference. In certain embodiments, the antibody or antigen-binding portion thereof binds specifically to PD-L1 and inhibits its interaction with PD-1, thereby increasing immune activity. Antibodies known in the art which bind to PD-L1 and disrupt the interaction between the PD-1 and PD-L1, and stimulates an anti-tumor immune response, are suitable for use in the methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743. It will be understood by one of ordinary skill that any antibody which binds to PD-1 or PD-L1, disrupts the PD-1/PD-L1 interaction, and stimulates an anti-tumor immune response, is suitable for use in the methods disclosed herein.

In certain embodiments, the inhibitory immunoregulator is a component of the CTLA4 signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets CTLA4 and disrupts its interaction with CD80 and CD86. Exemplary antibodies that target CTLA4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA4, disrupts its interaction with CD80 and CD86, and stimulates an anti-tumor immune response, is suitable for use in the methods disclosed herein.

In certain embodiments, the inhibitory immunoregulator is a component of the LAG3 (lymphocyte activation gene 3) signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets LAG3 and disrupts its interaction with MHC class II molecules. An exemplary antibody that targets LAG3 is IMP321 (Immutep), currently undergoing human trials. Other suitable antibodies that target LAG3 are disclosed in U.S. Patent Application 2011/0150892, herein incorporated by reference. It will be understood by one of ordinary skill that any antibody which binds to LAG3, disrupts its interaction with MHC class II molecules, and stimulates an anti-tumor immune response, is suitable for use in the methods disclosed herein.

In certain embodiments, the inhibitory immunoregulator is a component of the B7 family signaling pathway. In certain embodiments, the B7 family members are B7-H3 and B7-H4. Accordingly, certain embodiments of the disclosure provide methods for immunotherapy of a subject afflicted with cancer, which methods comprise administering to the subject a therapeutically effective amount of an antibody or an antigen-binding portion thereof that targets B7-H3 or H4. The B7 family does not have any defined receptors but these ligands are upregulated on tumor cells or tumor-infiltrating cells. Preclinical mouse models have shown that blockade of these ligands can enhance anti-tumor immunity. An exemplary antibody that targets B7-H3 is MGA271 (Macrogenics), currently undergoing human trials. Other suitable antibodies that target LAG3 are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the methods disclosed herein.

In certain embodiments, the inhibitory immunoregulator is a component of the TIM3 (T cell membrane protein 3) signaling pathway. Accordingly, certain embodiments of the disclosure provide methods for immunotherapy of a subject afflicted with cancer, which methods comprise administering to the subject a therapeutically effective amount of an antibody or an antigen-binding portion thereof that targets LAG3 and disrupts its interaction with galectin 9. Suitable antibodies that target TIM3 are disclosed in U.S. Patent Application 2013/0022623, herein incorporated by reference. It will be understood by one of ordinary skill that any antibody which binds to TIM3, disrupts its interaction with galectin 9, and stimulates an anti-tumor immune response, is suitable for use in the methods disclosed herein.

It should be understood that antibodies targeting immune checkpoints suitable for use in the methods disclosed herein are not limited to those described supra. Moreover, it will be understood by one of ordinary skill in the art that other immune checkpoint targets can also be targeted by antagonists or antibodies in the methods described herein, provided that the targeting results in the stimulation of an anti-tumor immune response as reflected in, e.g., an increase in T cell proliferation, enhanced T cell activation, and/or increased cytokine production (e.g., IFN-γ, IL-2).

Methods of Making Polypeptides

In some aspects, the polypeptides described herein (e.g., IL-2, such as extended-PK IL-2, a tumor targeting antibody, an integrin-binding polypeptide, and immune checkpoint inhibitor) are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making polypeptides also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be suitable for use in the methods disclosed herein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Expression of Polypeptides

The nucleic acid molecules described above can be contained within a vector that is capable of directing their expression in, for example, a cell that has been transduced with the vector. Accordingly, in addition to IL-2 (e.g., extended-PK IL-2), a tumor targeting antibody an integrin-binding polypeptide, and immune checkpoint inhibitor mutants, expression vectors containing a nucleic acid molecule encoding IL-2 (e.g., extended-PK IL-2), a tumor targeting antibody, an integrin-binding polypeptide or immune checkpoint inhibitor mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAK5 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes IL-2 (e.g., extended-PK IL-2), a tumor targeting antibody, an integrin-binding polypeptide, or an immune checkpoint inhibitor mutant are also features of the disclosure. A cell of the disclosure is a transfected cell, i.e., a cell into which a nucleic acid molecule, for example a nucleic acid molecule encoding an extended-PK IL-2 mutant or knottin-Fc, has been introduced by means of recombinant DNA techniques. The progeny of such a cell are also considered within the scope of the disclosure.

The precise components of the expression system are not critical. For example, IL-2 (e.g., extended-PK IL-2), a tumor targeting antibody, an integrin-binding polypeptide, or an immune checkpoint inhibitor mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

Pharmaceutical Compositions and Modes of Administration

In certain embodiments, the components of a priming dose combination immunotherapy are administered together (simultaneously or sequentially). For example, in some embodiments IL-2 (e.g., extended-PK IL-2) is administered together (simultaneously or sequentially) with a tumor targeting antibody or an integrin-binding polypeptide, and an immune checkpoint inhibitor. In certain embodiments, IL-2 (e.g., extended-PK IL-2) is administered prior to the administration of a a tumor targeting antibody or an integrin-binding polypeptide, and an immune checkpoint inhibitor. In certain embodiments, IL-2 (e.g., extended-PK IL-2) is administered concurrently with the administration of a a tumor targeting antibody or an integrin-binding polypeptide, and an immune checkpoint inhibitor. In certain embodiments, IL-2 (e.g., extended-PK IL-2) is administered subsequent to the administration of a tumor targeting antibody or an integrin-binding polypeptide, and an immune checkpoint inhibitor. In certain embodiments, the IL-2 (e.g., extended-PK IL-2), tumor targeting antibody or an integrin-binding polypeptide, and the immune checkpoint inhibitor are administered simultaneously. In other embodiments, the IL-2 (e.g., extended-PK IL-2), tumor targeting antibody or an integrin-binding polypeptide, and the immune checkpoint inhibitor are administered sequentially. In yet other embodiments, the IL-2, a tumor targeting antibody or an integrin-binding polypeptide, and the immune checkpoint inhibitor are administered within one, two, or three days of each other.

In certain embodiments, IL-2 (e.g., extended-PK IL-2), an immune checkpoint inhibitor, a tumor targeting antibody or an integrin-binding polypeptide, and optionally a cancer vaccine, are administered together (simultaneously or sequentially). In certain embodiments, IL-2 (e.g., extended-PK IL-2) and a tumor targeting antibody or an integrin-binding polypeptide are administered together (simultaneously or sequentially). In certain embodiments, IL-2 (e.g., extended-PK IL-2) and a cancer vaccine are administered together (simultaneously or sequentially). In certain embodiments, IL-2 (e.g., extended-PK IL-2) and an immune checkpoint inhibitor are administered together (simultaneously or sequentially). In certain embodiments, IL-2 (e.g., extended-PK IL-2), an immune checkpoint inhibitor, a tumor targeting antibody or an integrin-binding polypeptide, and optionally a cancer vaccine, are administered separately.

In certain embodiments, the disclosure provides for a pharmaceutical composition comprising IL-2 (e.g., extended-PK IL-2) with a pharmaceutically acceptable diluent, carrier, solubilizer, emulsifier, preservative and/or adjuvant, a pharmaceutical composition comprising a cancer vaccine with a pharmaceutically acceptable diluent, carrier, solubilizer, emulsifier, preservative and/or adjuvant, a pharmaceutical composition comprising an integrin-binding polypeptide with a pharmaceutically acceptable diluent, carrier, solubilizer, emulsifier, preservative and/or adjuvant, or a pharmaceutical composition comprising an immune checkpoint inhibitor with a pharmaceutically acceptable diluent, carrier, solubilizer, emulsifier, preservative and/or adjuvant.

In certain embodiments, the disclosure provides for pharmaceutical compositions comprising IL-2 (e.g., extended-PK IL-2), an immune checkpoint inhibitor, a tumor targeting antibody or an integrin-binding polypeptide, and/or a cancer vaccine, with a pharmaceutically acceptable diluent, carrier, solubilizer, emulsifier, preservative and/or adjuvant. In certain embodiments, each of the agents, e.g., IL-2 (e.g., extended-PK IL-2), an immune checkpoint inhibitor, a tumor targeting antibody or an integrin-binding polypeptide, and optionally a cancer vaccine can be formulated as separate compositions. In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of IL-2 (e.g., extended-PK IL-2), an immune checkpoint inhibitor, a tumor targeting antibody or an integrin-binding polypeptide, and optionally a cancer vaccine.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising IL-2 (e.g., extended-PK IL-2), an immune checkpoint inhibitor, a tumor targeting antibody or an integrin-binding polypeptide, and optionally a cancer vaccine, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising IL-2 (e.g., extended-PK IL-2), an immune checkpoint inhibitor, a tumor targeting antibody or an integrin-binding polypeptide, and optionally a cancer vaccine can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising IL-2 (e.g., extended-PK IL-2), an immune checkpoint inhibitor, a tumor targeting antibody or an integrin-binding polypeptide, and optionally a cancer vaccine, in a pharmaceutically acceptable vehicle. In certain embodiments, a vehicle for parenteral injection is sterile distilled water in which IL-2 (e.g., extended-PK IL-2), an immune checkpoint inhibitor, a tumor targeting antibody or an integrin-binding polypeptide, and optionally a cancer vaccine are formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, IL-2 (e.g., extended-PK IL-2), an immune checkpoint inhibitor, a tumor targeting antibody or an integrin-binding polypeptide, and optionally a cancer vaccine can be formulated as a dry powder for inhalation. In certain embodiments, an inhalation solution comprising IL-2 (e.g., extended-PK IL-2), an immune checkpoint inhibitor, a tumor targeting antibody or an integrin-binding polypeptide, and optionally a cancer vaccine can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, IL-2 (e.g., extended-PK IL-2), an immune checkpoint inhibitor, a tumor targeting antibody or an integrin-binding polypeptide, and optionally a cancer vaccine that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of IL-2 (e.g., extended-PK IL-2), the knottin-Fc, the cancer vaccine, and the optional immune checkpoint blocker. In certain embodiments, at least one additional agent can be included to facilitate absorption of IL-2 (e.g., extended-PK IL-2), the knottin-Fc, the immune checkpoint inhibitor, and the optional cancer vaccine. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of IL-2 (e.g., extended-PK IL-2), an immune checkpoint inhibitor, a tumor targeting antibody or an integrin-binding polypeptide, and optionally a cancer vaccine in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-2 (e.g., extended-PK IL-2), an immune checkpoint inhibitor, a tumor targeting antibody or an integrin-binding polypeptide, and optionally a cancer vaccine in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising IL-2 (e.g., extended-PK IL-2), an immune checkpoint inhibitor, a tumor targeting antibody or an integrin-binding polypeptide, and optionally a cancer vaccine to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which IL-2 (e.g., extended-PK IL-2), an immune checkpoint inhibitor, a tumor targeting antibody or an integrin-binding polypeptide, and optionally a cancer vaccine, are being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage for IL-2 (e.g., extended-PK IL-2) can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, a typical dosage for an immune checkpoint blocker can range from about 0.1 mg/kg to up to about 300 mg/kg or more, depending on the factors mentioned above. In certain embodiments, the dosage can range from 1 mg/kg up to about 300 mg/kg; or 5 mg/kg up to about 300 mg/kg; or 10 mg/kg up to about 300 mg/kg.

In some embodiments, the dosage of an integrin-binding polypeptide can range from about 5 mg/kg to about 50 mg/kg. In some embodiments, the dosage can range from about 10 mg/kg to about 40 mg/kg, about 10 mg/kg to about 30 mg/kg, about 10 mg/kg to about 25 mg/kg, about 5 mg/kg to about 20 mg/kg, about 5 mg/kg to about 15 mg/kg, or about 5 mg/kg to about 10 mg/kg. In some embodiments, the dosage is about 10 mg/kg.

IL-2 dosages can include but are not limited to high doses (HD): 0.72 MIU/kg every 8 hr.times.15 (80 MIU/m2/d); low dosages (LD): 8 MIU/m2/d; and subcutaneous dosages (SC): 250,000 U/kg/dose (9.25 MIU/m2/d, 5 days per week, dose halved in weeks 2-6). MIU refers to million international units. Subcutaneous IL-2 has been shown to be well tolerated and to exhibit a 10% response rate to subcutaneous IL-2 (see, for example, J Clin Oncol 21: 3127-3132, 2003). As such, Other subcutaneous IL-2 dosages can include 1 MIU/m2 d 2-7, 12-21; 12 MIU/m2 d 9-11 & 1-3 subsequent cycles (see, for example, Mani et al., Breast Cancer Research and Treatment, 117(1), 83-89. 2009) and 8.8 MIU/m2/d, 6.25 MIU/m2/d (14 MIU s.c. thrice weekly during weeks 2 to 5 and 10 MIU s.c. thrice weekly during weeks 6 to 9; see, for example, Clinical Cancer Research 12(23), 7046-7053, 2006). While the examples provide herein are directed to mice studies, such studies can be translated to human patients, including the IL-2 dosing. For example, 9 MIU/m2 in humans is equivalent to 3.6.mu.g in mice. The FDA human equivalent dose (HED) based on body area (see, for example, http://www.fda.gov/downloads/drugs/guidances/ucm078932.pdf; incorporated by reference herein; see tables 2 and 3 copied below). For example, 9 MIU/m2/(37 kg/m2)=0.24 MIU/kg.times.12.3=2.95 MIU/kg in mice and 2.95 MIU/kg/(16.4 MIU/mg)*0.02 kg/mouse=3.6 µg in mice.

TABLE 2

| Conversion of Animal Doses to Human Equivalent Doses Based on Body Surface Area | | |
|---|---|---|
| To Convert Animal Dose to dose in | To Convert Animal Dose in mg/kg to Dose in to HED[a] in mg/kg, Either: | |
| mg/m², Multiply by $k_m$ | Divide Animal Dose By | Multiply Animal Dose By |
| Species | | |
| Human — 37 | — | — |
| Child (20 kg)[b] — 25 | — | — |
| Mouse — 3 | 12.3 | 0.08 |
| Hamster — 5 | 7.4 | 0.13 |
| Rat — 6 | 6.2 | 0.16 |
| Ferret — 7 | 5.3 | 0.19 |
| Guinea Pig — 8 | 4.6 | 0.22 |
| Rabbit — 12 | 3.1 | 0.32 |
| Dog — 20 | 1.8 | 0.54 |
| Primates | | |
| Monkeys[c] — 12 | 3.1 | 0.32 |
| Mamoset — 6 | 6.2 | 0.16 |
| Squirrel monkey — 7 | 5.3 | 0.19 |
| Baboon — 20 | 1.8 | 0.54 |
| Micro-pig — 27 | 1.4 | 0.73 |
| Mini-pig — 35 | 1.1 | 0.95 |

[a]Assumes 60 kg human. For species not listed or for weight outside the standard ranges, HED can be calculated from the following formula HED = animal dose in mg/kg × (animal weight in kg/human weight in kg)$^{0.33}$

[b]This $k_m$ value is provided for reference only since healthy children will rarely be volunteers for phase I trials.

[c]For example, cynomolgus, rhesus and stamptail.

TABLE 3

Conversion of Animal Doses to Human Equivalent Doses Based on Body Surface Area

| | Reference body weight | Working weight range[a] (kg) | Body Surface Area (m²) | To Convert Animal Dose to dose in mg/m², Multiply by $k_m$ | To Convert Animal Dose in mg/kg mg/kg to Dose in to HED[b] in mg/kg, Either: | |
|---|---|---|---|---|---|---|
| | | | | | Divide Animal Dose By | Multiply Animal Dose By |
| Species | | | | | | |
| Human | 60 | — | 1.62 | 37 | — | — |
| Child (20 kg)[c] | 20 | — | 0.80 | 25 | — | — |
| Mouse | 0.020 | 0.011-0.034 | 0.007 | 3 | 12.3 | 0.081 |
| Hamster | 0.080 | 0.047-0.157 | 0.016 | 5 | 7.4 | 0.135 |
| Rat | 0.150 | 0.080-0.270 | 0.025 | 6 | 6.2 | 0.162 |
| Ferret | 0.300 | 0.160-0.540 | 0.043 | 7 | 5.3 | 0.189 |
| Guinea Pig | 0.400 | 0.208-0.700 | 0.05 | 8 | 4.6 | 0.216 |
| Rabbit | 1.8 | 0.9-3.0 | 0.15 | 12 | 3.1 | 0.324 |
| Dog | 10 | 5-17 | 0.5 | 20 | 1.8 | 0.541 |
| Primates | | | | | | |
| Monkeys[d] | 3 | 1.4-4.9 | 0.25 | 12 | 3.1 | 0.324 |
| Mamoset | 0.350 | 0.140-0.720 | 0.06 | 6 | 6.2 | 0.162 |
| Squirrel monkey | 0.600 | 0.290-0.970 | 0.09 | 7 | 5.3 | 0.189 |
| Baboon | 12 | 7-23 | 0.60 | 20 | 1.8 | 0.541 |
| Micro-pig | 20 | 10-33 | 0.74 | 27 | 1.4 | 0.730 |
| Mini-pig | 40 | 25-64 | 1.14 | 35 | 1.1 | 0.946 |

[a] For animal weights within the specified ranges, the HED for a 60 kg human calculated using the standard $k_m$ value will not vary more than ±20 percent from the HED calculated using a $k_m$ value based on the exact animal weight.
[b] Assumes 60 kg human. For species not listed or for weight outside the standard ranges, HED can be calculated from the following formula HED = animal dose in mg/kg × (animal weight in kg/human weight in kg)$^{0.33}$
[c] The $k_m$ value is provided for reference only since healthy children will rarely be volunteers for phase I trials.
[d] For example, cynomolgus, rhesus and stamptail.

Subcutaneous IL-2 has a plasma peak when 0.7 nM per MIU/m2 SC is dosed. The calculation is as follows:

10.6 CU/mL per MCU/m2;
10.6 CU/mL/(4×10^6 CU/mg)*1000 mL/L/(15,300 mg/mmol)×10^6 nmol/mmol=0.17 nM
16.4 MIU/mg/(4 MCU/mg)=4.1 MIU/MCU This has been described in, for example, Cancer Research 50. 2009-2017, '90, Table 4 of which is copied below as Table 4.

TABLE 4

Peak serum elvels after s.c. injections IL-2 was administered by s.c. injection at doses of 0.5 or 1.0 MU/m², and the activity was determined in serum taken at 0.5, 1, 2, 3, 4, 6, 8, and 24 h after injection. The median dose normalized peak level of 10.7 units/ml and time to peak of 180 min are similar to the corresponding values of 14.0 units/ml and 150 min observed after i.m. administration. The dose levels were lower in this study as compared to the i.m. trial, and meaningful values for AUC could not be obtained.

| Patient | Dose level (MU/m²) | Last time point (min) | Peak time (min) | Peak level (units/ml) | Peak level/ dose |
|---|---|---|---|---|---|
| 1 | 0.5 | 1440 | 120 | 6.7 | 13.4 |
| 2 | 0.5 | 1440 | 240 | 4.5 | 9.0 |
| 3 | 0.5 | 1440 | 360 | 7.5 | 15.0 |
| 4 | 1.0 | 1440 | 120 | 5.7 | 5.7 |
| 5 | 1.0 | 1440 | 120 | 11.8 | 11.8 |
| 7 | 1.0 | 1440 | 240 | 9.5 | 9.5 |
| Median | 0.8 | 1440 | 180 | 7.1 | 10.7 |
| Minimum | 0.5 | 1440 | 120 | 4.5 | 5.4 |
| Maximum | 1.0 | 1440 | 360 | 11.8 | 15.0 |
| Mean ± SD | | | | | 10.6 ± 3.5 |

With regard to Proleukin, it has a MW 15.3 kD and can be dosed at 16.4 MIU/mg. Other dosage units have been described, including "Cetus Units" and "Roche Units", and 1 Cetus Unit=3-6 IU (see, for example, http://cancerguide.org/rcc_il2.html Cancer Research 50. 2009-2017, '90).

With regard to surface area dosage conversion factors in IL-2 dosing, the following is applicable to the methods described herein. In adult humans, 100 mg/kg is equivalent to 100 mg/kg.times.37 kg/sq.m.=3700 mg/m2. A given mg/kg dose in mice can be divided by 12 to give an equivalent dose in man in terms of mg/m2. For example, a 60 kg human has 1.6 m2 surface area. See, for example, https://ncifrederick.cancer.gov/Lasp/Acuc/Frederick/Media/Documents/ACUC4-2.pdf.

In some embodiments, a typical dosage for an immune checkpoint inhibitor can range from about 0.1 mg/kg to up to about 300 mg/kg or more, depending on the factors mentioned above. In some embodiments, the dosage can range from 1 mg/kg up to about 300 mg/kg; or 5 mg/kg up to about 300 mg/kg; or 10 mg/kg up to about 300 mg/kg.

In some embodiments, the frequency of dosing will take into account the pharmacokinetic parameters of IL-2 (e.g., extended-PK IL-2), an immune checkpoint inhibitor, a tumor targeting antibody or an integrin-binding polypeptide, and optionally a cancer vaccine, in the formulation used. In some embodiments, a clinician will administer the composition until a dosage is reached that achieves the desired effect. In some embodiments, the composition can therefore be administered as a single dose, or as two or more doses (which may or may not contain the same amount of the desired molecule) over time, or as a continuous infusion via an implantation device or catheter. Further refinement of the appropriate dosage can be made by those of ordinary skill in the art and is within the ambit of tasks routinely performed by them. In some embodiments, appropriate dosages can be ascertained through use of appropriate dose-response data.

In some embodiments, the IL-2 is administered at a 12 MIU/m2 or lower daily dose. In some embodiments, the IL-2 dose is less than 14 MIU/m2, less than 12 MIU/m2, less than 10 MIU/m2, less than 8 MIU/m2, less than 6 MIU/m2, less than 4 MIU/m2, less than 2 MIU/m2 per day. In some embodiments, the IL-2 dose is about 14 MIU/m2 to about 6 MIU/m2 per day. In some embodiments, the IL-2 dose is about 12 MIU/m2 to about 8 MIU/m2 per day. In some embodiments, the IL-2 dose is about 12 MIU/m2 to about 10 MIU/m2 per day. In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes. In some embodiments, the priming dose and maintenance doses are administered by different routes. In some embodiments, the priming dose and maintenance doses are administered by the same route.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising IL-2 (e.g., extended-PK IL-2), an immune checkpoint inhibitor, a tumor targeting antibody or an integrin-binding polypeptide, and optionally a cancer vaccine in an ex vivo manner. In such instances, cells, tissues and/or organs that have been removed from the patient are exposed to a pharmaceutical composition IL-2 (e.g., extended-PK IL-2), an immune checkpoint inhibitor, a tumor targeting antibody or an integrin-binding polypeptide, and optionally a cancer vaccine after which the cells, tissues and/or organs are subsequently implanted back into the patient.

In certain embodiments, IL-2 (e.g., extended-PK IL-2), an immune checkpoint inhibitor, a tumor targeting antibody or an integrin-binding polypeptide, and optionally a cancer vaccine can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Kits

In some embodiments, the disclosure provides kits comprising IL-2, an immune checkpoint inhibitor, a tumor targeting antibody, an integrin-binding polypeptide, a cancer vaccine, or any combinations thereof, and instructions for use. The kits may comprise, in a suitable container, IL-2 (e.g., extended-PK IL-2), a cancer vaccine, the tumor targeting antibody or integrin-binding polypeptide, an immune checkpoint inhibitor, optionally a cancer vaccine, one or more controls, and various buffers, reagents, enzymes and other standard ingredients well known in the art. Certain embodiments include a kit with IL-2 (e.g., extended-PK IL-2), an immune checkpoint inhibitor, a tumor targeting antibody or an integrin-binding polypeptide, and optionally a cancer vaccine in the same vial. In certain embodiments, a kit includes IL-2 (e.g., extended-PK IL-2), an immune checkpoint inhibitor, a tumor targeting antibody or an integrin-binding polypeptide, and optionally a cancer vaccine in separate vials.

In some embodiments, a kit comprises a container comprising IL-2 and a package insert comprising instructions for administration of IL-2 in a priming dose comprising an immune checkpoint inhibitor polypeptide and a tumor targeting antibody or an integrin-binding polypeptide, wherein the priming dose is administered prior to administration of at least one maintenance dose comprising an immune checkpoint inhibitor polypeptide for treating or delaying progression of cancer or reducing or inhibiting tumor growth in a subject in need thereof.

In some embodiments, a kit comprises a container comprising a tumor targeting antibody and a package insert comprising instructions for administration of the tumor targeting antibody in a priming dose comprising an immune checkpoint inhibitor polypeptide and IL-2, wherein the priming dose is administered prior to administration of at least one maintenance dose comprising an immune checkpoint inhibitor polypeptide for treating or delaying progression of cancer or reducing or inhibiting tumor growth in a subject in need thereof.

In some embodiments, a kit comprises a container comprising an integrin-binding polypeptide and a package insert comprising instructions for administration of the integrin-binding polypeptide in a priming dose comprising an immune checkpoint inhibitor polypeptide and IL-2, wherein the priming dose is administered prior to administration of at least one maintenance dose comprising an immune checkpoint inhibitor polypeptide for treating or delaying progression of cancer or reducing or inhibiting tumor growth in a subject in need thereof.

In some embodiments, a kit comprises a container comprising an immune checkpoint inhibitor polypeptide and a package insert comprising instructions for administration of the immune checkpoint inhibitor polypeptide in a priming dose comprising IL-2 and a tumor targeting antibody or an integrin-binding polypeptide, wherein the priming dose is administered prior to administration of at least one maintenance dose comprising an immune checkpoint inhibitor polypeptide for treating or delaying progression of cancer or reducing or inhibiting tumor growth in a subject in need thereof.

The container can include at least one vial, well, test tube, flask, bottle, syringe, or other container means, into which IL-2 (e.g., extended-PK IL-2), an immune checkpoint inhibitor, a tumor targeting antibody or an integrin-binding polypeptide, and optionally a cancer vaccine may be placed, and in some instances, suitably aliquoted. Where an additional component is provided, the kit can contain additional containers into which this component may be placed. The kits can also include a means for containing IL-2 (e.g., extended-PK IL-2), an immune checkpoint inhibitor, a tumor targeting antibody or an integrin-binding polypeptide, and optionally a cancer vaccine, and any other reagent containers in close confinement for commercial sale. Such

Methods of Treatment

The IL-2 (e.g., extended-PK IL-2), immune checkpoint inhibitor, tumor targeting antibody, integrin-binding polypeptide, and optional cancer vaccine and/or nucleic acids expressing them, described herein, are useful for treating a disorder associated with abnormal apoptosis or a differentiative process (e.g., cellular proliferative disorders (e.g., hyperproliferaetive disorders) or cellular differentiative disorders, such as cancer). Non-limiting examples of cancers that are amenable to treatment with the methods of the present disclosure are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., IL-2 (e.g., extended-PK IL-2), an immune checkpoint inhibitor, a tumor targeting antibody, an integrin-binding polypeptide, and/or optional a cancer vaccine, can be administered to a patient who has cancer. In some embodiments, a priming dose comprising IL-2 (e.g., extended-PK IL-2), an immune checkpoint inhibitor, a tumor targeting antibody or an integrin-binding polypeptide, and optional a cancer vaccine is administered to a subject prior to at least one maintenance dose of an immune checkpoint inhibitor.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth). Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The priming dose and at least one maintenance dose described herein can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

In some embodiments, the priming dose comprising (i) IL-2; (ii) an immune checkpoint inhibitor polypeptide; (iii) a tumor targeting antibody or an integrin-binding polypeptide; and optionally (iv) a cancer vaccine, and at least one maintenance dose comprising an immune checkpoint inhibitor polypeptide as disclosed herein is used in a method of treating cancer in a subject, wherein the cancer comprises a cold tumor. As used herein, a "cold tumor" refers to a tumor comprising a tumor microenvironment with low infiltration of lymphocytes (e.g., CD8+ T cells) as described by Bonaventura, et al (2019) *Frontiers in Immunology* Vol. 10, Article 168. Methods of measuring quantity of tumor infiltrating lymphocytes (e.g., CD8+ T cell) and their proximity relative to the tumor margin are known in the art (see, e.g., Steele, et al. (2018) *J Immunother Cancer* 6:20). For example, tumor tissue samples isolated from a subject (e.g., tumor biopsy sample) are assessed by histological methods for infiltration of CD3+ T cells, CD4+ T cells, CD8+ T cells, or any combination thereof. Quantification of T cells in the tumor bed and tumor margin can be used to provide a score of T cell infiltration (see, e.g., Ascierto, et al (2013) *J Transl Med* 11:54; Galon, et al (2012) *J Transl Med* 10:1; Teng, et al (2015) *Cancer Res* 75:2139). While T cells may infiltrate the tumor margin, infiltration of the tumor bed is associated with an anti-tumor immune response.

In some embodiments, a priming dose and at least one maintenance dose are used in a method of treating a tumor with low infiltration of CD8+ T cells in the tumor. In some embodiment, a priming dose and at least one maintenance dose are used in a method of treating a tumor with low infiltration of CD8+ T cells in the tumor bed. In some embodiments, administration of priming dose and at least one maintenance dose as described herein induces increased infiltration of CD8+ T cells in the tumor bed. For example, CD8+ T cell infiltration in the tumor bed is increased by at least 5%, 10%, 15%, 20%, 25%, 30%, 35%, 40%, 45%, 50% or more than 50% relative to a tumor that did not receive a priming dose (e.g., tumor sample obtained prior to priming dose).

In some embodiments, sufficient priming of a cold tumor is evaluated in animal models. For example, certain syngeneic mouse models have been shown to have poor infiltration of lymphocytes (e.g, CD8+ T cells), including B16F10 melanoma (see, e.g., Yu et al (2018) *PLoS One* 13:e0206223), as well as genetically modified mouse (GEM) models, including the KP lung adenocarcinoma model (see, e.g., Schmidt, et al. (2019) *PNAS* 116:17460). In some embodiments, a priming dose induces increased infiltration of CD8+ T cells in a mouse tumor with low T cell infiltration (e.g., B16F10 melanoma tumor, e.g., KP lung tumor).

It will be appreciated by those skilled in the art that amounts for each of component of the combination immunotherapy (IL-2, immune checkpoint inhibitor, integrin-binding polypeptide or tumor targeting antibody, and optional cancer vaccine), and an immune checkpoint inhibitor that are sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis.

In certain embodiments, the priming and maintenance dosing methods disclosed herein are used to treat cancer.

In certain embodiments, the priming and maintenance dosing methods disclosed herein are used to treat melanoma, leukemia, lung cancer, breast cancer, prostate cancer, ovarian cancer, colon cancer, and brain cancer.

In certain embodiments, the priming and maintenance dosing methods disclosed herein inhibit the growth and/or proliferation of tumor cells.

In certain embodiments, the priming and maintenance dosing methods disclosed herein reduce tumor size.

In certain embodiments, the priming and maintenance dosing methods disclosed herein inhibit metastases of a primary tumor.

It will be appreciated by those skilled in the art that reference herein to treatment extends to prophylaxis as well as the treatment of the noted cancers and symptoms.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publication WO 13/177187, U.S. Pat. No. 8,536,301, and U.S. Patent Publication No. 2014/0073518 are expressly incorporated herein by reference.

Definitions

Terms used in the claims and specification are defined as set forth below unless otherwise specified. In the case of direct conflict with a term used in a parent provisional patent application, the term used in the instant application shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is a mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, "interleukin (IL)-2," refers to a pleiotropic cytokine that activates and induces proliferation of T cells and natural killer (NK) cells. IL-2 signals by binding its receptor, IL-2R, which is comprised of alpha, beta, and gamma subunits. IL-2 signaling stimulates proliferation of antigen-activated T cells.

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include PEG, human serum albumin (HSA) binders (as disclosed in U.S. Publication Nos. 2005/0287153 and 2007/0003549, PCT Publication Nos. WO 2009/083804 and WO 2009/133208, and SABA molecules as described in US2012/094909), serum albumin (e.g., HSA), Fc or Fc fragments and variants thereof, transferrin and variants thereof, and sugars (e.g., sialic acid). Other exemplary extended-PK groups are disclosed in Kontermann et al., Current Opinion in Biotechnology 2011; 22:868-876, which is herein incorporated by reference in its entirety. As used herein, an "extended-PK IL-2" refers to an IL-2 moiety in combination with an extended-PK group. In one embodiment, the extended-PK IL-2 is a fusion protein in which an IL-2 moiety is linked or fused to an extended-PK group. An exemplary fusion protein is an HSA/IL-2 fusion in which one or more IL-2 moieties are linked to HSA.

The term "extended-PK IL-2" is also intended to encompass IL-2 mutants with mutations in one or more amino acid residues that enhance the affinity of IL-2 for one or more of its receptors, for example, CD25. In one embodiment, the IL-2 moiety of extended-PK IL-2 is wild-type IL-2. In another embodiment, the IL-2 moiety is a mutant IL-2 which exhibits greater affinity for CD25 than wild-type IL-2. When a particular type of extended-PK group is indicated, such as HSA-IL-2, it should be understood that this encompasses both HSA or MSA fused to a wild-type IL-2 moiety or HSA or MSA fused to a mutant IL-2 moiety.

In certain aspects, the extended-PK IL-2 or integrin-binding polypeptide (e.g., knottin-Fc) described herein can employ one or more "linker domains," such as polypeptide linkers. As used herein, the term "linker" or "linker domain" refers to a sequence which connects two or more domains (e.g., the PK moiety and IL-2) in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to connect an IL-2 moiety to an Fc domain. Preferably, such polypeptide linkers can provide flexibility to the polypeptide molecule. In certain embodiments the polypeptide linker is used to connect (e.g., genetically fuse) one or more Fc domains and/or IL-2. In some embodiments, the polypeptide linker is used to connect (e.g., genetically engineer) one or more integrin-binding polypeptides to one or more Fc domains.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

The term "integrin" means a transmembrane heterodimeric protein important for cell adhesion. Integrins comprise an α and β subunit. These proteins bind to extracellular matrix components (e.g., fibronectin, collagen, laminin, etc.) and respond by inducing signaling cascades. Integrins bind to extracellular matrix components by recognition of the RGD motif. Certain integrins are found on the surface of tumor cells and therefore make promising therapeutic targets. In certain embodiments, the integrins being targeted are $\alpha_v\beta_3$, $\alpha_v\beta_5$, and $\alpha_5\beta_1$, individually or in combination.

The term "integrin-binding polypeptide" refers to a polypeptide which includes an integrin-binding domain or loop within a knottin polypeptide scaffold. The integrin binding domain or loop includes at least one RGD peptide. In certain embodiments, the RGD peptide is recognized by $\alpha_v\beta_3$, $\alpha_v\beta_5$, or $\alpha_5\beta_1$. In certain embodiments the RGD peptide binds to a combination of $\alpha_v\beta_3$, $\alpha_v\beta_5$, and/or $\alpha_5\beta_1$. These specific integrins are found on tumor cells and their vasculature and are therefore the targets of interest.

Protein binding to many different cell surface integrins can be mediated through the short peptide motif Arg-Gly-Asp (RGD) (Pierschbacher and Ruoslahti, 1984). These peptides have dual functions: They promote cell adhesion when immobilized onto a surface, and they inhibit cell adhesion when presented to cells in solution. Adhesion proteins that contain the RGD sequence include: fibronectin, vitronectin, osteopontin, fibrinogen, von Willebrand factor, thrombospondin, laminin, entactin, tenascin, and bone sialoprotein (Ruoslahti, 1996). The RGD sequence displays specificity to about half of the 20 known integrins including the $\alpha_5\beta_1$, $\alpha_v\beta_1$, $\alpha_v\beta_3$, $\alpha_v\beta_5$, $\alpha_v\beta_6$, $\alpha_5\beta_8$, and $\alpha_v\beta_3$ integrins, and, to a lesser extent, the $\alpha_2\beta_1$, $\alpha_3\beta_1$, or $\alpha_4\beta_1$, and $\alpha_7\beta_1$ (Ruoslahti, 1996). In particular, the $\alpha_v\beta_3$ integrin is capable of binding to a large variety of RGD containing proteins including fibronectin, fibrinogen, vitronectin, osteopontin, von Willebrand factor, and thrombospondin (Ruoslahti, 1996; Haubner et al., 1997), while the $\alpha_5\beta_1$ integrin is more specific and has only been shown to bind to fibronectin (D'Souza et al., 1991).

The linear peptide sequence RGD has a much lower affinity for integrins than the proteins from which it is derived (Hautanen et al., 1989). This due to conformational specificity afforded by folded protein domains not present in linear peptides. Increased functional integrin activity has resulted from preparation of cyclic RGD motifs, alteration of the residues flanking the RGD sequence, and synthesis of small molecule mimetics (reviewed in (Ruoslahti, 1996; Haubner et al., 1997)).

The term "loop domain" refers to an amino acid subsequence within a peptide chain that has no ordered secondary structure, and resides generally on the surface of the peptide.

The term "loop" is understood in the art as referring to secondary structures that are not ordered as in the form of an alpha helix, beta sheet, etc.

The term "integrin-binding loop" refers to a primary sequence of about 9-13 amino acids which is typically created ab initio through experimental methods such as directed molecular evolution to bind to integrins. In certain embodiments, the integrin-binding loop includes an RGD peptide sequence, or the like, placed between amino acids which are particular to the scaffold and the binding specificity desired. The RGD-containing peptide or like (RYD, etc) is generally not simply taken from a natural binding sequence of a known protein. The integrin-binding loop is preferably inserted within a knottin polypeptide scaffold between cysteine residues, and the length of the loop adjusted for optimal integrin-binding depending on the three-dimensional spacing between cysteine residues. For example, if the flanking cysteine residues in the knottin scaffold are linked to each other, the optimal loop may be shorter than if the flanking cysteine residues are linked to cysteine residues separated in primary sequence. Otherwise, particular amino acid substitutions can be introduced to constrain a longer RGD-containing loop into an optimal conformation for high affinity integrin binding. The knottin polypeptide scaffolds used herein may contain certain modifications made to truncate the native knottin, or to remove a loop or unnecessary cysteine residue or disulfide bond.

Incorporation of integrin-binding sequences into a molecular (e.g., knottin polypeptide) scaffold provides a framework for ligand presentation that is more rigid and stable than linear or cyclic peptide loops. In addition, the conformational flexibility of small peptides in solution is high, and results in large entropic penalties upon binding. Incorporation of an integrin-binding sequence into a knottin polypeptide scaffold provides conformational constraints that are required for high affinity integrin binding. Furthermore, the scaffold provides a platform to carry out protein engineering studies such as affinity or stability maturation.

As used herein, the term "knottin protein" refers to a structural family of small proteins, typically 25-40 amino acids, which bind to a range of molecular targets like proteins, sugars and lipids. Their three-dimensional structure is essentially defined by a peculiar arrangement of three to five disulfide bonds. A characteristic knotted topology with one disulfide bridge crossing the macro-cycle limited by the two other intra-chain disulfide bonds, which was found in several different microproteins with the same cystine network, lent its name to this class of biomolecules. Although their secondary structure content is generally low, the knottins share a small triple-stranded antiparallel n-sheet, which is stabilized by the disulfide bond framework. Biochemically well-defined members of the knottin family, also called cystine knot proteins, include the trypsin inhibitor EETI-II from Ecballium elaterium seeds, the neuronal N-type Ca2+ channel blocker w-conotoxin from the venom of the predatory cone snail Conus geographus, agouti-related protein (AgRP, See Millhauser et al., "Loops and Links: Structural Insights into the Remarkable Function of the Agouti-Related Protein," Ann. N.Y. Acad. Sci., Jun. 1, 2003; 994(1): 27-35), the omega agatoxin family, etc. A suitable agatoxin sequence [SEQ ID NO: 41] is given in U.S. Pat. No. 8,536,301. Other agatoxin sequences suitable for use in the methods disclosed herein include, Omega-agatoxin-Aa4b (GenBank Accession number P37045) and Omega-agatoxin-Aa3b (GenBank Accession number P81744). Other knottin sequences suitable for use in the methods disclosed herein include, knottin [*Bemisia tabaci*] (GenBank Accession number FJ601218.1), Omega-lycotoxin (Genbank Accession number P85079), mu-O conotoxin MrVIA=voltage-gated sodium channel blocker (Genbank Accession number AAB34917) and *Momordica cochinchinensis* Trypsin Inhibitor I (MCoTI-I) or II (McoTI-II) (Uniprot Accession numbers P82408 and P82409 respectively).

Knottin proteins have a characteristic disulfide linked structure. This structure is also illustrated in Gelly et al., "The KNOTTIN website and database: a new information system dedicated to the knottin scaffold," Nucleic Acids Research, 2004, Vol. 32, Database issue D156-D159. A triple-stranded n-sheet is present in many knottins. The spacing between cysteine residues is important, as is the molecular topology and conformation of the integrin-binding loop.

The term "molecular scaffold" means a polymer having a predefined three-dimensional structure, into which an integrin-binding loop is incorporated, such as an RGD peptide sequence as described herein. The term "molecular scaffold" has an art-recognized meaning (in other contexts), which is also intended here. For example, a review by Skerra, "Engineered protein scaffolds for molecular recognition," *J. Mol. Recognit.* 2000; 13:167-187 describes the following scaffolds: single domains of antibodies of the immunoglobulin superfamily, protease inhibitors, helix-bundle proteins, disulfide-knotted peptides and lipocalins. Guidance is given for the selection of an appropriate molecular scaffold.

The term "knottin polypeptide scaffold" refers to a knottin protein suitable for use as a molecular scaffold, as described herein. Characteristics of a desirable knottin polypeptide scaffold for engineering include 1) high stability in vitro and in vivo, 2) the ability to replace amino acid regions of the scaffold with other sequences without disrupting the overall fold, 3) the ability to create multifunctional or bispecific targeting by engineering separate regions of the molecule, and 4) a small size to allow for chemical synthesis and incorporation of non-natural amino acids if desired. Scaffolds derived from human proteins are favored for therapeutic applications to reduce toxicity or immunogenicity concerns, but are not always a strict requirement. Other scaffolds that have been used for protein design include fibronectin (Koide et al., 1998), lipocalin (Beste et al., 1999), cytotoxic T lymphocyte-associated antigen 4 (CTLA-4) (Hufton et al., 2000), and tendamistat (McConnell and Hoess, 1995; Li et al., 2003). While these scaffolds have proved to be useful frameworks for protein engineering, molecular scaffolds such as knottins have distinct advantages: their small size and high stability.

As used herein, the term "EETI" means Protein Data Bank Entry (PDB) 2ETI. Its entry in the Knottin database is EETI-II. It has the sequence:

(SEQ ID NO: 39)
GCPRILMRCKQDSDCLAGCVCGPNGFCG.

As used herein, the term "AgRP" means PDB entry 1HYK. Its entry in the Knottin database is SwissProt AGRP HUMAN, where the full-length sequence of 129 amino acids may be found. It comprises the sequence beginning at amino acid 87. An additional G is added to this construct. It also includes a C105A mutation described in Jackson, et al. 2002 Biochemistry, 41, 7565.

```
                                                          (SEQ ID NO: 40)
GCVRLHESCLGQQVPCCDPCATCYCRFFNAFCYCR-KLGTAMNPCSRT
```

The bold and underlined portion, from loop 4, is replaced by the RGD sequences described herein. Loops 1 and 3 are shown between brackets below:

```
                                                          (SEQ ID NO: 40)
GC[VRLHES]CLGQQVPCC[DPCAT]CYCRFFNAFCYCR-KLGTAMNPCSRT
```

As used herein, "integrin-binding-Fc fusion" is used interchangeably with "knottin-Fc" and refers to an integrin-binding polypeptide that includes an integrin-binding amino acid sequence within a knottin polypeptide scaffold and is operably linked to an Fc domain. In certain embodiments, the Fc domain is fused to the N-terminus of the integrin-binding polypeptide. In certain embodiments, the Fc domain is fused to the C-terminus of the integrin binding polypeptide. In some embodiments, the Fc domain is operably linked to the integrin-binding polypeptide via a linker.

As used herein, the term "Fc region" refers to the portion of a native immunoglobulin formed by the respective Fc domains (or Fc moieties) of its two heavy chains. As used herein, the term "Fc domain" refers to a portion of a single immunoglobulin (Ig) heavy chain wherein the Fc domain does not comprise an Fv domain. As such, an Fc domain can also be referred to as "Ig" or "IgG." In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 (i.e., SEQ ID NO: 1). In some embodiments, the Fc domain of human IgG1 comprises the amino acid sequence of SEQ ID NO: 2. In some embodiments, the Fc domain of human IgG1 with a deletion of the upper hinge region comprises the amino acid sequence of SEQ ID NO: 3. The Fc domain encompasses native Fc and Fc variant molecules. As with Fc variants and native Fc's, the term Fc domain includes molecules in monomeric or multimeric form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5th edition, Bethesda, Md.: NIH vol. 1:647-723 (1991); Kabat et al., "Introduction" Sequences of Proteins of Immunological Interest, US Dept of Health and Human Services, NIH, 5th edition, Bethesda, Md. vol. 1:xiii-xcvi (1991); Chothia & Lesk, J. Mol. Biol. 196:901-917 (1987); Chothia et al., Nature 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide of the disclosure may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

In certain embodiments, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In some embodiments, a polypeptide comprising IL-2 or a variant thereof, for use in extended-PK IL-2 consists of, consists essentially of, or comprises an amino acid sequence selected from SEQ ID Nos: 5, 7, 9, 11, 13, 15, 17, 19, 21, 23, 25, 27, 29, 31, 33, and 35. In some embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 5, 7, 9, 11, 13, 15, 17, 19, 21, 23, 25, 27, 29, 31, 33, and 35. In some embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 5, 7, 9, 11, 13, 15, 17, 19, 21, 23, 25, 27, 29, 31, 33, and 35. In some embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 5, 7, 9, 11, 13, 15, 17, 19, 21, 23, 25, 27, 29, 31, 33, and 35.

In some embodiments, the peptides are encoded by a nucleotide sequence. Nucleotide sequences can be useful for a number of applications, including: cloning, gene therapy, protein expression and purification, mutation introduction, DNA vaccination of a host in need thereof, antibody generation for, e.g., passive immunization, PCR, primer and probe generation, and the like. In some embodiments, the nucleotide sequence of the disclosure comprises, consists of, or consists essentially of, a nucleotide sequence of IL-2, or a variant thereof, selected from SEQ ID Nos: 4, 6, 8, 10, 12, 14, 16, 18, 20, 22, 24, 26, 28, 30, 32, and 34. In some embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID Nos: 4, 6, 8, 10, 12, 14, 16, 18, 20, 22, 24, 26, 28, 30, 32, and 34. In some embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID Nos: 4, 6, 8, 10, 12, 14, 16, 18, 20, 22, 24, 26, 28, 30, 32, and 34. In some embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in SEQ ID Nos: 4, 6, 8, 10, 12, 14, 16, 18, 20, 22, 24, 26, 28, 30, 32, and 34.

In some embodiments, a polypeptide comprising an integrin-binding peptide or a variant thereof, consists of, consists essentially of, or comprises an amino acid sequence selected from SEQ ID Nos: 59-125. In some embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 59-125. In some embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 59-125. In some embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 59-125.

It will also be understood by one of ordinary skill in the art that the IL-2 (e.g., extended-PK IL-2) or integrin-binding polypeptide (e.g., a knottin-Fc fusion suitable for use in the methods disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides described herein (e.g., IL-2, extended-PK IL-2, PK moieties, knottin, Fc, knottin-Fc, and the like) may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In certain embodiments, a string of amino acids can be replaced with a structurally similar string that differs in order and/or composition of side chain family members. Alternatively, in certain embodiments, mutations may be introduced randomly along all or part of a coding sequence, such as by saturation mutagenesis, and the resultant mutants can be incorporated into binding polypeptides of the disclosure and screened for their ability to bind to the desired target.

The term "ameliorating" refers to any therapeutically beneficial result in the treatment of a disease state, e.g., cancer, including prophylaxis, lessening in the severity or progression, remission, or cure thereof.

The term "in vivo" refers to processes that occur in a living organism.

The term "mammal" or "subject" or "patient" as used herein includes both humans and non-humans and includes, but is not limited to, humans, non-human primates, canines, felines, murines, bovines, equines, and porcines.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As used herein, the term "gly-ser polypeptide linker" refers to a peptide that consists of glycine and serine residues. An exemplary gly-ser polypeptide linker comprises the amino acid sequence Ser(Gly$_4$Ser)n (SEQ ID NO: 126). In certain embodiments, n=1. In certain embodiments, n=2. In certain embodiments, n=3, i.e., Ser(Gly$_4$Ser)3 (SEQ ID NO: 127). In certain embodiments, n=4, i.e., Ser(Gly$_4$Ser)4 (SEQ ID NO: 137). In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence (Gly$_4$Ser)n (SEQ ID NO: 128). In certain embodiments, n=1. In certain embodiments, n=2. In certain embodiments, n=3. In certain embodiments, n=4. In certain embodiments, n=5. In certain embodiments, n=6. Another exemplary gly-ser polypeptide linker comprises the amino acid sequence (Gly$_3$Ser)n (SEQ ID NO: 129). In certain embodiments, n=1. In certain embodiments, n=2. In certain embodiments, n=3. In certain embodiments, n=4. In certain embodiments, n=5. In certain embodiments, n=6.

As used herein, the terms "linked," "fused", or "fusion" are used interchangeably. These terms refer to the joining together of two or more elements or components or domains, by whatever means including chemical conjugation or recombinant means. Methods of chemical conjugation (e.g., using heterobifunctional crosslinking agents) are known in the art.

As used herein, "half-life" refers to the time taken for the serum or plasma concentration of a polypeptide to reduce by 50%, in vivo, for example due to degradation and/or clearance or sequestration by natural mechanisms. The extended-PK IL-2 suitable for use in the methods disclosed herein is stabilized in vivo and its half-life increased by, e.g., fusion to an Fc region, fusion to serum albumin (e.g., HSA or MSA), through PEGylation, or by binding to serum albumin molecules (e.g., human serum albumin) which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

A "therapeutic antibody" is an antibody, fragment of an antibody, or construct that is derived from an antibody, and can bind to a cell-surface antigen on a target cell to cause a therapeutic effect. Such antibodies can be chimeric, humanized or fully human antibodies. Methods are known in the art for producing such antibodies. Such antibodies include single chain Fc fragments of antibodies, minibodies and diabodies. Any of the therapeutic antibodies known in the art to be useful for cancer therapy can be used in the combination therapy suitable for use in the methods disclosed herein. Therapeutic antibodies may be monoclonal antibodies or polyclonal antibodies. In preferred embodiments, the therapeutic antibodies target cancer antigens.

As used herein, "cancer antigen" refers to (i) tumor-specific antigens, (ii) tumor-associated antigens, (iii) cells that express tumor-specific antigens, (iv) cells that express tumor-associated antigens, (v) embryonic antigens on tumors, (vi) autologous tumor cells, (vii) tumor-specific membrane antigens, (viii) tumor-associated membrane antigens, (ix) growth factor receptors, (x) growth factor ligands, and (xi) any other type of antigen or antigen-presenting cell or material that is associated with a cancer.

As used herein, "therapeutic protein" refers to any polypeptide, protein, protein variant, fusion protein and/or fragment thereof which may be administered to a subject as a medicament. An exemplary therapeutic protein is an interleukin, e.g., IL-7.

As used herein, "synergy" or "synergistic effect" with regard to an effect produced by two or more individual components refers to a phenomenon in which the total effect produced by these components, when utilized in combination, is greater than the sum of the individual effects of each component acting alone.

The term "sufficient amount" or "amount sufficient to" means an amount sufficient to produce a desired effect, e.g., an amount sufficient to reduce the size of a tumor.

The term "therapeutically effective amount" is an amount that is effective to ameliorate a symptom of a disease. A therapeutically effective amount can be a "prophylactically effective amount" as prophylaxis can be considered therapy.

As used herein, "combination therapy" embraces administration of each agent or therapy in a sequential manner in a regimen that will provide beneficial effects of the combination, and co-administration of these agents or therapies in a substantially simultaneous manner, such as in a single capsule having a fixed ratio of these active agents or in multiple, separate capsules for each agent. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, "cancer vaccine" refers to a treatment that induces the immune system to attack cells with one or more tumor associated antigens. The vaccine can treat existing cancer (e.g., therapeutic cancer vaccine) or prevent the development of cancer in certain individuals (e.g., prophylactic cancer vaccine). The vaccine creates memory cells that will recognize tumor cells with the antigen and therefore prevent tumor growth. In certain embodiments, the cancer vaccine comprises an immunostimulatory oligonucleotide.

As used herein, an "immunostimulatory oligonucleotide" is an oligonucleotide that can stimulate (e.g., induce or enhance) an immune response.

As used herein, "CG oligodeoxynucleotides (CG ODNs)", also referred to as "CpG ODNs", are short single-stranded synthetic DNA molecules that contain a cytosine nucleotide (C) followed by a guanine nucleotide (G). In certain embodiments, the immunostimulatory oligonucleotide is a CG ODN.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term "T cell" refers to a CD4+ T cell or a CD8+ T cell. The term T cell encompasses TH1 cells, TH2 cells and TH17 cells.

The term "T cell cytoxicity" includes any immune response that is mediated by CD8+ T cell activation. Exemplary immune responses include cytokine production, CD8+ T cell proliferation, granzyme or perforin production, and clearance of an infectious agent.

The "Programmed Death-1 (PD-1)" receptor refers to an immuno-inhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773 (SEQ ID NO: 52).

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7 (SEQ ID NO: 53).

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. P16410 (SEQ ID NO: 54):

"Lymphocyte Activation Gene-3 (LAG3)" is an inhibitory receptor associated with inhibition of lymphocyte activity by binding to MHC class II molecules. This receptor enhances the function of Treg cells and inhibits CD8+ effector T cell function. The term "LAG3" as used herein includes human LAG3 (hLAG3), variants, isoforms, and species homologs of hLAG3, and analogs having at least one common epitope. The complete hLAG3 sequence can be found under GenBank Accession No. P18627 (SEQ ID NO: 55).

"T Cell Membrane Protein-3 (TIM3)" is an inhibitory receptor involved in the inhibition of lymphocyte activity by inhibition of TH1 cells responses. Its ligand is galectin 9, which is upregulated in various types of cancers. The term "TIM3" as used herein includes human TIM3 (hTIM3), variants, isoforms, and species homologs of hTIM3, and analogs having at least one common epitope. The complete hTIM3 sequence can be found under GenBank Accession No. Q8TDQo (SEQ ID NO: 56).

The "B7 family" refers to inhibitory ligands with undefined receptors. The B7 family encompasses B7-H3 and B7-H4, both upregulated on tumor cells and tumor infiltrating cells. The complete hB7-H3 and hB7-H4 sequence can be found under GenBank Accession Nos. Q5ZPR3 and AAZ17406 (SEQ ID NOs: 57 and 58) respectively.

As used herein, "immune checkpoint" refers to co-stimulatory and inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG3 and MHC class II molecules. In certain embodiments, the inhibitory signal is the interaction between TIM3 and galectin 9.

As used herein, "immune checkpoint blocker" or "immune checkpoint inhibitor" refers to a molecule that totally or partially reduces, inhibits, interferes with or modulates one or more checkpoint proteins. In certain embodiments, the immune checkpoint blocker prevents inhibitory signals associated with the immune checkpoint. In certain embodiments, the immune checkpoint blocker is an antibody, or fragment thereof that disrupts inhibitory signaling associated with the immune checkpoint. In certain embodiments, the immune checkpoint blocker is a small molecule that disrupts inhibitory signaling. In certain embodiments, the immune checkpoint blocker is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint blocker is an antibody, or fragment thereof, that prevents the interaction between CTLA-4 and CD80 or CD86. In certain embodiments, the immune checkpoint blocker is an antibody, or fragment thereof, that prevents the interaction between LAG3 and its ligands, or TIM-3 and its ligands. The checkpoint blocker may also be in the form of the soluble form of the molecules (or variants thereof) themselves, e.g., a soluble PD-L1 or PD-L1 fusion.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, "priming dose" refers to a dose of combination immunotherapy that primes a subject for administration of a therapeutically effective dose or maintenance dose of an immune checkpoint inhibitor. In some embodiments, the priming dose of combination immunotherapy primes a subject having cancer for administration of a therapeutically effective dose or maintenance dose of an immune checkpoint inhibitor. In some embodiments, the priming dose of combination immunotherapy alters the tumor microenvironment (e.g., increased infiltration of cytotoxic T cells, cross presenting dendritic cells, NK cells), thereby priming the tumor for a therapeutically effective dose or maintenance dose of an immune checkpoint inhibitor. In some embodiments, the priming dose induces an anti-tumor immune response (e.g., T cell infiltration and activation). In some embodiments, the anti-tumor immune response is maintained by a therapeutically effective dose or maintenance dose of an immune checkpoint inhibitor. In some embodiments, a priming dose is administered one day, two days, three days, four days, five days, six days, seven days, eight days, nine days, ten days, eleven days, twelve days, thirteen days, fourteen days, fifteen days, sixteen days, seventeen days, eighteen days, nineteen days, twenty days, twenty one days or more than twenty one days prior to administration of a therapeutically effective dose or maintenance dose of an immune checkpoint inhibitor.

As used herein, "maintenance dose" refers to a dose intended to be a therapeutically effective dose. In some embodiments, the maintenance dose is an approved dose for an immune checkpoint inhibitor. In some embodiments, a maintenance dose maintains the anti-tumor immune response induced by a priming dose. In some embodiments, a maintenance dose comprises an approved dose of a single immune checkpoint inhibitor (e.g., anti-PD-1). In some embodiments, a maintenance dose comprises an approved dose of two or more immune checkpoint inhibitors (e.g., anti-PD-1 and anti-CTLA-4) administered as a combination therapy.

It must be noted that, as used in the specification and the appended claims, the singular forms "a," "an" and "the" include plural referents unless the context clearly dictates otherwise.

EXAMPLES

Below are examples of specific embodiments for carrying out the methods described herein. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for. The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992). Moreover, while the examples below employ extended-PK IL-2 of mouse origin (i.e., both the extended-PK group (mouse serum albumin) and IL-2 are of mouse origin), it should be understood that corresponding human extended-PK IL-2 (i.e., human serum albumin (HSA) and human IL-2, and variants thereof) can be readily generated by those of ordinary skill in the art using methods described supra, and used in the methods disclosed herein.

Example 1: Immunotherapy Combination Treatment Modulates Tumor Microenvironment

To assess the impact of an immunotherapy combination treatment on tumor microenvironments, the B16F10 melanoma mouse model was utilized. $1\times10^6$ B16F10 melanoma cells (ATCC), which are poorly immunogenic and aggressively form tumors, were subcutaneously injected into C57BL/6 mice. Immunotherapy was administered 8 days after tumor inoculation. This consisted of 100 µg TA99 ("A"; an anti-Trp-1 antibody, produced by researcher, see e.g., Zhu, E. et al. (2015) *Cancer Cell* 27:489-501), 30 µg mouse serum albumin (MSA)-IL-2 ("I"; produced by researcher, see e.g., Zhu, E. et al.), 200 µg anti-PD-1 antibody ("P"; clone 29F.1A12 from BioXcell), and an amphiphile-peptide cancer vaccine targeting Trp-2 ("V"). The vaccine included a lymph-node targeted molecular adjuvant in which a 20 base phosphorothioate (PS)-stabilized CpG oligonucleotide was linked at the 5' to diacyl lipid via a guanine linker (lipo-$G_2$-CpG) as described in Liu, H. et al., *Nature* 507: 519-522 (Mar. 27, 2014). Oligonucleotide amphiphiles were synthesized using an ABI 394 synthesizer on a 1.0 µmol scale. All lipophilic phosphoramidites were conjugated as a final 'base' on the 5'end of oligonucleotides. Lui, H. et al., *Angew. Chem. Int. Ed. Engl.* 50, 7052-7055 (2011). The tumor-associated self-antigen Trp2 from melanoma was conjugated to 1,2-distearoyl-sn-glycero-3-phoethanolamine-N-PEG (DSPE-PEG 2 kDa) to generate amph-peptides for vaccination studies. Antigen amphiphiles were synthesized by reacting N-terminal cysteine-modified peptides with maleimide-$PEG_{2000}$-DSPE in dimethly formamide.

Figure 1B:
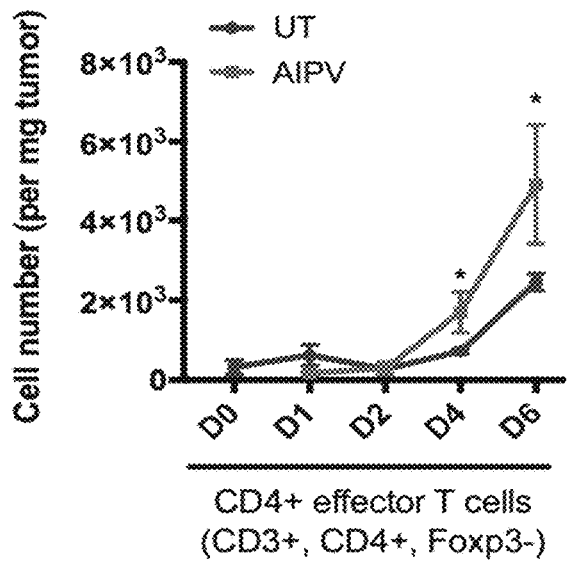
Figure 1C:
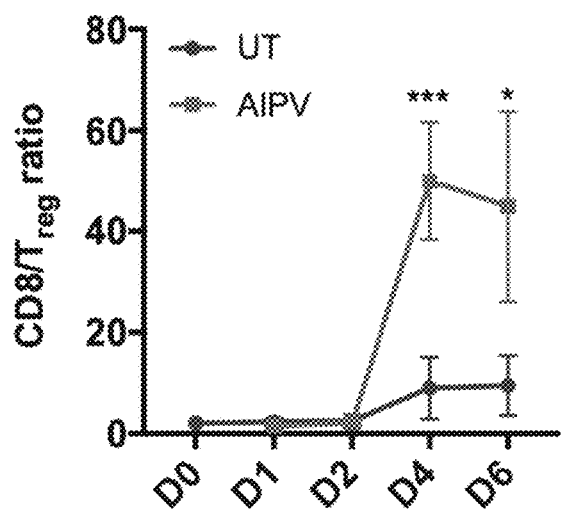

Tumors were isolated 1, 2, 4 and 6 days post treatment. The number of CD8+ T cells, CD4+ T cells (regulatory or non-regulatory) in the tumors or tumor draining lymph nodes were measured via flow cytometry as previously described (Zhu et al., *Cancer Cell* (2015) Vol 27:489-501). As shown in FIGS. 1A-1B the total number of CD8+ T cells (CD3+CD8+) and CD4+ effector T cells (CD3+CD4+Foxp3−) per mg of tumor, respectively, increased over time in mice that received the AIPV combination therapy. FIG. 1C shows the ratio of CD8+ T cells to CD4+Foxp3+CD25+ Treg cells increased in tumors over time. In addition, FIGS. 1D-1E show an increase in CD8+ T cells and CD4+ effector cells, respectively, in the tumor draining lymph node.

Figure 2:
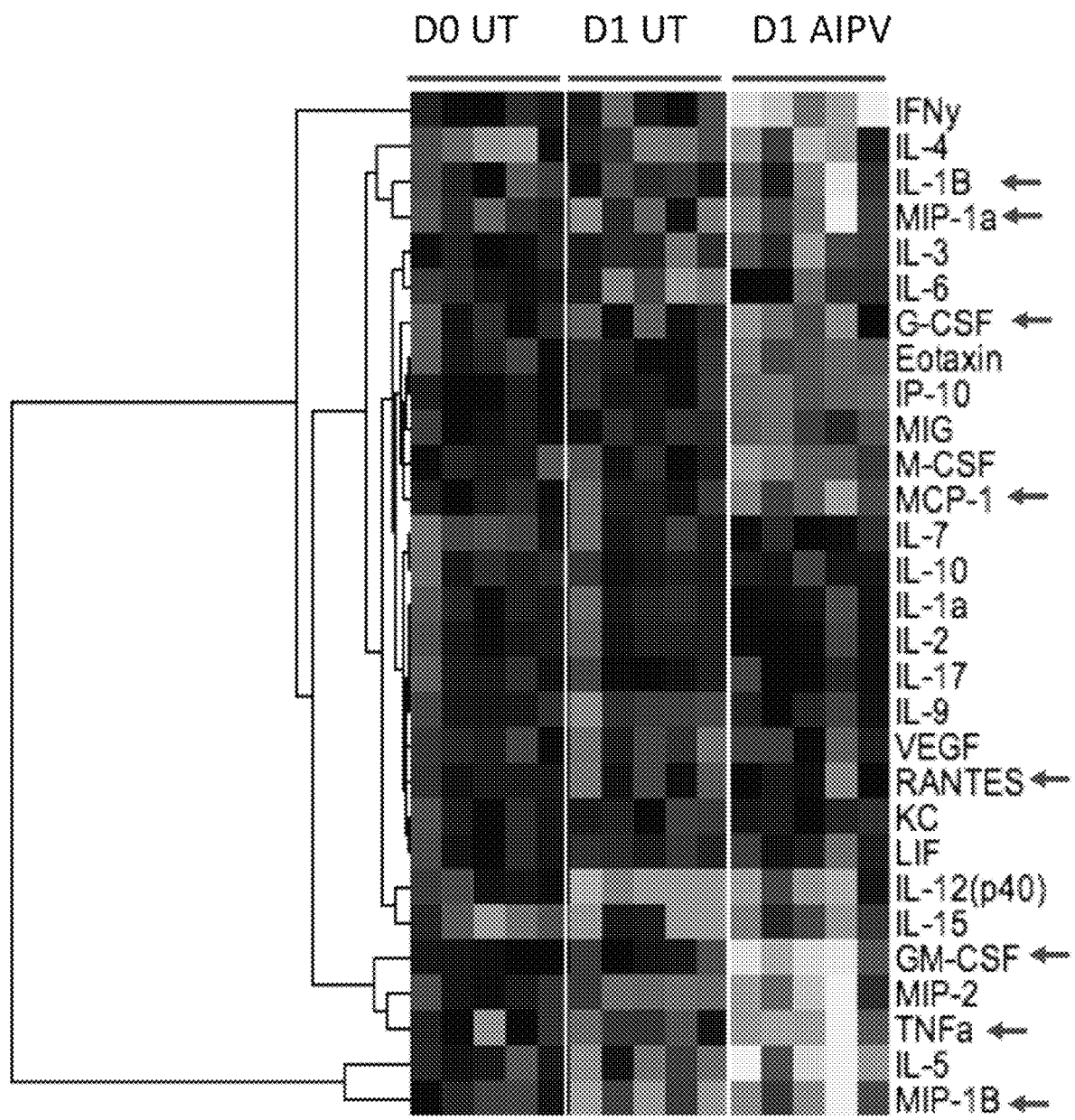
FIG. 2 provides a heat map showing changes in cytokine and chemokine levels in mice having B16F10 tumors and either untreated (UT) or treated with AIPV (combination of TA99 (anti-TRP1 antibody) (A), MSA-IL-2 (I), anti-PD-1 (P), and a cancer vaccine comprising amphiphilic Trp-2+ amphiphilic CpG (V)). Cytokine and chemokine levels in tumors were measured at day 0 and day 1 by Luminex.

To further analyze the changes in the tumor microenvironment after immunotherapy, tumors were isolated from mice bearing B16F10 tumors and treated with the AIPV combination on day 1 or left untreated on days 0 and 1. Cytokine and chemokine levels were measured by Luminex. Tumors were lysed in lysis buffer and processed in a bead beater. Lysates were diluted 1:1 with Assay Buffer and assayed using a Luminex bead-based ELISA (MILLIPLEX MAP Mouse Cytokine/Chemokine Magnetic Bead Panel, Millipore) for measurement of intratumoral cytokine and chemokine levels following manufacturer's instructions. FIG. 2 shows a significant change in cytokine and chemokine levels one day after AIPV treatment.

Overall, these results indicate the AIPV immunotherapy combination induced a more inflamed and cytotoxic T lymphocyte (CTL)-infiltrated tumor microenvironment.

Example 2: Priming Dose of Immunotherapy Combination Enhances Anti-Tumor Efficacy of Immune Checkpoint Blockade Based on the finding the immunotherapy combination changed the tumor microenvironment, it was next assessed whether this change was sufficient to sensitize the tumors to immune checkpoint blockade therapy. Mice bearing B16F10 tumors were administered the AIPV combination (as described in Example 1) on day 8, 15, and 21 after tumor inoculation, then subsequently administered A1 on day 28 and 36 days after tumor inoculation. Alternatively, tumor bearing mice were administered a single dose of the AIPV combination 8 days after tumor inoculation, followed by administration of immune checkpoint blockade therapy (anti-PD-1 and/or anti-CTLA-4) every 3 days for 4 weeks. Immune checkpoint blockade therapy was administered intraperitoneally at a dose of 200 µg.

Figure 3A:
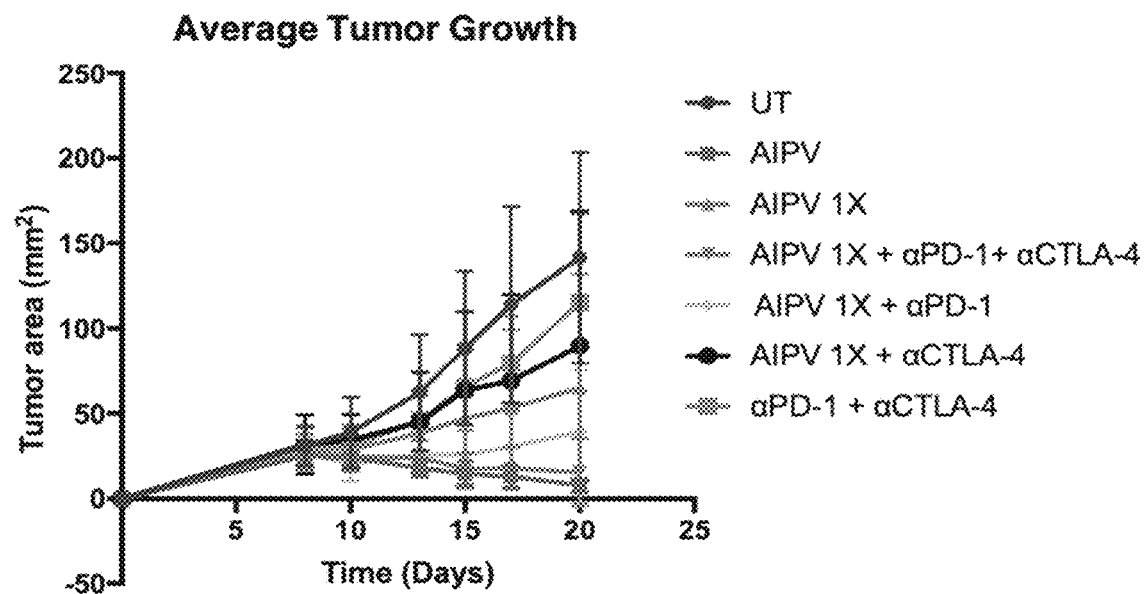
FIGS. 3A-3B show the enhanced anti-tumor efficacy of immune checkpoint blockade therapy in mice having B16F10 tumors that received a single priming dose of AIPV (TA99 (anti-TRP1 antibody) (A), MSA-IL-2 (I), anti-PD-1 (P) and a cancer vaccine comprising amphiphilic Trp-2+ amphiphilic CpG (V)). Mice received immune checkpoint blockade therapy (anti-PD-1 and/or anti-CTLA-4) or AIPV once 8 days after tumor cell inoculation, followed by immune checkpoint inhibitor therapy every 3 days for four weeks. Tumor growth is shown in FIG. 3A and survival is shown in FIG. 3B (*P<0.05; ****P<0.0001; versus AIPV by log-rank test).
Figure 3B:
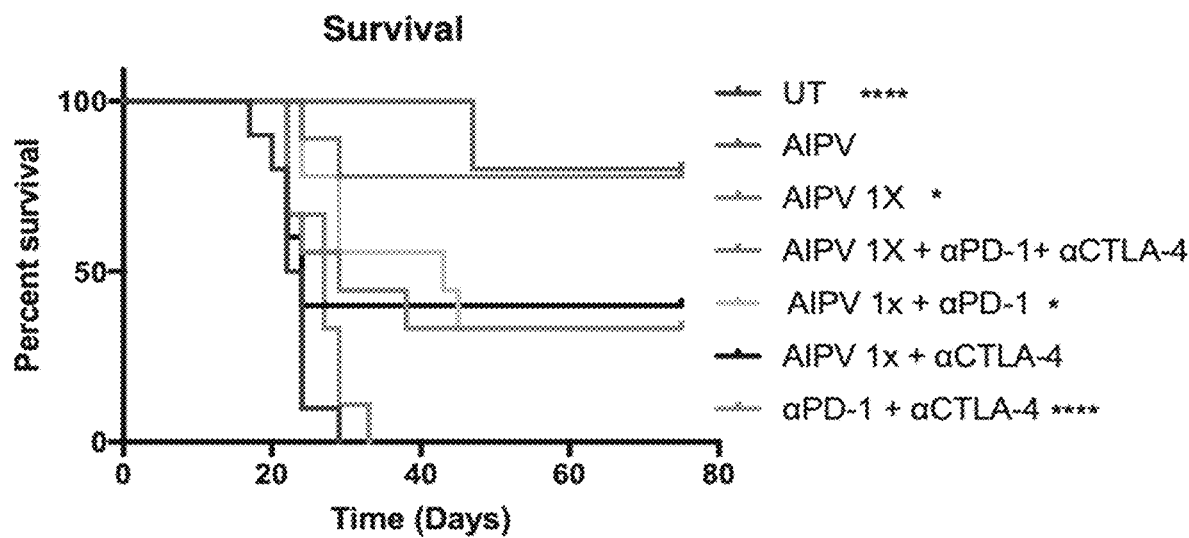

As shown in FIG. 3A, a single priming dose of AIPV prior to immune checkpoint blockade therapy with anti-PD-1 and anti-CTLA-4 resulted in reduced tumor growth compared to immune checkpoint blockade therapy alone. FIG. 3B shows an increase in survival in mice that received the single priming dose of AIPV prior to immune checkpoint blockade therapy compared to immune checkpoint blockade therapy alone.

Overall, these results indicate a single priming dose of an immunotherapy combination enhances the anti-tumor efficacy of immune checkpoint blockade therapy.

Example 3: Integrin-Targeting Polypeptide Effective in Priming Dose to Enhance Immune Checkpoint Blockade Therapy To broaden the applicability of the immunotherapy combination priming dose, a pan tumor-targeting antibody-like structure that binds integrins was investigated as a replacement for a tumor specific antibody to address the lack of general tumor-associated antigens. Specifically, a knottin-Fc protein capable of binding integrins was used, as integrins are overexpressed by many human and mouse tumors. The knottin-Fc protein comprises two parts: 1) an engineered cystine knot (knottin) peptide that binds with high affinity to tumor-associated $\alpha v \beta 3$, $\alpha v \beta 5$, and $\alpha 5 \beta 1$, integrin receptors (specifically 2.5F, SEQ ID NO: 86 or 88), and 2) an antibody Fc domain that mediates immune effector functions in vivo. The knottin-Fc used was 2.5F with a K15S substitution, fused to a mouse IgG2a Fc domain, SEQ ID NO: 45, unless stated otherwise.

To determine the effects of the knottin-Fc in a priming dose for immune checkpoint blockade therapy, $1 \times 10^6$ B16F10 murine melanoma cells were injected into the flanks of C57BL/6 mice subcutaneously. In the AIPV combination, knottin-Fc=A, which was administered at a dose of 400 µg. 8 days after tumor inoculation, mice were treated with a single priming dose of AIPV, AIP, AIV, IPV, AI, IP or AP, followed by administration of anti-PD-1 and anti-CTLA-4 intraperitoneally at a dose of 200 gig for each antibody every three days for four weeks.

Figure 4A:
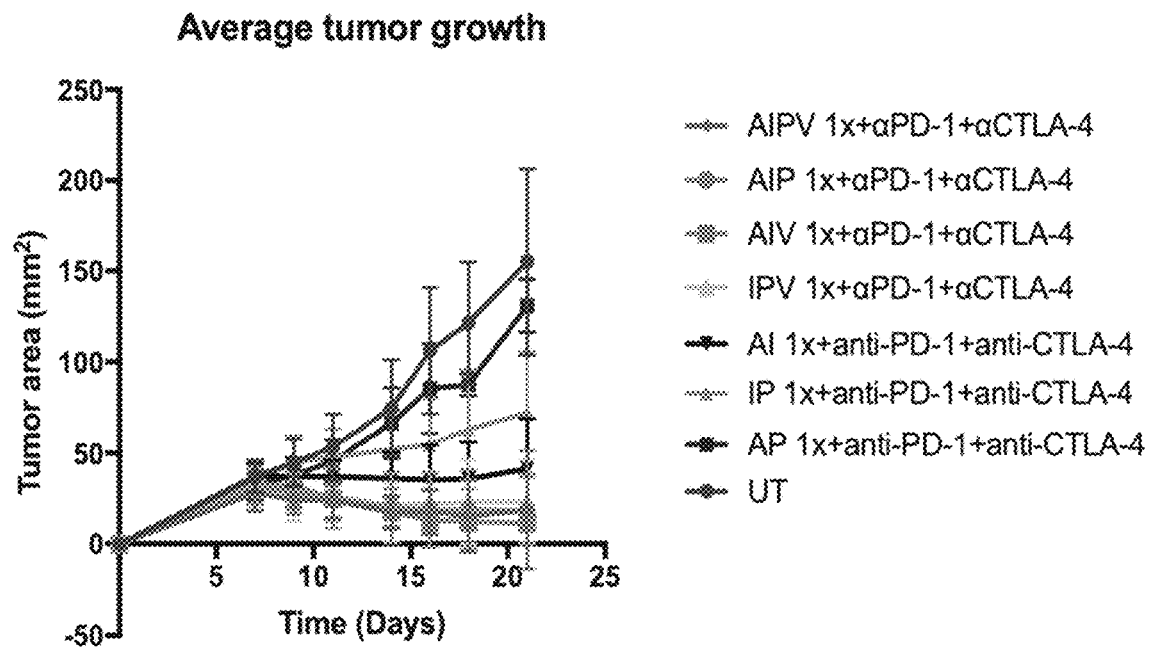
FIGS. 4A-4B show the enhanced anti-tumor efficacy of immune checkpoint blockade therapy in mice having B16F10 tumors that received a single priming dose of AIPV, AIP, AIV, IPV, AI, IP or AP. Mice received a single dose of the various AIPV combinations followed by immune checkpoint blockade therapy (anti-PD-1 and anti-CTLA-4) every 3 days for 4 weeks. Tumor growth is shown in FIG. 4A and survival is shown in FIG. 4B. A=integrin binding 2.5F-Fc; I=MSA-IL-2; P=anti-PD-1; V=amphiphilic Trp-2+amphiphilic CpG.
Figure 4B:
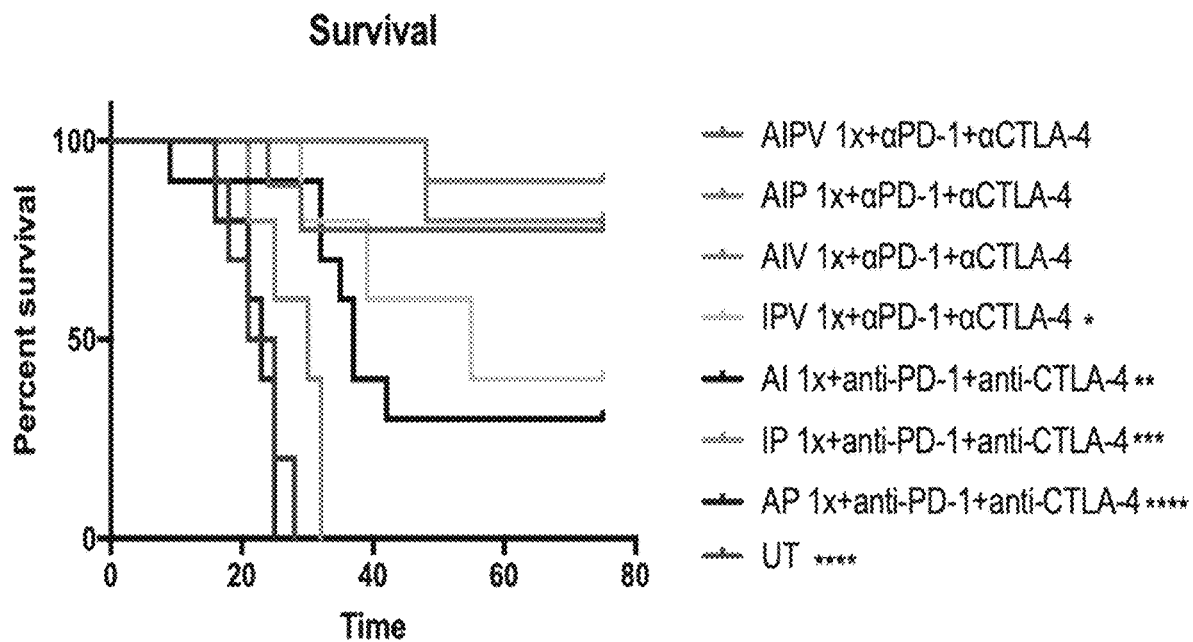
Figure 5:
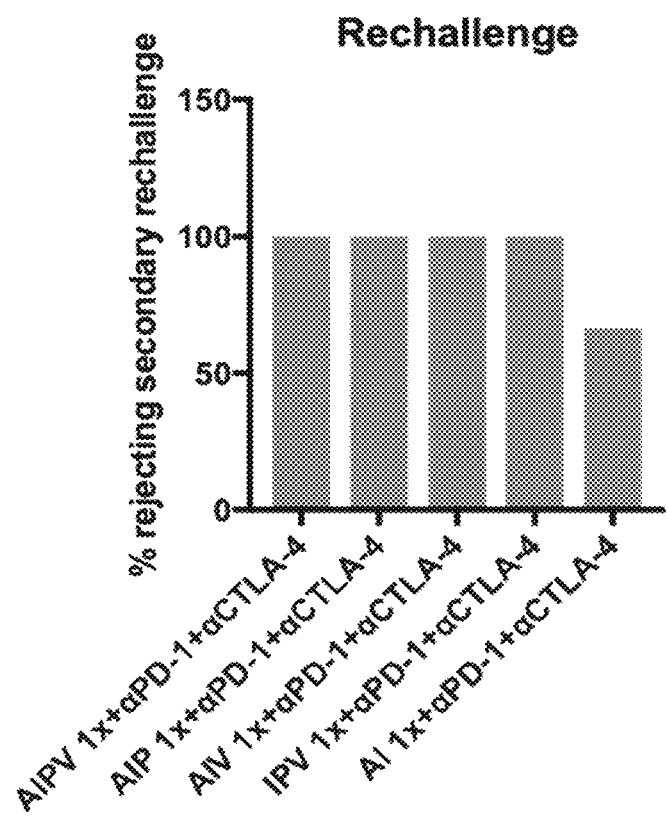
FIG. 5 shows the percentage of long-term survivors from FIGS. 4A-4B that rejected a re-challenge of B16F10 tumor cells on day 75.

As shown in FIGS. 4A-4B, the knottin-Fc was effective in the priming dose as reduced tumor growth and increased survival was observed. The combination of knottin-Fc+MSA-IL-2+anti-PD-1 (AIP) resulted in the highest percent survival relative to the various combinations of each immunotherapy component. To assess the memory of immune cells against tumor cells, long-term survivors were re-challenged with $1 \times 10^5$ B16F10 cells. As shown in FIG. 5, animals that received a priming dose of AIPV, AIP, AIV or IPV followed by immune checkpoint blockade therapy rejected the secondary challenged.

Figure 6A:
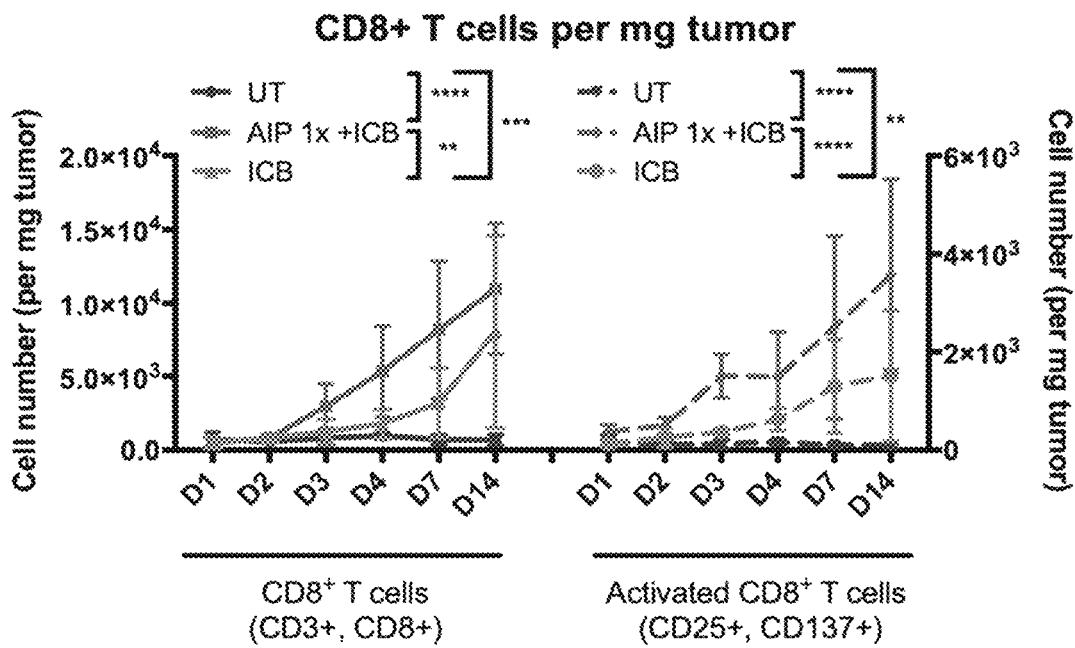
FIGS. 6A-6B provide graphs showing analysis of immune cells over time in mice having B16F10 tumors that were untreated or treated with a single priming dose of AIP followed by immune checkpoint blockade (ICB) therapy (anti-PD-1 and anti-CTLA-4), or ICB therapy alone.
Figure 6B:
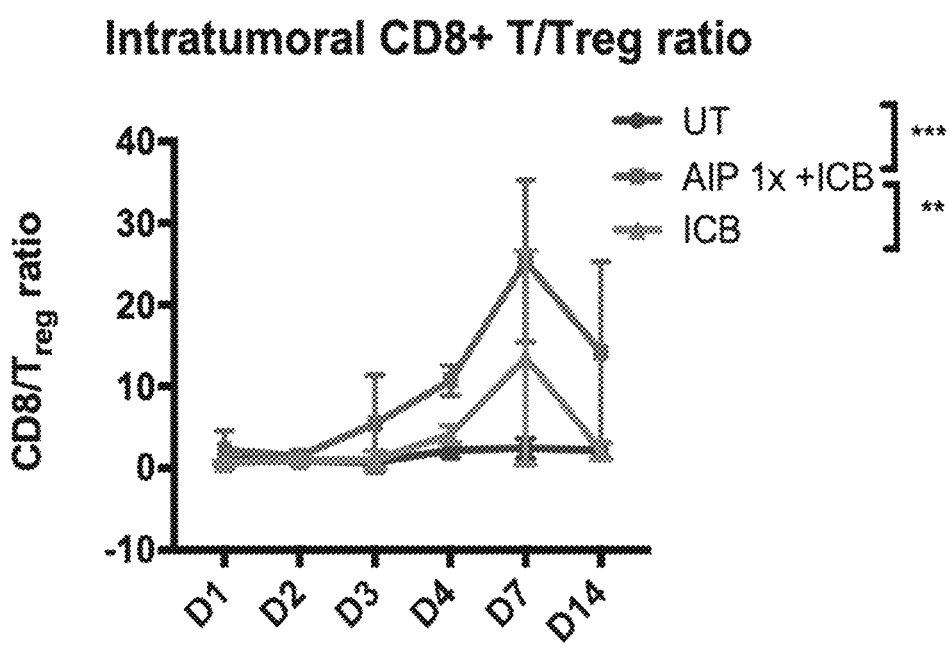

To confirm the priming dose having the knottin-Fc impacted the tumor microenvironments similarly to the tumor-specific antibody, mice with B16F10 tumors were treated with either: a single priming dose of AIP followed by immune checkpoint blockade (every 3 days for 4 weeks), or immune checkpoint blockade alone. In this experiment, immune checkpoint blockade (ICB) refers to a combination of anti-CTLA-4 and anti-PD-1. Tumors were isolated 1, 2, 3, 4, 7 and 14 days post treatment and analyzed via flow cytometry as described in Example 1. The single priming dose increased the total number of tumor infiltrating CD8+ T cells, and the number of activated CD8+ T cells compared to immune checkpoint blockade without the priming dose (FIG. 6A). The priming dose also increased the intratumoral CD8+/Treg ratio compared to immune checkpoint blockade without the priming dose (FIG. 6B).

Figure 7A:
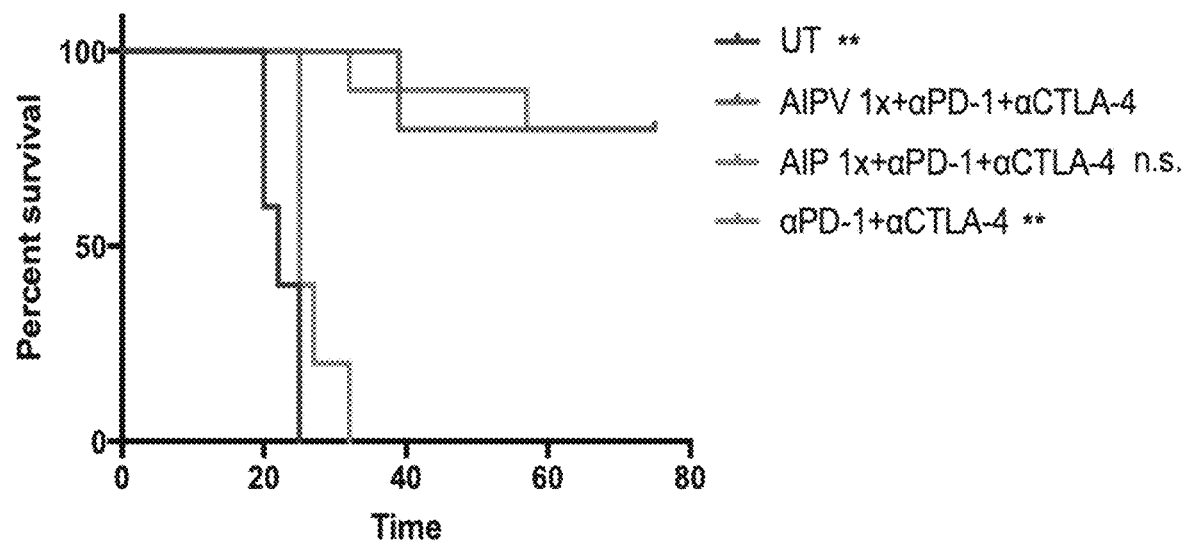
FIGS. 7A-7B are survival curves showing the enhanced anti-tumor efficacy of immune checkpoint blockade therapy (anti-PD-1+anti-CTLA-4) in mice having TC-1 (FIG. 7A), YUMM1.7 (melanoma) or YUMMER 1.7 (YUMM1.7 exposed to radiation) (FIG. 7B) tumors that received a single priming dose of AIPV or AIP. Mice received a single dose of AIP, AIPV or immune checkpoint blockade followed by immune checkpoint blockade therapy every 3 days for 4 weeks. A=integrin binding 2.5F-Fc; I=MSA-IL-2; P=anti-PD-1; V=amphiphilic HPV E7$_{43-62}$ amphiphilic CpG. *P<0.05; *P<0.01; ***P<0.001; versus AIPV 1x+αPD-1+αCTLA-4 by log-rank test if not otherwise indicated.
Figure 7B:
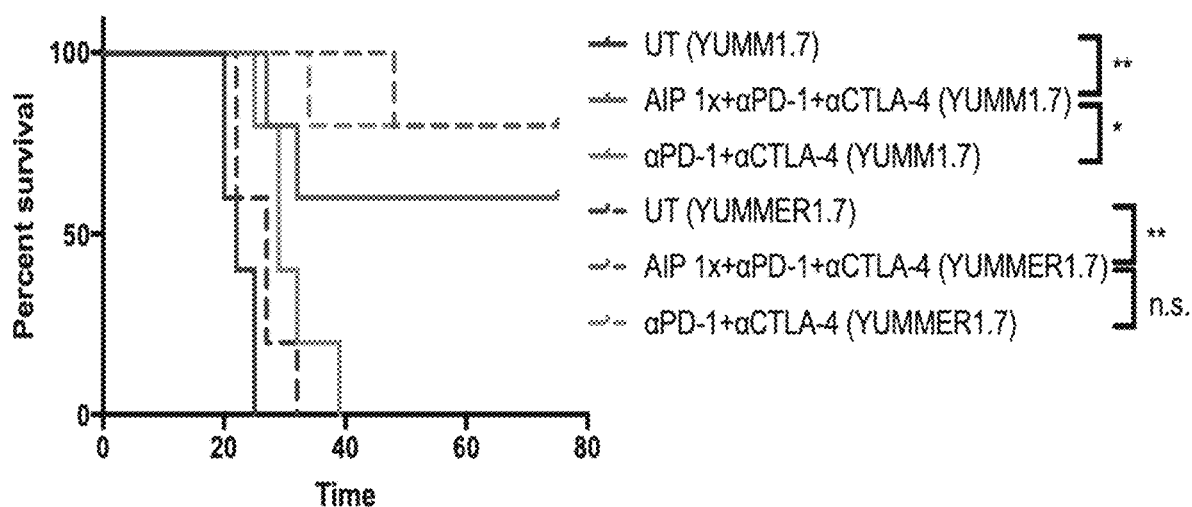

To confirm the findings in the B16F10 model, different tumor models were utilized. Specifically, $10^6$ TC-1 (lymphoblasts) YUMM1.7 or YUMMER1.7 (YUMM1.7 exposed to radiation) (melanoma) tumor cells were subcutaneously injected into the flanks of C57BL/6 mice. YUMM1.7 and YUMMER1.7 cells are described in Meeth, Katrina, et al. *Pigment Cell Melanoma Res.* (2016) 29.5: 590-597 and Jake, et al. *Pigment Cell Melanoma Res.* (2017) 30.4: 428-435. 8 days after tumor inoculation, mice were treated with anti-PD-1+anti-CTLA-4 every 3 days for 4 weeks, with or without a single priming dose of AIPV or AIP. For AIPV, the vaccine comprised an amph-peptide administered with lipo-$G_2$-CpG as described in Example 1, with the amph-peptide comprising the tumor-associated peptide antigen HPV $E7_{43-62}$ conjugated to DSPE-PEG 2 kDa. As shown in FIGS. 7A-7B, the single priming dose enhanced the anti-tumor efficacy of immune checkpoint blockade in these tumor models as shown by increasing survival.

Additionally, the combination therapy was further evaluated in a murine colon adenocarcinoma tumor model (MC-38) and mouse models of human non-small cell lung cancer (NSCLC). The NSCLC models were established using either KP tumor cells (Kras$^{LSL-G12D/+}$; p53$^{fl/fl}$) that comprise activation of oncogenic K-ras and loss of function of p53 as described in DuPage, M. et al. (2009) *Nat. Protoc.* 4:1064-1072 or KPM tumor cells (Kras$^{LSL-G12D/+}$; P53$^{fl/fl}$; Msh2$^{fl/fl}$) that further comprise loss of function of DNA mismatch repair protein MSH2. The MC-38 model was established by subcutaneous injection of $1 \times 10^6$ MC-38 tumor cells into the flanks of C57BL/6 mice. The NSCLC models were established by intratracheal inoculation of C57BL/6 mice with $0.5 \times 10^6$ KP or KPM tumor cells.

Figure 7C:
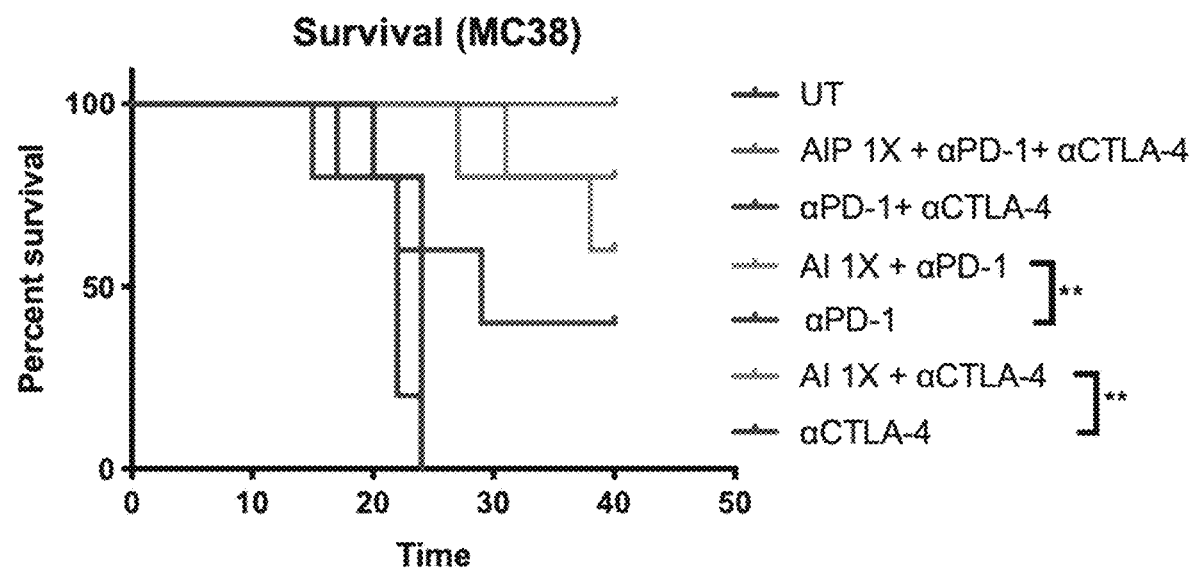
FIGS. 7C-7D are survival curves showing sensitization of tumors to immune checkpoint blockade therapy (anti-PD-1 and/or anti-CTLA-4) in mice having MC38 (FIG. 7C) or KP or KPM lung tumors (FIG. 7D) following a single priming dose of AIP or AI. Treatment components and regime as described in FIGS. 7A-7B. *P<0.05; *P<0.01; ***P<0.001 by log-rank test.
Figure 7D:
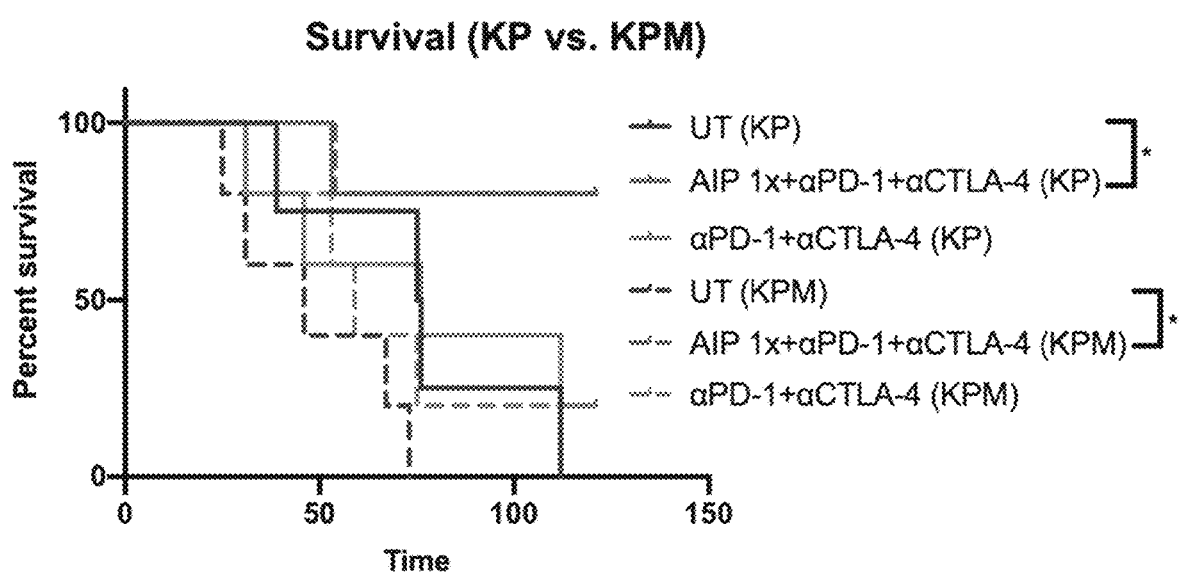

At 8 days post-inoculation, a single priming dose of AI, AIP or ICB was administered (A=knottin-Fc (2.5F-Fc); I=MSA-IL-2; P=anti-PD-1; ICB=anti-PD-1 and/or anti-CTLA-4 as indicated), The priming dose was followed by intraperitoneal administration of ICB (anti-PD-1 and/or anti-CTLA-4) at a dose of 200 µg of each antibody every 3 days for 4 weeks. Each treatment cohort comprised 5-10 mice. As shown in FIGS. 7C-7D, a single priming dose of AIP was most effective in the MC-38, KP and KPM tumor models, with all or a majority of animals rejecting tumor burden. Treatment with a single priming dose of AI was also effective in the MC-38 model, where animal survival was improved relative to treatment with ICB alone (FIG. 7C).

Overall, these results indicate a priming dose comprising an integrin binding polypeptide is sufficient to sensitize tumors to immune checkpoint blockade therapy, and that a memory immune response is developed in mice receiving the priming dose before immune checkpoint blockade therapy.

Example 4: Effect of Priming Dose Immune Checkpoint Inhibitor

The immune checkpoint inhibitor used in the priming dose was evaluated. Specifically, it was determined if the effect of the priming dose was comparable if the immune checkpoint inhibitor was anti-PD-1 or anti-CTLA-4. B16F10 tumors were established as described in the previous examples. On day 8 post tumor inoculation, B16F10-tumor bearing mice were administered AIP, AIC, or AIPC (A=knottin-Fc (2.5F-Fc); I=MSA-IL-2; P=anti-PD-1; C=anti-CTLA-4). The mice were subsequently administered ICB (anti-PD-1+anti-CTLA-4) every 3 days for 4 weeks and survival was monitored.

Figure 8A:
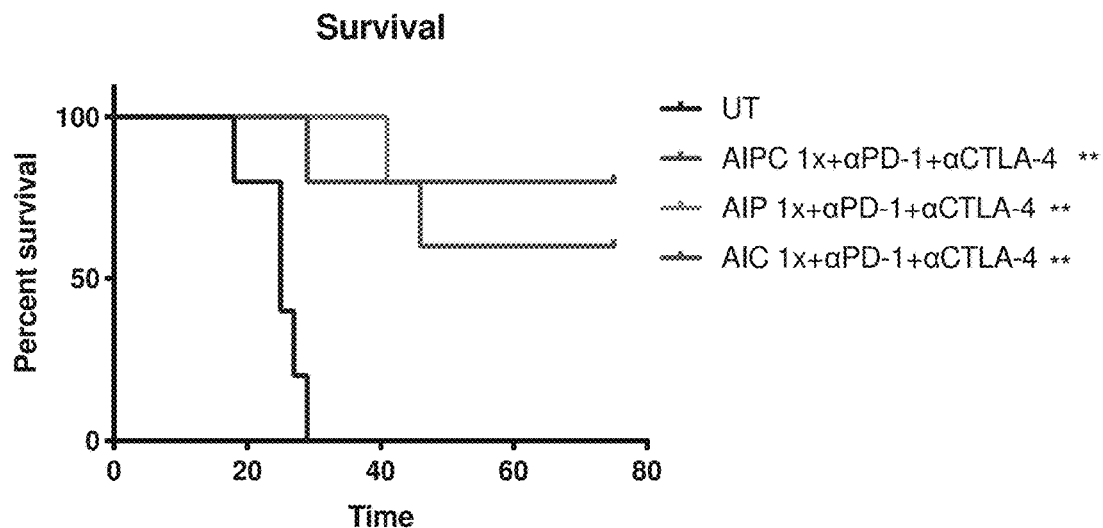
FIG. 8A is a survival graph showing B16F10 tumor-bearing mice administered a priming dose of AIPC, AIP, or AIC followed by immune checkpoint blockade (anti-PD-1+ anti-CTLA-4) every 3 days for 4 weeks as compared to untreated (UT) tumor-bearing mice. A=integrin binding 2.5F-Fc; I=MSA-IL-2; P=anti-PD-1; C=anti-CTLA-4. **P<0.01 compared to UT.

As show in FIG. 8A, survival for mice receiving a priming dose of AIP, AIC, or AIPC, followed by immune checkpoint blockade, was significantly improved compared to untreated mice. Thus, a priming dose comprising an immune checkpoint inhibitor targeting either PD-1 or CTLA-4 is effective for tumor eradication and long-term survival.

Example 5: Effect of Immune Cell Populations on Priming Dose and Immune Checkpoint Blockade Anti-Tumor Efficacy To assess the role of various immune cell populations in the observed improved survival of tumor-bearing mice treated with a single priming dose prior to immune checkpoint blockade, depletion antibodies were administered to B16F10 tumor-bearing mice one day prior to the priming dose of knottin-Fc+MSA-IL-2+anti-PD-1 (AIP). Cytotoxic lymphocytes were depleted with an anti-CD8α antibody (clone 2.43), natural killer cells were depleted with an anti-NK1.1 antibody (clone PK136), macrophages were depleted with an anti-CSF1R antibody (clone AFS98), and neutrophils were depleted with an anti-Ly6G antibody (clone 1A8). The anti-CD8α, anti-NK1.1 and anti-Ly6G antibodies were administered at 400 µg per dose twice weekly, while anti-CSF1R was administered at 300 µg per dose every other day. Immune checkpoint blockade (anti-PD-1+anti-CTLA-4) was administered every three days for four weeks.

Figure 8B:
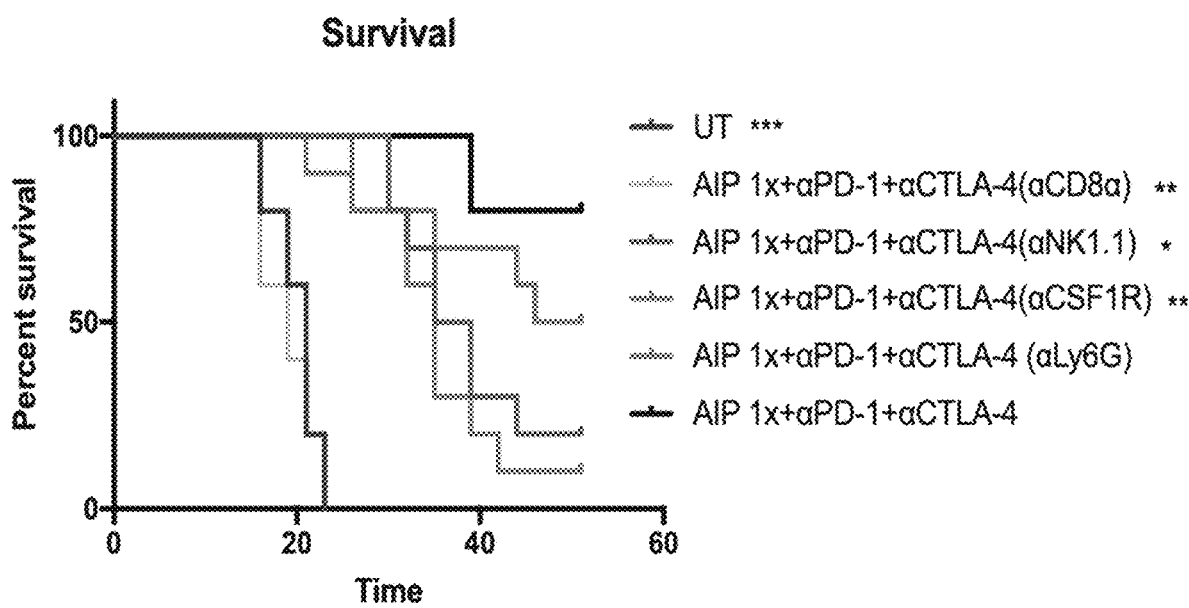
FIG. 8B is a survival graph showing the effect of depleting various immune cells from mice having B16F10 tumors that received a single priming dose of AIP followed by immune checkpoint blockade therapy (anti-CTLA-4+anti-PD-1). Depleting antibodies for CD8+ T cells (anti-CD8a), NK cells (anti-NK1.1), macrophages (anti-CSF1R) or neutrophils (anti-Ly6G) were administered one day prior to AIP dosing. A=integrin binding 2.5F-Fc; I=MSA-IL-2; P=anti-PD-1.

As shown in FIG. 8B, survival was reduced in mice that received any of the immune cell depleting antibodies. The most significant reduction was seen in mice that received the CD8+ T cell depleting antibody, indicating CD8+ T cells play an essential role in the observed anti-tumor efficacy of the priming dose and immune checkpoint blockade.

Figure 9:
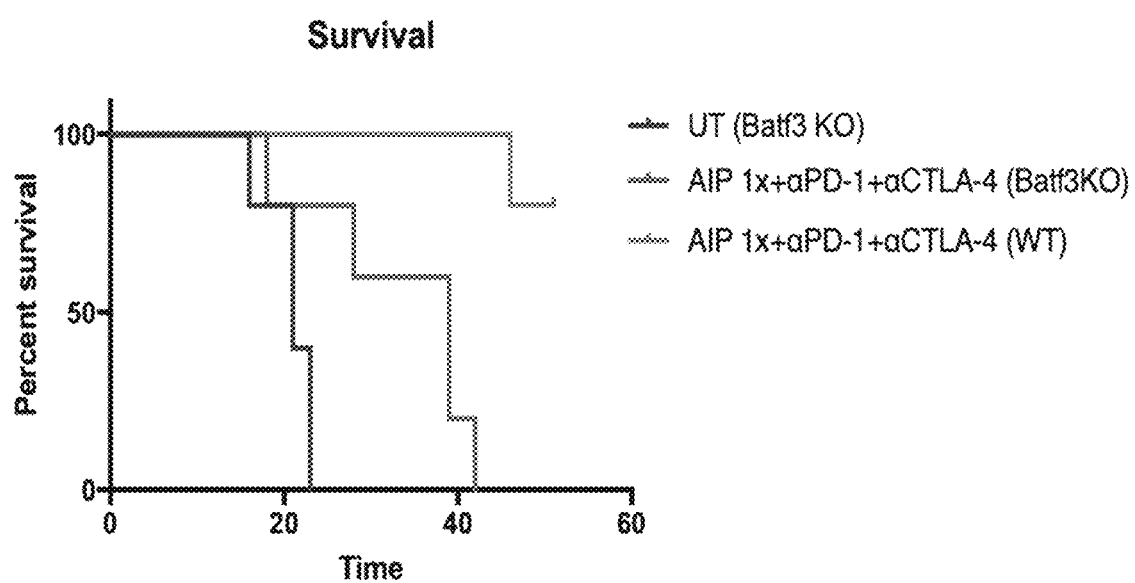
FIG. 9 is a survival curve showing decreased anti-tumor efficacy in Batf3−/− mice having B16F10 tumors and administered a single priming dose of AIP followed by immune checkpoint blockade therapy (anti-PD-1+anti-CTLA-4). A=integrin binding 2.5F-Fc; I=MSA-IL-2; P=anti-PD-1.

Example 6: Role of Dendritic Cells in Priming Dose for Immune Checkpoint Blockade To investigate the role of dendritic cells in sensitizing tumors for immune checkpoint blockade, cross-presenting dendritic cells were depleted using Batf3 −/− mice. Batf3 −/− mice lack the function of the basic leucine zipper transcription factor, ATF-like 3. Deletion of Batf3 has been shown to prevent the development of CD8+ dendritic cells, which are important for the cross-presentation of exogenous antigen on MHC Class I. B16F10 tumors were injected into wild-type or Batf3 −/− mice as described in Example 1. A single priming dose of knottin-Fc+MSA-IL-2+anti-PD-1, as described in Example 3, was administered prior to immune checkpoint blockade therapy with anti-PD-1+anti-CTLA-4. As shown in FIG. 9, reduced survival was observed in Batf3 −/− mice, indicating cross-presenting dendritic cells are necessary for anti-tumor efficacy.

Figures 10A, 10B:
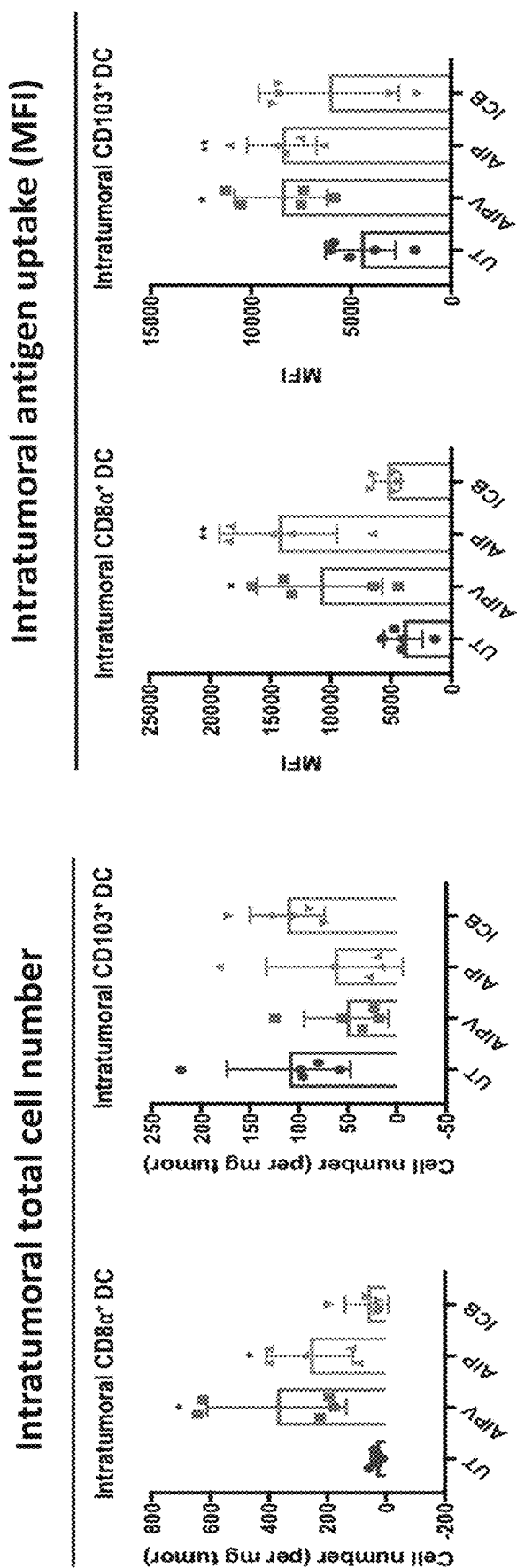
FIGS. 10A-10D provide graphs showing the number of dendritic cells and amount of antigen uptake in tumors (FIGS. 10A-10B) and tumor draining lymph nodes (FIGS. 10C-10D) of mice having B16F10-Zsgreen tumors. Mice were treated with AIPV, AIP or immune checkpoint blockade (ICB) (anti-PD-1+anti-CTLA-4), and tumors and tumor draining lymph nodes were isolated 2 days later. A=integrin binding 2.5F-Fc; I=MSA-IL-2; P=anti-PD-1; V=amphiphilic Trp-2+amphiphilic CpG. *$P<0.05$; $P<0.01$; **$P<0.0001$; versus untreated (UT) by log-rank test.
Figures 10C, 10D:
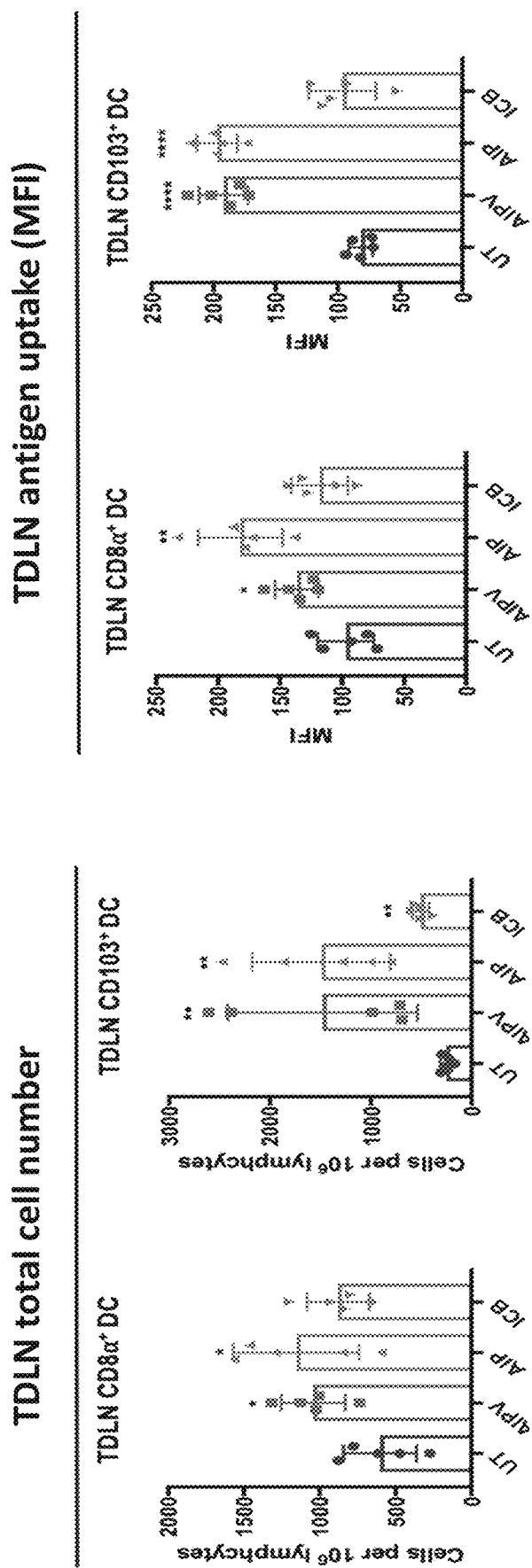

To further investigate the impact on dendritic cells, $10^6$ B16F10-Zsgreen cells were injected into mice. Eight days after tumor inoculation mice were treated with AIPV, AIP or immune checkpoint blockade (ICB; anti-CTLA-4+anti-PD-1). Two days after treatment, tumors and tumor draining lymph nodes were isolated and analyzed by flow cytometry. FIGS. 10A and 10C show the total number of CD8α+ or CD103+ dendritic cells found in tumors or tumor draining lymph nodes, respectively. FIGS. 10B and 10D show the mean fluorescent intensity of Zsgreen within those cells, which indicated antigen uptake by dendritic cells. This data shows that both single-dose AIPV and AIP were able to induce tumor antigen uptake by cross-presenting dendritic cells (CD8α+ and CD103+ dendritic cells) and their proliferation, followed by the migration of these cells, especially CD103+ dendritic cells, to tumor draining lymph nodes to engage adaptive immune responses.

Overall, these results indicate a single priming dose of the immunotherapy combination triggers migration of conventional dendritic cells, along with increasing antigen presentation in tumor draining lymph nodes.

Example 7: Adoptive Transfer Prior to Priming Dose

To confirm whether cross-presenting dendritic cells carrying tumor antigens were able to activate T cells and promote their proliferation in the tumor draining lymph node in AIPV or AIP treated mice, an adoptive transfer model was utilized. Specifically, seven days after subcutaneous injection of $1 \times 10^6$ B16F10 cells into mice, Pmel Thy1.1 T cells were adoptively transferred. Pmel T cells carry a T cell receptor specifically recognizing the melanocyte differentiation antigen gp100. One day after transfer, mice were administered either the AIPV or AIP immunotherapy combination (A=knottin-Fc), or immune checkpoint blockade (ICB; anti-CTLA-4+anti-PD-1). Tumors and tumor draining lymph nodes were isolated 24 hours later and analyzed via flow cytometry.

Figure 11A:
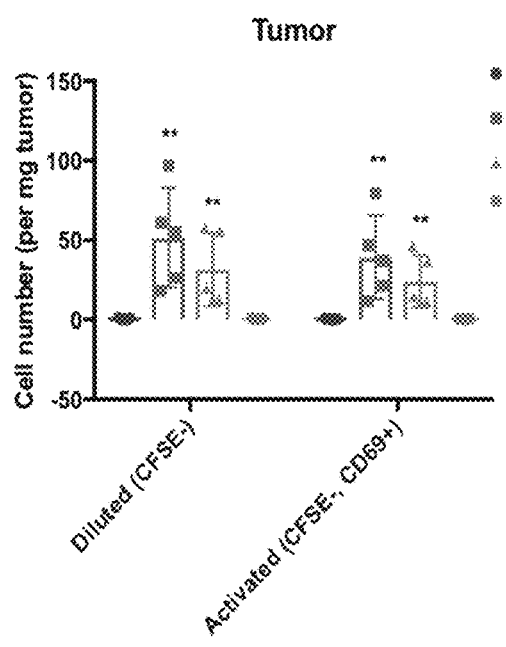
FIGS. 11A-11B show the number of pmel T cells and number of activated pmel T cells in mice bearing B16F10 tumors and adoptively transferred with labeled pmel T cells prior to treatment with AIPV, AIP or ICB (anti-PD-1+anti-CTLA-4). A=integrin binding 2.5F-Fc; I=MSA-IL-2; P=anti-PD-1; V=amphiphilic Trp-2+amphiphilic CpG.
Figure 11B:
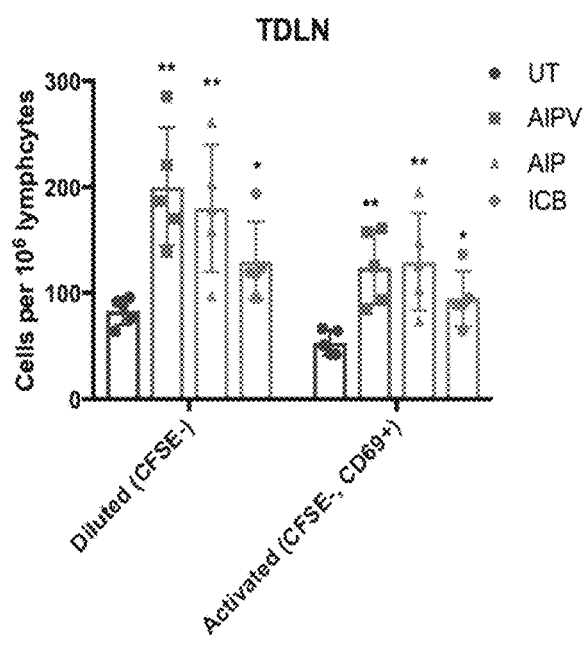

FIGS. 11A-11B show an increase in total number of pmel T cells and number of activated pmel T cells in both the tumor and the tumor draining lymph node in mice that received the immunotherapy combination compared to ICB treatment.

These results indicate that immunotherapy combination enhanced tumor antigen drainage and endogenous tumor antigen presentation by cross-presenting dendritic cells, resulting in antigen-specific T cell activation and proliferation in the tumor draining lymph node.

Figure 12:
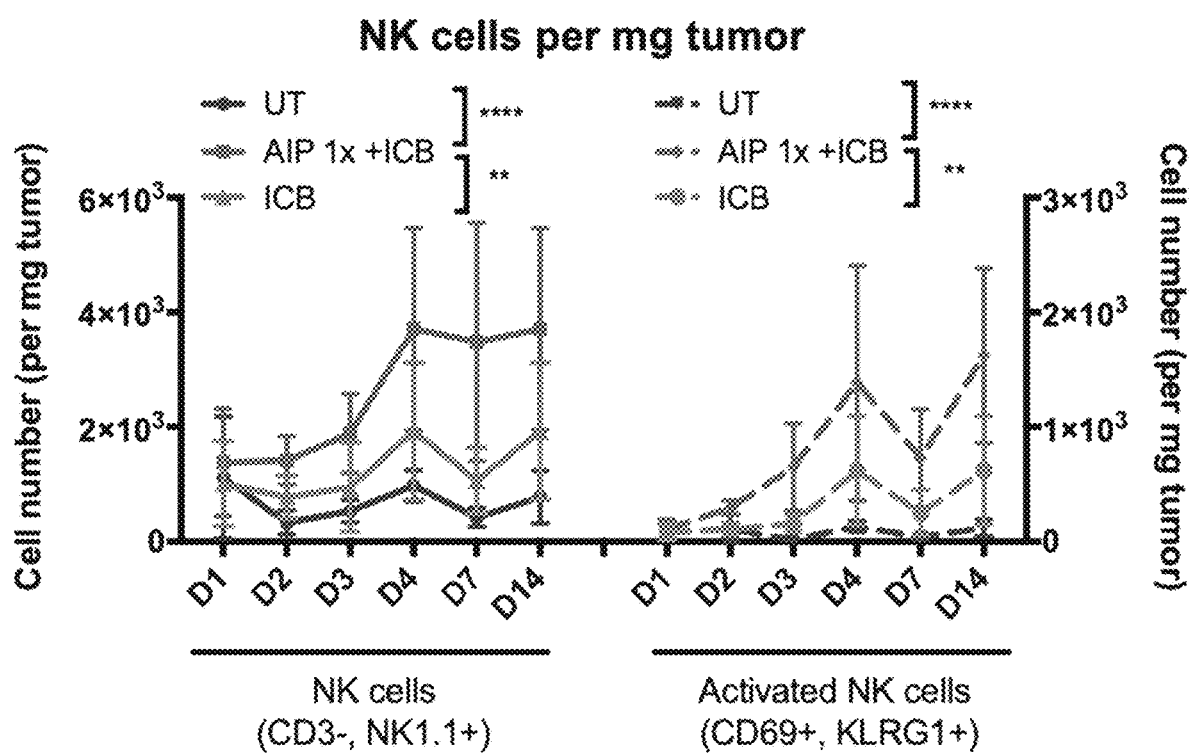
FIG. 12 is a graph showing the total number of NK cells and number of activated NK cells over time in mice with B16F10 tumors treated with a single priming dose of AIP followed by immune checkpoint blockade (ICB) therapy (anti-PD-1+anti-CTLA4), or only ICB therapy. A=integrin binding 2.5F-Fc; I=MSA-IL-2; P=anti-PD-1.

Example 8: Role of Natural Killer Cells in Priming Dose for Immune Checkpoint Blockade To investigate the role of natural killer cells in sensitizing tumors for immune checkpoint blockade, mice bearing B16F10 tumors as described in the above Examples were utilized. Mice were administered immune checkpoint blockade (ICB; anti-CTLA-4+anti-PD-1) every three days for four weeks with or without a single priming dose of AIP (A=knottin-Fc (2.5F-Fc)). Tumors were isolated 1, 2, 3, 4, 7 and 14 days post treatment and were analyzed by flow cytometry. FIG. 12 shows the total number of NK cells and total number of activated NK cells were increased in the tumors of mice that received the single priming dose prior to immune checkpoint blockade.

Figure 13A:
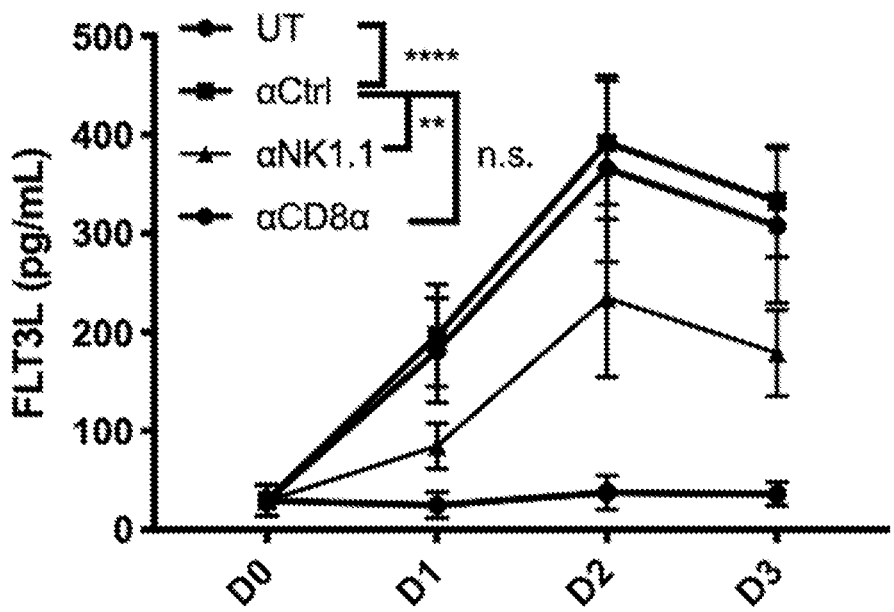
FIG. 13A-13B is a graph showing intratumoral expression of FLT3L (FIG. 13A) or XCL1 (FIG. 13B) measured by ELISA, in AIP treated mice bearing B16F10 tumors 0-3 days post treatment. 1 day prior to AIP treatment, mice were administered a depleting antibody against NK cells (anti-NK1.1) or cytotoxic T cells (anti-CD8α) or a non-depleting control antibody. A=integrin binding 2.5F-Fc; P=anti-PD-1.
Figure 13B:
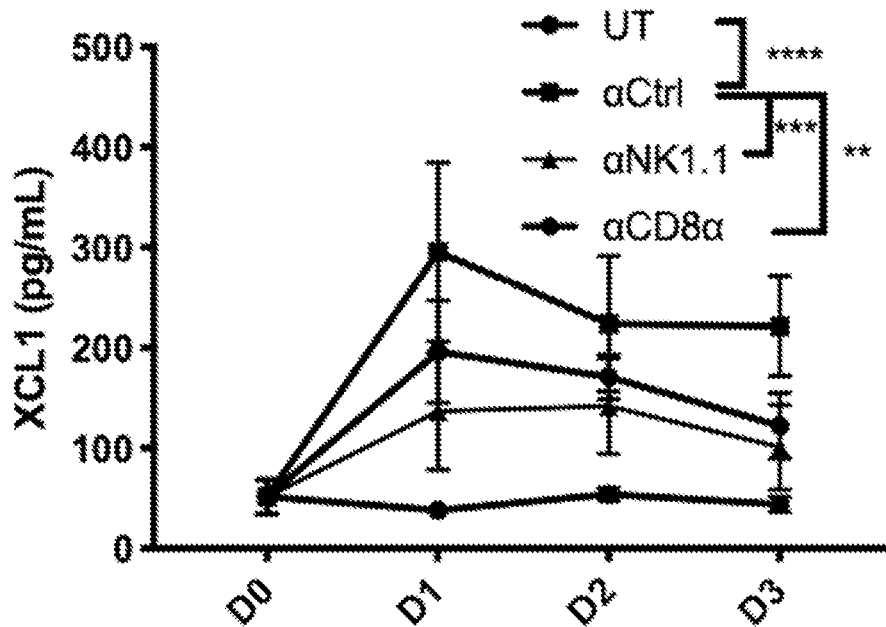
Figure 13C:
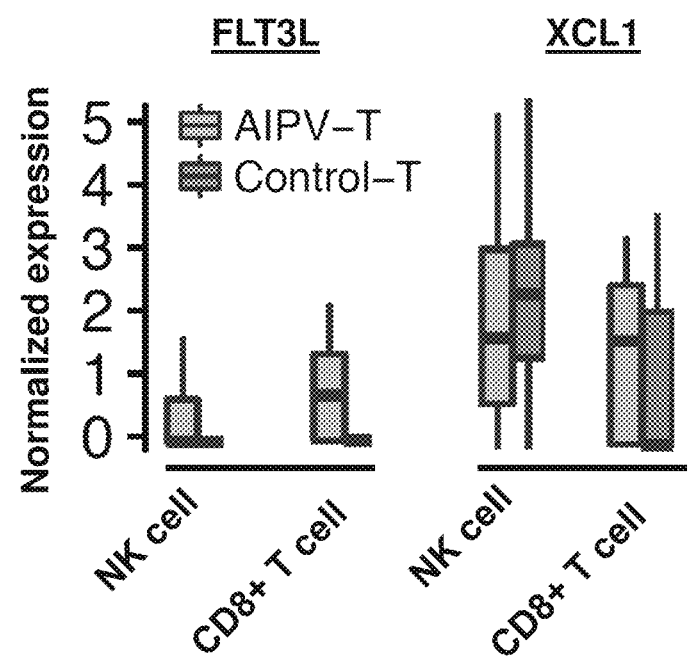

In addition, tumors from mice that received combination immunotherapy were analyzed over time for production of FLT3L and XCL1 by ELISA. C57BL/6 mice were first treated with either depleting antibodies against CD8 T cells (anti-CD8α; clone 2.43) or NK cells (anti-NK1.1; clone PK136) or a non-depleting control antibody as described in Example 4. One day later, the animals received a priming dose of AIP. Intratumoral levels of FLT3L and XCL1 were then measured on day 0, 1, 2, or 3 following AIP administration. FIGS. 13A-13B show a significant increase in FLT3L and XCL1 intratumoral expression in mice that received AIP treatment in combination with control antibody. Treatment with anti-CD8a depleting antibody had no effect on intratumoral FLT3L expression relative to treatment with AIP+control antibody, while treatment with anti-NK1.1 depleting antibody resulted in diminished intratumoral FLT3L levels (FIG. 13A). In contrast, treatment with either anti-CD8a or anti-NK1.1 depleting antibody resulted in significantly decreased intratumoral XCL1 levels compared to treatment with AIP+control antibody (FIG. 13B).

Figure 14:
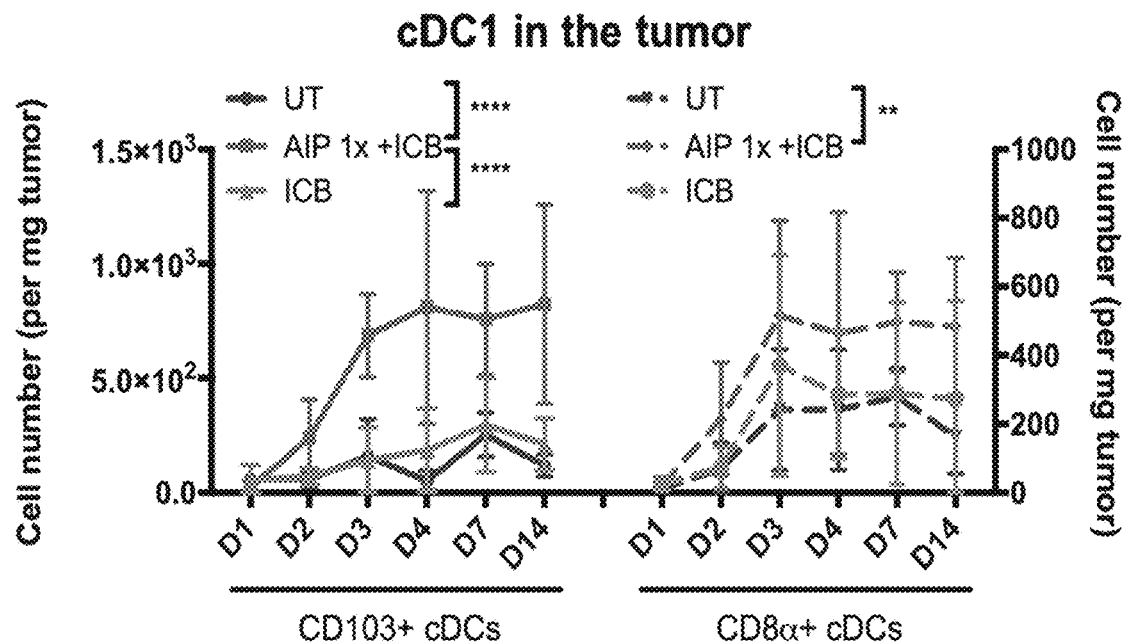
FIG. 14 is a graph showing the total number of tumor infiltrating dendritic cells and number of activated dendritic cells in mice with B16F10 tumors treated with a single priming dose of AIP followed by immune checkpoint blockade therapy (ICB) or only ICB therapy. A=integrin binding 2.5F-Fc; I=MSA-IL-2; P=anti-PD-1.

Conventional DC1 cells (cDC1 cells, CD8α+ or CD103+) were also measured in mice that received immune checkpoint blockade with or without a single priming dose of AIP. Tumors were isolated 1, 2, 3, 4, 7 and 14 days post-treatment and analyzed by flow cytometry. FIG. 14 shows an increase in cDC1 cells over time in the tumors of mice that received the single priming dose of the immunotherapy combination.

Figure 15A:
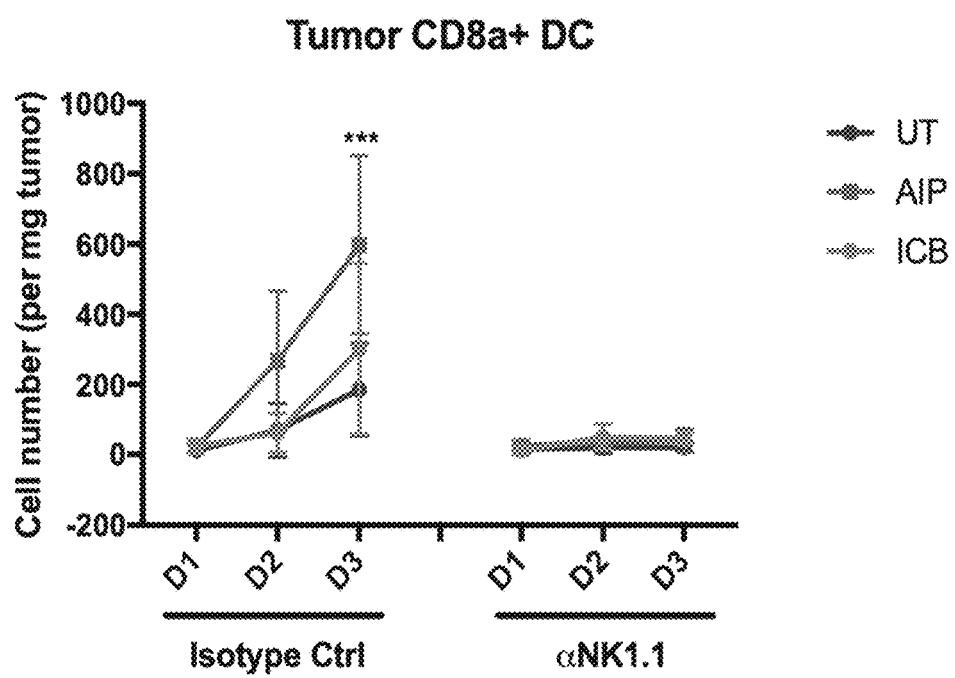
FIGS. 15A-15C provide graphs showing decreased tumor infiltrating CD8+ dendritic cells (FIG. 15A), CD103+ dendritic cells (FIG. 15B), and activated CD8+ T cells (FIG. 15C) in mice bearing B16F10 tumors treated with anti-NK1.1 antibody every three days for one week starting one day before treatment with AIP or immune checkpoint blockade (ICB). A=integrin binding 2.5F-Fc; I=MSA-IL-2; P=anti-PD-1.
Figure 15B:
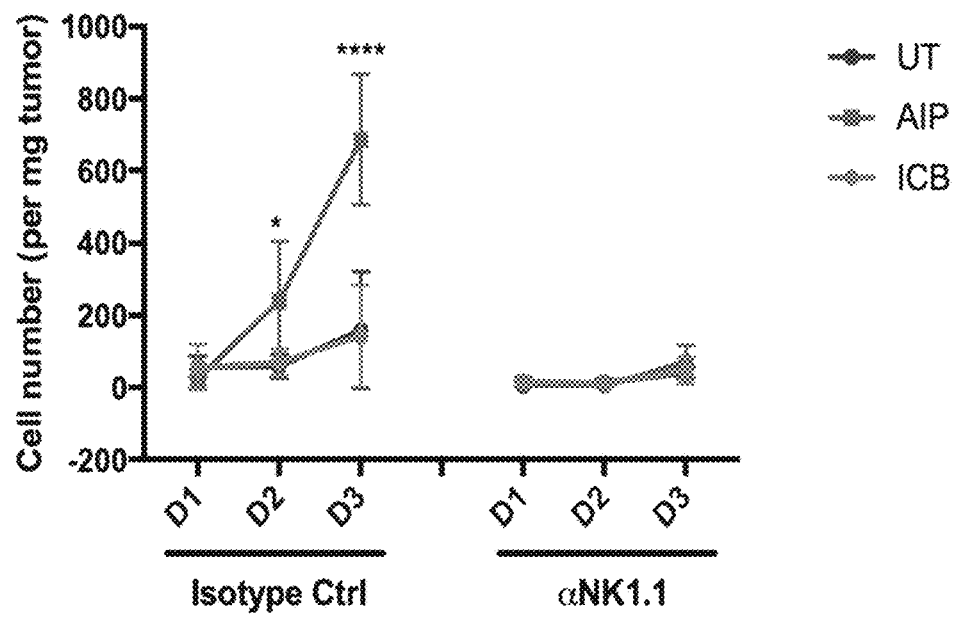
Figure 15C:
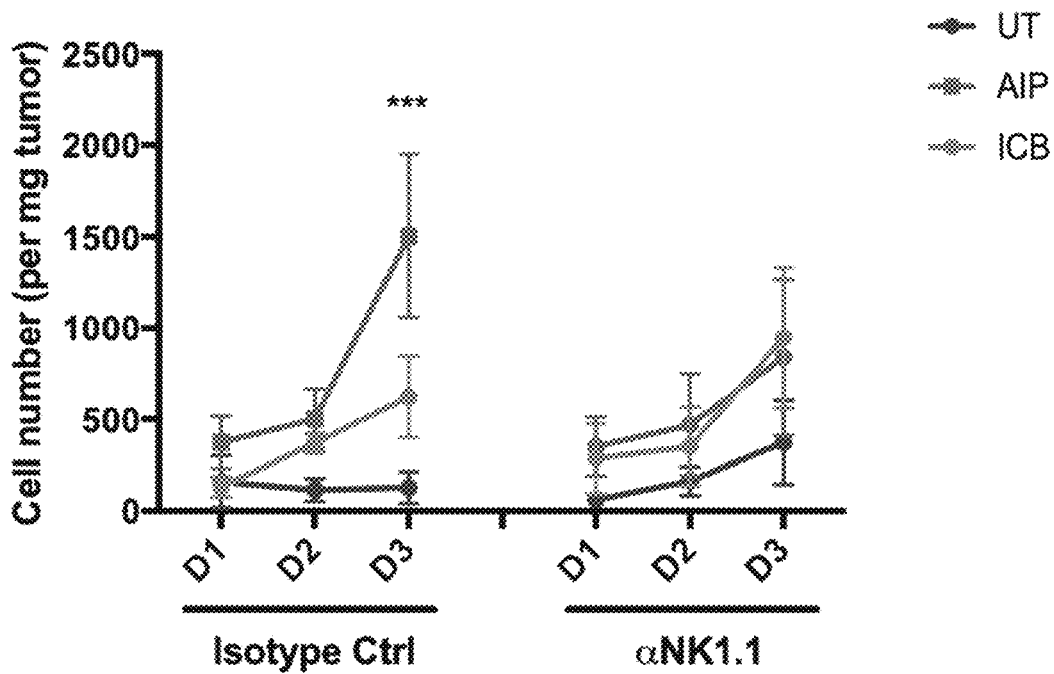
Figure 16A:
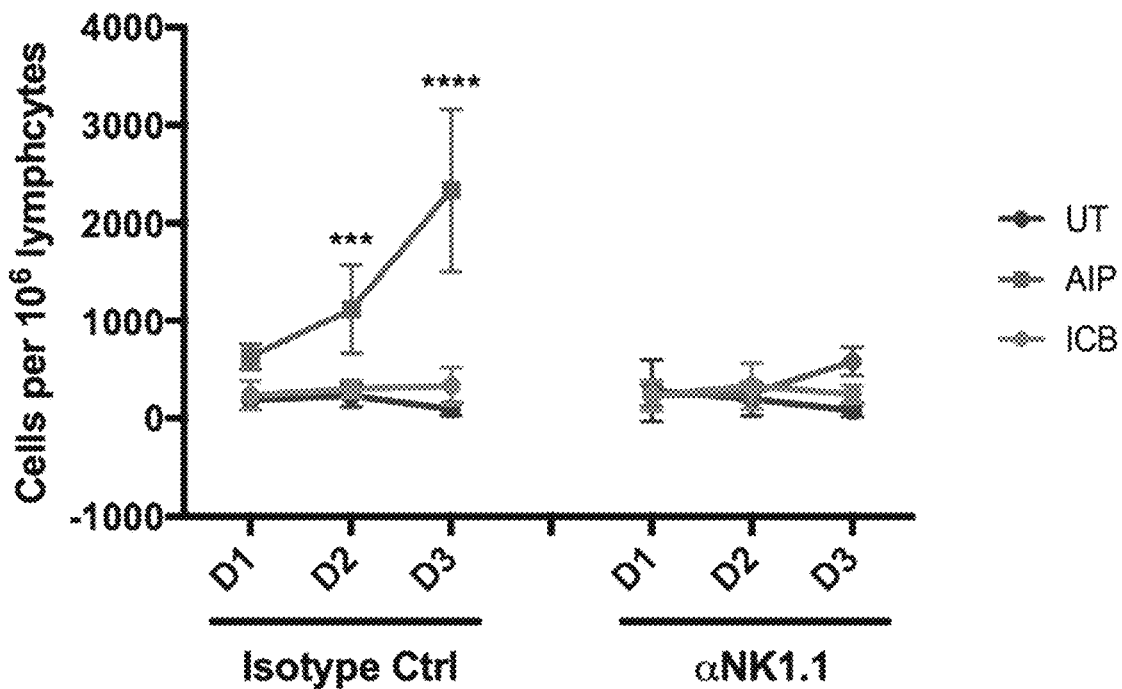
FIGS. 16A-16B provide graphs quantifying CD103+ dendritic cells (FIG. 16A) and activated CD8+ T cells (FIG. 16B) present in tumor draining lymph nodes isolated from B16F10 tumor-bearing mice that were administered anti-NK1.1 antibody or non-depleting isotype control antibody every three days for one week starting 1 day prior to treatment with AIP or ICB. Treatment regimen and components as in FIGS. 15A-15C.
Figure 16B:
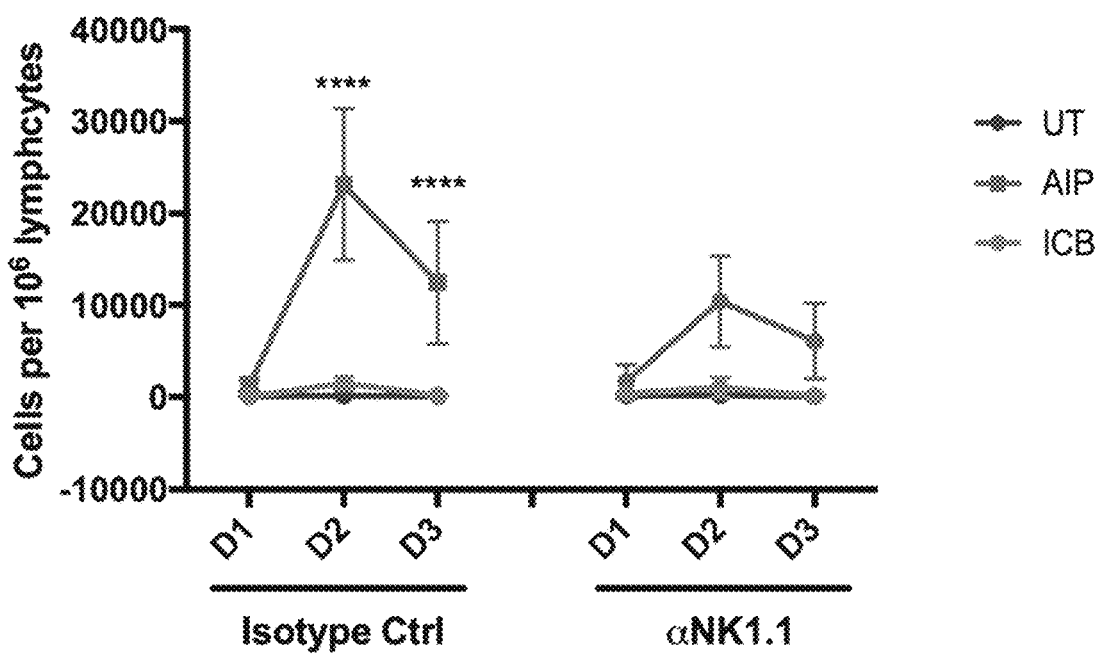

To further assess the role of natural killer cells, NK cells were depleted in B16F10-bearing mice. Specifically, mice were treated with anti-NK1.1 antibody every three days for one week starting one day before treatment with AIP or ICB (i.e., NK depleting antibody administered on day 7 and 10 following tumor inoculation). Tumors and tumor draining lymph nodes (TDLNs) were isolated one, two and three days after treatment and analyzed by flow cytometry for CD8α+ or CD103+ dendritic cells or activated CD8+ T cells. Additionally, tumor draining lymph nodes were isolated one, two, and three days after treatment and analyzed by flow cytometry for CD103+ dendritic cells and activated CD8+ T cells. FIGS. 15A-15C show natural killer cells are required for recruitment and maintenance of cDC1s and activated CD8+ T cells in tumors. FIGS. 16A-16B further show that natural killer cells promote migration of dendritic cells to TDLNs (FIG. 16A) and elevated levels of activated CD8+ T cells in TDLNs (FIG. 16B).

Overall, these results indicate natural killer cells are essential for sensitizing tumors to immune checkpoint blockade therapy following a priming dose of AIP, at least because they recruit and maintain dendritic cells and CD8+ T cells in the tumor. Additionally, they play a role in promoting migration of cross presenting dendritic cells to TDLNs where they can promote activation of tumor-specific cytotoxic T cells.

Example 9: Innate Immune Cells Promote Tumor Cell Killing and Function of Dendritic Cells in Response to Priming Dose of Immunotherapy The role of various immune cell populations was further explored by evaluating their effect on tumor cell killing in response to a single priming dose of an immunotherapy combination. Specifically, B16F10 tumors were established in C57BL/6 mice as described in the previous Examples. At 8 days post tumor inoculation, mice were administered immune checkpoint blockade (ICB; anti-CTLA-4+anti-PD-1) or a single priming dose of AIP (A=knottin-Fc (2.5F-Fc); I=MSA-IL-2; P=anti-PD-1). To determine the effect of specific immune cell populations, animal cohorts receiving AIP were administered a depleting antibody or a non-depleting isotype control antibody one day prior to AIP therapy. Depleting antibodies evaluated included an anti-CD8a antibody (clone 2.43) to deplete cytotoxic T cells, an anti-NK1.1 antibody (clone PK136) to deplete natural killer cells, an anti-F4/80 (clone CI:A3-1) antibody to deplete macrophages, and an anti-GR-1 antibody (clone RB6-8C5) to deplete neutrophils.

Figure 17A:
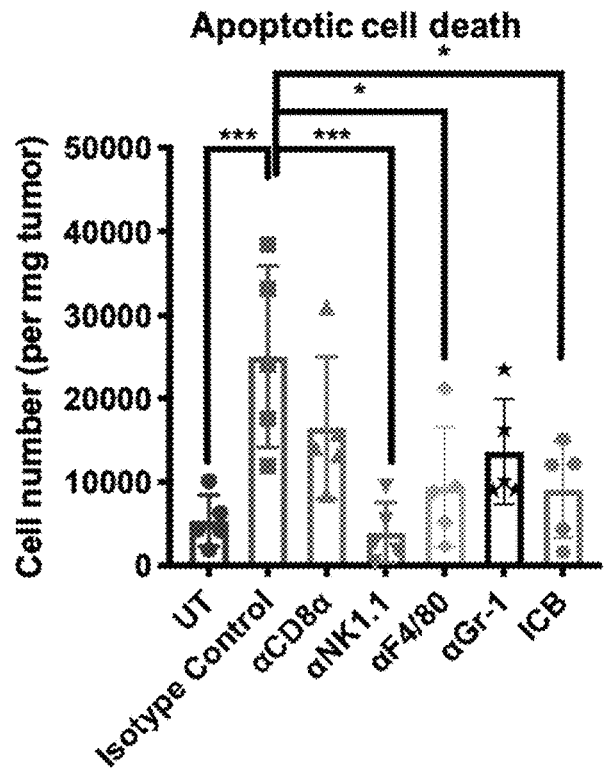
FIGS. 17A-17B provide graphs showing quantification by flow cytometry of tumor cells undergoing apoptotic cell death (FIG. 17A) and immunogenic cell death (FIG. 17B) in B16F10 tumors that were isolated from mice at 1 day following administration of AIP or ICB therapy. Mice receiving a priming dose of AIP were administered depleting antibodies against NK cells (anti-NK1.1), macrophages (anti-F4/80), cytotoxic T cells (anti-CD8α), and neutrophils (anti-Gr-1) or a non-depleting antibody isotype control at 1 day prior to AIP administration. A=integrin binding 2.5F-Fc; I=MSA-IL-2; P=anti-PD-1.
Figure 17B:
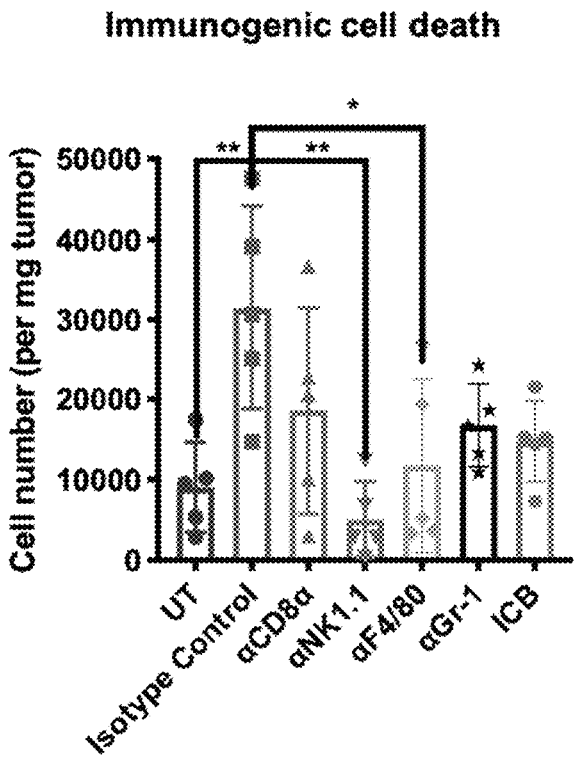

Tumors were isolated at 1 day following administration of AIP or ICB. The tumors were evaluated by flow cytometry for the quantity of tumor cells undergoing apoptosis (characterized by positive staining with Annexin V and propidium iodide (PI)) and for the quantity of tumor cells undergoing immunogenic cell death (characterized by positive staining for surface exposed calreticulin). As shown in FIGS. 17A-17B, a single priming dose of AIP therapy resulted in a dramatic increase in the number of tumor cells undergoing apoptosis or immunogenic cell death compared to tumors in untreated or ICB-treated mice. The quantity was substantially reduced in mice that received depleting antibodies against natural killer cells (anti-NK1.1) or macrophages (anti-F4/80). Thus, these cell populations are expected to have a significant role in inducing tumor cell apoptosis and immunogenic cell death following a single priming dose of AIP therapy.

Following immunogenic tumor cell killing, cross-presenting dendritic cells (CD103+ cDC1s) transport tumor antigens to the tumor draining lymph nodes and present antigen for activation of tumor-specific cytotoxic T cells (see e.g., Fu, C. (2018) *Front. Immunol.* 9:1). Given that natural killer cells and macrophages contribute to tumor cell killing in response to a priming dose of AIP as described above, it was evaluated whether they are necessary for subsequent antigen uptake and trafficking by cross-presenting dendritic cells. Specifically, $1 \times 10^6$ B16F10 tumor cells expressing Zsgreen (B16F10-Zsgreen) were inoculated in C57BL/6 mice by subcutaneous injection. At 8 days post tumor inoculation, mice were administered a single priming dose of AIP (A=knottin-Fc (2.5F-Fc); I=MSA-IL-2; P=anti-PD-1). Additionally, mouse cohorts received an anti-CD8α, anti-NK1.1, or anti-F4/80 depleting antibody or a non-depleting isotype control antibody one day prior to AIP administration as described above. Tumor draining lymph nodes were isolated from mice 1 day following AIP administration. Quantification of total numbers of CD103+ DCs or CD8α+ DCs in the TDLN was determined by flow cytometry, as well as the number of CD103+ DCs or CD8α+ DCs that were positive for Zsgreen tumor antigen.

Figure 18A:
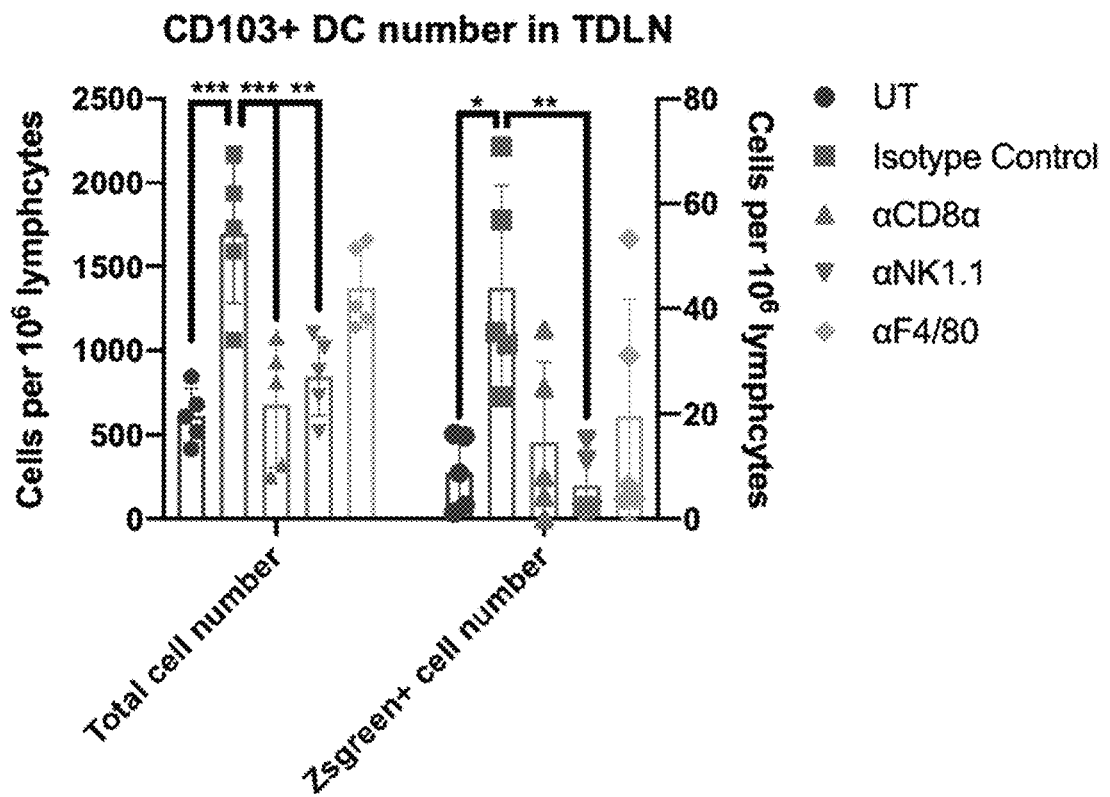
FIGS. 18A-18B provide graphs showing quantification by flow cytometry of total cell number and number of cells internalizing tumor antigen that were CD103+ dendritic cells (FIG. 18A) and CD8α+ dendritic cells (FIG. 18B) in the tumor draining lymph nodes of mice bearing Zsgreen-expressing B16F10 tumors that were untreated (UT) or isolated at 1 day following administration a priming dose of AIP. Mice receiving a priming dose of AIP were administered depleting antibodies against NK cells (anti-NK1.1), macrophages (anti-F4/80), or cytotoxic T cells (anti-CD8α) or a non-depleting antibody isotype control 1 day prior to treatment with AIP. AIP components as in FIGS. 17A-17B.
Figure 18B:
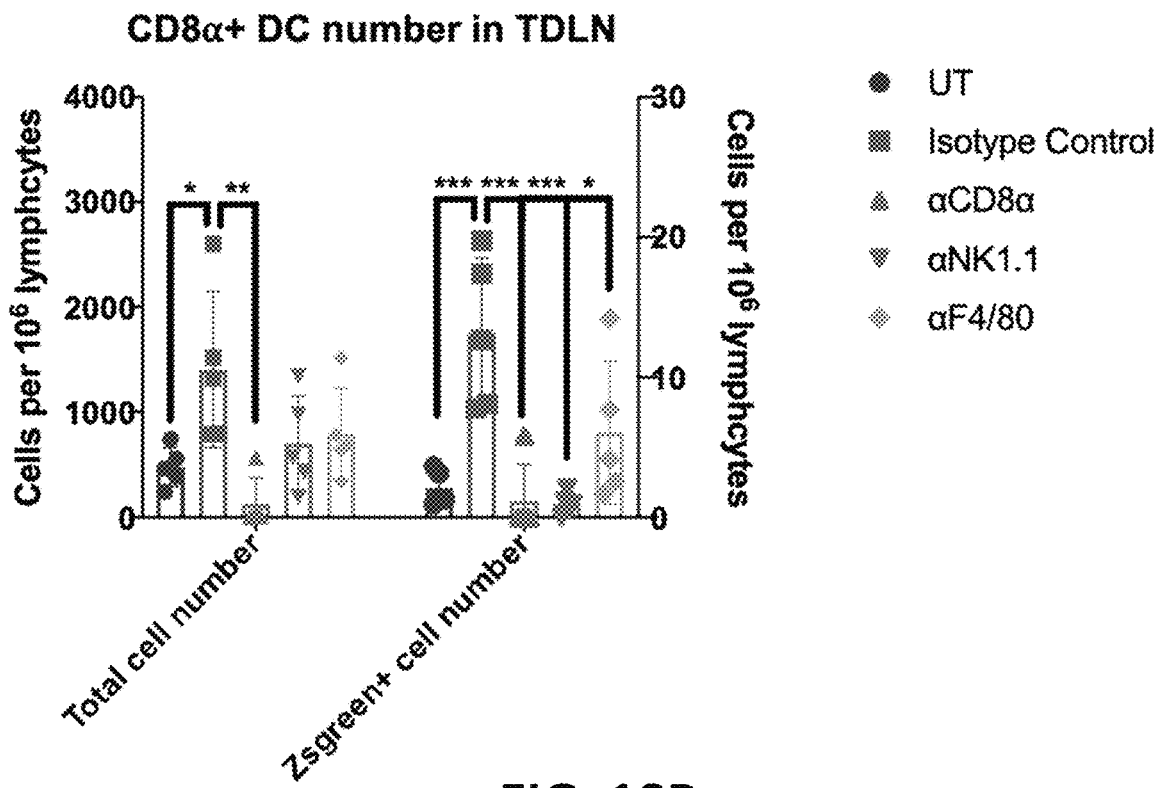

As shown in FIGS. 18A-18B, a single priming dose of AIP resulted in substantial increase in the total quantity of CD103+ DCs or CD8α+ DCs in the TDLN, as well as those positive for tumor antigen uptake. By comparison, depletion of NK cells in particular resulted in significantly fewer CD103+ DCs in the TDLN that were positive for tumor antigen uptake (FIG. 18A), while depletion of either NK cells or macrophages resulted in significantly fewer CD8α+ DCs in the TDLN that were positive for tumor antigen uptake (FIG. 18B).

Thus, NK cells and macrophages are essential for sensitizing tumors to immune checkpoint blockade by inducing tumor cell apoptosis and immunogenic cell death and promoting tumor antigen uptake and transport to lymphatic tissues by cross-presenting dendritic cells.

Example 10: Effect of Integrin-Targeting Polypeptide Fc Domain on Efficacy of Priming Dose The impact of the Fc-domain of knottin-Fc on the efficacy of the immunotherapy combination priming dose was evaluated. Tumor targeting antibodies are known to potentiate anti-tumor effects by antibody-dependent cell-mediated cytotoxicity (ADCC) and complement-dependent cytotoxicity that is mediated via the antibody Fc domain (see, e.g., Bakema, J. et al (2014) Curr Top Microbiol Immunol 382: 373-92). Thus, it was evaluated whether the efficacy of the AIP priming dose was dependent upon treatment with A=knottin-Fc comprising a functional Fc domain.

Specifically, variants of 2.5F-Fc were generated comprising a 2.5F knottin peptide (2.5F with a K15S substitution) fused to a modified antibody Fc domain. The modified Fc domain was either a mouse IgG2a with substitution of aspartic acid with alanine at position 265 (D265A) or mouse IgG2a with substitution of leucine with alanine at positions 234 and 235 and substitution of proline with glycine at position 329 (LALA-PG). The D265A substitution eliminates interaction of the Fc domain with Fcγ receptors (see, e.g., Baudino, L. (2008) J. Immunol. 181:6664-6669), while the LALA-PG substitutions eliminate Fc-dependent binding and fixation of complement proteins (see, e.g., Lo, M. et al (2017) J. Biol. Chem. 292:3900-3908). The amino acid sequence for 2.5F-Fc with a D265A mutation is set forth by SEQ ID NO: 132; the amino acid sequence for 2.5F-Fc with a LALA-PG mutation is set forth by SEQ ID NO: 134.

B16F10 tumors were established in C57BL/6 mice as described in the previous Examples. On day 8 following tumor inoculation, a single priming dose of AIP (A=2.5F-Fc, 2.5F-Fc (D265A), or 2.5F-Fc (LALA-PG); I=MSA-IL-2; P=anti-PD-1) was administered, with subsequent administration of ICB (anti-PD-1+anti-CTLA-4) every 3 days for 4 weeks as described in Example 3. The animals were treated with the same molar dose of 2.5F-Fc, 2.5F-Fc (D265A) or 2.5F-Fc (LALA-PG).

Figure 19A:
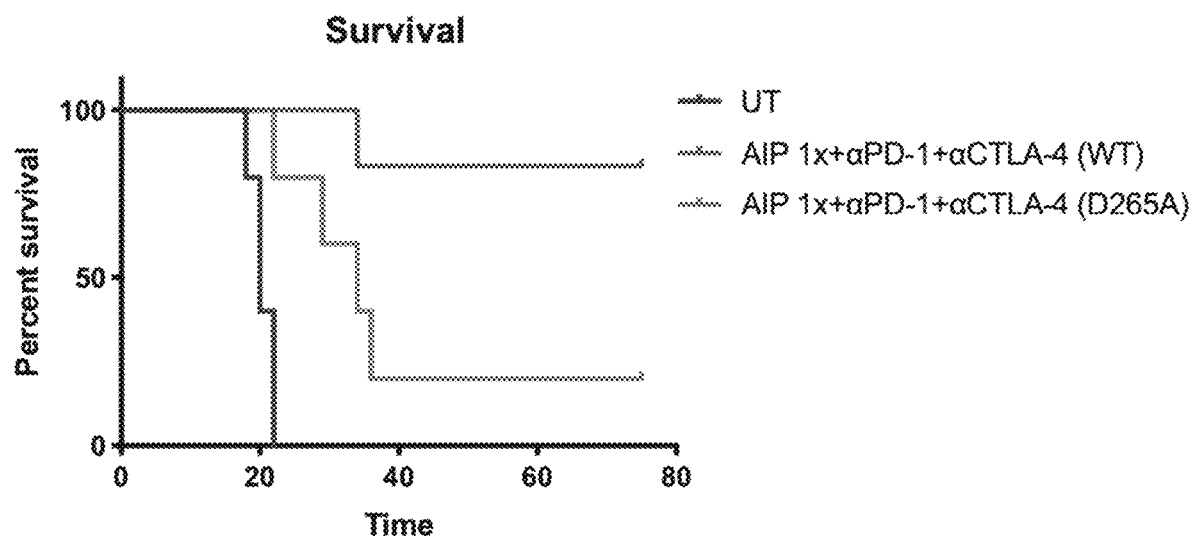
FIGS. 19A-19B provide graphs showing percent survival of B16F10 tumor-bearing mice administered a single priming dose of AIP followed by immune checkpoint blockade (anti-PD-1+anti-CTLA-4) therapy every 3 days for 4 weeks. AIP therapy comprised I=MSA-IL-2; P=anti-PD-1; and A=integrin binding 2.5F-Fc, wherein the 2.5F-Fc comprised a wild-type (WT) Fc domain or an Fc domain variant that was either an Fc domain with D265A mutation (FIG. 19A) or an Fc domain with LALA-PG mutations (FIG. 19B).
Figure 19B:
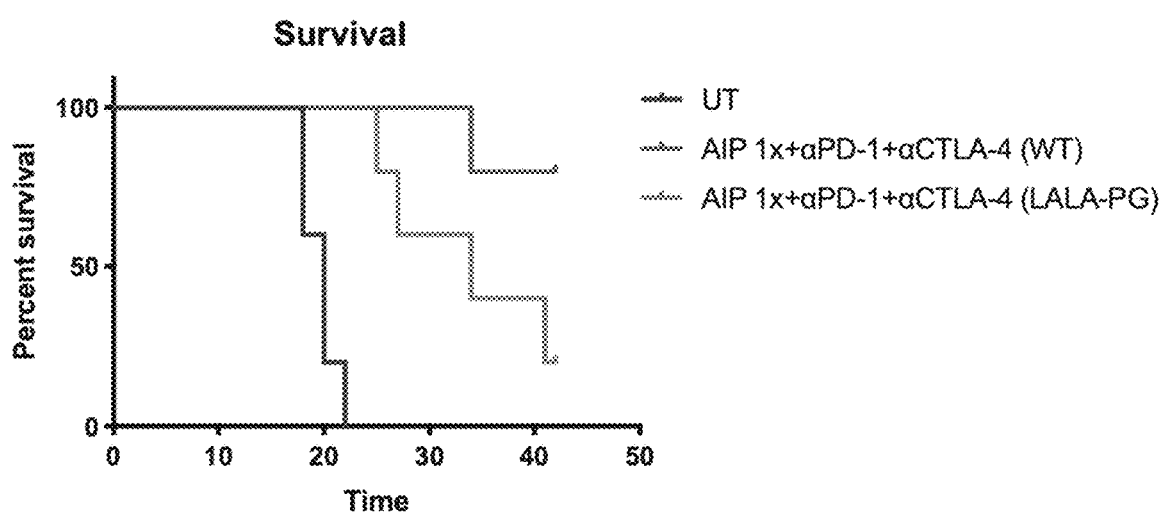

As shown in FIGS. 19A-19B, survival of animals was significantly reduced for the immunotherapy combination priming dose comprising a knottin-Fc protein lacking a functional Fc domain (D265A mutation or LALA-PG mutation) compared to the priming dose with knottin-Fc protein comprising a wild-type Fc domain.

Figure 20:
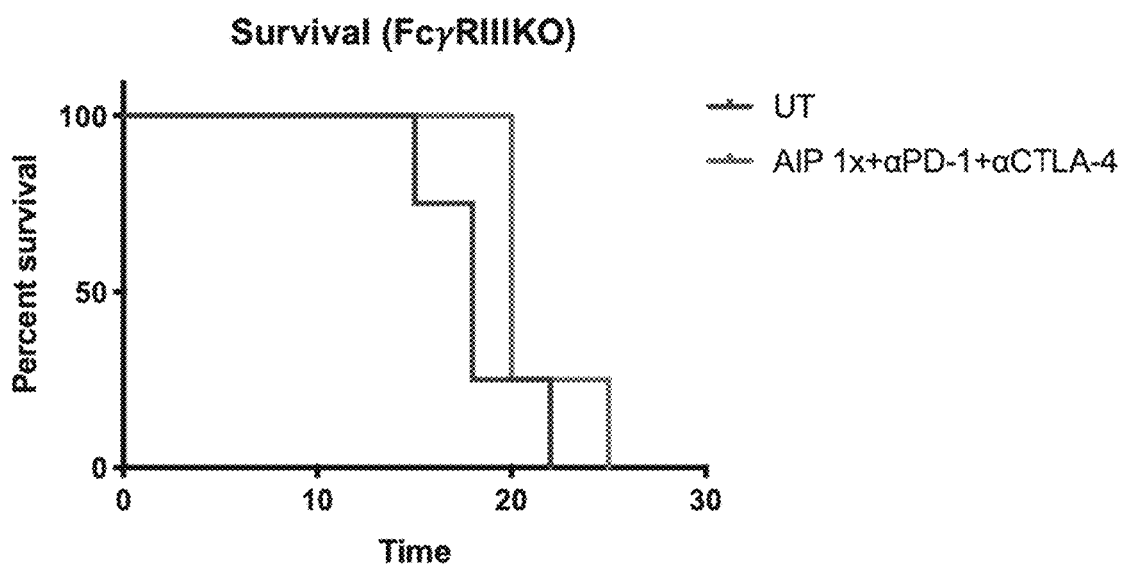
FIG. 20 provides a graph comparing survival of untreated B16F10 tumor-bearing wild-type mice to B16F10 tumor-bearing mice deficient for FcγIII receptor and administered a single priming dose of AIP followed by immune checkpoint blockade (anti-PD-1+anti-CTLA-4) therapy every 3 days. A=integrin binding 2.5F-Fc; I=MSA-IL-2; P=anti-PD-1.

To further demonstrate the impact of Fc-engagement, the immunotherapy combination priming dose was evaluated in mice lacking activating FcγIII receptor. The FcγIII receptor-deficient mice were inoculated with 1×10$^6$ B16F10 melanoma cells. On day 8 post-tumor inoculation, the animals were treated with a single priming dose of AIP (A=knottin-Fc (2.5F-Fc); I=MSA-IL-2; P=anti-PD-1), followed by administration of ICB (anti-PD-1+anti-CTLA-4) as described in Example 3 through the duration of the experiment. While this treatment regime dramatically improved survival in wild-type mice bearing B16F10 tumors (see FIG. 4B), it provided no survival benefit in mice lacking FcγIII receptors compared to untreated mice (FIG. 20).

Together these data demonstrate that engagement of Fcγ receptors by the knottin-Fc component of the single priming dose of immunotherapy is needed to sensitize tumors to subsequent immune checkpoint blockade therapy.

Example 11: Effect of Extended-PK IL-2 on Efficacy of Priming Dose

The impact of increased half-life of an extended-PK IL-2 on the efficacy of the immunotherapy combination priming dose was evaluated. The single priming dose of AIP comprises MSA-IL-2, which as described in Example 1, has been shown to have prolonged circulation half-life relative to soluble IL-2 (see, e.g., Zhu, E. et al. (2015) Cancer Cell 27:489-501). The impact of prolonged half-life of IL-2 on the efficacy of the AIP priming dose was evaluated.

Specifically, a comparison of single priming dose of AIP comprising I=MSA-IL-2 or a single priming dose of AIP comprising I=soluble IL-2 was made. B16F10 tumors were established in C57BL/6 mice as described in the previous Examples. On day 8 following tumor inoculation, a single priming dose of AIP (A=knottin-Fc (2.5F-Fc); I=MSA-IL-2 or soluble IL-2; P=anti-PD-1) was administered, with subsequent administration of ICB (anti-PD-1+anti-CTLA-4) every 3 days for 4 weeks as described in Example 3. The mice were treated with either 30 µg MSA-IL-2 or the molar equivalent of soluble murine IL-2.

Figure 21:
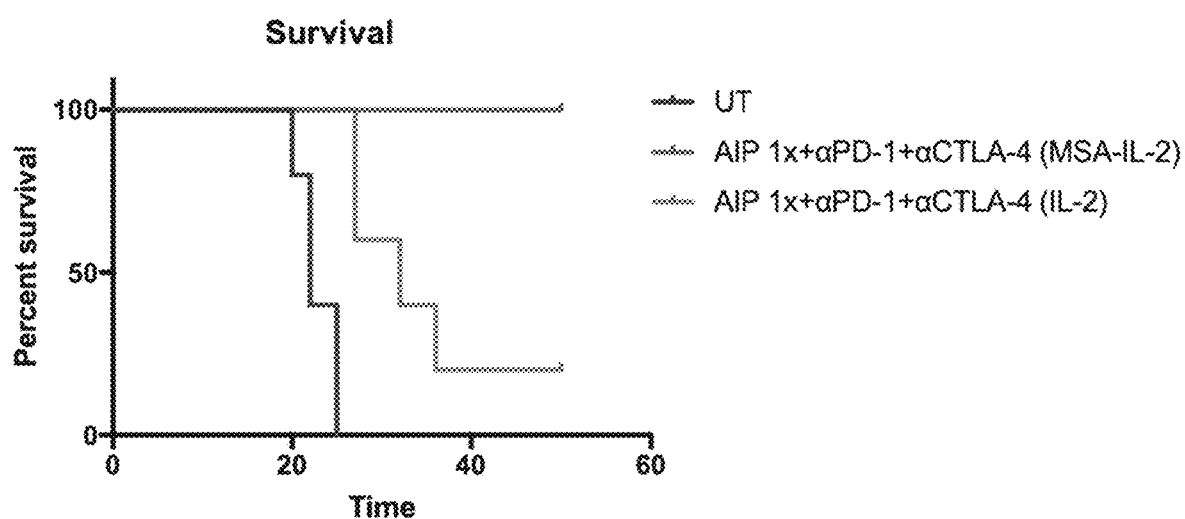
FIG. 21 provides a graph showing percent survival of B16F10 tumor-bearing mice untreated (UT) or administered a single priming dose of AIP followed by immune checkpoint blockade (anti-PD-1+anti-CTLA-4) therapy every 3 days for 4 weeks. AIP therapy comprised P=anti-PD-1; A=integrin binding 2.5F-Fc; and I=MSA-IL-2 or soluble murine IL-2.

As shown in FIG. 21, survival following a priming dose of AIP and subsequent administration of ICB was greatly reduced if AIP comprised soluble IL-2 rather than extended-PK IL-2. Thus, an IL-2 component with longer circulation half-life (i.e., extended-PK IL-2) in the priming dose of an immunotherapy combination is more effective for sensitizing a tumor microenvironment to subsequent ICB therapy.

Example 12: Therapeutic Components that Promote FLT3L Production by Natural Killer Cells FLT3L is known to promote expansion of dendritic cells and is predominantly produced by lymphocytes, notably natural killer cells (see, e.g., Barry, K. et al (2018) Nat. Med. 24:1178-1191). As shown in FIG. 13A, a priming dose of AIP results in increased intratumoral FLT3L production that is dependent upon natural killer cells. To determine which components of AIP therapy contribute to FLT3L production by NK cells, isolated NK cells were stimulated in vitro with AIP and various subcombinations. Specifically, NK cells were isolated from murine splenocytes using a NK cell isolation kit (STEMCELL) by negative selection. The isolated NK cells were seeded with PBS as a control or in combination with B16F10 melanoma cells at a ratio of 1:1 NK cells:tumor cells. The control culture or co-culture of NK and B16F10 cells was treated with the following therapeutic combinations: A, I, P, AI, IP, AP, or AIP. In vitro treatment comprised A=knottin-Fc (2.5F-Fc) at a concentration of 5 ug/mL, I=MSA-IL-2 at a concentration of 60 ng/mL, and P=anti-PD-1 at a concentration of 4 ug/mL. Following treatment, the cultures were incubated at 37° C. for 48 hours. The concentration of FLT3L in the cell culture supernatant was measured by ELISA.

Figure 22:
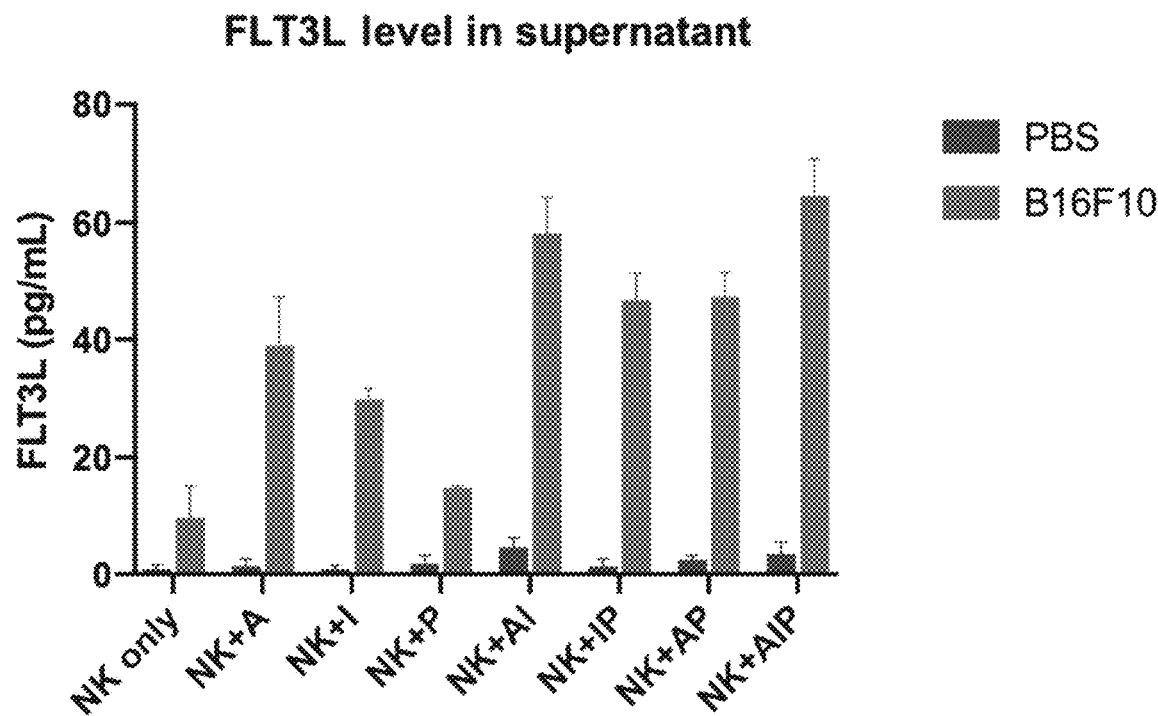
FIG. 22 provides a bar graph showing in vitro production of FLT3L measured by ELISA in cultures comprising natural killer cells isolated from mouse splenocytes either alone or in combination with B16F10 tumor cells and treated with A, I, P, AI, IP, AP, or AIP. A=integrin binding 2.5F-Fc; 1=MSA-IL-2; P=anti-PD-1.

As shown in FIG. 22, A and I were the most effective single treatments for inducing FLT3L production by NK cells in response to B16F10 tumor cells. The combination of AI resulted in a further increase that was comparable to that induced by the triple AIP combination. Based upon these mechanistic studies, a priming dose of AIP is able to activate FLT3 production by NK cells, notably through Fc receptor and IL-2R engagement by the A and I therapeutic components. Thus, the priming dose of immunotherapy stimulates FLT3 production by NK cells, thereby promoting subsequent expansion of cross presenting dendritic cells, activation of tumor specific cytotoxic T cells, and sensitization of the tumor to immune checkpoint blockade.

Example 13: Response of Natural Killer Cells to Priming Dose of Immunotherapy Sensitizes Tumors to Immune Checkpoint Blockade As described in the previous Examples, the priming efficacy of an immunotherapy combination is dependent upon NK cells for FLT3L production, induction of immunogenic tumor cell death, and tumor antigen uptake and subsequent migration to lymphatic tissues by cross-presenting dendritic cells. To further demonstrate the crucial role of NK cells in sensitizing tumors to immune checkpoint blockade, NK cells were depleted and the effect on animal survival in response to AIP+ICB therapy was evaluated. Specifically, B16F10 tumors were established in C57BL/6 mice as described in the previous Examples, with treatment cohorts consisting of 5 animals per group. On day 8 following tumor inoculation, a single priming dose of AIP (knottin-Fc (2.5F-Fc)+MSA-IL-2+anti-PD-1) was administered, with subsequent administration of ICB (anti-PD-1+anti-CTLA-4) as described in Example 3. Additionally, the animals were treated with anti-NK1.1 antibody to induce depletion of natural killer cells. The anti-NK1.1 antibody (clone PK136) was administered every 3 days by intraperitoneal injection at 400 µg starting 1 day prior to AIP (early NK cell depletion) or starting 3 days post AIP (late NK cell depletion) and continued through the duration of the study.

Figure 23:
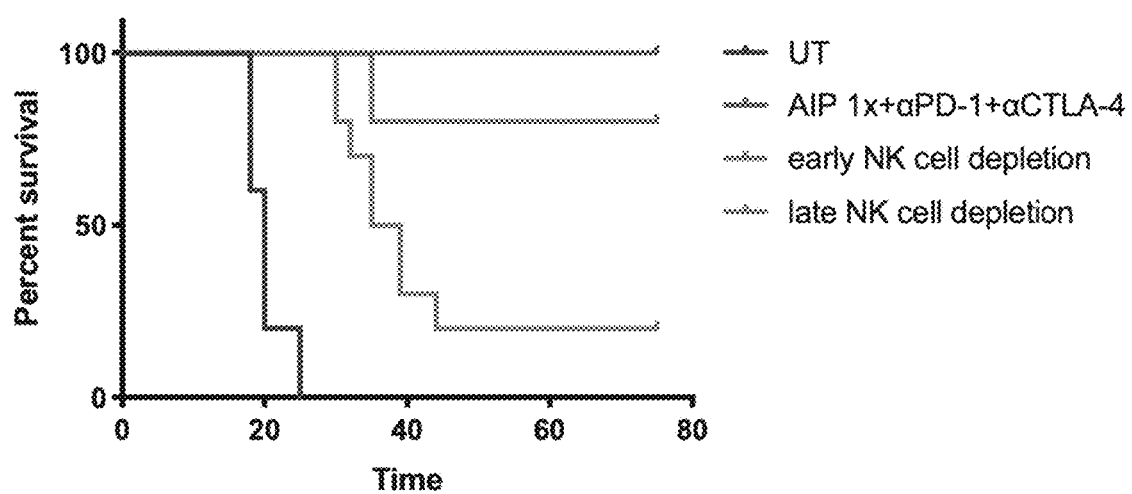
FIG. 23 provides a graph showing survival of B16F10-bearing mice that were untreated (UT) or received a single priming dose of AIP followed by immune checkpoint blockade (anti-PD-1+anti-CTLA-4) therapy every 3 days for 4 weeks. The treated mice were administered depleting antibody against NK cells (anti-NK1.1) 1 day prior to AIP (early NK cell depletion) or 3 days following AIP (late NK cell depletion). A=integrin binding 2.5F-Fc; I=MSA-IL-2; P=anti-PD-1.

As shown in FIG. 23, all animals receiving a single priming dose of AIP and subsequent ICB therapy rejected tumor burden. By comparison, survival in animals receiving early NK cell depletion was greatly reduced, further demonstrating the essential role of NK cells for altering the tumor microenvironment in response to a single priming dose of an immunotherapy combination. However, late depletion of NK cells did not substantially alter survival, indicating that presence of NK cells at the time of the priming dose is both necessary and sufficient for anti-tumor efficacy in response to the priming dose of immunotherapy combination.

Example 14: Combination Therapy Results in Normalization of Tumor Vessels

Abnormal tumor vasculature contributes to hypoxia, acidity and elevated interstitial fluid pressure in the tumor microenvironment. Such effects contribute to tumor progression, treatment resistance, and immune evasion (see, e.g., Martin, J. et al (2019) *Ann Rev Physiol* 81:505-534). Hallmarks of abnormal tumor vasculature comprise enlarged blood vessels, disorganized vasculature, detached pericytes, and large gaps between endothelial cells (see, e.g., Jain, R. (2013) *J. Clin. Oncol.* 31:2205-2218). Increasingly, it is appreciated that normalization of tumor vasculature is associated with restoration of tumor immune surveillance (see, e.g., Schaaf, M. et al (2018) *Cell Death & Disease* 9:115; Tian, L. et al (2017) *Nature* 544:250-254; Huang, Y. et al (2012) *PNAS* 109:17561-17566).

To evaluate whether a single priming dose of an immunotherapy combination contributes to anti-tumor immunity through normalization of the tumor vasculature, treated tumors were isolated and tumor vasculature was assessed by flow cytometry and confocal microscopy. Specifically, B16F10 melanoma tumors were established in mice as described in Example 1. At 8 days following tumor inoculation, mice were administered AIP (A=knottin-Fc (2.5F-Fc); I-MSA-IL-2; P=anti-PD-1) or ICB (anti-PD-1+anti-CTLA-4) as described in Example 3. Tumors were isolated at 3 days following administration of AIP or ICB and analyzed to quantify intratumoral endothelial cells and pericytes. Endothelial cells and pericytes present in single cell isolates were characterized by staining with antibodies against CD31 (marker for endothelial cells) and NG2 (marker for pericytes). Endothelial cells were further characterized for expression of adhesion and activation markers using antibodies against E-selectin, VCAM-1, and VEGFR2. Following staining, cells were quantified by flow cytometry.

As shown in FIG. 24A, the total quantity of endothelial cells, as well as the quantity of endothelial cells expressing the adhesion markers E-selectin and VCAM-1 and proliferation marker VEGFR2, was significantly elevated in tumors administered AIP compared to untreated tumors or tumors administered ICB. The increased expression of endothelial adhesion factors may contribute to recruitment and infiltration of tumor targeting lymphocytes following treatment with a single priming dose of an immunotherapy combination.

Additionally, as shown in FIG. 24B, the ratio of endothelial cells to pericytes was greatly reduced in tumors administered either AIP or ICB compared to untreated tumors. Given that abnormal vasculature is characterized by decreased pericyte coverage of blood vessels, the increased presence of pericytes in tumors administered AIP is indicative of normalization of the tumor vasculature.

Additionally, at 3 days following treatment of B16F10 tumor-bearing mice as described above, mice were intravenously injected with 1000 µg of 2000 kDa dextran-rhodamine. The mice were then perfused systemically with PBS and the tumors were isolated. The tumors were fixed using paraformaldehyde and embedded in agarose. Agarose embedded tumors were cut into 100 µm sections using vibratome (Leica Biosystems). The tumor tissue sections were cleared using CUBIC-R optical clearing technique (see, e.g., Susaki, Etsuo A., et al. Nature protocols 10.11 (2015): 1709) and subsequently imaged using confocal microscopy, with labeling by dextran-rhodamine used to identify tumor blood vessels. The images were analyzed to determine the size of tumor vasculature in untreated tumors or tumors administered either AIP or ICB. As shown in FIG. 25, administration of AIP resulted in a significant reduction in tumor vessel radius and reduced variability in tumor vessel size compared to untreated or ICB-treated tumors, indicating the immunotherapy combination causes reduction of enlarged tumor vessels that are associated with abnormal tumor vasculature.

Abnormal tumor blood vessels are prone to excessive leakiness, resulting in increased transvascular transport (i.e., vascular permeability). Additionally, though tumor blood vessels can be highly permeable, blood perfusion in tumors is heterogenous, with areas of the tumor having reduced or no blood flow due to pinched and irregular vessels. This heterogeneity can result in reduced access of blood-borne molecules (e.g., blood-borne therapeutics) to poorly perfused regions of the tumor (see, e.g., Jain, R. (1996) *Ann Biomed Eng* 24:457-473).

To evaluate the effect of the immunotherapy combination on vascular permeability and tumor perfusion level, B16F10 tumor-bearing mice were administered AIP or ICB as described above. Additionally, the mice receiving AIP were administered depleting antibodies or a non-depleting isotype control antibody 1 day prior to treatment. Depleting antibodies included: 500 µg anti-TNFα antibody (clone XT3.11) for depletion of TNFα, 400 µg anti-NK1.1 antibody (clone PK136) for depletion of NK cells, 400 µg anti-F4/80 antibody (clone CI:A3-1) for depletion of macrophages. At 3 days following administration, the mice were intravenously injected with 1000 µg of 70 kDa dextran-rhodamine and 200 µg Hoechst DNA-staining dye. The mice were systemically perfused with PBS, and tumors were isolated, sectioned, stained with anti-CD31, and imaged by confocal microscopy as described above.

To evaluate vasculature permeability in the tumor, blood vessel endothelial cells (CD31-positive cells) with dextran labeling were quantified. Increased quantity of CD31+, dextran+ cells indicates that dextran was retained by blood vessel endothelial cells, with less dextran crossing the vasculature into the tumor (i.e., reduced transvascular permeability). As shown in FIG. 26, a priming dose of AIP resulted in a significant increase in quantity of CD31+, dextran+ cells compared to untreated tumors or ICB treated tumors, indicating the immunotherapy combination normalizes the tumor vasculature by reducing vessel permeability (leakiness). Inflammatory cytokines such as TNFα are produced by NK cells and macrophages and are essential for blood vessel remodeling, thus depletion of NK cells, macrophages, or TNFα are expected to inhibit vasculature normalization. Indeed, NK cells, macrophages, and TNFα were required for reduced vasculature permeability induced by a priming dose of AIP immunotherapy combination (FIG. 26).

To evaluate blood perfusion in the tumor, tumor area positive for staining with Hoeschst dye was quantified, with increased Hoeschst staining indicative of improved tumor perfusion. As shown in FIG. 27, a priming dose of AIP therapy resulted in dramatically improved tumor perfusion level relative to untreated tumors or ICB treated tumors. Additionally, NK cells, macrophages, and TNFα were required for this effect (FIG. 27).

Having demonstrated that AIP combination contributes to normalization of tumor vasculature, it was further determined if such normalization was associated with reduced tumor hypoxia. Briefly, B16F10 tumor bearing mice were administered AIP or ICB as described above. 3 days following treatment, the mice were intravenously injected with the hypoxia-detecting agent EF5. The mice were systemically perfused with PBS, and tumors were immediately isolated, fixed, and prepared for frozen sectioning by embedding in OCT compound. Tumors were sectioned by cryostat to provide sections of 8 µm thickness. The sections were stained with fluorescent antibody against the hypoxia-detecting agent EF5. The sections were imaged by confocal microscopy and the tumor area positive for EF5 was quantified. As shown in FIG. 28, the hypoxic area of the tumor was dramatically reduced in tumors that received a priming dose of AIP relative to untreated or ICB-treated tumors.

Together, these results indicate that tumors primed with a dose AIP immunotherapy have a vasculature normalization phenotype (i.e., reduced vessel size, reduced tumor hypoxia, reduced vessel permeability, increased pericytes, improved tumor perfusion). Additionally, NK cells and macrophages are essential for normalization of the tumor vasculature in response to the priming dose of immunotherapy combination. Without being bound by theory, normalization of the tumor vasculature in response to a priming dose of immunotherapy combination is thought to sensitize the tumor to immune checkpoint blockade by enabling tumor infiltration by cytotoxic T cells and improved tumor perfusion with subsequent doses of ICB therapy.

TABLE 5

Sequence Summary

| SEQ ID NO | Description | Sequence |
| --- | --- | --- |
| 1 | Human IgG1 constant region (amino acid sequence) | ASTKGPSVFPLAPSSKSTSGGTAALGCLVKDYFPEPVT VSWNSGALTSGVHTFPAVLQSSGLYSLSSVVTVPSSSL GTQTYICNVNHKPSNTKVDKKVEPKSCDKTHTCPPCP APELLGGPSVFLFPPKPKDTLMISRTPEVTCVVVDVSHE DPEVKFNWYVDGVEVHNAKTKPREEQYNSTYRVVSV LTVLHQDWLNGKEYKCKVSNKALPAPIEKTISKAKGQ PREPQVYTLPPSRDELTKNQVSLTCLVKGFYPSDIAVE WESNGQPENNYKTTPPVLDSDGSFFLYSKLTVDKSRW QQGNVFSCSVMHEALHNHYTQKSLSLSPGK |
| 2 | Human IgG1 Fc domain (amino acid sequence) | EPKSCDKTHTCPPCPAPELLGGPSVFLFPPKPKDTLMIS RTPEVTCVVVDVSHEDPEVKFNWYVDGVEVHNAKTK PREEQYNSTYRVVSVLTVLHQDWLNGKEYKCKVSNK ALPAPIEKTISKAKGQPREPQVYTLPPSRDELTKNQVSL TCLVKGFYPSDIAVEWESNGQPENNYKTTPPVLDSDGS FFLYSKLTVDKSRWQQGNVFSCSVMHEALHNHYTQK SLSLSPGK |
| 3 | Human IgG1 Fc domain (amino acid sequence) Deletion (ΔEPKSC) Upper Hinge | DKTHTCPPCPAPELLGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALPAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK |
| 4 | Mouse IL-2 (nucleic acid sequence) | GCACCCACTTCAAGCTCCACTTCAAGCTCTACAGCG GAAGCACAGCAGCAGCAGCAGCAGCAGCAGCAGCA GCAGCAGCACCTGGAGCAGCTGTTGATGGACCTACA GGAGCTCCTGAGCAGGATGGAGAATTACAGGAACCT GAAACTCCCCAGGATGCTCACCTTCAAATTTTACTTG CCCAAGCAGGCCACAGAATTGAAAGATCTTCAGTGC |

TABLE 5-continued

Sequence Summary

| SEQ ID NO | Description | Sequence |
|---|---|---|
| | | CTAGAAGATGAACTTGGACCTCTGCGGCATGTTCTG<br>GATTTGACTCAAAGCAAAAGCTTTCAATTGGAAGAT<br>GCTGAGAATTTCATCAGCAATATCAGAGTAACTGTT<br>GTAAAACTAAAGGGCTCTGACAACACATTTGAGTGC<br>CAATTCGATGATGAGTCAGCAACTGTGGTGGACTTT<br>CTGAGGAGATGGATAGCCTTCTGTCAAAGCATCATC<br>TCAACAAGCCCTCAA |
| 5 | Mouse IL-2 (amino acid sequence) | APTSSSTSSSTAEAQQQQQQQQQQQQHLEQLLMDLQE<br>LLSRMENYRNLKLPRMLTFKFYLPKQATELKDLQCLE<br>DELGPLRHVLDLTQSKSFQLEDAENFISNIRVTVVKLK<br>GSDNTFECQFDDESATVVDFLRRWIAFCQSIISTSPQ |
| 6 | QQ6210 (nucleic acid sequence) | GCACCCACTTCAAGCTCCACTTCAAGCTCTACAGCG<br>GAAGCACAACAGCAGCAGCAGCAGCAGCAGCAGCA<br>GCAGCAGCACCTGGAGCAGCTGTTGATGGACCTACA<br>GGAACTCCTGAGTAGGATGGAGGATCACAGGAACCT<br>GAGACTCCCCAGGATGCTCACCTTCAAATTTTACTTG<br>CCCGAGCAGGCCACAGAATTGGAAGATCTTCAGTGC<br>CTAGAAGATGAACTTGAACCACTGCGGCAAGTTCTG<br>GATTTGACTCAAAGCAAAAGCTTTCAATTGGAAGAT<br>GCTGAGAATTTCATCAGCAATATCAGAGTAACTGTT<br>GTAAAACTAAAGGGCTCTGACAACACATTTGAGTGC<br>CAATTCGACGATGAGCCAGCAACTGTGGTGGACTTT<br>CTGAGGAGATGGATAGCCTTCTGTCAAAGCATCATC<br>TCAACAAGCCCTCAA |
| 7 | QQ6210 (amino acid sequence) | APTSSSTSSSTAEAQQQQQQQQQQQQHLEQLLMDLQE<br>LLSRMEDHRNLRLPRMLTFKFYLPEQATELEDLQCLED<br>ELEPLRQVLDLTQSKSFQLEDAENFISNIRVTVVKLKGS<br>DNTFECQFDDEPATVVDFLRRWIAFCQSIISTSPQ |
| 8 | E76A (nucleic acid sequence) | GCACCCACTTCAAGCTCCACTTCAAGCTCTACAGCG<br>GAAGCACAGCAGCAGCAGCAGCAGCAGCAGCAGCA<br>GCAGCAGCACCTGGAGCAGCTGTTGATGGACCTACA<br>GGAGCTCCTGAGCAGGATGGAGAATTACAGGAACCT<br>GAAACTCCCCAGGATGCTCACCTTCAAATTTTACTTG<br>CCCAAGCAGGCCACAGAATTGAAAGATCTTCAGTGC<br>CTAGAAGATGCTCTTGGACCTCTGCGGCATGTTCTG<br>GATTTGACTCAAAGCAAAAGCTTTCAATTGGAAGAT<br>GCTGAGAATTTCATCAGCAATATCAGAGTAACTGTT<br>GTAAAACTAAAGGGCTCTGACAACACATTTGAGTGC<br>CAATTCGATGATGAGTCAGCAACTGTGGTGGACTTT<br>CTGAGGAGATGGATAGCCTTCTGTCAAAGCATCATC<br>TCAACAAGCCCTCAA |
| 9 | E76A (amino acid sequence) | APTSSSTSSSTAEAQQQQQQQQQQQQHLEQLLMDLQE<br>LLSRMENYRNLKLPRMLTFKFYLPKQATELKDLQCLE<br>DALGPLRHVLDLTQSKSFQLEDAENFISNIRVTVVKLK<br>GSDNTFECQFDDESATVVDFLRRWIAFCQSIISTSPQ |
| 10 | E76G (nucleic acid sequence) | GCACCCACTTCAAGCTCCACTTCAAGCTCTACAGCG<br>GAAGCACAGCAGCAGCAGCAGCAGCAGCAGCAGCA<br>GCAGCAGCACCTGGAGCAGCTGTTGATGGACCTACA<br>GGAGCTCCTGAGCAGGATGGAGAATTACAGGAACCT<br>GAAACTCCCCAGGATGCTCACCTTCAAATTTTACTTG<br>CCCAAGCAGGCCACAGAATTGAAAGATCTTCAGTGC<br>CTAGAAGATGGTCTTGGACCTCTGCGGCATGTTCTG<br>GATTTGACTCAAAGCAAAAGCTTTCAATTGGAAGAT<br>GCTGAGAATTTCATCAGCAATATCAGAGTAACTGTT<br>GTAAAACTAAAGGGCTCTGACAACACATTTGAGTGC<br>CAATTCGATGATGAGTCAGCAACTGTGGTGGACTTT<br>CTGAGGAGATGGATAGCCTTCTGTCAAAGCATCATC<br>TCAACAAGCCCTCAA |
| 11 | E76G (amino acid sequence) | APTSSSTSSSTAEAQQQQQQQQQQQQHLEQLLMDLQE<br>LLSRMENYRNLKLPRMLTFKFYLPKQATELKDLQCLE<br>DGLGPLRHVLDLTQSKSFQLEDAENFISNIRVTVVKLK<br>GSDNTFECQFDDESATVVDFLRRWIAFCQSIISTSPQ |

TABLE 5-continued

Sequence Summary

| SEQ ID NO | Description | Sequence |
|---|---|---|
| 12 | D265AFc/Flag (nucleic acid sequence) (C-terminal flag tag is underlined) | ATGAGGGTCCCCGCTCAGCTCCTGGGGCTCCTGCTG CTCTGGCTCCCAGGTGCACGATGTGAGCCCAGAGTG CCCATAACACAGAACCCCTGTCCTCCACTCAAAGAG TGTCCCCCATGCGCAGCTCCAGACCTCTTGGGTGGA CCATCCGTCTTCATCTTCCCTCCAAAGATCAAGGATG TACTCATGATCTCCCTGAGCCCCATGGTCACATGTGT GGTGGTGGCCGTGAGCGAGGATGACCCAGACGTCCA GATCAGCTGGTTTGTGAACAACGTGGAAGTACACAC AGCTCAGACACAAACCCATAGAGAGGATTACAACA GTACTCTCCGGGTGGTCAGTGCCCTCCCCATCCAGC ACCAGGACTGGATGAGTGGCAAGGAGTTCAAATGC AAGGTCAACAACAGAGCCCTCCCATCCCCCATCGAG AAAACCATCTCAAAACCCAGAGGGCCAGTAAGAGC TCCACAGGTATATGTCTTGCCTCCACCAGCAGAAGA GATGACTAAGAAAGAGTTCAGTCTGACCTGCATGAT CACAGGCTTCTTACCTGCCGAAATTGCTGTGGACTG GACCAGCAATGGGCGTACAGAGCAAAACTACAAGA ACACCGCAACAGTCCTGGACTCTGATGGTTCTTACTT CATGTACAGCAAGCTCAGAGTACAAAAGAGCACTTG GGAAAGAGGAAGTCTTTTCGCCTGCTCAGTGGTCCA CGAGGGTCTGCACAATCACCTTACGACTAAGACCAT CTCCCGGTCTCTGGGTAAAGGTGGCGGATCT<u>GACTA CAAGGACGACGATGACAAGTGATAA</u> |
| 13 | D265AFc/Flag (amino acid sequence) (C-terminal flag tag is underlined) | MRVPAQLLGLLLLWLPGARCEPRVPITQNPCPPLKECP PCAAPDLLGGPSVFIFPPKIKDVLMISLSPMVTCVVVAV SEDDPDVQISWFVNNVEVHTAQTQTHREDYNSTLRVV SALPIQHQDWMSGKEFKCKVNNRALPSPIEKTISKPRG PVRAPQVYVLPPPAEEMTKKEFSLTCMITGFLPAEIAV DWTSNGRTEQNYKNTATVLDSDGSYFMYSKLRVQKS TWERGSLFACSVVHEGLHNHLTTKTISRSLGKGGGS<u>D YKDDDDK</u> |
| 14 | D265AFc/wt mIL-2 (nucleic acid sequence) (C-terminal 6x his tag is underlined) | ATGAGGGTCCCCGCTCAGCTCCTGGGGCTCCTGCTG CTCTGGCTCCCAGGTGCACGATGTGAGCCCAGAGTG CCCATAACACAGAACCCCTGTCCTCCACTCAAAGAG TGTCCCCCATGCGCAGCTCCAGACCTCTTGGGTGGA CCATCCGTCTTCATCTTCCCTCCAAAGATCAAGGATG TACTCATGATCTCCCTGAGCCCCATGGTCACATGTGT GGTGGTGGCCGTGAGCGAGGATGACCCAGACGTCCA GATCAGCTGGTTTGTGAACAACGTGGAAGTACACAC AGCTCAGACACAAACCCATAGAGAGGATTACAACA GTACTCTCCGGGTGGTCAGTGCCCTCCCCATCCAGC ACCAGGACTGGATGAGTGGCAAGGAGTTCAAATGC AAGGTCAACAACAGAGCCCTCCCATCCCCCATCGAG AAAACCATCTCAAAACCCAGAGGGCCAGTAAGAGC TCCACAGGTATATGTCTTGCCTCCACCAGCAGAAGA GATGACTAAGAAAGAGTTCAGTCTGACCTGCATGAT CACAGGCTTCTTACCTGCCGAAATTGCTGTGGACTG GACCAGCAATGGGCGTACAGAGCAAAACTACAAGA ACACCGCAACAGTCCTGGACTCTGATGGTTCTTACTT CATGTACAGCAAGCTCAGAGTACAAAAGAGCACTTG GGAAAGAGGAAGTCTTTTCGCCTGCTCAGTGGTCCA CGAGGGTCTGCACAATCACCTTACGACTAAGACCAT CTCCCGGTCTCTGGGTAAAGGAGGGGCTCCGCACC CACTTCAAGCTCCACTTCAAGCTCTACAGCGGAAGC ACAGCAGCAGCAGCAGCAGCAGCAGCAGCAGC AGCACCTGGAGCAGCTGTTGATGGACCTACAGGAGC TCCTGAGCAGGATGGAGAATTACAGGAACCTGAAAC TCCCCAGGATGCTCACCTTCAAATTTTACTTGCCCAA GCAGGCCACAGAATTGAAAGATCTTCAGTGCCTAGA AGATGAACTTGGACCTCTGCGGCATGTTCTGGATTT GACTCAAAGCAAAAGCTTTCAATTGGAAGATGCTGA GAATTTCATCAGCAATATCAGAGTAACTGTTGTAAA ACTAAAGGGCTCTGACAACACATTTGAGTGCCAATT CGATGATGAGTCAGCAACTGTGGTGGACTTTCTGAG GAGATGGATAGCTTCTGTCAAAGCATCATCTCAAC AAGCCCTCAA<u>CACCATCACCACCATCACT</u>GATAA |

TABLE 5-continued

Sequence Summary

| SEQ ID NO | Description | Sequence |
|---|---|---|
| 15 | D265AFc/wt mIL-2 (amino acid sequence) (C-terminal 6x his tag is underlined) | MRVPAQLLGLLLLWLPGARCEPRVPITQNPCPPLKECP PCAAPDLLGGPSVFIFPPKIKDVLMISLSPMVTCVVVAV SEDDPDVQISWFVNNVEVHTAQTQTHREDYNSTLRVV SALPIQHQDWMSGKEFKCKVNNRALPSPIEKTISKPRG PVRAPQVYVLPPPAEEMTKKEFSLTCMITGFLPAEIAV DWTSNGRTEQNYKNTATVLDSDGSYFMYSKLRVQKS TWERGSLFACSVVHEGLHNHLTTKTISRSLGKGGGSAP TSSSTSSSTAEAQQQQQQQQQQQQHLEQLLMDLQELL SRMENYRNLKLPRMLTFKFYLPKQATELKDLQCLEDE LGPLRHVLDLTQSKSFQLEDAENFISNIRVTVVKLKGS DNTFECQFDDESATVVDFLRRWIAFCQSIISTSPQ<u>HHHH HH</u>** |
| 16 | D265AFc /QQ6210 (nucleic acid sequence) (C-terminal 6x his tag is underlined) | ATGAGGGTCCCCGCTCAGCTCCTGGGGCTCCTGCTG CTCTGGCTCCCAGGTGCACGATGTGAGCCCAGAGTG CCCATAACACAGAACCCCTGTCCTCCACTCAAAGAG TGTCCCCCATGCGCAGCTCCAGACCTCTTGGGTGGA CCATCCGTCTTCATCTTCCCTCCAAAGATCAAGGATG TACTCATGATCTCCCTGAGCCCCATGGTCACATGTGT GGTGGTGGCCGTGAGCGAGGATGACCCAGACGTCCA GATCAGCTGGTTTGTGAACAACGTGGAAGTACACAC AGCTCAGACACAAACCCATAGAGAGGATTACAACA GTACTCTCCGGGTGGTCAGTGCCCTCCCCATCCAGC ACCAGGACTGGATGAGTGGCAAGGAGTTCAAATGC AAGGTCAACAACAGAGCCCTCCCATCCCCCATCGAG AAAACCATCTCAAAACCCAGAGGGCCAGTAAGAGC TCCACAGGTATATGTCTTGCCTCCACCAGCAGAAGA GATGACTAAGAAAGAGTTCAGTCTGACCTGCATGAT CACAGGCTTCTTACCTGCCGAAATTGCTGTGGACTG GACCAGCAATGGGCGTACAGAGCAAAACTACAAGA ACACCGCAACAGTCCTGGACTCTGATGGTTCTTACTT CATGTACAGCAAGCTCAGAGTACAAAAGAGCACTTG GGAAAGAGGAAGTCTTTTCGCCTGCTCAGTGGTCCA CGAGGGTCTGCACAATCACCTTACGACTAAGACCAT CTCCCGGTCTCTGGGTAAAGGAGGGGGCTCCGCACC CACTTCAAGCTCCACTTCAAGCTCTACAGCGGAAGC ACAACAGCAGCAGCAGCAGCAGCAGCAGCAGCAGC AGCACCTGGAGCAGCTGTTGATGGACCTACAGGAAC TCCTGAGTAGGATGGAGGATCACAGGAACCTGAGAC TCCCCAGGATGCTCACCTTCAAATTTTACTTGCCCGA GCAGGCCACAGAATTGGAAGATCTTCAGTGCCTAGA AGATGAACTTGAACCACTGCGGCAAGTTCTGGATTT GACTCAAAGCAAAAGCTTTCAATTGGAAGATGCTGA GAATTTCATCAGCAATATCAGAGTAACTGTTGTAAA ACTAAAGGGCTCTGACAACACATTTGAGTGCCAATT CGACGATGAGCCAGCAACTGTGGTGGACTTTCTGAG GAGATGGATAGCCTTCTGTCAAAGCATCATCTCAAC AAGCCCTCAA<u>CACCATCACCACCATCAC</u>TGATAA |
| 17 | D265AFc /QQ6210 (amino acid sequence) (C-terminal 6x his tag is underlined) | MRVPAQLLGLLLLWLPGARCEPRVPITQNPCPPLKECP PCAAPDLLGGPSVFIFPPKIKDVLMISLSPMVTCVVVAV SEDDPDVQISWFVNNVEVHTAQTQTHREDYNSTLRVV SALPIQHQDWMSGKEFKCKVNNRALPSPIEKTISKPRG PVRAPQVYVLPPPAEEMTKKEFSLTCMITGFLPAEIAV DWTSNGRTEQNYKNTATVLDSDGSYFMYSKLRVQKS TWERGSLFACSVVHEGLHNHLTTKTISRSLGKGGGSAP TSSSTSSSTAEAQQQQQQQQQQQQHLEQLLMDLQELL SRMEDHRNLRLPRMLTFKFYLPEQATELEDLQCLEDEL EPLRQVLDLTQSKSFQLEDAENFISNIRVTVVKLKGSD NTFECQFDDEPATVVDFLRRWIAFCQSIISTSPQ<u>HHHHH H</u> |
| 18 | D265AFc / E76A (nucleic acid sequence) (C-terminal 6x his tag is underlined) | ATGAGGGTCCCCGCTCAGCTCCTGGGGCTCCTGCTG CTCTGGCTCCCAGGTGCACGATGTGAGCCCAGAGTG CCCATAACACAGAACCCCTGTCCTCCACTCAAAGAG TGTCCCCCATGCGCAGCTCCAGACCTCTTGGGTGGA CCATCCGTCTTCATCTTCCCTCCAAAGATCAAGGATG TACTCATGATCTCCCTGAGCCCCATGGTCACATGTGT GGTGGTGGCCGTGAGCGAGGATGACCCAGACGTCCA GATCAGCTGGTTTGTGAACAACGTGGAAGTACACAC AGCTCAGACACAAACCCATAGAGAGGATTACAACA GTACTCTCCGGGTGGTCAGTGCCCTCCCCATCCAGC ACCAGGACTGGATGAGTGGCAAGGAGTTCAAATGC AAGGTCAACAACAGAGCCCTCCCATCCCCCATCGAG |

TABLE 5-continued

Sequence Summary

| SEQ ID NO | Description | Sequence |
|---|---|---|
| | | AAAACCATCTCAAAACCCAGAGGGCCAGTAAGAGC TCCACAGGTATATGTCTTGCCTCCACCAGCAGAAGA GATGACTAAGAAAGAGTTCAGTCTGACCTGCATGAT CACAGGCTTCTTACCTGCCGAAATTGCTGTGGACTG GACCAGCAATGGGCGTACAGAGCAAAACTACAAGA ACACCGCAACAGTCCTGGACTCTGATGGTTCTTACTT CATGTACAGCAAGCTCAGAGTACAAAAGAGCACTTG GGAAAGAGGAAGTCTTTTCGCCTGCTCAGTGGTCCA CGAGGGTCTGCACAATCACCTTACGACTAAGACCAT CTCCCGGTCTCTGGGTAAAGGAGGGGGCTCCGCACC CACTTCAAGCTCCACTTCAAGCTCTACAGCGGAAGC ACAGCAGCAGCAGCAGCAGCAGCAGCAGCAGCAGC AGCACCTGGAGCAGCTGTTGATGGACCTACAGGAGC TCCTGAGCAGGATGGAGAATTACAGGAACCTGAAAC TCCCCAGGATGCTCACCTTCAAATTTTACTTGCCCAA GCAGGCCACAGAATTGAAAGATCTTCAGTGCCTAGA AGATGCTCTTGGACCTCTGCGGCATGTTCTGGATTTG ACTCAAAGCAAAAGCTTTCAATTGGAAGATGCTGAG AATTTCATCAGCAATATCAGAGTAACTGTTGTAAAA CTAAAGGGCTCTGACAACACATTTGAGTGCCAATTC GATGATGAGTCAGCAACTGTGGTGGACTTTCTGAGG AGATGGATAGCCTTCTGTCAAAGCATCATCTCAACA AGCCCTCAA<u>CACCATCACCACCATCACT</u>GATAA |
| 19 | D265AFc / E76A (amino acid sequence) (C-terminal 6x his tag is underlined) | MRVPAQLLGLLLLWLPGARCEPRVPITQNPCPPLKECP PCAAPDLLGGPSVFIFPPKIKDVLMISLSPMVTCVVVAV SEDDPDVQISWFVNNVEVHTAQTQTHREDYNSTLRVV SALPIQHQDWMSGKEFKCKVNNRALPSPIEKTISKPRG PVRAPQVYVLPPPAEEMTKKEFSLTCMITGFLPAEIAV DWTSNGRTEQNYKNTATVLDSDGSYFMYSKLRVQKS TWERGSLFACSVVHEGLHNHLTTKTISRSLGKGGGSAP TSSSTSSSTAEAQQQQQQQQQQQQHLEQLLMDLQELL SRMENYRNLKLPRMLTFKFYLPKQATELKDLQCLEDA LGPLRHVLDLTQSKSFQLEDAENFISNIRVTVVKLKGS DNTFECQFDDESATVVDFLRRWIAFCQSIISTSPQ<u>HHHH HH</u> |
| 20 | D265AFc / E76G (nucleic acid sequence) (C-terminal 6x his tag is underlined) | ATGAGGGTCCCCGCTCAGCTCCTGGGGCTCCTGCTG CTCTGGCTCCCAGGTGCACGATGTGAGCCCAGAGTG CCCATAACACAGAACCCCTGTCCTCCACTCAAAGAG TGTCCCCCATGCGCAGCTCCAGACCTCTTGGGTGGA CCATCCGTCTTCATCTTCCCTCCAAAGATCAAGGATG TACTCATGATCTCCCTGAGCCCCATGGTCACATGTGT GGTGGTGGCCGTGAGCGAGGATGACCCAGACGTCCA GATCAGCTGGTTTGTGAACAACGTGGAAGTACACAC AGCTCAGACACAAACCCATAGAGAGGATTACAACA GTACTCTCCGGGTGGTCAGTGCCCTCCCCATCCAGC ACCAGGACTGGATGAGTGGCAAGGAGTTCAAATGC AAGGTCAACAACAGAGCCCTCCCATCCCCCATCGAG AAAACCATCTCAAAACCCAGAGGGCCAGTAAGAGC TCCACAGGTATATGTCTTGCCTCCACCAGCAGAAGA GATGACTAAGAAAGAGTTCAGTCTGACCTGCATGAT CACAGGCTTCTTACCTGCCGAAATTGCTGTGGACTG GACCAGCAATGGGCGTACAGAGCAAAACTACAAGA ACACCGCAACAGTCCTGGACTCTGATGGTTCTTACTT CATGTACAGCAAGCTCAGAGTACAAAAGAGCACTTG GGAAAGAGGAAGTCTTTTCGCCTGCTCAGTGGTCCA CGAGGGTCTGCACAATCACCTTACGACTAAGACCAT CTCCCGGTCTCTGGGTAAAGGAGGGGGCTCCGCACC CACTTCAAGCTCCACTTCAAGCTCTACAGCGGAAGC ACAGCAGCAGCAGCAGCAGCAGCAGCAGCAGCAGC AGCACCTGGAGCAGCTGTTGATGGACCTACAGGAGC TCCTGAGCAGGATGGAGAATTACAGGAACCTGAAAC TCCCCAGGATGCTCACCTTCAAATTTTACTTGCCCAA GCAGGCCACAGAATTGAAAGATCTTCAGTGCCTAGA AGATGGTCTTGGACCTCTGCGGCATGTTCTGGATTTG ACTCAAAGCAAAAGCTTTCAATTGGAAGATGCTGAG AATTTCATCAGCAATATCAGAGTAACTGTTGTAAAA CTAAAGGGCTCTGACAACACATTTGAGTGCCAATTC GATGATGAGTCAGCAACTGTGGTGGACTTTCTGAGG AGATGGATAGCCTTCTGTCAAAGCATCATCTCAACA AGCCCTCAA<u>CACCATCACCACCATCACT</u>GATAA |

TABLE 5-continued

Sequence Summary

| SEQ ID NO | Description | Sequence |
|---|---|---|
| 21 | D265AFc / E76G (amino acid sequence) (C-terminal 6x his tag is underlined) | MRVPAQLLGLLLLWLPGARCEPRVPITQNPCPPLKECP PCAAPDLLGGPSVFIFPPKIKDVLMISLSPMVTCVVVAV SEDDPDVQISWFVNNVEVHTAQTQTHREDYNSTLRVV SALPIQHQDWMSGKEFKCKVNNRALPSPIEKTISKPRG PVRAPQVYVLPPPAEEMTKKEFSLTCMITGFLPAEIAV DWTSNGRTEQNYKNTATVLDSDGSYFMYSKLRVQKS TWERGSLFACSVVHEGLHNHLTTKTISRSLGKGGGSAP TSSSTSSSTAEAQQQQQQQQQQQQHLEQLLMDLQELL SRMENYRNLKLPRMLTFKFYLPKQATELKDLQCLEDG LGPLRHVLDLTQSKSFQLEDAENFISNIRVTVVKLKGS DNTFECQFDDESATVVDFLRRWIAFCQSIISTSPQ<u>HHHH HH</u> |
| 22 | mIL-2 QQ 6.2-4 (nucleic acid sequence) | GCACCCACCTCAAGCTCCACTTCAAGCTCTACAGCG GAAGCACAACAGCAGCAGCAGCAGCAGCAGCAGCA GCAGCAGCACCTGGAGCAGCTGTTGATGGACCTACA GGAGCTCCTGAGCAGGATGGAGGATTCCAGGAACCT GAGACTCCCCAGGATGCTCACCTTCAAATTTTACTTG CCCAAGCAGGCCACAGAATTGGAAGATCTTCAGTGC CTAGAAGATGAACTTGAACCTCTGCGGCAAGTTCTG GATTTGACTCAAAGCAAAAGCTTTCAATTGGAAGAT GCTGAGAATTTCATCAGCAATATCAGAGTAACTGTT GTAAAACTAAAGGGCTCTGACAACACATTTGAGTGC CAATTCGATGATGAGCCAGCAACTGTGGTGGGCTTT CTGAGGAGATGGATAGCCTTCTGTCAAAGCATCATC TCAACGAGCCCTCAA |
| 23 | mIL-2 QQ 6.2-4 (amino acid sequence) | APTSSSTSSSTAEAQQQQQQQQQQQQHLEQLLMDLQE LLSRMEDSRNLRLPRMLTFKFYLPKQATELEDLQCLED ELEPLRQVLDLTQSKSFQLEDAENFISNIRVTVVKLKGS DNTFECQFDDEPATVVGFLRRWIAFCQSIISTSPQ |
| 24 | mIL-2 QQ 6.2-8 (nucleic acid sequence) | GCACCCACCTCAAGCTCCACTTCAAGCTCTACAGCG GAAGCACAACAGCAGCAGCAGCAGCAGCAGCACCT GGAGCAGCTGTTGATGGACCTACAGGAGCTCCTGAG TAGGATGGAGGATCACAGGAACCTGAGACTCCCCAG GATGCTCACCTTCAAATTTTACTTGCCCAAGCAGGCC ACAGAATTGGAAGATCTTCAGTGCCTAGAAGATGAA CTTGAACCTCTGCGGCAAGTTCTGGATTTGACTCAA AGCAAAAGCTTTCAATTGGAAGATGCTGAGAATTTC ATCAGCAATATCAGAGTAACTGTTGTAAAACTAAAG GGCTCTGACAACACATTTGAGTGCCAATTCGATGAT GAGCCAGCAACTGTGGTGGACTTTCTGAGGAGATGG ATAGCCTTCTGTCAAAGCATCATCTCAACAAGCCCT CGA |
| 25 | mIL-2 QQ 6.2-8 (amino acid sequence) | APTSSSTSSSTAEAQQQQQQQQHLEQLLMDLQELLSR MEDHRNLRLPRMLTFKFYLPKQATELEDLQCLEDELEP LRQVLDLTQSKSFQLEDAENFISNIRVTVVKLKGSDNT FECQFDDEPATVVDFLRRWIAFCQSIISTSPR |
| 26 | mIL-2 QQ 6.2-10 (nucleic acid sequence) | GCACCCACCTCAAGCTCCACTTCAAGCTCTACAGCG GAAGCACAACAGCAGCAGCAGCAGCAGCAGCAGCA GCAGCAGCACCTGGAGCAGCTGTTGATGGACCTACA GGAACTCCTGAGTAGGATGGAGGATCACAGGAACCT GAGACTCCCCAGGATGCTCACCTTCAAATTTTACTTG CCCGAGCAGGCCACAGAATTGGAAGATCTTCAGTGC CTAGAAGATGAACTTGAACCACTGCGGCAAGTTCTG GATTTGACTCAAAGCAAAAGCTTTCAATTGGAAGAT GCTGAGAATTTCATCAGCAATATCAGAGTAACTGTT GTAAAACTAAAGGGCTCTGACAACACATTTGAGTGC CAATTCGACGATGAGCCAGCAACTGTGGTGGACTTT CTGAGGAGATGGATAGCCTTCTGTCAAAGCATCATC TCAACAAGCCCTCAG |
| 27 | mIL-2 QQ 6.2-10 (amino acid sequence) | APTSSSTSSSTAEAQQQQQQQQQQQQHLEQLLMDLQE LLSRMEDHRNLRLPRMLTFKFYLPEQATELEDLQCLED ELEPLRQVLDLTQSKSFQLEDAENFISNIRVTVVKLKGS DNTFECQFDDEPATVVDFLRRWIAFCQSIISTSPQ |

TABLE 5-continued

Sequence Summary

| SEQ ID NO | Description | Sequence |
|---|---|---|
| 28 | mIL-2 QQ 6.2-11 (nucleic acid sequence) | GCACCCACCTCAAGCTCCACTTCAAGCTCTACAGCG GAAGCACAACAGCAGCAGCAGCAGCAGCAGCAGCA CCTGGAGCAGCTGTTGATGGACCTACAGGAGCTCCT GAGCAGGATGGAGGATTCCAGGAACCTGAGACTCCC CAGAATGCTCACCTTCAAATTTTACTTGCCCGAGCA GGCCACAGAATTGAAAGATCTCCAGTGCCTAGAAGA TGAACTTGAACCTCTGCGGCAAGTTCTGGATTTGACT CAAAGCAAAAGCTTTCAATTGGAAGATGCTGAGAAT TTCATCAGCAATATCAGAGTAACTGTTGTAAAACTA AAGGGCTCTGACAACACATTTGAGTGCCAATTCGAC GATGAGCCAGCAACTGTGGTGGACTTTCTGAGGAGA TGGATAGCCTTCTGTCAAAGCATCATCTCAACAAGC CCTCAG |
| 29 | mIL-2 QQ 6.2-11 (amino acid sequence) | APTSSSTSSSTAEAQQQQQQQQHLEQLLMDLQELLSR MEDSRNLRLPRMLTFKFYLPEQATELKDLQCLEDELEP LRQVLDLTQSKSFQLEDAENFISNIRVTVVKLKGSDNT FECQFDDEPATVVDFLRRWIAFCQSIISTSPQ |
| 30 | mIL-2 QQ 6.2-13 (nucleic acid sequence) | GCACCCACCTCAAGCTCCACTTCAAGCTCTACAGCG GAAGCACAACAGCAGCAGCAGCAGCAGCAGCAGCA GCAGCAGCACCTGGAGCAGCTGTTGATGGACCTACA GGAGCTCCTGAGTAGGATGGAGGATCACAGGAACCT GAGACTCCCCAGGATGCTCACCTTCAAATTTTACTTG CCCGAGCAGGCCACAGAATTGAAAGATCTCCAGTGC CTAGAAGATGAACTTGAACCTCTGCGGCAGGTTCTG GATTTGACTCAAAGCAAAAGCTTTCAATTGGAAGAT GCTGAGAATTTCATCAGCAATATCAGAGTAACTGTT GTAAAACTAAAGGGCTCTGACAACACATTTGAGTGC CAATTCGATGATGAGCCAGCAACTGTGGTGGACTTT CTGAGGAGATGGATAGCCTTCTGTCAAAGCATCATC TCAACAAGCCCTCAG |
| 31 | mIL-2 QQ 6.2-13 (amino acid sequence) | APTSSSTSSSTAEAQQQQQQQQQQQHLEQLLMDLQE LLSRMEDHRNLRLPRMLTFKFYLPEQATELKDLQCLE DELEPLRQVLDLTQSKSFQLEDAENFISNIRVTVVKLKG SDNTFECQFDDEPATVVDFLRRWIAFCQSIISTSPQ |
| 32 | Full length human IL-2 (nucleic acid sequence) | ATGTACAGGATGCAACTCCTGTCTTGCATTGCACTA AGTCTTGCACTTGTCACAAACAGTGCACCTACTTCA AGTTCTACAAAGAAAACACAGCTACAACTGGAGCAT TTACTGCTGGATTTACAGATGATTTTGAATGGAATTA ATAATTACAAGAATCCCAAACTCACCAGGATGCTCA CATTTAAGTTTTACATGCCCAAGAAGGCCACAGAAC TGAAACATCTTCAGTGTCTAGAAGAAGAACTCAAAC CTCTGGAGGAAGTGCTAAATTTAGCTCAAAGCAAAA ACTTTCACTTAAGACCCAGGGACTTAATCAGCAATA TCAACGTAATAGTTCTGGAACTAAAGGGATCTGAAA CAACATTCATGTGTAATATGCTGATGAGACAGCAAC CATTGTAGAATTTCTGAACAGATGGATTACCTTTTGT CAAAGCATCATCTCAACACTGACTTGA |
| 33 | Full length human IL-2 (amino acid sequence) | MYRMQLLSCIALSLALVTNSAPTSSSTKKTQLQLEHLL LDLQMILNGINNYKNPKLTRMLTFKFYMPKKATELKH LQCLEEELKPLEEVLNLAQSKNFHLRPRDLISNINVIVL ELKGSETTFMCEYADETATIVEFLNRWITFCQSIISTLT |
| 34 | Human IL-2 without signal peptide (nucleic acid sequence) | GCACCTACTTCAAGTTCTACAAAGAAAACACAGCTA CAACTGGAGCATTTACTGCTGGATTTACAGATGATTT TGAATGGAATTAATAATTACAAGAATCCCAAACTCA CCAGGATGCTCACATTTAAGTTTTACATGCCCAAGA AGGCCACAGAACTGAAACATCTTCAGTGTCTAGAAG AAGAACTCAAACCTCTGGAGGAAGTGCTAAATTTAG CTCAAAGCAAAAACTTTCACTTAAGACCCAGGGACT TAATCAGCAATATCAACGTAATAGTTCTGGAACTAA AGGGATCTGAAACAACATTCATGTGTAATATGCTGA TGAGACAGCAACCATTGTAGAATTTCTGAACAGATG GATTACCTTTTGTCAAAGCATCATCTCAACACTGACT TGA |

TABLE 5-continued

Sequence Summary

| SEQ ID NO | Description | Sequence |
|---|---|---|
| 35 | Human IL-2 without signal peptide (amino acid sequence) | APTSSSTKKTQLQLEHLLLDLQMILNGINNYKNPKLTR MLTFKFYMPKKATELKHLQCLEEELKPLEEVNLAQS KNFHLRPRDLISNINVIVLELKGSETTFMCEYADETATI VEFLNRWITFCQSIISTLT |
| 36 | Human serum albumin (amino acid sequence) | MDMRVPAQLLGLLLLWLPGARCADAHKSEVAHRFKD LGEENFKALVLIAFAQYLQQCPFEDHVKLVNEVTEFAK TCVADESAENCDKSLHTLFGDKLCTVATLRETYGEMA DCCAKQEPERNECFLQHKDDNPNLPRLVRPEVDVMCT AFHDNEETFLKKYLYEIARRHPYFYAPELLFFAKRYKA AFTECCQAADKAACLLPKLDELRDEGKASSAKQRLKC ASLQKFGERAFKAWAVARLSQRFPKAEFAEVSKLVTD LTKVHTECCHGDLLECADDRADLAKYICENQDSISSKL KECCEKPLLEKSHCIAEVENDEMPADLPSLAADFVESK DVCKNYAEAKDVFLGMFLYEYARRHPDYSVVLLLRL AKTYETTLEKCCAAADPHECYAKVFDEFKPLVEEPQN LIKQNCELFEQLGEYKFQNALLVRYTKKVPQVSTPTLV EVSRNLGKVGSKCCKHPEAKRMPCAEDYLSVVLNQLC VLHEKTPVSDRVTKCCTESLVNRRPCFSALEVDETYVP KEFNAETFTFHADICTLSEKERQIKKQTALVELVKHKP KATKEQLKAVMDDFAAFVEKCCKADDKETCFAEEGK KLVAASQAALGLGGGSAPTSSSTKKTQLQLEHLLLDL QMILNGINNYKNPKLTRMLTFKFYMPKKATELKHLQC LEEELKPLEEVNLAQSKNFHLRPRDLISNINVIVLELK GSETTFMCEYADETATIVEFLNRWITFCQSIISTLTGGGS |
| 37 | Mature HSA (amino acid sequence) | DAHKSEVAHRFKDLGEENFKALVLIAFAQYLQQCPFE DHVKLVNEVTEFAKTCVADESAENCDKSLHTLFGDKL CTVATLRETYGEMADCCAKQEPERNECFLQHKDDNPN LPRLVRPEVDVMCTAFHDNEETFLKKYLYEIARRHPYF YAPELLFFAKRYKAAFTECCQAADKAACLLPKLDELR DEGKASSAKQRLKCASLQKFGERAFKAWAVARLSQRF PKAEFAEVSKLVTDLTKVHTECCHGDLLECADDRADL AKYICENQDSISSKLKECCEKPLLEKSHCIAEVENDEMP ADLPSLAADFVESKDVCKNYAEAKDVFLGMFLYEYA RRHPDYSVVLLLRLAKTYETTLEKCCAAADPHECYAK VFDEFKPLVEEPQNLIKQNCELFEQLGEYKFQNALLVR YTKKVPQVSTPTLVEVSRNLGKVGSKCCKHPEAKRMP CAEDYLSVVLNQLCVLHEKTPVSDRVTKCCTESLVNR RPCFSALEVDETYVPKEFNAETFTFHADICTLSEKERQI KKQTALVELVKHKPKATKEQLKAVMDDFAAFVEKCC KADDKETCFAEEGKKLVAASQAALGLGGGSAPTSSST KKTQLQLEHLLLDLQMILNGINNYKNPKLTRMLTFKF YMPKKATELKHLQCLEEELKPLEEVNLAQSKNFHLR PRDLISNINVIVLELKGSETTFMCEYADETATIVEFLNR WITFCQSIISTLTGGGS |
| 38 | Human serum albumin (nucleic acid sequence) | ATGGATATGCGGGTGCCTGCTCAGCTGCTGGGACTG CTGCTGCTGTGGCTGCCTGGGGCTAGATGCGCCGAT GCTCACAAAAGCGAAGTCGCACACAGGTTCAAAGAT CTGGGGGAGGAAAACTTTAAGGCTCTGGTGCTGATT GCATTCGCCCAGTACCTGCAGCAGTGCCCCTTTGAG GACCACGTGAAACTGGTCAACGAAGTGACTGAGTTC GCCAAGACCTGCGTGGCCGACGAATCTGCTGAGAAT TGTGATAAAAGTCTGCATACTCTGTTTGGGGATAAG CTGTGTACAGTGGCCACTCTGCGAGAAACCTATGGA GAGATGGCAGACTGCTGTGCCAAACAGGAACCCGA GCGGAACGAATGCTTCCTGCAGCATAAGGACGATAA CCCCAATCTGCCTCGCCTGGTGCGACCTGAGGTGGA CGTCATGTGTACAGCCTTCCACGATAATGAGGAAAC TTTTCTGAAGAAATACCTGTACGAAATCGCTCGGAG ACATCCTTACTTTTATGCACCAGAGCTGCTGTTCTTT GCCAAACGCTACAAGGCCGCTTTCACCGAGTGCTGT CAGGCAGCCGATAAAGCTGCATGCCTGCTGCCTAAG CTGGACGAACTGAGGGATGAGGGCAAGGCCAGCTC CGCTAAACAGCGCCTGAAGTGTGCTAGCCTGCAGAA ATTCGGGGAGCGAGCCTTCAAGGCTTGGGCAGTGGC ACGGCTGAGTCAGAGATTCCCAAAGGCAGAATTTGC CGAGGTCTCAAAACTGGTGACCGACCTGACAAAGGT GCACACCGAATGCTGTCATGGCGACCTGCTGGAGTG CGCCGACGATCGAGCTGATCTGGCAAAGTATATTTG TGAGAACCAGGACTCCATCTCTAGTAAGCTGAAAGA ATGCTGTGAGAAACCACTGCTGGAAAAGTCTCACTG CATTGCCGAAGTGGAGAACGACGAGATGCCAGCTG |

TABLE5-continued

Sequence Summary

| SEQ ID NO | Description | Sequence |
|---|---|---|
| | | ATCTGCCCTCACTGGCCGCTGACTTCGTCGAAAGCA AAGATGTGTGTAAGAATTACGCTGAGGCAAAGGATG TGTTCCTGGGAATGTTTCTGTACGAGTATGCCAGGC GCCACCCAGACTACTCCGTGGTCCTGCTGCTGAGGC TGGCTAAAACATATGAAACCACACTGGAGAAGTGCT GTGCAGCCGCTGATCCCCATGAATGCTATGCCAAAG TCTTCGACGAGTTTAAGCCCCTGGTGGAGGAACCTC AGAACCTGATCAAACAGAATTGTGAACTGTTTGAGC AGCTGGGCGAGTACAAGTTCCAGAACGCCCTGCTGG TGCGCTATACCAAGAAAGTCCCACAGGTGTCCACAC CCACTCTGGTGGAGGTGAGCCGGAATCTGGGCAAAG TGGGGAGTAAATGCTGTAAGCACCCTGAAGCCAAGA GGATGCCATGCGCTGAGGATTACCTGAGTGTGGTCC TGAATCAGCTGTGTGTCCTGCATGAAAAAACACCTG TCAGCGACCGGGTGACAAAGTGCTGTACTGAGTCAC TGGTGAACCGACGGCCCTGCTTTAGCGCCCTGGAAG TCGATGAGACTTATGTGCCTAAAGAGTTCAACGCTG AGACCTTCACATTTCACGCAGACATTTGTACCCTGA GCGAAAAGGAGAGACAGATCAAGAAACAGACAGCC CTGGTCGAACTGGTGAAGCATAAACCCAAGGCCACA AAAGAGCAGCTGAAGGCTGTCATGGACGATTTCGCA GCCTTTGTGGAAAAATGCTGTAAGGCAGACGATAAG GAGACTTGCTTTGCCGAGGAAGGAAAGAAACTGGTG GCTGCATCCCAGGCAGCTCTGGGACTGGGAGGAGGA TCTGCCCCTACCTCAAGCTCCACTAAGAAAACCCAG CTGCAGCTGGAGCACCTGCTGCTGGACCTGCAGATG ATTCTGAACGGGATCAACAATTACAAAAATCCAAAG CTGACCCGGATGCTGACATTCAAGTTTTATATGCCCA AGAAAGCCACAGAGCTGAAACACCTGCAGTGCCTG GAGGAAGAGCTGAAGCCTCTGGAAGAGGTGCTGAA CCTGGCCCAGAGCAAGAATTTCCATCTGAGACCAAG GGATCTGATCTCCAACATTAATGTGATCGTCCTGGA ACTGAAGGGATCTGAGACTACCTTTATGTGCGAATA CGCTGACGAGACTGCAACCATTGTGGAGTTCCTGAA CAGATGGATCACCTTCTGCCAGTCCATCATTTCTACT CTGACAGGCGGGGGAGC |
| 39 | EETI-II from Knottin Database | GC PRILMR CKQDSDCLAGCVCGPNGFCG |
| 40 | AgRP from Knottin Database "-" indicates where mini protein can be formed | GCVRLHESCLGQQVPCCDPCATCYCRFFNAFCYCR-KLGTAMNPCSRT |
| 41 | Omega agatoxin from Knottin Database "-" indicates where mini Protein can be formed | EDN--CIAEDYGKCTWGGTKCCRGRPCRC SMIGTN CECTPRLIMEGLSFA |
| 42 | EETI-II Library | GCX$_1$X$_2$X$_3$RGDX$_7$X$_8$X$_9$X$_{10}$X$_{11}$CKQDSDCLAGCVCGPNGF CG |
| 43 | EETI-II K15S Mutation Library | GCX$_1$X$_2$X$_3$RGDX$_7$X$_8$X$_9$X$_{10}$X$_{11}$CSQDSDCLAGCVCGPNGF CG |
| 44 | 2.5F- (K15S) mIgG2aFc Nucleic Acid Sequence | GGTTGTCCAAGACCAAGAGGTGATAATCCACCATTG ACTTGTTCTCAAGATTCTGATTGTTTGGCTGGTTGTG TTTGTGGTCCAAATGGTTTTTGTGGTGGTCGACTAGA GCCCAGAGTGCCCATAACACAGAACCCCTGTCCTCC ACTCAAAGAGTGTCCCCCATGCGCAGCTCCAGACCT CTTGGGTGGACCATCCGTCTTCATCTTCCCTCCAAAG ATCAAGGATGTACTCATGATCTCCCTGAGCCCCATG GTCACATGTGTGGTGGTGGATGTGAGCGAGGATGAC CCAGACGTCCAGATCAGCTGGTTTGTGAACAACGTG GAAGTACACACAGCTCAGACACAAACCCATAGAGA GGATTACAACAGTACTCTCCGGGTGGTCAGTGCCCT CCCCATCCAGCACCAGGACTGGATGAGTGGCAAGGA GTTCAAATGCAAGGTCAACAACAGAGCCCTCCCATC CCCCATCGAGAAAACCATCTCAAAACCCAGAGGGCC AGTAAGAGCTCCACAGGTATATGTCTTGCCTCCACC AGCAGAAGAGATGACTAAGAAAGAGTTCAGTCTGA CCTGCATGATCACAGGCTTCTTACCTGCCGAAATTGC TGTGGACTGGACCAGCAATGGGCGTACAGAGCAAA ACTACAAGAACACCGCAACAGTCCTGGACTCTGATG |

TABLE 5-continued

Sequence Summary

| SEQ ID NO | Description | Sequence |
|---|---|---|
| | | GTTCTTACTTCATGTACAGCAAGCTCAGAGTACAAA AGAGCACTTGGGAAAGAGGAAGTCTTTTCGCCTGCT CAGTGGTCCACGAGGGTCTGCACAATCACCTTACGA CTAAGACCATCTCCCGGTCTCTGGGTAAA |
| 45 | 2.5F- (K15S) mIgG2aFc Amino Acid Sequence | GCPRPRGDNPPLTCSQDSDCLAGCVCGPNGFCGEPRVP ITQNPCPPLKECPPCAAPDLLGGPSVFIFPPKIKDVLMIS LSPMVTCVVVDVSEDDPDVQISWFVNNVEVHTAQTQT HREDYNSTLRVVSALPIQHQDWMSGKEFKCKVNNRA LPSPIEKTISKPRGPVRAPQVYVLPPPAEEMTKKEFSLT CMITGFLPAEIAVDWTSNGRTEQNYKNTATVLDSDGS YFMYSKLRVQKSTWERGSLFACSVVHEGLHNHLTTKT ISRSLGK |
| 46 | 2.5D- (K15S) mIgG2aFc Nucleic Acid Sequence | GGTTGTCCACAAGGCAGAGGTGATTGGGCTCCAACT TCTTGTTCTCAAGATTCTGATTGTTTGGCTGGTTGTG TTTGTGGTCCAAATGGTTTTTGTGGTGGTCGACTAGA GCCCAGAGTGCCCATAACACAGAACCCCTGTCCTCC ACTCAAAGAGTGTCCCCCATGCGCAGCTCCAGACCT CTTGGGTGGACCATCCGTCTTCATCTTCCCTCCAAAG ATCAAGGATGTACTCATGATCTCCCTGAGCCCCATG GTCACATGTGTGGTGGTGGATGTGAGCGAGGATGAC CCAGACGTCCAGATCAGCTGGTTTGTGAACAACGTG GAAGTACACACAGCTCAGACACAAACCCATAGAGA GGATTACAACAGTACTCTCCGGGTGGTCAGTGCCCT CCCCATCCAGCACCAGGACTGGATGAGTGGCAAGGA GTTCAAATGCAAGGTCAACAACAGAGCCCTCCCATC CCCCATCGAGAAAACCATCTCAAACCCAGAGGGCC AGTAAGAGCTCCACAGGTATATGTCTTGCCTCCACC AGCAGAAGAGATGACTAAGAAAGAGTTCAGTCTGA CCTGCATGATCACAGGCTTCTTACCTGCCGAAATTGC TGTGGACTGGACCAGCAATGGGCGTACAGAGCAAA ACTACAAGAACACCGCAACAGTCCTGGACTCTGATG GTTCTTACTTCATGTACAGCAAGCTCAGAGTACAAA AGAGCACTTGGGAAAGAGGAAGTCTTTTCGCCTGCT CAGTGGTCCACGAGGGTCTGCACAATCACCTTACGA CTAAGACCATCTCCCGGTCTCTGGGTAAA |
| 47 | 2.5D- (K15S) mIgG2aFc Amino Acid Sequence | GCPQGRGDWAPTSCSQDSDCLAGCVCGPNGFCGEPRV PITQNPCPPLKECPPCAAPDLLGGPSVFIFPPKIKDVLMI SLSPMVTCVVVDVSEDDPDVQISWFVNNVEVHTAQTQ THREDYNSTLRVVSALPIQHQDWMSGKEFKCKVNNR ALPSPIEKTISKPRGPVRAPQVYVLPPPAEEMTKKEFSL TCMITGFLPAEIAVDWTSNGRTEQNYKNTATVLDSDG SYFMYSKLRVQKSTWERGSLFACSVVHEGLHNHLTTK TISRSLGK |
| 48 | 2.5F- (K15S) hIgG1Fc Amino Acid Sequence | GCPRPRGDNPPLTCSQDSDCLAGCVCGPNGFCGEPKSC DKTHTCPPCPAPELLGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALPAPI EKTISKAKGQPREPQVYTLPPSREEMTKNQVSLTCLVK GFYPSDIAVEWESNGQPENNYKTTPPVLDSDGSFFLYS KLTVDKSRWQQGNVFSCSVMHEALHNHYTQKSLSLSP GK |
| 49 | 2.5F- (K15S) hIgG1Fc Fc Upper Hinge Deletion (ΔEPKSC) Amino Acid Sequence | GCPRPRGDNPPLTCSQDSDCLAGCVCGPNGFCGDKTH TCPPCPAPELLGGPSVFLFPPKPKDTLMISRTPEVTCVV VDVSHEDPEVKFNWYVDGVEVHNAKTKPREEQYNST YRVVSVLTVLHQDWLNGKEYKCKVSNKALPAPIEKTI SKAKGQPREPQVYTLPPSREEMTKNQVSLTCLVKGFYP SDIAVEWESNGQPENNYKTTPPVLDSDGSFFLYSKLTV DKSRWQQGNVFSCSVMHEALHNHYTQKSLSLSPGK |
| 50 | 2.5D- (K15S) hIgG1Fc Amino Acid Sequence | GCPQGRGDWAPTSCSQDSDCLAGCVCGPNGFCGEPKS CDKTHTCPPCPAPELLGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALPA PIEKTISKAKGQPREPQVYTLPPSREEMTKNQVSLTCLV KGFYPSDIAVEWESNGQPENNYKTTPPVLDSDGSFFLY SKLTVDKSRWQQGNVFSCSVMHEALHNHYTQKSLSLS PGK |

TABLE 5-continued

Sequence Summary

| SEQ ID NO | Description | Sequence |
|---|---|---|
| 51 | 2.5D- (K15S) hIgG1Fc Fc Upper Hinge Deletion (ΔEPKSC) Amino Acid Sequence | GCPQGRGDWAPTSCSQDSDCLAGCVCGPNGFCGDKT HTCPPCPAPELLGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALPAPIEKT ISKAKGQPREPQVYTLPPSREEMTKNQVSLTCLVKGFY PSDIAVEWESNGQPENNYKTTPPVLDSDGSFFLYSKLT VDKSRWQQGNVFSCSVMHEALHNHYTQKSLSLSPGK |
| 52 | hPD-1 amino acid sequence | MQIPQAPWPVVWAVLQLGWRPGWFLDSPDPWNPPTF FPALLVVTEGDNATFTCSFSNTSESFVLNWYRMSPSNQ TDKLAAFPEDRSQPGQDCRFRVTQLPNGRDFHMSVVR ARRNDSGTYLCGAISLAPKAQIKESLRAELRVTERRAE VPTAHPSPSPRPAGQFQTLVVGVVGGLLGSLVLLVWV LAVICSRAARGTIGARRTGQPLKEDPSAVPVFSVDYGE LDFQWREKTPEPPVPCVPEQTEYATIVFPSGMGTSSPA RRGSADGPRSAQPLRPEDGHCSWPL |
| 53 | hPD-L-1 amino acid sequence | MRIFAVFIFMTYWHLLNAFTVTVPKDLYVVEYGSNMT IECKFPVEKQLDLAALIVYWEMEDKNIIQFVHGEEDLK VQHSSYRQRARLLKDQLSLGNAALQITDVKLQDAGVY RCMISYGGADYKRITVKVNAPYNKINQRILVVDPVTSE HELTCQAEGYPKAEVIWTSSDHQVLSGKTTTTNSKREE KLFNVTSTLRINTTTNEIFYCTFRRLDPEENHTAELVIPE LPLAHPPNERTHLVILGAILLC LGVALTFIFR LRKGRMMDVKKCGIQDTNSK KQSDTHLEET |
| 54 | hCTLA-4 amino acid sequence | MACLGFQRHKAQLNLATRTWPCTLFFLLFIPVFCKA MHVAQPAVVLASSRGIASFVCEYASPGKATEVRVTVL RQADSQVTEVCAATYMMGNELTFLDDSICTGTSSGNQ VNLTIQGLRAMDTGLYICKVELMYPPPYY LGIGNGTQIY VIDPEPCPDS DFLLWILAAVSSGLFFYSFL LTAVSLSKML KKRSPLTTGVYVKMPPTEPE CEKQFQPYFI PIN |
| 55 | hLAG3 amino acid sequence | MWEAQFLGLLFLQPLWVAPVKPLQPGAEVPVVWAQE GAPAQLPCSPTIPLQDLSLLRRAGVTWQHQPDSGPPAA APGHPLAPGPHPAAPSSWGPRPRRYTVLSVGPGGLRSG RLPLQPRVQLDERGRQRGDFSLWLRPARRADAGEYRA AVHLRDRALSCRLRLRLGQASMTASPPGSLRASDWVI LNCSFSRPDRPASVHWFRNRGQGRVPVRESPHHHLAE SFLFLPQVSPMDSGPWGCILTYRDGFNVSIMYNLTVLG LEPPTPLTVYAGAGSRVGLPCRLPAGVGTRSFLTAKWT PPGGGPDLLVTGDNGDFTLRLEDVSQAQAGTYTCHIH LQEQQLNATVTLAIITVTPKSFGSPGSLGKLLCEVTPVS GQERFVWSSLDTPSQRSFSGPWLEAQEAQLLSQPWQC QLYQGERLLGAAVYFTELSSPGAQRSGRAPGALPAGH L LLFLILGVLSLLLLVTGAFGFHLWRRQWRPRRFSALEQ GIHPPQAQSKIE ELEQEPEPEP EPEPEPEPEP EPEQL |
| 56 | hTIM3 amino acid sequence | MFSHLPFDCVLLLLLLLTRSSEVEYRAEVGQNAYLPC FYTPAAPGNLVPVCWGKGACPVFECGNVVLRTDERD VNYWTSRYWLNGDFRKGDVSLTIENVTLADSGIYCCR IQIPGIMNDEKFNLKLVIKPAKVTPAPTR QRDFTAAFPR MLTTRGHGPA ETQTLGSLPDINLTQISTLA NELRDSRLANDLRDSGATIRGIYIGAGICAGLALALIFG ALIFKWYSHSKEKIQNLSLISLANLPPSGLANAVAEGIR SEENIYTIEENVYEVEEPNEYYCYVSSRQQPSQPLGCRF AMP |
| 57 | hB7-H3 amino acid sequence | MLRRRGSPGMGVHVGAALGALWFCLTGALEVQVPED PVVALVGTDATLCCSFSPEPGFSLQLNLIWQLTDTKQL VHSFAEGQDQGSAYANRTALFPDLLAQGNASLRLQRV RVADEGSFCFVSIRDFGSAAVSLQVAA PYSKPSMTLEPNKDLRPGDTVTITCSSYQGYPEAEVFW QD GQGVPLTGNVTTSQMANEQGLFDVHSILRVVLGANGT YSCLVRNPVLQQDAHSSVTITPQRSPTGAVEVQVPEDP VVALVGTDATLRCSF SPEPGFSLAQLNLIWQLTDTKQLVHSFTEGRDQGSAYA NRTALFPDLLAQ GNASLRLQRVRVADEGSFTCFVSIRDFGSAAVSLQVAA PY |

TABLE 5-continued

Sequence Summary

| SEQ ID NO | Description | Sequence |
|---|---|---|
| | | SKPSMTLEPNKDLRPGDTVTITCSSYRGYPEAEVFWQD GQGVPLTGNVTTSQMANEQGLFDVHSVLRVVLGANG TYSCLVRNPVLQQDAHGSVTITGQPMTFPPEALWVTV GLSVCLIALLVALAFVCWRKIKQSCEEEN AGAEDQDGEGEGSKTALQPLKHSDSKEDDGQEIA |
| 58 | hB7-H4 amino acid sequence | MASLGQILFWSIISIIIILAGAIALIIGFGISAFSMPEVNVD YNASSETLRCEAPRWFPQPTVVWASQVDQGANFSEVS NTSFELNSENVTMKVVSVLYN VTINNTYSCM IENDIAKATGDIKVTESEIKRRSHLQLLNS KASLCVSSFFAISWALLPLSPYLMLK |
| 59 | EETI-II 1.4A | GCAEPRGDMPWTWCKQDSDCLAGCVCGPNGFCG |
| 60 | EETI-II 1.4B | GCVGGRGDWSPKWCKQDSDCPAGCVCGPNGFCG |
| 61 | EETI-II 1.4C | GC AELRGDRSYPE CKQDSDCLAGCVCGPNGFCG |
| 62 | EETI-II 1.4E | GC RLPRGDVPRPH CKQDSDCQAGCVCGPNGFCG |
| 63 | EETI-II 1.4H | GC YPLRGDNPYAA CKQDSDCRAGCVCGPNGFCG |
| 64 | EETI-II 1.5B | GC TIGRGDWAPSE CKQDSDCLAGCVCGPNGFCG |
| 65 | EETI-II 1.5F | GC HPPRGDNPPVT CKQDSDCLAGCVCGPNGFCG |
| 66 | EETI-II 2.3A | GC PEPRGDNPPPS CKQDSDCRAGCVCGPNGFCG |
| 67 | EETI-II 2.3B | GC LPPRGDNPPPS CKQDSDCQAGCVCGPNGFCG |
| 68 | EETI-II 2.3C | GCHLGRGDWAPVGCKQDSDCPAGCVCGPNGFCG |
| 69 | EETI-II 2.3D | GC NVGRGDWAPSECKQDSDCPAGCVCGPNGFCG |
| 70 | EETI-II 2.3E | GC FPGRGDWAPSSCKQDSDCRAGCVCGPNGFCG |
| 71 | EETI-II 2.3F | GC PLPRGDNPPTE CKQDSDCQAGCVCGPNGFCG |
| 72 | EETI-II 2.3G | GC SEARGDNPRLS CKQDSDCRAGCVCGPNGFCG |
| 73 | EETI-II 2.3H | GCLLGRGDWAPEACKQDSDCRAGCVCGPNGFCG |
| 74 | EETI-II 2.3I | GCHVGRGDWAPLKCKQDSDCQAGCVCGPNGFCG |
| 75 | EETI-II 2.3J | GC VRGRGDWAPPSCKQDSDCPAGCVCGPNGFCG |
| 76 | EETI-II 2.4A | GCLGGRGDWAPPACKQDSDCRAGCVCGPNGFCG |
| 77 | EETI-II 2.4C | GC FVGRGDWAPLTCKQDSDCQAGCVCGPNGFCG |
| 78 | EETI-II 2.4D | GC PVGRGDWSPASCKQDSDCRAGCVCGPNGFCG |
| 79 | EETI-II 2.4E | GC PRPRGDNPPLTCKQDSDCLAGCVCGPNGFCG |
| 80 | EETI-II 2.4F | GC YQGRGDWSPSSCKQDSDCPAGCVCGPNGFCG |
| 81 | EETI-II 2.4G | GC APGRGDWAPSECKQDSDCQAGCVCGPNGFCG |
| 82 | EETI-II 2.4J | GC VQGRGDWSPPSCKQDSDCPAGCVCGPNGFCG |
| 83 | EETI-II 2.5A | GC HVGRGDWAPEECKQDSDCQAGCVCGPNGFCG |
| 84 | EETI-II 2.5C | GC DGGRGDWAPPACKQDSDCRAGCVCGPNGFCG |
| 85 | EETI-II 2.5D | GC PQGRGDWAPTSCKQDSDCRAGCVCGPNGFCG |
| 86 | EETI-II 2.5F | GC PRPRGDNPPLTCKQDSDCLAGCVCGPNGFCG |
| 87 | EETI-II 2.5DK15S Mutant | GCPQGRGDWAPTSCSQDSDCLAGCVCGPNGFCG |
| 88 | EETI-II 2.5FK15S Mutant | GCPRPRGDNPPLTCSQDSDCLAGCVCGPNGFCG |
| 89 | EETI-II 2.5H | GCPQGRGDWAPEWCKQDSDCPAGCVCGPNGFCG |

TABLE 5-continued

Sequence Summary

| SEQ ID NO | Description | Sequence |
|---|---|---|
| 90 | EETI-II 2.5J | GCPRGRGDWSPPACKQDSDCQAGCVCGPNGFCG |
| 91 | AgRp 3A | GCVRLHESCLGQQVPCCDPAATCYCVVRGDWRKRCYCR |
| 92 | AgRp 3B | GCVRLHESCLGQQVPCCDPAATCYCEERGDMLEKCYCR |
| 93 | AgRp 3C | GCVRLHESCLGQQVPCCDPAATCYCETRGDGKEKCYCR |
| 94 | AgRp 3D | GCVRLHESCLGQQVPCCDPAATCYCQWRGDGDVKCYCR |
| 95 | AgRp 3E | GCVRLHESCLGQQVPCCDPAATCYCSRRGDMRERCYCR |
| 96 | AgRp 3F | GCVRLHESCLGQQVPCCDPAATCYCQYRGDGMKHCYCR |
| 97 | AgRp 3G | GCVRLHESCLGQQVPCCDPAATCYCTGRGDTKVLCYCR |
| 98 | AgRp 3H | GCVRLHESCLGQQVPCCDPAATCYCVERGDMKRRCYCR |
| 99 | AgRp 3I | GCVRLHESCLGQQVPCCDPAATCYCTGRGDVRMNCYCR |
| 100 | AgRp 3J | GCVRLHESCLGQQVPCCDPAATCYCVERGDGMSKCYCR |
| 101 | AgRp 4A | GCVRLHESCLGQQVPCCDPAATCYCRGRGDMRRECYCR |
| 102 | AgRp 4B | GCVRLHESCLGQQVPCCDPAATCYCEGRGDVKVNCYCR |
| 103 | AgRp 4C | GCVRLHESCLGQQVPCCDPAATCYCVGRGDEKMSCYCR |
| 104 | AgRp 4D | GCVRLHESCLGQQVPCCDPAATCYCVSRGDMRKRCYCR |
| 105 | AgRp 4E | GCVRLHESCLGQQVPCCDPAATCYCERRGDSVKKCYCR |
| 106 | AgRp 4F | GCVRLHESCLGQQVPCCDPAATCYCEGRGDTRRRCYCR |
| 107 | AgRp 4G | GCVRLHESCLGQQVPCCDPAATCYCEGRGDVVRRCYCR |
| 108 | AgRp 4H | GCVRLHESCLGQQVPCCDPAATCYCKGRGDNKRKCYCR |
| 109 | AgRp 4I | GCVRLHESCLGQQVPCCDPAXTCYCKGRGDVRRVCYCR |
| 110 | AgRp 4J | GCVRLHESCLGQQVPCCDPAATCYCVGRGDNKVKCYCR |
| 111 | AgRp 5A | GCVRLHESCLGQQVPCCDPAATCYCVGRGDNRLKCYCR |
| 112 | AgRp 5B | GCVRLHESCLGQQVPCCDPAATCYCVERGDGMKKCYCR |
| 113 | AgRp 5C | GCVRLHESCLGQQVPCCDPAATCYCEGRGDMRRRCYCR |
| 114 | AgRp 5D | GCVRLHESCLGQQVPCCDPAATCYCQGRGDGDVKCYCR |

TABLE 5-continued

Sequence Summary

| SEQ ID NO | Description | Sequence |
|---|---|---|
| 115 | AgRp 5E | GCVRLHESCLGQQVPCCDPAATCYCSGRGDNDLVCYCR |
| 116 | AgRp 5F | GCVRLHESCLGQQVPCCDPAATCYCVERGDMIRCYCR |
| 117 | AgRp 5G | GCVRLHESCLGQQVPCCDPAATCYCSGRGDNDLVCYCR |
| 118 | AgRp 5H | GCVRLHESCLGQQVPCCDPAATCYCEGRGDMKMKCYCR |
| 119 | AgRp 5I | GCVRLHESCLGQQVPCCDPAATCYCIGRGDVRRRCYCR |
| 120 | AgRp 5J | GCVRLHESCLGQQVPCCDPAATCYCEERGDGRKKCYCR |
| 121 | AgRp 6B | GCVRLHESCLGQQVPCCDPAATCYCEGRGDRDMKCYCR |
| 122 | AgRp 6C | GCVRLHESCLGQQVPCCDPAATCYCTGRGDEKLRCYCR |
| 123 | AgRp 6E | GCVRLHESCLGQQVPCCDPAATCYCVERGDGNRRCYCR |
| 124 | AgRp 6F | GCVRLHESCLGQQVPCCDPAATCYCESRGDVVRKCYCR |
| 125 | AgRp 7C | GCVRLHESCLGQQVPCCDPAATCYCYGRGDNDLRCYCR |
| 126 | Linker | Ser(Gly$_4$Ser)n |
| 127 | Linker | Ser(Gly$_4$Ser)3 |
| 128 | Linker | (Gly$_4$Ser)n |
| 129 | Linker | (Gly$_3$Ser)n |
| 130 | lipophilic-CpG oligonucleotide conjugate | 5'-L-G$_n$TCCATGACGTTCCTGACGTT-3'  L = lipophilic compound; Gn = guanine repeat linker; n = 1, 2, 3, 4 or 5. |
| 131 | 2.5F- (K15S) mIgG2aFc (Amino Acid Sequence with D265A mutation; signal peptide in bold) | MRVPAQLLGLLLLWLPGARCGCPRPRGDNPPLTCSQDSDCLAGCVCGPNGFCGGRLEPRVPITQNPCPPLKECPPCAAPDLLGGPSVFIFPPKIKDVLMISLSPMVTCVVVDVSEDDPDVQISWFVNNVEVHTAQTQTHREDYNSTLRVVSALPIQHQDWMSGKEFKCKVNNRALPSPIEKTISKPRGPVRAPQVYVLPPPAEEMTKKEFSLTCMITGFLPAEIAVDWTSNGRTEQNYKNTATVLDSDGSYFMYSKLRVQKSTWERGSLFACSVVHEGLHNHLTTKTISRSLGK |
| 132 | Mature 2.5F- (K15S) mIgG2aFc (Amino Acid Sequence with D265A mutation) | GCPRPRGDNPPLTCSQDSDCLAGCVCGPNGFCGGRLEPRVPITQNPCPPLKECPPCAAPDLLGGPSVFIFPPKIKDVLMISLSPMVTCVVVDVSEDDPDVQISWFVNNVEVHTAQTQTHREDYNSTLRVVSALPIQHQDWMSGKEFKCKVNNRALPSPIEKTISKPRGPVRAPQVYVLPPPAEEMTKKEFSLTCMITGFLPAEIAVDWTSNGRTEQNYKNTATVLDSDGSYFMYSKLRVQKSTWERGSLFACSVVHEGLHNHLTTKTISRSLGK |
| 133 | 2.5F- (K15S) mIgG2aFc (Amino Acid Sequence with LALA-PG mutation; signal peptide in bold) | MDAMKRGLCCVLLLCGAVFVSPSGCPRPRGDNPPLTCSQDSDCLAGCVCGPNGFCGGRLEPRVPITQNPCPPLKECPPCAAPDAAGGPSVFIFPPKIKDVLMISLSPMVTCVVVDVSEDDPDVQISWFVNNVEVHTAQTQTHREDYNSTLRVVSALPIQHQDWMSGKEFKCKVNNRALGSPIEKTISKPRGPVRAPQVYVLPPPAEEMTKKEFSLTCMITGFLPAEIAVDWTSNGRTEQNYKNTATVLDSDGSYFMYSKLRVQKSTWERGSLFACSVVHEGLHNHLTTKTISRSLGK |

TABLE 5-continued

Sequence Summary

| SEQ ID NO | Description | Sequence |
|---|---|---|
| 134 | Mature 2.5F- (K15S) mIgG2aFc (Amino Acid Sequence with LALA-PGmutation) | GCPRPRGDNPPLTCSQDSDCLAGCVCGPNGFCGGRLEP RVPITQNPCPPLKECPPCAAPDAAGGPSVFIFPPPKIKDVL MISLSPMVTCVVVDVSEDDPDVQISWFVNNVEVHTAQ TQTHREDYNSTLRVVSALPIQHQDWMSGKEFKCKVNN RALGSPIEKTISKPRGPVRAPQVYVLPPPAEEMTKKEFS LTCMITGFLPAEIAVDWTSNGRTEQNYKNTATVLDSD GSYFMYSKLRVQKSTWERGSLFACSVVHEGLHNHLTT KTISRSLGK |
| 135 | Human IgG1 Fc upper hinge | EPKSC |
| 136 | Integrin binding loop | $X_1X_2X_3RGD_X7X_8X_9X_{10}X_{11}$   X = any amino acid |
| 137 | Linker | Ser(Gly$_4$Ser)4 |
| 138 | Lipid-linker | lipo-G$_6$T$_4$-CG   lipo = lipid tail (diacyl tail) |

EQUIVALENTS

Those skilled in the art will recognize or be able to ascertain, using no more than routine experimentation, many equivalents of the specific embodiments described herein described herein. Such equivalents are intended to be encompassed by the following claims.

---

The invention claimed is:

1. A method for treating a cancer in a subject, comprising administering to the subject:
   (a) a priming dose comprising (i) interleukin (IL)-2, (ii) an immune checkpoint inhibitor polypeptide, and (iii) an integrin-binding polypeptide, wherein the priming dose induces or enhances an anti-tumor immune response in the subject; and
   (b) at least one maintenance dose comprising an immune checkpoint inhibitor polypeptide,
   wherein the priming dose is administered at least four days prior to the at least one maintenance dose, thereby treating cancer in the subject.

2. The method of claim 1, wherein IL-2 is Proleukin.

3. The method of claim 1, wherein IL-2 is administered at a dose of less than 14 MIU/m$^2$, less than 12 MIU/m$^2$, less than 10 MIU/m$^2$, less than 8 MIU/m$^2$, less than 6 MIU/m$^2$, less than 4 MIU/m$^2$, or less than 2 MIU/m$^2$.

4. The method of claim 1, wherein IL-2 is an extended pharmacokinetic (PK) IL-2.

5. The method of claim 4, wherein the extended-PK IL-2 comprises a fusion protein.

6. The method of claim 5, wherein the fusion protein comprises an IL-2 moiety and a moiety selected from the group consisting of an immunoglobulin fragment, an immunoglobulin Fc domain, human serum albumin, and Fn3.

7. The method of claim 4, wherein the extended-PK IL-2 comprises an IL-2 moiety conjugated to a non-protein polymer.

8. The method of claim 1, wherein the immune checkpoint inhibitor polypeptide of the priming dose is:
   (i) an antibody or antibody fragment targeting PD-1, PD-L1, CTLA-4, LAG3, TIM3, or a member of the B7 ligand family;
   (ii) an antibody or antibody fragment targeting PD-1;
   (iii) an antibody or antibody fragment targeting PD-1 selected from the group consisting of: nivolumab and pembrolizumab;
   (iv) an antibody or antibody fragment targeting PD-L1;
   (v) an antibody or antibody fragment targeting PD-L1 selected from the group consisting of: atezolizumab, avelumab, and durvalumab;
   (vi) an antibody or antibody fragment targeting CTLA-4; or
   (v) an antibody or antibody fragment targeting CTLA-4 selected from the group consisting of: tremelimumab and ipilimumab.

9. The method of claim 1, wherein the integrin-binding polypeptide comprises an integrin-binding loop and a knottin polypeptide scaffold, and wherein the integrin-binding polypeptide binds to a tumor-associated integrin selected from the group consisting of $\alpha_v\beta_3$, $\alpha_v\beta_5$, $\alpha_5\beta_1$, or combination thereof.

10. The method of claim 1, wherein the integrin-binding polypeptide is operably linked to an immunoglobulin Fc domain.

11. The method of claim 9, wherein the knottin polypeptide scaffold comprises at least three cysteine disulfide linkages or crosslinked cysteine residues, and wherein the integrin-binding loop is adjacent to cysteine residues of the knottin polypeptide scaffold, or wherein the knottin polypeptide scaffold is derived from a knottin peptide selected from the group consisting of EETI-II, AgRP, and agatoxin.

12. The method of claim 9, wherein the knottin polypeptide scaffold is derived from EETI-II and the integrin-binding loop comprises the sequence $X_1X_2X_3RGDX_7X_8X_9X_{10}X_{11}$ (SEQ ID NO: 136), wherein each X represents any amino acid, wherein the loop is inserted between 2 cysteine residues in the EETI-II sequence and replaces the native EETI-II sequence.

13. The method of claim 1, wherein the integrin-binding polypeptide comprises;
(i) the amino acid sequence set forth SEQ ID NO: 42 or 43, wherein X1 is selected from the group consisting of A, V, L, P, F, Y, S, H, D, and N; X2 is selected from the group consisting of G, V, L, P, R, E, and Q; X3 is selected from the group consisting of G, A, and P; X7 is selected from the group consisting of W and N; Xg is selected from the group consisting of A, P, and S; X9 is selected from the group consisting of P and R; X10 is selected from the group consisting of A, V, L, P, S, T, and E; and Xn is selected from the group consisting of G, A, W, S, T, K, and E;
(ii) an amino acid sequence selected from the group consisting of SEQ ID NOs: 59-125; or
(iii) the amino acid sequence of SEQ ID NO: 86 or 88.

14. The method of claim 10, wherein the integrin-binding polypeptide operably linked to an immunoglobulin Fc domain comprises the amino acid sequence of SEQ ID NO: 48, 49, 50, or 51.

15. The method of claim 1, wherein the immune checkpoint inhibitor polypeptide of the maintenance dose is:
(i) an antibody or antibody fragment targeting PD-1, PD-L1, CTLA-4, LAG3, TIM3, or a member of the B7 ligand family;
(ii) an antibody or antibody fragment targeting PD-1;
(iii) an antibody or antibody fragment targeting PD-1 is selected from the group consisting of: nivolumab and pembrolizumab;
(iv) an antibody or antibody fragment targeting PD-L1;
(v) an antibody or antibody fragment targeting PD-L1 is selected from the group consisting of: atezolizumab, avelumab, and durvalumab;
(vi) an antibody or antibody fragment targeting CTLA-4; or
(vii) an antibody or antibody fragment targeting CTLA-4 is selected from the group consisting of: tremelimumab and ipilimumab.

16. The method of claim 1, wherein the maintenance dose comprises a second different immune checkpoint inhibitor polypeptide.

17. The method of claim 16, wherein the second different immune checkpoint inhibitor polypeptide is an antibody or antibody fragment targeting PD-1, PD-L1, CTLA-4, LAG3, TIM3, or a member of the B7 ligand family.

18. The method of claim 16, wherein the maintenance dose comprises an antibody or antibody fragment targeting PD-1 and an antibody or antibody fragment targeting CTLA-4.

19. The method of claim 1, wherein the priming dose:
(i) induces infiltration of immune cells in a tumor, wherein the immune cells are CD8+ T cells, natural killer cells, dendritic cells, or any combination thereof;
(ii) induces or promotes tumor cell apoptosis;
(iii) induces or promotes tumor cell immunogenic cell death;
(iv) induces migration of dendritic cells to a tumor draining lymph node;
(v) induces tumor antigen uptake by dendritic cells in the tumor, tumor draining lymph nodes, or both;
(vi) induces expression of at least one cytokine or chemokine;
(vii) induces expression of at least one cytokine or chemokine selected from the group consisting of: IFN-γ, IL-1β, MIP-1α, G-CSF, Eotaxin, IP-10, MIG, M-CSF, MCP-1, RANTES, IL-12, GM-CSF, MIP-2, TNFα, IL-5, MIP-1β or any combination thereof;
(viii) induces expression of FLT3L and XCL1 in a tumor;
(ix) induces or promotes normalization of vasculature within the tumor; or
(x) a combination of (i)-(ix).

20. The method of claim 1, wherein the priming dose is administered five days, six days or seven days before the at least one maintenance dose.

21. The method of claim 1, wherein (i), (ii) and (iii) of the priming dose:
(i) are formulated in the same composition;
(ii) are formulated in different compositions, wherein (i), (ii), and (iii) are administered simultaneously; or
(iii) are formulated in different compositions, wherein the (i), (ii), and (iii) are administered sequentially.

22. The method of claim 21, wherein the compositions are administered by the same route of administration, or wherein the compositions are administered by different routes of administration.

23. The method of claim 1, wherein the priming dose and at least one maintenance dose are administered by the same route of administration, or by different routes of administration.

24. The method of claim 1, wherein the cancer comprises tumor cells expressing a tumor-associated integrin, and wherein the integrin-binding polypeptide binds to the tumor cells expressing the tumor-associated integrin.

* * * * *

SEQUENCE LISTING

<160> NUMBER OF SEQ ID NOS: 143

<210> SEQ ID NO 1
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1 constant region (amino acid sequence)

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 232
<212> TYPE: PRT
<213> ORGANISM: Homo sapiens
<220> FEATURE:
<221> NAME/KEY: misc_feature
<222> LOCATION: (1)..(232)
<223> OTHER INFORMATION: Human IgG1 Fc domain (amino acid sequence)

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
        210                 215                 220

Ser Leu Ser Leu Ser Pro Gly Lys
225             230

<210> SEQ ID NO 3
<211> LENGTH: 227
<212> TYPE: PRT
<213> ORGANISM: Homo sapiens
<220> FEATURE:
<221> NAME/KEY: misc_feature
<222> LOCATION: (1)..(227)
<223> OTHER INFORMATION: Human IgG1 Fc domain (amino acid sequence)
      Deletion (DEPKSC) Upper Hinge

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 447
<212> TYPE: DNA
<213> ORGANISM: Mus musculus
<220> FEATURE:
```

<221> NAME/KEY: misc_feature
<222> LOCATION: (1)..(447)
<223> OTHER INFORMATION: Mouse IL-2 (nucleic acid sequence)

<400> SEQUENCE: 4

```
gcacccactt caagctccac ttcaagctct acagcggaag cacagcagca gcagcagcag      60
cagcagcagc agcagcagca cctggagcag ctgttgatgg acctacagga gctcctgagc     120
aggatggaga attacaggaa cctgaaactc cccaggatgc tcaccttcaa attttacttg     180
cccaagcagg ccacagaatt gaaagatctt cagtgcctag aagatgaact tggacctctg     240
cggcatgttc tggatttgac tcaaagcaaa agctttcaat tggaagatgc tgagaatttc     300
atcagcaata tcagagtaac tgttgtaaaa ctaaagggct ctgacaacac atttgagtgc     360
caattcgatg atgagtcagc aactgtggtg gactttctga ggagatggat agccttctgt     420
caaagcatca tctcaacaag ccctcaa                                         447
```

<210> SEQ ID NO 5
<211> LENGTH: 149
<212> TYPE: PRT
<213> ORGANISM: Mus musculus
<220> FEATURE:
<221> NAME/KEY: misc_feature
<222> LOCATION: (1)..(149)
<223> OTHER INFORMATION: Mouse IL-2 (amino acid sequence)

<400> SEQUENCE: 5

```
Ala Pro Thr Ser Ser Thr Ser Ser Ser Thr Ala Glu Ala Gln Gln
1               5                   10                  15

Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 6
<211> LENGTH: 447
<212> TYPE: DNA
<213> ORGANISM: Artificial Sequence
<220> FEATURE:
<223> OTHER INFORMATION: Synthetic: QQ6210 (nucleic acid sequence)

<400> SEQUENCE: 6

```
gcacccactt caagctccac ttcaagctct acagcggaag cacaacagca gcagcagcag      60
cagcagcagc agcagcagca cctggagcag ctgttgatgg acctacagga actcctgagt     120
aggatggagg atcacaggaa cctgagactc cccaggatgc tcaccttcaa attttacttg     180
```

```
cccgagcagg ccacagaatt ggaagatctt cagtgcctag aagatgaact tgaaccactg      240
cggcaagttc tggatttgac tcaaagcaaa agctttcaat tggaagatgc tgagaatttc      300
atcagcaata tcagagtaac tgttgtaaaa ctaaagggct ctgacaacac atttgagtgc      360
caattcgacg atgagccagc aactgtggtg gactttctga ggagatggat agccttctgt      420
caaagcatca tctcaacaag ccctcaa                                          447

<210> SEQ ID NO 7
<211> LENGTH: 149
<212> TYPE: PRT
<213> ORGANISM: Artificial Sequence
<220> FEATURE:
<223> OTHER INFORMATION: Synthetic: QQ6210 (amino acid sequence)

<400> SEQUENCE: 7

Ala Pro Thr Ser Ser Thr Ser Ser Thr Ala Glu Ala Gln Gln
 1               5                  10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
         35                  40                  45

Arg Leu Pro Arg Met Leu Thr Phe Lys Phe Tyr Leu Pro Glu Gln Ala
     50                  55                  60

Thr Glu Leu Glu Asp Leu Gln Cys Leu Glu Asp Glu Leu Glu Pro Leu
 65                  70                  75                  80

Arg Gln Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 8
<211> LENGTH: 447
<212> TYPE: DNA
<213> ORGANISM: Artificial Sequence
<220> FEATURE:
<223> OTHER INFORMATION: Synthetic: E76A (nucleic acid sequence)

<400> SEQUENCE: 8
gcacccactt caagctccac ttcaagctct acagcggaag cacagcagca gcagcagcag       60
cagcagcagc agcagcagca cctggagcag ctgttgatgg acctacagga gctcctgagc      120
aggatggaga attacaggaa cctgaaactc cccaggatgc tcaccttcaa attttacttg      180
cccaagcagg ccacagaatt gaaagatctt cagtgcctag aagatgctct ggacctctg      240 cggcatgttc tggatttgac tcaaagcaaa agctttcaat tggaagatgc tgagaatttc      300
atcagcaata tcagagtaac tgttgtaaaa ctaaagggct ctgacaacac atttgagtgc      360
caattcgatg atgagtcagc aactgtggtg gactttctga ggagatggat agccttctgt      420
caaagcatca tctcaacaag ccctcaa                                          447

<210> SEQ ID NO 9
```

<211> LENGTH: 149
<212> TYPE: PRT
<213> ORGANISM: Artificial Sequence
<220> FEATURE:
<223> OTHER INFORMATION: Synthetic: E76A (amino acid sequence)

<400> SEQUENCE: 9

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Ala Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 10
<211> LENGTH: 447
<212> TYPE: DNA
<213> ORGANISM: Artificial Sequence
<220> FEATURE:
<223> OTHER INFORMATION: Synthetic: E76G (nucleic acid sequence)

<400> SEQUENCE: 10
gcacccactt caagctccac ttcaagctct acagcggaag cacagcagca gcagcagcag     60
cagcagcagc agcagcagca cctggagcag ctgttgatgg acctacagga gctcctgagc    120
aggatggaga attacaggaa cctgaaactc cccaggatgc tcaccttcaa attttacttg    180
cccaagcagg ccacagaatt gaaagatctt cagtgcctag aagatggtct tggacctctg    240
cggcatgttc tggatttgac tcaaagcaaa gctttcaat tggaagatgc tgagaatttc     300
atcagcaata tcagagtaac tgttgtaaaa ctaaagggct ctgacaacac atttgagtgc    360
caattcgatg atgagtcagc aactgtggtg gactttctga ggagatggat agccttctgt    420
caaagcatca tctcaacaag ccctcaa                                        447

<210> SEQ ID NO 11
<211> LENGTH: 149
<212> TYPE: PRT
<213> ORGANISM: Artificial Sequence
<220> FEATURE:
<223> OTHER INFORMATION: Synthetic: E76G (amino acid sequence)

<400> SEQUENCE: 11

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
         35                  40                  45

Lys Leu Pro Arg Met Leu Thr Phe Lys Phe Tyr Leu Pro Lys Gln Ala
     50                  55                  60

Thr Glu Leu Lys Asp Leu Gln Cys Leu Glu Asp Gly Leu Gly Pro Leu
 65                  70                  75                  80

Arg His Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
             100                 105                 110

Gly Ser Asp Asn Thr Phe Glu Cys Gln Phe Asp Asp Glu Ser Ala Thr
         115                 120                 125

Val Val Asp Phe Leu Arg Arg Trp Ile Ala Phe Cys Gln Ser Ile Ile
     130                 135                 140

Ser Thr Ser Pro Gln
145

<210> SEQ ID NO 12
<211> LENGTH: 816
<212> TYPE: DNA
<213> ORGANISM: Artificial Sequence
<220> FEATURE:
<223> OTHER INFORMATION: Synthetic: D265A Fc/Flag (nucleic acid
      sequence)

<400> SEQUENCE: 12
atgagggtcc ccgctcagct cctggggctc ctgctgctct ggctcccagg tgcacgatgt      60
gagcccagag tgcccataac acagaacccc tgtcctccac tcaaagagtg tccccccatgc   120 gcagctccag acctcttggg tggaccatcc gtcttcatct ccctccaaa gatcaaggat     180 gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta aacagtact ctccgggtgg tcagtgccct ccccatccag     360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct acctgccga aattgctgtg gactggacca gcaatgggcg tacagagcaa    600
aactacaaga caccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaaggtggc   780
ggatctgact acaaggacga cgatgacaag tgataa                               816

<210> SEQ ID NO 13
<211> LENGTH: 270
<212> TYPE: PRT
<213> ORGANISM: Artificial Sequence
<220> FEATURE:
<223> OTHER INFORMATION: Synthetic: D265A Fc/Flag (amino acid sequence)

<400> SEQUENCE: 13

Met Arg Val Pro Ala Gln Leu Leu Gly Leu Leu Leu Leu Trp Leu Pro
  1               5                  10                  15

Gly Ala Arg Cys Glu Pro Arg Val Pro Ile Thr Gln Asn Pro Cys Pro
             20                  25                  30

```
Pro Leu Lys Glu Cys Pro Pro Cys Ala Ala Pro Asp Leu Leu Gly Gly
         35                  40                  45

Pro Ser Val Phe Ile Phe Pro Pro Lys Ile Lys Asp Val Leu Met Ile
 50                  55                  60

Ser Leu Ser Pro Met Val Thr Cys Val Val Ala Val Ser Glu Asp
 65                  70                  75                  80

Asp Pro Asp Val Gln Ile Ser Trp Phe Val Asn Asn Val Glu Val His
                     85                  90                  95

Thr Ala Gln Thr Gln Thr His Arg Glu Asp Tyr Asn Ser Thr Leu Arg
             100                 105                 110

Val Val Ser Ala Leu Pro Ile Gln His Gln Asp Trp Met Ser Gly Lys
         115                 120                 125

Glu Phe Lys Cys Lys Val Asn Asn Arg Ala Leu Pro Ser Pro Ile Glu
130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                    165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Asp Tyr Lys Asp Asp Asp Lys
            260                 265                 270

<210> SEQ ID NO 14
<211> LENGTH: 1257
<212> TYPE: DNA
<213> ORGANISM: Artificial Sequence
<220> FEATURE:
<223> OTHER INFORMATION: Synthetic: D265A Fc/wt mIL-2 (nucleic acid
      sequence)

<400> SEQUENCE: 14
atgagggtcc ccgctcagct cctggggctc ctgctgctct ggctcccagg tgcacgatgt      60
gagcccagag tgcccataac acagaacccc tgtcctccac tcaaagagtg tccccccatgc    120 gcagctccag acctcttggg tggaccatcc gtcttcatct ccctccaaa gatcaaggat      180 gtactcatga tctccctgag ccccatggtc acatgtgtgg tggtggccgt gagcgaggat    240
gacccagacg tccagatcag ctggtttgtg aacaacgtgg aagtacacac agctcagaca    300 caaaccccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga gagatgact aagaaagagt tcagtctgac ctgcatgatc    540
acaggcttct acctgccga aattgctgtg actggaccga gcaatgggcg tacagagcaa    600
aactacaaga acaccgcaac agtcctggac tctgatggtt cttacttcat gtacagcaag    660
```

-continued

```
ctcagagtac aaaagagcac ttgggaaaga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca gcagcagcag    840
cagcagcagc agcagcagca gcagcacctg gagcagctgt tgatggacct acaggagctc    900
ctgagcagga tggagaatta caggaacctg aaactcccca ggatgctcac cttcaaattt    960
tacttgccca agcaggccac agaattgaaa gatcttcagt gcctagaaga tgaacttgga   1020
cctctgcggc atgttctgga tttgactcaa agcaaaagct ttcaattgga agatgctgag   1080
aatttcatca gcaatatcag agtaactgtt gtaaaactaa agggtctga caacacattt    1140 gagtgccaat tcgatgatga gtcagcaact gtggtggact ttctgaggag atggatagcc   1200
ttctgtcaaa gcatcatctc aacaagccct caacaccatc accaccatca ctgataa      1257
```

<210> SEQ ID NO 15
<211> LENGTH: 417
<212> TYPE: PRT
<213> ORGANISM: Artificial Sequence
<220> FEATURE:
<223> OTHER INFORMATION: Synthetic: D265A Fc/wt mIL-2 (amino acid sequence)

<400> SEQUENCE: 15

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255
```

```
Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Glu Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His
                405                 410                 415

His
```

```
<210> SEQ ID NO 16
<211> LENGTH: 1257
<212> TYPE: DNA
<213> ORGANISM: Artificial Sequence
<220> FEATURE:
<223> OTHER INFORMATION: Synthetic: D265A Fc /QQ6210 (nucleic acid
      sequence)

<400> SEQUENCE: 16
atgagggtcc ccgctcagct cctggggctc ctgctgctct ggctcccagg tgcacgatgt      60
gagcccagag tgcccataac acagaacccc tgtcctccac tcaaagagtg tccccatgc     120 gcagctccag acctcttggg tggaccatcc gtcttcatct ccctccaaa gatcaaggat      180 gtactcatga tctccctgag ccccatggtc acatgtgtgg tggtggccgt gagcgaggat     240
gacccagacg tccagatcag ctggtttgtg aacaacgtgg aagtacacac agctcagaca     300
caaacccata gagaggatta caacagtact ctccgggtgg tcagtgccct ccccatccag     360
caccaggact ggatgagtgg caaggagttc aaatgcaagg tcaacaacag agccctccca     420
tcccccatcg agaaaccat ctcaaaaccc agagggccag taagagctcc acaggtatat     480
gtcttgcctc caccagcaga agagatgact aagaaagagt tcagtctgac ctgcatgatc     540
acaggcttct acctgccga aattgctgtg gactggacca gcaatgggcg tacagagcaa     600
aactacaaga caccgcaac agtcctggac tctgatggtt cttacttcat gtacagcaag     660
ctcagagtac aaaagagcac ttgggaaaga ggaagtcttt tcgcctgctc agtggtccac     720
gagggtctgc acaatcacct tacgactaag accatctccc ggtctctggg taaaggaggg     780
ggctccgcac ccacttcaag ctccacttca agctctacag cggaagcaca acagcagcag     840
cagcagcagc agcagcagca gcagcacctg gagcagctgt tgatggacct acaggaactc     900
ctgagtagga tggaggatca caggaacctg agactcccca ggatgctcac cttcaaattt     960
tacttgcccg agcaggccac agaattggaa gatcttcagt gcctagaaga tgaacttgaa    1020
ccactgcggc aagttctgga tttgactcaa agcaaaagct tcaattgga agatgctgag    1080
```

```
aatttcatca gcaatatcag agtaactgtt gtaaaactaa agggctctga caacacattt    1140
gagtgccaat cgacgatga gccagcaact gtggtggact ttctgaggag atggatagcc    1200
ttctgtcaaa gcatcatctc aacaagccct caacaccatc accaccatca ctgataa     1257
```

<210> SEQ ID NO 17
<211> LENGTH: 417
<212> TYPE: PRT
<213> ORGANISM: Artificial Sequence
<220> FEATURE:
<223> OTHER INFORMATION: Synthetic: D265A Fc /QQ6210 (amino acid
      sequence)

<400> SEQUENCE: 17

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asp His Arg Asn Leu Arg Leu Pro Arg Met Leu Thr Phe Lys Phe
305                 310                 315                 320

Tyr Leu Pro Glu Gln Ala Thr Glu Leu Glu Asp Leu Gln Cys Leu Glu
                325                 330                 335
```

Asp Glu Leu Glu Pro Leu Arg Gln Val Leu Asp Leu Thr Gln Ser Lys
                340                 345                 350

Ser Phe Gln Leu Glu Asp Ala Glu Asn Phe Ile Ser Asn Ile Arg Val
            355                 360                 365

Thr Val Val Lys Leu Lys Gly Ser Asp Asn Thr Phe Glu Cys Gln Phe
    370                 375                 380

Asp Asp Glu Pro Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415

His

<210> SEQ ID NO 18
<211> LENGTH: 1257
<212> TYPE: DNA
<213> ORGANISM: Artificial Sequence
<220> FEATURE:
<223> OTHER INFORMATION: Synthetic: D265A Fc / E76A (nucleic acid
      sequence)

<400> SEQUENCE: 18

| | | | | |
|---|---|---|---|---|
| atgagggtcc | ccgctcagct | cctggggctc | ctgctgctct | ggctcccagg | tgcacgatgt | 60 |
| gagcccagag | tgcccataac | acagaacccc | tgtcctccac | tcaaagagtg | tccccccatgc | 120 |
| gcagctccag | acctcttggg | tggaccatcc | gtcttcatct | tccctccaaa | gatcaaggat | 180 |
| gtactcatga | tctccctgag | ccccatggtc | acatgtgtgg | tggtggccgt | gagcgaggat | 240 |
| gacccagacg | tccagatcag | ctggtttgtg | aacaacgtgg | aagtacacac | agctcagaca | 300 |
| caaacccata | gagaggatta | caacagtact | ctccgggtgg | tcagtgccct | ccccatccag | 360 |
| caccaggact | ggatgagtgg | caaggagttc | aaatgcaagg | tcaacaacag | agccctccca | 420 |
| tcccccatcg | agaaaaccat | ctcaaaaccc | agagggccag | taagagctcc | acaggtatat | 480 |
| gtcttgcctc | caccagcaga | agagatgact | aagaaagagt | tcagtctgac | ctgcatgatc | 540 |
| acaggcttct | acctgccga | aattgctgtg | gactggacca | gcaatgggcg | tacagagcaa | 600 |
| aactacaaga | acaccgcaac | agtcctggac | tctgatggtt | cttacttcat | gtacagcaag | 660 |
| ctcagagtac | aaaagagcac | ttgggaaaga | ggaagtcttt | tcgcctgctc | agtggtccac | 720 |
| gagggtctgc | acaatcacct | tacgactaag | accatctccc | ggtctctggg | taaaggaggg | 780 |
| ggctccgcac | ccacttcaag | ctccacttca | agctctacag | cggaagcaca | gcagcagcag | 840 |
| cagcagcagc | agcagcagca | gcagcacctg | gagcagctgt | tgatggacct | acaggagctc | 900 |
| ctgagcagga | tggagaatta | caggaacctg | aaactcccca | ggatgctcac | cttcaaattt | 960 |
| tacttgccca | gcaggccac | agaattgaaa | gatcttcagt | gcctagaaga | tgctcttgga | 1020 |
| cctctgcggc | atgttctgga | tttgactcaa | agcaaaagct | tcaattgga | agatgctgag | 1080 |
| aatttcatca | gcaatatcag | agtaactgtt | gtaaaactaa | agggctctga | caacacattt | 1140 |
| gagtgccaat | tcgatgatga | gtcagcaact | gtggtggact | ttctgaggag | atggatagcc | 1200 |
| ttctgtcaaa | gcatcatctc | aacaagccct | caacaccatc | accaccatca | ctgataa | 1257 |

<210> SEQ ID NO 19
<211> LENGTH: 417
<212> TYPE: PRT
<213> ORGANISM: Artificial Sequence
<220> FEATURE:
<223> OTHER INFORMATION: Synthetic: D265A Fc / E76A (amino acid
      sequence)

<400> SEQUENCE: 19

| | | | | | | | | | | | | | | |
|---|---|---|---|---|---|---|---|---|---|---|---|---|---|---|
| Met | Arg | Val | Pro | Ala | Gln | Leu | Leu | Gly | Leu | Leu | Leu | Trp | Leu | Pro |
| 1 | | | | 5 | | | | | 10 | | | | | 15 |

Gly Ala Arg Cys Glu Pro Arg Val Pro Ile Thr Gln Asn Pro Cys Pro
                    20                 25                 30

Pro Leu Lys Glu Cys Pro Pro Cys Ala Ala Pro Asp Leu Leu Gly Gly
            35               40                45

Pro Ser Val Phe Ile Phe Pro Pro Lys Ile Lys Asp Val Leu Met Ile
50                          55                          60

Ser Leu Ser Pro Met Val Thr Cys Val Val Ala Val Ser Glu Asp
65                70                      75                 80

Asp Pro Asp Val Gln Ile Ser Trp Phe Val Asn Asn Val Glu Val His
                    85                  90                      95

Thr Ala Gln Thr Gln Thr His Arg Glu Asp Tyr Asn Ser Thr Leu Arg
                100                 105                 110

Val Val Ser Ala Leu Pro Ile Gln His Gln Asp Trp Met Ser Gly Lys
            115                 120                 125

Glu Phe Lys Cys Lys Val Asn Asn Arg Ala Leu Pro Ser Pro Ile Glu
130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Ala Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His His

His

<210> SEQ ID NO 20
<211> LENGTH: 1257
<212> TYPE: DNA
<213> ORGANISM: Artificial Sequence
<220> FEATURE:
<223> OTHER INFORMATION: Synthetic: D265A Fc / E76G (nucleic acid sequence)

<400> SEQUENCE: 20

| | | |
|---|---|---|
| atgagggtcc cgctcagct cctggggctc ctgctgctct ggctcccagg tgcacgatgt | 60 |
| gagcccagag tgcccataac acagaacccc tgtcctccac tcaaagagtg tcccccatgc | 120 |
| gcagctccag acctcttggg tggaccatcc gtcttcatct ccctccaaa gatcaaggat | 180 |
| gtactcatga tctccctgag ccccatggtc acatgtgtgg tggtggccgt gagcgaggat | 240 |
| gacccagacg tccagatcag ctggtttgtg aacaacgtgg aagtacacac agctcagaca | 300 |
| caaacccata gagaggatta aacagtact ctccgggtgg tcagtgccct ccccatccag | 360 |
| caccaggact ggatgagtgg caaggagttc aaatgcaagg tcaacaacag agccctccca | 420 |
| tcccccatcg agaaaaccat ctcaaaaccc agagggccag taagagctcc acaggtatat | 480 |
| gtcttgcctc caccagcaga agagatgact aagaaagagt tcagtctgac ctgcatgatc | 540 |
| acaggcttct acctgccga aattgctgtg gactggacca gcaatgggcg tacagagcaa | 600 |
| aactacaaga caccgcaac agtcctggac tctgatggtt cttacttcat gtacagcaag | 660 |
| ctcagagtac aaaagagcac ttgggaaaga ggaagtcttt tcgcctgctc agtggtccac | 720 |
| gagggtctgc acaatcacct tacgactaag accatctccc ggtctctggg taaaggaggg | 780 |
| ggctccgcac ccacttcaag ctccacttca agctctacag cggaagcaca gcagcagcag | 840 |
| cagcagcagc agcagcagca gcagcacctg gagcagctgt tgatggacct acaggagctc | 900 |
| ctgagcagga tggagaatta caggaacctg aaactcccca ggatgctcac cttcaaattt | 960 |
| tacttgccca gcaggccac agaattgaaa gatcttcagt gcctagaaga tggtcttgga | 1020 |
| cctctgcggc atgttctgga tttgactcaa gcaaaagct tcaattgga agatgctgag | 1080 |
| aatttcatca gcaatatcag agtaactgtt gtaaaactaa agggctctga caacacattt | 1140 |
| gagtgccaat cgatgatga gtcagcaact gtggtggact tctgaggag atggatagcc | 1200 |
| ttctgtcaaa gcatcatctc aacaagccct caacaccatc accaccatca ctgataa | 1257 |

<210> SEQ ID NO 21
<211> LENGTH: 417
<212> TYPE: PRT
<213> ORGANISM: Artificial Sequence
<220> FEATURE:
<223> OTHER INFORMATION: Synthetic: D265A Fc / E76G (amino acid sequence)

<400> SEQUENCE: 21

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Ala Val Ser Glu Asp
 65                  70                  75                  80

Asp Pro Asp Val Gln Ile Ser Trp Phe Val Asn Asn Val Glu Val His
                 85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Gly Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415

His

<210> SEQ ID NO 22
<211> LENGTH: 447
<212> TYPE: DNA
<213> ORGANISM: Artificial Sequence
<220> FEATURE:
<223> OTHER INFORMATION: Synthetic: mIL-2 QQ 6.2-4 (nucleic acid
      sequence)

<400> SEQUENCE: 22

```
gcacccacct caagctccac ttcaagctct acagcggaag cacaacagca gcagcagcag      60
cagcagcagc agcagcagca cctggagcag ctgttgatgg acctacagga gctcctgagc     120
aggatggagg attccaggaa cctgagactc cccaggatgc tcaccttcaa attttacttg     180
cccaagcagg ccacagaatt ggaagatctt cagtgcctag aagatgaact tgaacctctg     240
cggcaagttc tggatttgac tcaaagcaaa agctttcaat tggaagatgc tgagaatttc     300
atcagcaata tcagagtaac tgttgtaaaa ctaaagggct ctgacaacac atttgagtgc     360
caattcgatg atgagccagc aactgtggtg ggctttctga ggagatggat agccttctgt     420
caaagcatca tctcaacgag ccctcaa                                         447
```

<210> SEQ ID NO 23
<211> LENGTH: 149
<212> TYPE: PRT
<213> ORGANISM: Artificial Sequence
<220> FEATURE:
<223> OTHER INFORMATION: Synthetic: mIL-2 QQ 6.2-4 (amino acid sequence)

<400> SEQUENCE: 23

```
Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asp Ser Arg Asn Leu
            35                  40                  45

Arg Leu Pro Arg Met Leu Thr Phe Lys Phe Tyr Leu Pro Lys Gln Ala
 50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145
```

<210> SEQ ID NO 24
<211> LENGTH: 435
<212> TYPE: DNA
<213> ORGANISM: Artificial Sequence
<220> FEATURE:
<223> OTHER INFORMATION: Synthetic: mIL-2 QQ 6.2-8 (nucleic acid
    sequence)

<400> SEQUENCE: 24

```
gcacccacct caagctccac ttcaagctct acagcggaag cacaacagca gcagcagcag      60
cagcagcacc tggagcagct gttgatggac ctacaggagc tcctgagtag gatggaggat     120
cacaggaacc tgagactccc caggatgctc accttcaaat tttacttgcc caagcaggcc     180
acagaattgg aagatcttca gtgcctagaa gatgaacttg aacctctgcg gcaagttctg     240
gatttgactc aaagcaaaag ctttcaattg gaagatgctg agaatttcat cagcaatatc     300
agagtaactg ttgtaaaact aaagggctct gacaacacat ttgagtgcca attcgatgat     360
```

```
gagccagcaa ctgtggtgga ctttctgagg agatggatag ccttctgtca aagcatcatc    420
tcaacaagcc ctcga                                                     435

<210> SEQ ID NO 25
<211> LENGTH: 145
<212> TYPE: PRT
<213> ORGANISM: Artificial Sequence
<220> FEATURE:
<223> OTHER INFORMATION: Synthetic: mIL-2 QQ 6.2-8 (amino acid sequence)

<400> SEQUENCE: 25

Ala Pro Thr Ser Ser Thr Ser Ser Ser Thr Ala Glu Ala Gln Gln
1               5                   10                  15

Gln Gln Gln Gln Gln Gln His Leu Glu Gln Leu Leu Met Asp Leu Gln
            20                  25                  30

Glu Leu Leu Ser Arg Met Glu Asp His Arg Asn Leu Arg Leu Pro Arg
        35                  40                  45

Met Leu Thr Phe Lys Phe Tyr Leu Pro Lys Gln Ala Thr Glu Leu Glu
    50                  55                  60

Asp Leu Gln Cys Leu Glu Asp Glu Leu Glu Pro Leu Arg Gln Val Leu
65                  70                  75                  80

Asp Leu Thr Gln Ser Lys Ser Phe Gln Leu Glu Asp Ala Glu Asn Phe
                85                  90                  95

Ile Ser Asn Ile Arg Val Thr Val Val Lys Leu Lys Gly Ser Asp Asn
            100                 105                 110

Thr Phe Glu Cys Gln Phe Asp Asp Glu Pro Ala Thr Val Val Asp Phe
        115                 120                 125

Leu Arg Arg Trp Ile Ala Phe Cys Gln Ser Ile Ile Ser Thr Ser Pro
    130                 135                 140

Arg
145

<210> SEQ ID NO 26
<211> LENGTH: 447
<212> TYPE: DNA
<213> ORGANISM: Artificial Sequence
<220> FEATURE:
<223> OTHER INFORMATION: Synthetic: mIL-2 QQ 6.2-10 (nucleic acid
      sequence)

<400> SEQUENCE: 26
gcacccacct caagctccac ttcaagctct acagcggaag cacaacagca gcagcagcag     60
cagcagcagc agcagcagca cctggagcag ctgttgatgg acctacagga actcctgagt    120
aggatggagg atcacaggaa cctgagactc cccaggatgc tcaccttcaa attttacttg    180
cccgagcagg ccacagaatt ggaagatctt cagtgcctag aagatgaact tgaaccactg    240
cggcaagttc tggatttgac tcaaagcaaa gctttcaat ggaagatgc tgagaatttc     300 atcagcaata tcagagtaac tgttgtaaaa ctaaagggct ctgacaacac atttgagtgc    360
caattcgacg atgagccagc aactgtggtg gactttctga ggagatggat agccttctgt    420
caaagcatca tctcaacaag ccctcag                                        447

<210> SEQ ID NO 27
<211> LENGTH: 149
<212> TYPE: PRT
<213> ORGANISM: Artificial Sequence
<220> FEATURE:
<223> OTHER INFORMATION: Synthetic: mIL-2 QQ 6.2-10 (amino acid
``` sequence)

<400> SEQUENCE: 27

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asp His Arg Asn Leu
            35                  40                  45

Arg Leu Pro Arg Met Leu Thr Phe Lys Phe Tyr Leu Pro Glu Gln Ala
        50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 28
<211> LENGTH: 438
<212> TYPE: DNA
<213> ORGANISM: Artificial Sequence
<220> FEATURE:
<223> OTHER INFORMATION: Synthetic: mIL-2 QQ 6.2-11 (nucleic acid
      sequence)

<400> SEQUENCE: 28
gcacccacct caagctccac ttcaagctct acagcggaag cacaacagca gcagcagcag      60
cagcagcagc acctggagca gctgttgatg gacctacagg agctcctgag caggatggag     120
gattccagga acctgagact ccccagaatg ctcaccttca aatttactt gcccgagcag      180
gccacagaat tgaaagatct ccagtgccta gaagatgaac ttgaacctct gcggcaagtt     240
ctggatttga ctcaaagcaa aagctttcaa ttggaagatg ctgagaattt catcagcaat     300
atcagagtaa ctgttgtaaa actaaagggc tctgacaaca catttgagtg ccaattcgac     360
gatgagccag caactgtggt ggactttctg aggagatgga tagccttctg tcaaagcatc     420
atctcaacaa gccctcag                                                   438

<210> SEQ ID NO 29
<211> LENGTH: 146
<212> TYPE: PRT
<213> ORGANISM: Artificial Sequence
<220> FEATURE:
<223> OTHER INFORMATION: Synthetic: mIL-2 QQ 6.2-11 (amino acid
      sequence)

<400> SEQUENCE: 29

Ala Pro Thr Ser Ser Thr Ser Ser Ser Thr Ala Glu Ala Gln Gln
1               5                   10                  15

Gln Gln Gln Gln Gln Gln Gln His Leu Glu Gln Leu Leu Met Asp Leu
                20                  25                  30

Gln Glu Leu Leu Ser Arg Met Glu Asp Ser Arg Asn Leu Arg Leu Pro

```
                35                  40                  45
Arg Met Leu Thr Phe Lys Phe Tyr Leu Pro Glu Gln Ala Thr Glu Leu
 50                  55                  60

Lys Asp Leu Gln Cys Leu Glu Asp Glu Leu Glu Pro Leu Arg Gln Val
 65                  70                  75                  80

Leu Asp Leu Thr Gln Ser Lys Ser Phe Gln Leu Glu Asp Ala Glu Asn
                 85                  90                  95

Phe Ile Ser Asn Ile Arg Val Thr Val Val Lys Leu Lys Gly Ser Asp
                100                 105                 110

Asn Thr Phe Glu Cys Gln Phe Asp Asp Glu Pro Ala Thr Val Val Asp
                115                 120                 125

Phe Leu Arg Arg Trp Ile Ala Phe Cys Gln Ser Ile Ile Ser Thr Ser
130                 135                 140

Pro Gln
145

<210> SEQ ID NO 30
<211> LENGTH: 447
<212> TYPE: DNA
<213> ORGANISM: Artificial Sequence
<220> FEATURE:
<223> OTHER INFORMATION: Synthetic: mIL-2 QQ 6.2-13 (nucleic acid
      sequence)

<400> SEQUENCE: 30
gcacccacct caagctccac ttcaagctct acagcggaag cacaacagca gcagcagcag    60
cagcagcagc agcagcagca cctggagcag ctgttgatgg acctacagga gctcctgagt   120
aggatggagg atcacaggaa cctgagactc cccaggatgc tcaccttcaa attttacttg   180
cccgagcagg ccacagaatt gaaagatctc cagtgcctag aagatgaact tgaacctctg   240
cggcaggttc tggatttgac tcaaagcaaa agctttcaat ggaagatgc tgagaatttc   300 atcagcaata tcagagtaac tgttgtaaaa ctaaagggct ctgacaacac atttgagtgc   360
caattcgatg atgagccagc aactgtggtg gactttctga ggagatggat agccttctgt   420
caaagcatca tctcaacaag ccctcag                                       447

<210> SEQ ID NO 31
<211> LENGTH: 149
<212> TYPE: PRT
<213> ORGANISM: Artificial Sequence
<220> FEATURE:
<223> OTHER INFORMATION: Synthetic: mIL-2 QQ 6.2-13 (amino acid
      sequence)

<400> SEQUENCE: 31

Ala Pro Thr Ser Ser Thr Ser Ser Ser Thr Ala Glu Ala Gln Gln
 1               5                  10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asp His Arg Asn Leu
                35                  40                  45

Arg Leu Pro Arg Met Leu Thr Phe Lys Phe Tyr Leu Pro Glu Gln Ala
 50                  55                  60

Thr Glu Leu Lys Asp Leu Gln Cys Leu Glu Asp Glu Leu Glu Pro Leu
 65                  70                  75                  80

Arg Gln Val Leu Asp Leu Thr Gln Ser Lys Ser Phe Gln Leu Glu Asp
                 85                  90                  95
```

```
Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 32
<211> LENGTH: 461
<212> TYPE: DNA
<213> ORGANISM: Homo sapiens
<220> FEATURE:
<221> NAME/KEY: misc_feature
<222> LOCATION: (1)..(461)
<223> OTHER INFORMATION: Full length human IL-2 (nucleic acid sequence)

<400> SEQUENCE: 32
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat acaagaatc ccaaactcac caggatgctc      180
acatttaagt tttacatgcc caagaaggcc acagaactga acatcttca gtgtctagaa      240 gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtaatat gctgatgaga cagcaaccat gtagaatttt ctgaacagat     420
ggattacctt ttgtcaaagc atcatctcaa cactgacttg a                         461

<210> SEQ ID NO 33
<211> LENGTH: 153
<212> TYPE: PRT
<213> ORGANISM: Homo sapiens
<220> FEATURE:
<221> NAME/KEY: misc_feature
<222> LOCATION: (1)..(153)
<223> OTHER INFORMATION: Full length human IL-2 (amino acid sequence)

<400> SEQUENCE: 33

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140
```

```
Cys Gln Ser Ile Ile Ser Thr Leu Thr
145                 150
```

<210> SEQ ID NO 34
<211> LENGTH: 401
<212> TYPE: DNA
<213> ORGANISM: Homo sapiens
<220> FEATURE:
<221> NAME/KEY: misc_feature
<222> LOCATION: (1)..(401)
<223> OTHER INFORMATION: Human IL-2 without signal peptide (nucleic acid sequence)

<400> SEQUENCE: 34

```
gcacctactt caagttctac aaagaaaaca cagctacaac tggagcattt actgctggat     60
ttacagatga ttttgaatgg aattaataat tacaagaatc ccaaactcac caggatgctc    120
acatttaagt tttacatgcc caagaaggcc acagaactga acatcttca gtgtctagaa     180
gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtaatat gctgatgaga cagcaaccat tgtagaattt ctgaacagat    360
ggattacctt ttgtcaaagc atcatctcaa cactgacttg a                       401
```

<210> SEQ ID NO 35
<211> LENGTH: 133
<212> TYPE: PRT
<213> ORGANISM: Homo sapiens
<220> FEATURE:
<221> NAME/KEY: misc_feature
<222> LOCATION: (1)..(133)
<223> OTHER INFORMATION: Human IL-2 without signal peptide (amino acid sequence)

<400> SEQUENCE: 35

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 36
<211> LENGTH: 749
<212> TYPE: PRT
<213> ORGANISM: Homo sapiens
<220> FEATURE:
<221> NAME/KEY: misc_feature
<222> LOCATION: (1)..(749)
<223> OTHER INFORMATION: Human serum albumin (amino acid sequence)

<400> SEQUENCE: 36

| | | | | | | | | | | | | | | |
|---|---|---|---|---|---|---|---|---|---|---|---|---|---|---|
| Met | Asp | Met | Arg | Val | Pro | Ala | Gln | Leu | Leu | Gly | Leu | Leu | Leu | Trp |
| 1 | | | | 5 | | | | | 10 | | | | | 15 |
| Leu | Pro | Gly | Ala | Arg | Cys | Ala | Asp | Ala | His | Lys | Ser | Glu | Val | Ala | His |
| | | | 20 | | | | | 25 | | | | | 30 | | |
| Arg | Phe | Lys | Asp | Leu | Gly | Glu | Glu | Asn | Phe | Lys | Ala | Leu | Val | Leu | Ile |
| | | | 35 | | | | | 40 | | | | | 45 | | |
| Ala | Phe | Ala | Gln | Tyr | Leu | Gln | Gln | Cys | Pro | Phe | Glu | Asp | His | Val | Lys |
| | 50 | | | | | 55 | | | | | 60 | | | | |
| Leu | Val | Asn | Glu | Val | Thr | Glu | Phe | Ala | Lys | Thr | Cys | Val | Ala | Asp | Glu |
| 65 | | | | | 70 | | | | | 75 | | | | | 80 |
| Ser | Ala | Glu | Asn | Cys | Asp | Lys | Ser | Leu | His | Thr | Leu | Phe | Gly | Asp | Lys |
| | | | | 85 | | | | | 90 | | | | | 95 | |
| Leu | Cys | Thr | Val | Ala | Thr | Leu | Arg | Glu | Thr | Tyr | Gly | Glu | Met | Ala | Asp |
| | | | 100 | | | | | 105 | | | | | 110 | | |
| Cys | Cys | Ala | Lys | Gln | Glu | Pro | Glu | Arg | Asn | Glu | Cys | Phe | Leu | Gln | His |
| | | | 115 | | | | | 120 | | | | | 125 | | |
| Lys | Asp | Asp | Asn | Pro | Asn | Leu | Pro | Arg | Leu | Val | Arg | Pro | Glu | Val | Asp |
| | 130 | | | | | 135 | | | | | 140 | | | | |
| Val | Met | Cys | Thr | Ala | Phe | His | Asp | Asn | Glu | Glu | Thr | Phe | Leu | Lys | Lys |
| 145 | | | | | 150 | | | | | 155 | | | | | 160 |
| Tyr | Leu | Tyr | Glu | Ile | Ala | Arg | Arg | His | Pro | Tyr | Phe | Tyr | Ala | Pro | Glu |
| | | | | 165 | | | | | 170 | | | | | 175 | |
| Leu | Leu | Phe | Phe | Ala | Lys | Arg | Tyr | Lys | Ala | Ala | Phe | Thr | Glu | Cys | Cys |
| | | | 180 | | | | | 185 | | | | | 190 | | |
| Gln | Ala | Ala | Asp | Lys | Ala | Ala | Cys | Leu | Leu | Pro | Lys | Leu | Asp | Glu | Leu |
| | | | 195 | | | | | 200 | | | | | 205 | | |
| Arg | Asp | Glu | Gly | Lys | Ala | Ser | Ser | Ala | Lys | Gln | Arg | Leu | Lys | Cys | Ala |
| | 210 | | | | | 215 | | | | | 220 | | | | |
| Ser | Leu | Gln | Lys | Phe | Gly | Glu | Arg | Ala | Phe | Lys | Ala | Trp | Ala | Val | Ala |
| 225 | | | | | 230 | | | | | 235 | | | | | 240 |
| Arg | Leu | Ser | Gln | Arg | Phe | Pro | Lys | Ala | Glu | Phe | Ala | Glu | Val | Ser | Lys |
| | | | | 245 | | | | | 250 | | | | | 255 | |
| Leu | Val | Thr | Asp | Leu | Thr | Lys | Val | His | Thr | Glu | Cys | Cys | His | Gly | Asp |
| | | | 260 | | | | | 265 | | | | | 270 | | |
| Leu | Leu | Glu | Cys | Ala | Asp | Asp | Arg | Ala | Asp | Leu | Ala | Lys | Tyr | Ile | Cys |
| | | | 275 | | | | | 280 | | | | | 285 | | |
| Glu | Asn | Gln | Asp | Ser | Ile | Ser | Ser | Lys | Leu | Lys | Glu | Cys | Cys | Glu | Lys |
| | 290 | | | | | 295 | | | | | 300 | | | | |
| Pro | Leu | Leu | Glu | Lys | Ser | His | Cys | Ile | Ala | Glu | Val | Glu | Asn | Asp | Glu |
| 305 | | | | | 310 | | | | | 315 | | | | | 320 |
| Met | Pro | Ala | Asp | Leu | Pro | Ser | Leu | Ala | Ala | Asp | Phe | Val | Glu | Ser | Lys |
| | | | | 325 | | | | | 330 | | | | | 335 | |
| Asp | Val | Cys | Lys | Asn | Tyr | Ala | Glu | Ala | Lys | Asp | Val | Phe | Leu | Gly | Met |
| | | | 340 | | | | | 345 | | | | | 350 | | |
| Phe | Leu | Tyr | Glu | Tyr | Ala | Arg | Arg | His | Pro | Asp | Tyr | Ser | Val | Val | Leu |
| | | | 355 | | | | | 360 | | | | | 365 | | |
| Leu | Leu | Arg | Leu | Ala | Lys | Thr | Tyr | Glu | Thr | Thr | Leu | Glu | Lys | Cys | Cys |
| | 370 | | | | | 375 | | | | | 380 | | | | |
| Ala | Ala | Ala | Asp | Pro | His | Glu | Cys | Tyr | Ala | Lys | Val | Phe | Asp | Glu | Phe |
| 385 | | | | | 390 | | | | | 395 | | | | | 400 |
| Lys | Pro | Leu | Val | Glu | Glu | Pro | Gln | Asn | Leu | Ile | Lys | Gln | Asn | Cys | Glu |

```
                405                 410                 415
Leu Phe Glu Gln Leu Gly Glu Tyr Lys Phe Gln Asn Ala Leu Leu Val
        420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
                500                 505                 510

Ala Leu Glu Val Asp Glu Thr Tyr Val Pro Lys Glu Phe Asn Ala Glu
                515                 520                 525

Thr Phe Thr Phe His Ala Asp Ile Cys Thr Leu Ser Glu Lys Glu Arg
        530                 535                 540

Gln Ile Lys Lys Gln Thr Ala Leu Val Glu Leu Val Lys His Lys Pro
545                 550                 555                 560

Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
                580                 585                 590

Glu Glu Gly Lys Lys Leu Val Ala Ala Ser Gln Ala Ala Leu Gly Leu
                595                 600                 605

Gly Gly Gly Ser Ala Pro Thr Ser Ser Ser Thr Lys Lys Thr Gln Leu
        610                 615                 620

Gln Leu Glu His Leu Leu Leu Asp Leu Gln Met Ile Leu Asn Gly Ile
625                 630                 635                 640

Asn Asn Tyr Lys Asn Pro Lys Leu Thr Arg Met Leu Thr Phe Lys Phe
                645                 650                 655

Tyr Met Pro Lys Lys Ala Thr Glu Leu Lys His Leu Gln Cys Leu Glu
                660                 665                 670

Glu Glu Leu Lys Pro Leu Glu Glu Val Leu Asn Leu Ala Gln Ser Lys
        675                 680                 685

Asn Phe His Leu Arg Pro Arg Asp Leu Ile Ser Asn Ile Asn Val Ile
        690                 695                 700

Val Leu Glu Leu Lys Gly Ser Glu Thr Thr Phe Met Cys Glu Tyr Ala
705                 710                 715                 720

Asp Glu Thr Ala Thr Ile Val Glu Phe Leu Asn Arg Trp Ile Thr Phe
                725                 730                 735

Cys Gln Ser Ile Ile Ser Thr Leu Thr Gly Gly Gly Ser
                740                 745

<210> SEQ ID NO 37
<211> LENGTH: 726
<212> TYPE: PRT
<213> ORGANISM: Artificial Sequence
<220> FEATURE:
<223> OTHER INFORMATION: Synthetic: Mature HSA (amino acid sequence)

<400> SEQUENCE: 37

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

-continued

```
                    20                  25                  30
        Gln Cys Pro Phe Glu Asp His Val Lys Leu Val Asn Glu Val Thr Glu
                     35                  40                  45

Phe Ala Lys Thr Cys Val Ala Asp Glu Ser Ala Glu Asn Cys Asp Lys
         50                  55                  60

Ser Leu His Thr Leu Phe Gly Asp Lys Leu Cys Thr Val Ala Thr Leu
         65                  70                  75                  80

Arg Glu Thr Tyr Gly Glu Met Ala Asp Cys Cys Ala Lys Gln Glu Pro
                         85                  90                  95

Glu Arg Asn Glu Cys Phe Leu Gln His Lys Asp Asp Asn Pro Asn Leu
                    100                 105                 110

Pro Arg Leu Val Arg Pro Glu Val Asp Val Met Cys Thr Ala Phe His
                    115                 120                 125

Asp Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
        145                 150                 155                 160

Tyr Lys Ala Ala Phe Thr Glu Cys Cys Gln Ala Ala Asp Lys Ala Ala
                        165                 170                 175

Cys Leu Leu Pro Lys Leu Asp Glu Leu Arg Asp Glu Gly Lys Ala Ser
                    180                 185                 190

Ser Ala Lys Gln Arg Leu Lys Cys Ala Ser Leu Gln Lys Phe Gly Glu
                    195                 200                 205

Arg Ala Phe Lys Ala Trp Ala Val Ala Arg Leu Ser Gln Arg Phe Pro
                    210                 215                 220

Lys Ala Glu Phe Ala Glu Val Ser Lys Leu Val Thr Asp Leu Thr Lys
        225                 230                 235                 240

Val His Thr Glu Cys Cys His Gly Asp Leu Leu Glu Cys Ala Asp Asp
                        245                 250                 255

Arg Ala Asp Leu Ala Lys Tyr Ile Cys Glu Asn Gln Asp Ser Ile Ser
                    260                 265                 270

Ser Lys Leu Lys Glu Cys Cys Glu Lys Pro Leu Leu Glu Lys Ser His
                    275                 280                 285

Cys Ile Ala Glu Val Glu Asn Asp Glu Met Pro Ala Asp Leu Pro Ser
                    290                 295                 300

Leu Ala Ala Asp Phe Val Glu Ser Lys Asp Val Cys Lys Asn Tyr Ala
        305                 310                 315                 320

Glu Ala Lys Asp Val Phe Leu Gly Met Phe Leu Tyr Glu Tyr Ala Arg
                        325                 330                 335

Arg His Pro Asp Tyr Ser Val Val Leu Leu Leu Arg Leu Ala Lys Thr
                    340                 345                 350

Tyr Glu Thr Thr Leu Glu Lys Cys Cys Ala Ala Ala Asp Pro His Glu
                    355                 360                 365

Cys Tyr Ala Lys Val Phe Asp Glu Phe Lys Pro Leu Val Glu Glu Pro
                    370                 375                 380

Gln Asn Leu Ile Lys Gln Asn Cys Glu Leu Phe Glu Gln Leu Gly Glu
        385                 390                 395                 400

Tyr Lys Phe Gln Asn Ala Leu Leu Val Arg Tyr Thr Lys Lys Val Pro
                        405                 410                 415

Gln Val Ser Thr Pro Thr Leu Val Glu Val Ser Arg Asn Leu Gly Lys
                    420                 425                 430

Val Gly Ser Lys Cys Cys Lys His Pro Glu Ala Lys Arg Met Pro Cys
                    435                 440                 445
```

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Ala Pro Thr
            580                 585                 590

Ser Ser Ser Thr Lys Lys Thr Gln Leu Gln Leu Glu His Leu Leu Leu
        595                 600                 605

Asp Leu Gln Met Ile Leu Asn Gly Ile Asn Asn Tyr Lys Asn Pro Lys
    610                 615                 620

Leu Thr Arg Met Leu Thr Phe Lys Phe Tyr Met Pro Lys Lys Ala Thr
625                 630                 635                 640

Glu Leu Lys His Leu Gln Cys Leu Glu Glu Leu Lys Pro Leu Glu
                645                 650                 655

Glu Val Leu Asn Leu Ala Gln Ser Lys Asn Phe His Leu Arg Pro Arg
            660                 665                 670

Asp Leu Ile Ser Asn Ile Asn Val Ile Val Leu Glu Leu Lys Gly Ser
        675                 680                 685

Glu Thr Thr Phe Met Cys Glu Tyr Ala Asp Glu Thr Ala Thr Ile Val
    690                 695                 700

Glu Phe Leu Asn Arg Trp Ile Thr Phe Cys Gln Ser Ile Ile Ser Thr
705                 710                 715                 720

Leu Thr Gly Gly Gly Ser
                725

<210> SEQ ID NO 38
<211> LENGTH: 2247
<212> TYPE: DNA
<213> ORGANISM: Homo sapiens
<220> FEATURE:
<221> NAME/KEY: misc_feature
<222> LOCATION: (1)..(2247)
<223> OTHER INFORMATION: Human serum albumin (nucleic acid sequence)

<400> SEQUENCE: 38
atggatatgc gggtgcctgc tcagctgctg ggactgctgc tgctgtggct gcctggggct    60
agatgcgccg atgctcacaa aagcgaagtc gcacacaggt tcaaagatct gggggaggaa   120
aactttaagg ctctggtgct gattgcattc gcccagtacc tgcagcagtg ccccttgag   180 gaccacgtga aactggtcaa cgaagtgact gagttcgcca agaccctgcgt ggccgacgaa   240 tctgctgaga attgtgataa aagtctgcat actctgtttg gggataagct gtgtacagtg   300
gccactctgc gagaaaccta tggagagatg gcagactgct gtgccaaaca ggaacccgag   360

```
cggaacgaat gcttcctgca gcataaggac gataacccca atctgcctcg cctggtgcga    420
cctgaggtgg acgtcatgtg tacagccttc cacgataatg aggaaacttt tctgaagaaa    480
tacctgtacg aaatcgctcg gagacatcct tactttatg caccagagct gctgttcttt     540
gccaaacgct acaaggccgc tttcaccgag tgctgtcagg cagccgataa agctgcatgc    600
ctgctgccta agctggacga actgagggat gagggcaagg ccagctccgc taaacagcgc    660
ctgaagtgtg ctagcctgca gaaattcggg gagcgagcct tcaaggcttg ggcagtggca    720
cggctgagtc agagattccc aaaggcagaa tttgccgagg tctcaaaact ggtgaccgac    780
ctgacaaagg tgcacaccga atgctgtcat ggcgacctgc tggagtgcgc cgacgatcga    840
gctgatctgg caaagtatat ttgtgagaac caggactcca tctctagtaa gctgaaagaa    900
tgctgtgaga accactgct ggaaaagtct cactgcattg ccgaagtgga aacgacgag      960 atgccagctg atctgccctc actggccgct gacttcgtcg aaagcaaaga tgtgtgtaag   1020
aattacgctg aggcaaagga tgtgttcctg ggaatgtttc tgtacgagta tgccaggcgc   1080
cacccagact actccgtggt cctgctgctg aggctggcta aacatatga accacactg     1140 gagaagtgct gtgcagccgc tgatccccat gaatgctatg ccaaagtctt cgacgagttt   1200
aagcccctgg tggaggaacc tcagaacctg atcaaacaga attgtgaact gtttgagcag   1260
ctgggcgagt acaagttcca gaacgccctg ctggtgcgct ataccaagaa agtcccacag   1320
gtgtccacac ccactctggt ggaggtgagc cggaatctgg gcaaagtggg gagtaaatgc   1380
tgtaagcacc ctgaagccaa gaggatgcca tgcgctgagg attacctgag tgtggtcctg   1440
aatcagctgt gtgtcctgca tgaaaaaaca cctgtcagcg accgggtgac aaagtgctgt   1500
actgagtcac tggtgaaccg acggccctgc tttagcgccc tggaagtcga tgagacttat   1560
gtgcctaaag agttcaacgc tgagaccttc acatttcacg cagacatttg taccctgagc   1620
gaaaaggaga gacagatcaa gaaacagaca gccctggtcg aactggtgaa gcataaaccc   1680
aaggccacaa aagagcagct gaaggctgtc atggacgatt cgcagccctt tgtggaaaaa   1740
tgctgtaagg cagacgataa ggagacttgc tttgccgagg aaggaaagaa actggtggct   1800
gcatcccagc agctctggg actgggagga ggatctgccc ctacctcaag ctccactaag    1860
aaaacccagc tgcagctgga gcacctgctg ctggacctgc agatgattct gaacgggatc   1920
aacaattaca aaaatccaaa gctgacccgg atgctgacat tcaagtttta tatgcccaag   1980
aaagccacag agctgaaaca cctgcagtgc ctggaggaag agctgaagcc tctggaagag   2040
gtgctgaacc tggcccagag caagaatttc catctgagac aagggatct gatctccaac    2100 attaatgtga tcgtcctgga actgaaggga tctgagacta cctttatgtg cgaatacgct   2160
gacgagactg caaccattgt ggagttcctg aacagatgga tcaccttctg ccagtccatc   2220
atttctactc tgacaggcgg ggggagc                                       2247
```

<210> SEQ ID NO 39
<211> LENGTH: 28
<212> TYPE: PRT
<213> ORGANISM: Artificial Sequence
<220> FEATURE:
<223> OTHER INFORMATION: Synthetic: EETI-II from Knottin Database

<400> SEQUENCE: 39

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 40
<211> LENGTH: 47
<212> TYPE: PRT
<213> ORGANISM: Artificial Sequence
<220> FEATURE:
<223> OTHER INFORMATION: Synthetic: AgRP from Knottin Database

<400> SEQUENCE: 40

Gly Cys Val Arg Leu His Glu Ser Cys Leu Gly Gln Gln Val Pro Cys
1               5                   10                  15

Cys Asp Pro Cys Ala Thr Cys Tyr Cys Arg Phe Phe Asn Ala Phe Cys
            20                  25                  30

Tyr Cys Arg Lys Leu Gly Thr Ala Met Asn Pro Cys Ser Arg Thr
        35                  40                  45

<210> SEQ ID NO 41
<211> LENGTH: 48
<212> TYPE: PRT
<213> ORGANISM: Artificial Sequence
<220> FEATURE:
<223> OTHER INFORMATION: Synthetic: Omega agatoxin from Knottin Database

<400> SEQUENCE: 41

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
            20                  25                  30

Asn Cys Glu Cys Thr Pro Arg Leu Ile Met Glu Gly Leu Ser Phe Ala
        35                  40                  45

<210> SEQ ID NO 42
<211> LENGTH: 33
<212> TYPE: PRT
<213> ORGANISM: Artificial Sequence
<220> FEATURE:
<223> OTHER INFORMATION: Synthetic: EETI-II Library
<220> FEATURE:
<221> NAME/KEY: misc_feature
<222> LOCATION: (3)..(3)
<223> OTHER INFORMATION: X is selected from the group consisting of A,
    V, L, P, F, Y, S, H, D, and N
<220> FEATURE:
<221> NAME/KEY: misc_feature
<222> LOCATION: (4)..(4)
<223> OTHER INFORMATION: X is selected from the group consisting of G,
    V, L, P, R, E, and Q
<220> FEATURE:
<221> NAME/KEY: misc_feature
<222> LOCATION: (5)..(5)
<223> OTHER INFORMATION: X is selected from the group consisting of G,
    A, and P
<220> FEATURE:
<221> NAME/KEY: misc_feature
<222> LOCATION: (9)..(9)
<223> OTHER INFORMATION: X is selected from the group consisting of W
    and N
<220> FEATURE:
<221> NAME/KEY: misc_feature
<222> LOCATION: (10)..(10)
<223> OTHER INFORMATION: X is selected from the group consisting of A,
    P, and S
<220> FEATURE:
<221> NAME/KEY: misc_feature
<222> LOCATION: (11)..(11)
<223> OTHER INFORMATION: X is selected from the group consisting of P
    and R
<220> FEATURE:
<221> NAME/KEY: misc_feature
<222> LOCATION: (12)..(12)

```
<223> OTHER INFORMATION: X is selected from the group consisting of A,
      V, L, P, S, T, and E
<220> FEATURE:
<221> NAME/KEY: misc_feature
<222> LOCATION: (13)..(13)
<223> OTHER INFORMATION: X is selected from the group consisting of G,
      A, W, S, T, K, and E

<400> SEQUENCE: 42

Gly Cys Xaa Xaa Xaa Arg Gly Asp Xaa Xaa Xaa Xaa Xaa Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 43
<211> LENGTH: 33
<212> TYPE: PRT
<213> ORGANISM: Artificial Sequence
<220> FEATURE:
<223> OTHER INFORMATION: Synthetic: EETI-II K15S Mutation Library
<220> FEATURE:
<221> NAME/KEY: misc_feature
<222> LOCATION: (3)..(3)
<223> OTHER INFORMATION: X is selected from the group consisting of A,
      V, L, P, F, Y, S, H, D, and N
<220> FEATURE:
<221> NAME/KEY: misc_feature
<222> LOCATION: (4)..(4)
<223> OTHER INFORMATION: X is selected from the group consisting of G,
      V, L, P, R, E, and Q
<220> FEATURE:
<221> NAME/KEY: misc_feature
<222> LOCATION: (5)..(5)
<223> OTHER INFORMATION: X is selected from the group consisting of G,
      A, and P
<220> FEATURE:
<221> NAME/KEY: misc_feature
<222> LOCATION: (9)..(9)
<223> OTHER INFORMATION: X is selected from the group consisting of W
      and N
<220> FEATURE:
<221> NAME/KEY: misc_feature
<222> LOCATION: (10)..(10)
<223> OTHER INFORMATION: X is selected from the group consisting of A,
      P, and S
<220> FEATURE:
<221> NAME/KEY: misc_feature
<222> LOCATION: (11)..(11)
<223> OTHER INFORMATION: X is selected from the group consisting of P
      and R
<220> FEATURE:
<221> NAME/KEY: misc_feature
<222> LOCATION: (12)..(12)
<223> OTHER INFORMATION: X is selected from the group consisting of A,
      V, L, P, S, T, and E
<220> FEATURE:
<221> NAME/KEY: misc_feature
<222> LOCATION: (13)..(13)
<223> OTHER INFORMATION: X is selected from the group consisting of G,
      A, W, S, T, K, and E

<400> SEQUENCE: 43

Gly Cys Xaa Xaa Xaa Arg Gly Asp Xaa Xaa Xaa Xaa Xaa Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 44
<211> LENGTH: 822
```

```
<212> TYPE: DNA
<213> ORGANISM: Artificial Sequence
<220> FEATURE:
<223> OTHER INFORMATION: Synthetic: 2.5F- (K15S) mIgG2aFc  Nucleic Acid
      Sequence

<400> SEQUENCE: 44
ggttgtccaa gaccaagagg tgataatcca ccattgactt gttctcaaga ttctgattgt    60
ttggctggtt gtgtttgtgg tccaaatggt ttttgtggtg gtcgactaga gcccagagtg   120
cccataacac agaacccctg tcctccactc aaagagtgtc cccatgcgc agctccagac    180 ctcttgggtg gaccatccgt cttcatcttc cctccaaaga tcaaggatgt actcatgatc   240
tccctgagcc ccatggtcac atgtgtggtg gtggatgtga gcgaggatga cccagacgtc   300
cagatcagct ggtttgtgaa caacgtggaa gtacacacag ctcagacaca aacccataga   360
gaggattaca acagtactct ccgggtggtc agtgccctcc ccatccagca ccaggactgg   420
atgagtggca aggagttcaa atgcaaggtc aacaacagag ccctcccatc ccccatcgag   480
aaaaccatct caaacccag agggccagta agagctccac aggtatatgt cttgcctcca   540
ccagcagaag agatgactaa gaaagagttc agtctgacct gcatgatcac aggcttctta   600
cctgccgaaa ttgctgtgga ctggaccagc aatgggcgta cagagcaaaa ctacaagaac   660
accgcaacag tcctggactc tgatggttct tacttcatgt acagcaagct cagagtacaa   720
aagagcactt gggaaagagg aagtcttttc gcctgctcag tggtccacga gggtctgcac   780 aatcaccta cgactaagac catctcccgg tctctgggta aa                      822

<210> SEQ ID NO 45
<211> LENGTH: 271
<212> TYPE: PRT
<213> ORGANISM: Artificial Sequence
<220> FEATURE:
<223> OTHER INFORMATION: Synthetic: 2.5F- (K15S) mIgG2aFc  Amino Acid
      Sequence

<400> SEQUENCE: 45

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
        35                  40                  45

Glu Cys Pro Pro Cys Ala Ala Pro Asp Leu Leu Gly Gly Pro Ser Val
    50                  55                  60

Phe Ile Phe Pro Pro Lys Ile Lys Asp Val Leu Met Ile Ser Leu Ser
65                  70                  75                  80

Pro Met Val Thr Cys Val Val Val Asp Val Ser Glu Asp Asp Pro Asp
                85                  90                  95

Val Gln Ile Ser Trp Phe Val Asn Asn Val Glu Val His Thr Ala Gln
            100                 105                 110

Thr Gln Thr His Arg Glu Asp Tyr Asn Ser Thr Leu Arg Val Val Ser
        115                 120                 125

Ala Leu Pro Ile Gln His Gln Asp Trp Met Ser Gly Lys Glu Phe Lys
    130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                165                 170                 175
```

```
Pro Pro Ala Glu Glu Met Thr Lys Lys Glu Phe Ser Leu Thr Cys Met
            180                 185                 190

Ile Thr Gly Phe Leu Pro Ala Glu Ile Ala Val Asp Trp Thr Ser Asn
        195                 200                 205

Gly Arg Thr Glu Gln Asn Tyr Lys Asn Thr Ala Thr Val Leu Asp Ser
    210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly Lys
            260                 265                 270

<210> SEQ ID NO 46
<211> LENGTH: 822
<212> TYPE: DNA
<213> ORGANISM: Artificial Sequence
<220> FEATURE:
<223> OTHER INFORMATION: Synthetic: 2.5D- (K15S) mIgG2aFc Nucleic Acid
      Sequence

<400> SEQUENCE: 46
ggttgtccac aaggcagagg tgattgggct ccaacttctt gttctcaaga ttctgattgt    60
ttggctggtt gtgtttgtgg tccaaatggt ttttgtggtg gtcgactaga gcccagagtg   120
cccataacac agaaccctg tcctccactc aaagagtgtc ccccatgcgc agctccagac    180
ctcttgggtg gaccatccgt cttcatcttc cctccaaaga tcaaggatgt actcatgatc   240
tccctgagcc ccatggtcac atgtgtggtg gtggatgtga gcgaggatga cccagacgtc   300
cagatcagct ggtttgtgaa caacgtggaa gtacacacag ctcagacaca aacccataga   360
gaggattaca acagtactct ccgggtggtc agtgccctcc ccatccagca ccaggactgg   420
atgagtggca aggagttcaa atgcaaggtc aacaacagag ccctcccatc ccccatcgag   480
aaaaccatct caaacccag agggccagta agagctccac aggtatatgt cttgcctcca   540
ccagcagaag atgactaa gaaagagttc agtctgacct gcatgatcac aggcttctta    600
cctgccgaaa ttgctgtgga ctggaccagc aatgggcgta cagagcaaaa ctacaagaac   660
accgcaacag tcctggactc tgatggttct tacttcatgt acagcaagct cagagtacaa   720
aagagcactt gggaaagagg aagtcttttc gcctgctcag tggtccacga gggtctgcac   780
aatcacctta cgactaagac catctcccgg tctctgggta aa                     822

<210> SEQ ID NO 47
<211> LENGTH: 271
<212> TYPE: PRT
<213> ORGANISM: Artificial Sequence
<220> FEATURE:
<223> OTHER INFORMATION: Synthetic: 2.5D- (K15S) mIgG2aFc Amino Acid
      Sequence

<400> SEQUENCE: 47

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
        35                  40                  45

Glu Cys Pro Pro Cys Ala Ala Pro Asp Leu Leu Gly Gly Pro Ser Val
```

```
            50                  55                  60
Phe Ile Phe Pro Pro Lys Ile Lys Asp Val Leu Met Ile Ser Leu Ser
 65                  70                  75                  80

Pro Met Val Thr Cys Val Val Asp Val Ser Glu Asp Asp Pro Asp
                 85                  90                  95

Val Gln Ile Ser Trp Phe Val Asn Asn Val Glu Val His Thr Ala Gln
                100                 105                 110

Thr Gln Thr His Arg Glu Asp Tyr Asn Ser Thr Leu Arg Val Val Ser
            115                 120                 125

Ala Leu Pro Ile Gln His Gln Asp Trp Met Ser Gly Lys Glu Phe Lys
        130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                165                 170                 175

Pro Pro Ala Glu Glu Met Thr Lys Lys Glu Phe Ser Leu Thr Cys Met
            180                 185                 190

Ile Thr Gly Phe Leu Pro Ala Glu Ile Ala Val Asp Trp Thr Ser Asn
        195                 200                 205

Gly Arg Thr Glu Gln Asn Tyr Lys Asn Thr Ala Thr Val Leu Asp Ser
    210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly Lys
            260                 265                 270

<210> SEQ ID NO 48
<211> LENGTH: 265
<212> TYPE: PRT
<213> ORGANISM: Artificial Sequence
<220> FEATURE:
<223> OTHER INFORMATION: Synthetic: 2.5F- (K15S) hIgG1Fc Amino Acid
      Sequence

<400> SEQUENCE: 48

Gly Cys Pro Arg Pro Arg Gly Asp Asn Pro Leu Thr Cys Ser Gln
 1               5                  10                  15

Asp Ser Asp Cys Leu Ala Gly Cys Val Cys Gly Pro Asn Gly Phe Cys
                 20                  25                  30

Gly Glu Pro Lys Ser Cys Asp Lys Thr His Thr Cys Pro Cys Pro
            35                  40                  45

Ala Pro Glu Leu Leu Gly Gly Pro Ser Val Phe Leu Phe Pro Pro Lys
        50                  55                  60

Pro Lys Asp Thr Leu Met Ile Ser Arg Thr Pro Glu Val Thr Cys Val
 65                  70                  75                  80

Val Val Asp Val Ser His Glu Asp Pro Glu Val Lys Phe Asn Trp Tyr
                 85                  90                  95

Val Asp Gly Val Glu Val His Asn Ala Lys Thr Lys Pro Arg Glu Glu
                100                 105                 110

Gln Tyr Asn Ser Thr Tyr Arg Val Val Ser Val Leu Thr Val Leu His
            115                 120                 125

Gln Asp Trp Leu Asn Gly Lys Glu Tyr Lys Cys Lys Val Ser Asn Lys
        130                 135                 140
```

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
            165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
            210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
            245                 250                 255

Lys Ser Leu Ser Leu Ser Pro Gly Lys
            260                 265

<210> SEQ ID NO 49
<211> LENGTH: 260
<212> TYPE: PRT
<213> ORGANISM: Artificial Sequence
<220> FEATURE:
<223> OTHER INFORMATION: Synthetic: 2.5F- (K15S) hIgG1Fc Fc Upper Hinge
      Deletion (DEPKSC) Amino Acid Sequence

<400> SEQUENCE: 49

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Asp Lys Thr His Thr Cys Pro Pro Cys Pro Ala Pro Glu Leu Leu
            35                  40                  45

Gly Gly Pro Ser Val Phe Leu Phe Pro Pro Lys Pro Lys Asp Thr Leu
            50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
            85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
            115                 120                 125

Gly Lys Glu Tyr Lys Cys Lys Val Ser Asn Lys Ala Leu Pro Ala Pro
            130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
            165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
            195                 200                 205

Pro Val Leu Asp Ser Asp Gly Ser Phe Phe Leu Tyr Ser Lys Leu Thr
            210                 215                 220

Val Asp Lys Ser Arg Trp Gln Gln Gly Asn Val Phe Ser Cys Ser Val
225                 230                 235                 240

```
Met His Glu Ala Leu His Asn His Tyr Thr Gln Lys Ser Leu Ser Leu
            245                 250                 255

Ser Pro Gly Lys
            260
```

<210> SEQ ID NO 50
<211> LENGTH: 265
<212> TYPE: PRT
<213> ORGANISM: Artificial Sequence
<220> FEATURE:
<223> OTHER INFORMATION: Synthetic: 2.5D- (K15S) hIgG1Fc  Amino Acid
      Sequence

<400> SEQUENCE: 50

```
Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Lys Ser Cys Asp Lys Thr His Thr Cys Pro Pro Cys Pro
        35                  40                  45

Ala Pro Glu Leu Leu Gly Gly Pro Ser Val Phe Leu Phe Pro Pro Lys
    50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
    210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly Lys
            260                 265
```

<210> SEQ ID NO 51
<211> LENGTH: 260
<212> TYPE: PRT
<213> ORGANISM: Artificial Sequence
<220> FEATURE:
<223> OTHER INFORMATION: Synthetic: 2.5D- (K15S) hIgG1Fc  Fc Upper Hinge
      Deletion (DEPKSC) Amino Acid Sequence

<400> SEQUENCE: 51

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Asp Lys Thr His Thr Cys Pro Pro Cys Pro Ala Pro Glu Leu Leu
            35                  40                  45

Gly Gly Pro Ser Val Phe Leu Phe Pro Pro Lys Pro Lys Asp Thr Leu
    50                  55                  60

Met Ile Ser Arg Thr Pro Glu Val Thr Cys Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
                100                 105                 110

Tyr Arg Val Val Ser Val Leu Thr Val Leu His Gln Asp Trp Leu Asn
            115                 120                 125

Gly Lys Glu Tyr Lys Cys Lys Val Ser Asn Lys Ala Leu Pro Ala Pro
        130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
        260

<210> SEQ ID NO 52
<211> LENGTH: 287
<212> TYPE: PRT
<213> ORGANISM: Artificial Sequence
<220> FEATURE:
<223> OTHER INFORMATION: Synthetic: hPD-1  amino acid sequence

<400> SEQUENCE: 52

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp Asn
            20                  25                  30

Pro Pro Thr Phe Phe Pro Ala Leu Leu Val Val Thr Glu Gly Asp Asn
            35                  40                  45

Ala Thr Phe Thr Cys Ser Phe Ser Asn Thr Ser Glu Ser Phe Val Leu
        50                  55                  60

Asn Trp Tyr Arg Met Ser Pro Ser Asn Gln Thr Asp Lys Leu Ala Ala
65                  70                  75                  80

Phe Pro Glu Asp Arg Ser Gln Pro Gly Gln Asp Cys Arg Phe Arg Val
                85                  90                  95

```
Thr Gln Leu Pro Asn Gly Arg Asp Phe His Met Ser Val Val Arg Ala
            100                 105                 110

Arg Arg Asn Asp Ser Gly Thr Tyr Leu Cys Gly Ala Ile Ser Leu Ala
            115                 120                 125

Pro Lys Ala Gln Ile Lys Glu Ser Leu Arg Ala Glu Leu Arg Val Thr
            130                 135                 140

Glu Arg Arg Ala Glu Val Pro Thr Ala His Pro Ser Pro Ser Pro Arg
145                 150                 155                 160

Pro Ala Gly Gln Phe Gln Thr Leu Val Val Gly Val Val Gly Gly Leu
                    165                 170                 175

Leu Gly Ser Leu Val Leu Leu Val Trp Val Leu Ala Val Ile Cys Ser
            180                 185                 190

Arg Ala Ala Arg Gly Thr Ile Gly Ala Arg Arg Thr Gly Gln Pro Leu
            195                 200                 205

Lys Glu Asp Pro Ser Ala Val Pro Val Phe Ser Val Asp Tyr Gly Glu
            210                 215                 220

Leu Asp Phe Gln Trp Arg Glu Lys Thr Pro Glu Pro Pro Val Pro Cys
225                 230                 235                 240

Val Pro Glu Gln Thr Glu Tyr Ala Thr Ile Val Phe Pro Ser Gly Met
                    245                 250                 255

Gly Thr Ser Ser Pro Ala Arg Arg Gly Ser Ala Asp Gly Pro Arg Ser
            260                 265                 270

Ala Gln Pro Leu Arg Pro Glu Asp Gly His Cys Ser Trp Pro Leu
            275                 280                 285

<210> SEQ ID NO 53
<211> LENGTH: 290
<212> TYPE: PRT
<213> ORGANISM: Artificial Sequence
<220> FEATURE:
<223> OTHER INFORMATION: Synthetic: hPD-L-1 amino acid sequence

<400> SEQUENCE: 53

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                    85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                    165                 170                 175
```

```
Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
                275                 280                 285

Glu Thr
    290

<210> SEQ ID NO 54
<211> LENGTH: 223
<212> TYPE: PRT
<213> ORGANISM: Artificial Sequence
<220> FEATURE:
<223> OTHER INFORMATION: Synthetic: hCTLA-4 amino acid sequence

<400> SEQUENCE: 54

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
        210                 215                 220

<210> SEQ ID NO 55
```

```
<211> LENGTH: 525
<212> TYPE: PRT
<213> ORGANISM: Artificial Sequence
<220> FEATURE:
<223> OTHER INFORMATION: Synthetic: hLAG3 amino acid sequence

<400> SEQUENCE: 55
```

| | | | | | | | | | | | | | | |
|---|---|---|---|---|---|---|---|---|---|---|---|---|---|---|
| Met | Trp | Glu | Ala | Gln | Phe | Leu | Gly | Leu | Leu | Phe | Leu | Gln | Pro | Trp |
| 1 | | | | 5 | | | | | 10 | | | | | 15 |
| Val | Ala | Pro | Val | Lys | Pro | Leu | Gln | Pro | Gly | Ala | Glu | Val | Pro | Val |
| | | | 20 | | | | | 25 | | | | | 30 | |
| Trp | Ala | Gln | Glu | Gly | Ala | Pro | Ala | Gln | Leu | Pro | Cys | Ser | Pro | Thr | Ile |
| | | 35 | | | | | 40 | | | | | 45 | | | |
| Pro | Leu | Gln | Asp | Leu | Ser | Leu | Leu | Arg | Arg | Ala | Gly | Val | Thr | Trp | Gln |
| 50 | | | | | 55 | | | | | 60 | | | | | |
| His | Gln | Pro | Asp | Ser | Gly | Pro | Pro | Ala | Ala | Pro | Gly | His | Pro | Leu |
| 65 | | | | | 70 | | | | | 75 | | | | | 80 |
| Ala | Pro | Gly | Pro | His | Pro | Ala | Ala | Pro | Ser | Ser | Trp | Gly | Pro | Arg | Pro |
| | | | | 85 | | | | | 90 | | | | | 95 | |
| Arg | Arg | Tyr | Thr | Val | Leu | Ser | Val | Gly | Pro | Gly | Gly | Leu | Arg | Ser | Gly |
| | | | 100 | | | | | 105 | | | | | 110 | | |
| Arg | Leu | Pro | Leu | Gln | Pro | Arg | Val | Gln | Leu | Asp | Glu | Arg | Gly | Arg | Gln |
| | | | 115 | | | | | 120 | | | | | 125 | | |
| Arg | Gly | Asp | Phe | Ser | Leu | Trp | Leu | Arg | Pro | Ala | Arg | Arg | Ala | Asp | Ala |
| | | 130 | | | | | 135 | | | | | 140 | | | |
| Gly | Glu | Tyr | Arg | Ala | Ala | Val | His | Leu | Arg | Asp | Arg | Ala | Leu | Ser | Cys |
| 145 | | | | | 150 | | | | | 155 | | | | | 160 |
| Arg | Leu | Arg | Leu | Arg | Leu | Gly | Gln | Ala | Ser | Met | Thr | Ala | Ser | Pro | Pro |
| | | | | 165 | | | | | 170 | | | | | 175 | |
| Gly | Ser | Leu | Arg | Ala | Ser | Asp | Trp | Val | Ile | Leu | Asn | Cys | Ser | Phe | Ser |
| | | | 180 | | | | | 185 | | | | | 190 | | |
| Arg | Pro | Asp | Arg | Pro | Ala | Ser | Val | His | Trp | Phe | Arg | Asn | Arg | Gly | Gln |
| | | | 195 | | | | | 200 | | | | | 205 | | |
| Gly | Arg | Val | Pro | Val | Arg | Glu | Ser | Pro | His | His | His | Leu | Ala | Glu | Ser |
| | 210 | | | | | 215 | | | | | 220 | | | | |
| Phe | Leu | Phe | Leu | Pro | Gln | Val | Ser | Pro | Met | Asp | Ser | Gly | Pro | Trp | Gly |
| 225 | | | | | 230 | | | | | 235 | | | | | 240 |
| Cys | Ile | Leu | Thr | Tyr | Arg | Asp | Gly | Phe | Asn | Val | Ser | Ile | Met | Tyr | Asn |
| | | | | 245 | | | | | 250 | | | | | 255 | |
| Leu | Thr | Val | Leu | Gly | Leu | Glu | Pro | Pro | Thr | Pro | Leu | Thr | Val | Tyr | Ala |
| | | | 260 | | | | | 265 | | | | | 270 | | |
| Gly | Ala | Gly | Ser | Arg | Val | Gly | Leu | Pro | Cys | Arg | Leu | Pro | Ala | Gly | Val |
| | | | 275 | | | | | 280 | | | | | 285 | | |
| Gly | Thr | Arg | Ser | Phe | Leu | Thr | Ala | Lys | Trp | Thr | Pro | Pro | Gly | Gly | Gly |
| | | 290 | | | | | 295 | | | | | 300 | | | |
| Pro | Asp | Leu | Leu | Val | Thr | Gly | Asp | Asn | Gly | Asp | Phe | Thr | Leu | Arg | Leu |
| 305 | | | | | 310 | | | | | 315 | | | | | 320 |
| Glu | Asp | Val | Ser | Gln | Ala | Gln | Ala | Gly | Thr | Tyr | Thr | Cys | His | Ile | His |
| | | | | 325 | | | | | 330 | | | | | 335 | |
| Leu | Gln | Glu | Gln | Gln | Leu | Asn | Ala | Thr | Val | Thr | Leu | Ala | Ile | Ile | Thr |
| | | | 340 | | | | | 345 | | | | | 350 | | |
| Val | Thr | Pro | Lys | Ser | Phe | Gly | Ser | Pro | Gly | Ser | Leu | Gly | Lys | Leu | Leu |
| | | 355 | | | | | 360 | | | | | 365 | | | |
| Cys | Glu | Val | Thr | Pro | Val | Ser | Gly | Gln | Glu | Arg | Phe | Val | Trp | Ser | Ser |
| | | 370 | | | | | 375 | | | | | 380 | | | |

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
            405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
            450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
            485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
            515                 520                 525

<210> SEQ ID NO 56
<211> LENGTH: 300
<212> TYPE: PRT
<213> ORGANISM: Artificial Sequence
<220> FEATURE:
<223> OTHER INFORMATION: Synthetic: hTIM3 amino acid sequence

<400> SEQUENCE: 56

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
        130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Gly Ile Tyr Ile Gly Ala Gly Ile
        195                 200                 205

Cys Ala Gly Leu Ala Leu Ala Leu Ile Phe Gly Ala Leu Ile Phe Lys
    210                 215                 220

```
Trp Tyr Ser His Ser Lys Glu Lys Ile Gln Asn Leu Ser Leu Ile Ser
225                 230                 235                 240

Leu Ala Asn Leu Pro Pro Ser Gly Leu Ala Asn Ala Val Ala Glu Gly
                245                 250                 255

Ile Arg Ser Glu Glu Asn Ile Tyr Thr Ile Glu Glu Asn Val Tyr Glu
            260                 265                 270

Val Glu Glu Pro Asn Glu Tyr Tyr Cys Tyr Val Ser Ser Arg Gln Gln
        275                 280                 285

Pro Ser Gln Pro Leu Gly Cys Arg Phe Ala Met Pro
    290                 295                 300

<210> SEQ ID NO 57
<211> LENGTH: 532
<212> TYPE: PRT
<213> ORGANISM: Artificial Sequence
<220> FEATURE:
<223> OTHER INFORMATION: Synthetic: hB7-H3 amino acid sequence

<400> SEQUENCE: 57

Met Leu Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Gln Leu Asn Leu
        50                  55                  60

Ile Trp Gln Leu Thr Asp Thr Lys Gln Leu Val His Ser Phe Ala Glu
65                  70                  75                  80

Gly Gln Asp Gln Gly Ser Ala Tyr Ala Asn Arg Thr Ala Leu Phe Pro
                85                  90                  95

Asp Leu Leu Ala Gln Gly Asn Ala Ser Leu Arg Leu Gln Arg Val Arg
            100                 105                 110

Val Ala Asp Glu Gly Ser Phe Cys Phe Val Ser Ile Arg Asp Phe Gly
        115                 120                 125

Ser Ala Ala Val Ser Leu Gln Val Ala Ala Pro Tyr Ser Lys Pro Ser
    130                 135                 140

Met Thr Leu Glu Pro Asn Lys Asp Leu Arg Pro Gly Asp Thr Val Thr
145                 150                 155                 160

Ile Thr Cys Ser Ser Tyr Gln Gly Tyr Pro Glu Ala Glu Val Phe Trp
                165                 170                 175

Gln Asp Gly Gln Gly Val Pro Leu Thr Gly Asn Val Thr Thr Ser Gln
            180                 185                 190

Met Ala Asn Glu Gln Gly Leu Phe Asp Val His Ser Ile Leu Arg Val
        195                 200                 205

Val Leu Gly Ala Asn Gly Thr Tyr Ser Cys Leu Val Arg Asn Pro Val
    210                 215                 220

Leu Gln Gln Asp Ala His Ser Ser Val Thr Ile Thr Pro Gln Arg Ser
225                 230                 235                 240

Pro Thr Gly Ala Val Glu Val Gln Val Pro Glu Asp Pro Val Val Ala
                245                 250                 255

Leu Val Gly Thr Asp Ala Thr Leu Arg Cys Ser Phe Ser Pro Glu Pro
            260                 265                 270

Gly Phe Ser Leu Ala Gln Leu Asn Leu Ile Trp Gln Leu Thr Asp Thr
        275                 280                 285
```

Lys Gln Leu Val His Ser Phe Thr Glu Gly Arg Asp Gln Gly Ser Ala
            290                 295                 300

Tyr Ala Asn Arg Thr Ala Leu Phe Pro Asp Leu Leu Ala Gln Gly Asn
305                 310                 315                 320

Ala Ser Leu Arg Leu Gln Arg Val Arg Val Ala Asp Glu Gly Ser Phe
                325                 330                 335

Thr Cys Phe Val Ser Ile Arg Asp Phe Gly Ser Ala Ala Val Ser Leu
            340                 345                 350

Gln Val Ala Ala Pro Tyr Ser Lys Pro Ser Met Thr Leu Glu Pro Asn
        355                 360                 365

Lys Asp Leu Arg Pro Gly Asp Thr Val Thr Ile Thr Cys Ser Ser Tyr
370                 375                 380

Arg Gly Tyr Pro Glu Ala Glu Val Phe Trp Gln Asp Gly Gln Gly Val
385                 390                 395                 400

Pro Leu Thr Gly Asn Val Thr Thr Ser Gln Met Ala Asn Glu Gln Gly
                405                 410                 415

Leu Phe Asp Val His Ser Val Leu Arg Val Val Leu Gly Ala Asn Gly
            420                 425                 430

Thr Tyr Ser Cys Leu Val Arg Asn Pro Val Leu Gln Gln Asp Ala His
        435                 440                 445

Gly Ser Val Thr Ile Thr Gly Gln Pro Met Thr Phe Pro Pro Glu Ala
450                 455                 460

Leu Trp Val Thr Val Gly Leu Ser Val Cys Leu Ile Ala Leu Leu Val
465                 470                 475                 480

Ala Leu Ala Phe Val Cys Trp Arg Lys Ile Lys Gln Ser Cys Glu Glu
                485                 490                 495

Glu Asn Ala Gly Ala Glu Asp Gln Asp Gly Glu Gly Glu Gly Ser Lys
            500                 505                 510

Thr Ala Leu Gln Pro Leu Lys His Ser Asp Ser Lys Glu Asp Asp Gly
        515                 520                 525

Gln Glu Ile Ala
    530

<210> SEQ ID NO 58
<211> LENGTH: 166
<212> TYPE: PRT
<213> ORGANISM: Artificial Sequence
<220> FEATURE:
<223> OTHER INFORMATION: Synthetic: hB7-H4 amino acid sequence

<400> SEQUENCE: 58

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Ala Phe Ser Met Pro Glu Val Asn Val Asp Tyr Asn Ala Ser Ser Glu
            35                  40                  45

Thr Leu Arg Cys Glu Ala Pro Arg Trp Phe Pro Gln Pro Thr Val Val
        50                  55                  60

Trp Ala Ser Gln Val Asp Gln Gly Ala Asn Phe Ser Glu Val Ser Asn
65                  70                  75                  80

Thr Ser Phe Glu Leu Asn Ser Glu Asn Val Thr Met Lys Val Val Ser
                85                  90                  95

Val Leu Tyr Asn Val Thr Ile Asn Asn Thr Tyr Ser Cys Met Ile Glu
                100                 105                 110

Asn Asp Ile Ala Lys Ala Thr Gly Asp Ile Lys Val Thr Glu Ser Glu
        115                 120                 125

Ile Lys Arg Arg Ser His Leu Gln Leu Leu Asn Ser Lys Ala Ser Leu
    130                 135                 140

Cys Val Ser Ser Phe Phe Ala Ile Ser Trp Ala Leu Leu Pro Leu Ser
145                 150                 155                 160

Pro Tyr Leu Met Leu Lys
                165

<210> SEQ ID NO 59
<211> LENGTH: 33
<212> TYPE: PRT
<213> ORGANISM: Artificial Sequence
<220> FEATURE:
<223> OTHER INFORMATION: Synthetic: EETI-II 1.4A

<400> SEQUENCE: 59

Gly Cys Ala Glu Pro Arg Gly Asp Met Pro Trp Thr Trp Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 60
<211> LENGTH: 33
<212> TYPE: PRT
<213> ORGANISM: Artificial Sequence
<220> FEATURE:
<223> OTHER INFORMATION: Synthetic: EETI-II 1.4B

<400> SEQUENCE: 60

Gly Cys Val Gly Gly Arg Gly Asp Trp Ser Pro Lys Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 61
<211> LENGTH: 33
<212> TYPE: PRT
<213> ORGANISM: Artificial Sequence
<220> FEATURE:
<223> OTHER INFORMATION: Synthetic: EETI-II 1.4C

<400> SEQUENCE: 61

Gly Cys Ala Glu Leu Arg Gly Asp Arg Ser Tyr Pro Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 62
<211> LENGTH: 33
<212> TYPE: PRT
<213> ORGANISM: Artificial Sequence
<220> FEATURE:
<223> OTHER INFORMATION: Synthetic: EETI-II 1.4E

<400> SEQUENCE: 62

Gly Cys Arg Leu Pro Arg Gly Asp Val Pro Arg Pro His Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 63
<211> LENGTH: 33
<212> TYPE: PRT
<213> ORGANISM: Artificial Sequence
<220> FEATURE:
<223> OTHER INFORMATION: Synthetic: EETI-II 1.4H

<400> SEQUENCE: 63

Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 64
<211> LENGTH: 33
<212> TYPE: PRT
<213> ORGANISM: Artificial Sequence
<220> FEATURE:
<223> OTHER INFORMATION: Synthetic: EETI-II 1.5B

<400> SEQUENCE: 64

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 65
<211> LENGTH: 33
<212> TYPE: PRT
<213> ORGANISM: Artificial Sequence
<220> FEATURE:
<223> OTHER INFORMATION: Synthetic: EETI-II 1.5F

<400> SEQUENCE: 65

Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 66
<211> LENGTH: 33
<212> TYPE: PRT
<213> ORGANISM: Artificial Sequence
<220> FEATURE:
<223> OTHER INFORMATION: Synthetic: EETI-II 2.3A

<400> SEQUENCE: 66

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

```
<210> SEQ ID NO 67
<211> LENGTH: 33
<212> TYPE: PRT
<213> ORGANISM: Artificial Sequence
<220> FEATURE:
<223> OTHER INFORMATION: Synthetic: EETI-II 2.3B

<400> SEQUENCE: 67

Gly Cys Leu Pro Pro Arg Gly Asp Asn Pro Pro Ser Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 68
<211> LENGTH: 33
<212> TYPE: PRT
<213> ORGANISM: Artificial Sequence
<220> FEATURE:
<223> OTHER INFORMATION: Synthetic: EETI-II 2.3C

<400> SEQUENCE: 68

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 69
<211> LENGTH: 33
<212> TYPE: PRT
<213> ORGANISM: Artificial Sequence
<220> FEATURE:
<223> OTHER INFORMATION: Synthetic: EETI-II 2.3D

<400> SEQUENCE: 69

Gly Cys Asn Val Gly Arg Gly Asp Trp Ala Pro Ser Glu Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 70
<211> LENGTH: 33
<212> TYPE: PRT
<213> ORGANISM: Artificial Sequence
<220> FEATURE:
<223> OTHER INFORMATION: Synthetic: EETI-II 2.3E

<400> SEQUENCE: 70

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 71
<211> LENGTH: 33
<212> TYPE: PRT
<213> ORGANISM: Artificial Sequence
<220> FEATURE:
<223> OTHER INFORMATION: Synthetic: EETI-II 2.3F
```

-continued

```
<400> SEQUENCE: 71

Gly Cys Pro Leu Pro Arg Gly Asp Asn Pro Thr Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 72
<211> LENGTH: 33
<212> TYPE: PRT
<213> ORGANISM: Artificial Sequence
<220> FEATURE:
<223> OTHER INFORMATION: Synthetic: EETI-II 2.3G

<400> SEQUENCE: 72

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 73
<211> LENGTH: 32
<212> TYPE: PRT
<213> ORGANISM: Artificial Sequence
<220> FEATURE:
<223> OTHER INFORMATION: Synthetic: EETI-II 2.3H

<400> SEQUENCE: 73

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Pro Asn Gly Phe Cys Gly
            20                  25                  30

<210> SEQ ID NO 74
<211> LENGTH: 33
<212> TYPE: PRT
<213> ORGANISM: Artificial Sequence
<220> FEATURE:
<223> OTHER INFORMATION: Synthetic: EETI-II 2.3I

<400> SEQUENCE: 74

Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 75
<211> LENGTH: 33
<212> TYPE: PRT
<213> ORGANISM: Artificial Sequence
<220> FEATURE:
<223> OTHER INFORMATION: Synthetic: EETI-II 2.3J

<400> SEQUENCE: 75

Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly
```

<210> SEQ ID NO 76
<211> LENGTH: 33
<212> TYPE: PRT
<213> ORGANISM: Artificial Sequence
<220> FEATURE:
<223> OTHER INFORMATION: Synthetic: EETI-II 2.4A

<400> SEQUENCE: 76

Gly Cys Leu Gly Gly Arg Gly Asp Trp Ala Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 77
<211> LENGTH: 33
<212> TYPE: PRT
<213> ORGANISM: Artificial Sequence
<220> FEATURE:
<223> OTHER INFORMATION: Synthetic: EETI-II 2.4C

<400> SEQUENCE: 77

Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 78
<211> LENGTH: 33
<212> TYPE: PRT
<213> ORGANISM: Artificial Sequence
<220> FEATURE:
<223> OTHER INFORMATION: Synthetic: EETI-II 2.4D

<400> SEQUENCE: 78

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 79
<211> LENGTH: 33
<212> TYPE: PRT
<213> ORGANISM: Artificial Sequence
<220> FEATURE:
<223> OTHER INFORMATION: Synthetic: EETI-II 2.4E

<400> SEQUENCE: 79

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 80
<211> LENGTH: 33
<212> TYPE: PRT
<213> ORGANISM: Artificial Sequence
<220> FEATURE:

<223> OTHER INFORMATION: Synthetic: EETI-II 2.4F

<400> SEQUENCE: 80

Gly Cys Tyr Gln Gly Arg Gly Asp Trp Ser Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 81
<211> LENGTH: 33
<212> TYPE: PRT
<213> ORGANISM: Artificial Sequence
<220> FEATURE:
<223> OTHER INFORMATION: Synthetic: EETI-II 2.4G

<400> SEQUENCE: 81

Gly Cys Ala Pro Gly Arg Gly Asp Trp Ala Pro Ser Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 82
<211> LENGTH: 33
<212> TYPE: PRT
<213> ORGANISM: Artificial Sequence
<220> FEATURE:
<223> OTHER INFORMATION: Synthetic: EETI-II 2.4J

<400> SEQUENCE: 82

Gly Cys Val Gln Gly Arg Gly Asp Trp Ser Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 83
<211> LENGTH: 33
<212> TYPE: PRT
<213> ORGANISM: Artificial Sequence
<220> FEATURE:
<223> OTHER INFORMATION: Synthetic: EETI-II 2.5A

<400> SEQUENCE: 83

Gly Cys His Val Gly Arg Gly Asp Trp Ala Pro Glu Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 84
<211> LENGTH: 33
<212> TYPE: PRT
<213> ORGANISM: Artificial Sequence
<220> FEATURE:
<223> OTHER INFORMATION: Synthetic: EETI-II 2.5C

<400> SEQUENCE: 84

Gly Cys Asp Gly Gly Arg Gly Asp Trp Ala Pro Pro Ala Cys Lys Gln
1               5                   10                  15

```
Asp Ser Asp Cys Arg Ala Gly Cys Val Cys Gly Pro Asn Gly Phe Cys
            20                  25                  30

Gly

<210> SEQ ID NO 85
<211> LENGTH: 33
<212> TYPE: PRT
<213> ORGANISM: Artificial Sequence
<220> FEATURE:
<223> OTHER INFORMATION: Synthetic: EETI-II 2.5D

<400> SEQUENCE: 85

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 86
<211> LENGTH: 33
<212> TYPE: PRT
<213> ORGANISM: Artificial Sequence
<220> FEATURE:
<223> OTHER INFORMATION: Synthetic: EETI-II 2.5F

<400> SEQUENCE: 86

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 87
<211> LENGTH: 33
<212> TYPE: PRT
<213> ORGANISM: Artificial Sequence
<220> FEATURE:
<223> OTHER INFORMATION: Synthetic: EETI-II 2.5D K15S Mutant

<400> SEQUENCE: 87

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 88
<211> LENGTH: 33
<212> TYPE: PRT
<213> ORGANISM: Artificial Sequence
<220> FEATURE:
<223> OTHER INFORMATION: Synthetic: EETI-II 2.5F K15S Mutant

<400> SEQUENCE: 88

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 89
```

```
<211> LENGTH: 33
<212> TYPE: PRT
<213> ORGANISM: Artificial Sequence
<220> FEATURE:
<223> OTHER INFORMATION: Synthetic: EETI-II 2.5H

<400> SEQUENCE: 89

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 90
<211> LENGTH: 33
<212> TYPE: PRT
<213> ORGANISM: Artificial Sequence
<220> FEATURE:
<223> OTHER INFORMATION: Synthetic: EETI-II 2.5J

<400> SEQUENCE: 90

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 91
<211> LENGTH: 38
<212> TYPE: PRT
<213> ORGANISM: Artificial Sequence
<220> FEATURE:
<223> OTHER INFORMATION: Synthetic: AgRp 3A

<400> SEQUENCE: 91

Gly Cys Val Arg Leu His Glu Ser Cys Leu Gly Gln Gln Val Pro Cys
1               5                   10                  15

Cys Asp Pro Ala Ala Thr Cys Tyr Cys Val Val Arg Gly Asp Trp Arg
            20                  25                  30

Lys Arg Cys Tyr Cys Arg
        35

<210> SEQ ID NO 92
<211> LENGTH: 38
<212> TYPE: PRT
<213> ORGANISM: Artificial Sequence
<220> FEATURE:
<223> OTHER INFORMATION: Synthetic: AgRp 3B

<400> SEQUENCE: 92

Gly Cys Val Arg Leu His Glu Ser Cys Leu Gly Gln Gln Val Pro Cys
1               5                   10                  15

Cys Asp Pro Ala Ala Thr Cys Tyr Cys Glu Glu Arg Gly Asp Met Leu
            20                  25                  30

Glu Lys Cys Tyr Cys Arg
        35

<210> SEQ ID NO 93
<211> LENGTH: 38
<212> TYPE: PRT
<213> ORGANISM: Artificial Sequence
<220> FEATURE:
<223> OTHER INFORMATION: Synthetic: AgRp 3C
```

<400> SEQUENCE: 93

Gly Cys Val Arg Leu His Glu Ser Cys Leu Gly Gln Gln Val Pro Cys
1               5                   10                  15

Cys Asp Pro Ala Ala Thr Cys Tyr Cys Glu Thr Arg Gly Asp Gly Lys
            20                  25                  30

Glu Lys Cys Tyr Cys Arg
        35

<210> SEQ ID NO 94
<211> LENGTH: 38
<212> TYPE: PRT
<213> ORGANISM: Artificial Sequence
<220> FEATURE:
<223> OTHER INFORMATION: Synthetic: AgRp 3D

<400> SEQUENCE: 94

Gly Cys Val Arg Leu His Glu Ser Cys Leu Gly Gln Gln Val Pro Cys
1               5                   10                  15

Cys Asp Pro Ala Ala Thr Cys Tyr Cys Gln Trp Arg Gly Asp Gly Asp
            20                  25                  30

Val Lys Cys Tyr Cys Arg
        35

<210> SEQ ID NO 95
<211> LENGTH: 38
<212> TYPE: PRT
<213> ORGANISM: Artificial Sequence
<220> FEATURE:
<223> OTHER INFORMATION: Synthetic: AgRp 3E

<400> SEQUENCE: 95

Gly Cys Val Arg Leu His Glu Ser Cys Leu Gly Gln Gln Val Pro Cys
1               5                   10                  15

Cys Asp Pro Ala Ala Thr Cys Tyr Cys Ser Arg Arg Gly Asp Met Arg
            20                  25                  30

Glu Arg Cys Tyr Cys Arg
        35

<210> SEQ ID NO 96
<211> LENGTH: 38
<212> TYPE: PRT
<213> ORGANISM: Artificial Sequence
<220> FEATURE:
<223> OTHER INFORMATION: Synthetic: AgRp 3F

<400> SEQUENCE: 96

Gly Cys Val Arg Leu His Glu Ser Cys Leu Gly Gln Gln Val Pro Cys
1               5                   10                  15

Cys Asp Pro Ala Ala Thr Cys Tyr Cys Gln Tyr Arg Gly Asp Gly Met
            20                  25                  30

Lys His Cys Tyr Cys Arg
        35

<210> SEQ ID NO 97
<211> LENGTH: 38
<212> TYPE: PRT
<213> ORGANISM: Artificial Sequence
<220> FEATURE:
<223> OTHER INFORMATION: Synthetic: AgRp 3G

<400> SEQUENCE: 97

-continued

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Thr Lys
            20                  25                  30

Val Leu Cys Tyr Cys Arg
        35

<210> SEQ ID NO 98
<211> LENGTH: 38
<212> TYPE: PRT
<213> ORGANISM: Artificial Sequence
<220> FEATURE:
<223> OTHER INFORMATION: Synthetic: AgRp 3H

<400> SEQUENCE: 98

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Met Lys
            20                  25                  30

Arg Arg Cys Tyr Cys Arg
        35

<210> SEQ ID NO 99
<211> LENGTH: 38
<212> TYPE: PRT
<213> ORGANISM: Artificial Sequence
<220> FEATURE:
<223> OTHER INFORMATION: Synthetic: AgRp 3I

<400> SEQUENCE: 99

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Val Arg
            20                  25                  30

Met Asn Cys Tyr Cys Arg
        35

<210> SEQ ID NO 100
<211> LENGTH: 38
<212> TYPE: PRT
<213> ORGANISM: Artificial Sequence
<220> FEATURE:
<223> OTHER INFORMATION: Synthetic: AgRp 3J

<400> SEQUENCE: 100

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Ser Lys Cys Tyr Cys Arg
        35

<210> SEQ ID NO 101
<211> LENGTH: 38
<212> TYPE: PRT
<213> ORGANISM: Artificial Sequence
<220> FEATURE:
<223> OTHER INFORMATION: Synthetic: AgRp 4A

<400> SEQUENCE: 101

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Met Arg
            20                  25                  30

Arg Glu Cys Tyr Cys Arg
        35

<210> SEQ ID NO 102
<211> LENGTH: 38
<212> TYPE: PRT
<213> ORGANISM: Artificial Sequence
<220> FEATURE:
<223> OTHER INFORMATION: Synthetic: AgRp 4B

<400> SEQUENCE: 102

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Lys
            20                  25                  30

Val Asn Cys Tyr Cys Arg
        35

<210> SEQ ID NO 103
<211> LENGTH: 38
<212> TYPE: PRT
<213> ORGANISM: Artificial Sequence
<220> FEATURE:
<223> OTHER INFORMATION: Synthetic: AgRp 4C

<400> SEQUENCE: 103

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Glu Lys
            20                  25                  30

Met Ser Cys Tyr Cys Arg
        35

<210> SEQ ID NO 104
<211> LENGTH: 38
<212> TYPE: PRT
<213> ORGANISM: Artificial Sequence
<220> FEATURE:
<223> OTHER INFORMATION: Synthetic: AgRp 4D

<400> SEQUENCE: 104

Gly Cys Val Arg Leu His Glu Ser Cys Leu Gly Gln Gln Val Pro Cys
1               5                   10                  15

Cys Asp Pro Ala Ala Thr Cys Tyr Cys Val Ser Arg Gly Asp Met Arg
            20                  25                  30

Lys Arg Cys Tyr Cys Arg
        35

<210> SEQ ID NO 105
<211> LENGTH: 38
<212> TYPE: PRT
<213> ORGANISM: Artificial Sequence
<220> FEATURE:
<223> OTHER INFORMATION: Synthetic: AgRp 4E

<400> SEQUENCE: 105

Gly Cys Val Arg Leu His Glu Ser Cys Leu Gly Gln Gln Val Pro Cys
1               5                   10                  15

Cys Asp Pro Ala Ala Thr Cys Tyr Cys Glu Arg Arg Gly Asp Ser Val
            20                  25                  30

Lys Lys Cys Tyr Cys Arg
        35

<210> SEQ ID NO 106
<211> LENGTH: 38
<212> TYPE: PRT
<213> ORGANISM: Artificial Sequence
<220> FEATURE:
<223> OTHER INFORMATION: Synthetic: AgRp 4F

<400> SEQUENCE: 106

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Thr Arg
            20                  25                  30

Arg Arg Cys Tyr Cys Arg
        35

<210> SEQ ID NO 107
<211> LENGTH: 38
<212> TYPE: PRT
<213> ORGANISM: Artificial Sequence
<220> FEATURE:
<223> OTHER INFORMATION: Synthetic: AgRp 4G

<400> SEQUENCE: 107

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Val
            20                  25                  30

Arg Arg Cys Tyr Cys Arg
        35

<210> SEQ ID NO 108
<211> LENGTH: 38
<212> TYPE: PRT
<213> ORGANISM: Artificial Sequence
<220> FEATURE:
<223> OTHER INFORMATION: Synthetic: AgRp 4H

<400> SEQUENCE: 108

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Asn Lys
            20                  25                  30

Arg Lys Cys Tyr Cys Arg
        35

<210> SEQ ID NO 109
<211> LENGTH: 38
<212> TYPE: PRT
<213> ORGANISM: Artificial Sequence
<220> FEATURE:
<223> OTHER INFORMATION: Synthetic: AgRp 4I
<220> FEATURE:
<221> NAME/KEY: misc_feature
<222> LOCATION: (21)..(21)
<223> OTHER INFORMATION: Xaa can be any naturally occurring amino acid

<400> SEQUENCE: 109

Gly Cys Val Arg Leu His Glu Ser Cys Leu Gly Gln Gln Val Pro Cys
1               5                   10                  15

Cys Asp Pro Ala Xaa Thr Cys Tyr Cys Lys Gly Arg Gly Asp Val Arg
            20                  25                  30

```
Arg Val Cys Tyr Cys Arg
        35

<210> SEQ ID NO 110
<211> LENGTH: 38
<212> TYPE: PRT
<213> ORGANISM: Artificial Sequence
<220> FEATURE:
<223> OTHER INFORMATION: Synthetic: AgRp 4J

<400> SEQUENCE: 110

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Lys
            20                  25                  30

Val Lys Cys Tyr Cys Arg
        35

<210> SEQ ID NO 111
<211> LENGTH: 38
<212> TYPE: PRT
<213> ORGANISM: Artificial Sequence
<220> FEATURE:
<223> OTHER INFORMATION: Synthetic: AgRp 5A

<400> SEQUENCE: 111

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Arg
            20                  25                  30

Leu Lys Cys Tyr Cys Arg
        35

<210> SEQ ID NO 112
<211> LENGTH: 38
<212> TYPE: PRT
<213> ORGANISM: Artificial Sequence
<220> FEATURE:
<223> OTHER INFORMATION: Synthetic: AgRp 5B

<400> SEQUENCE: 112

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Lys Lys Cys Tyr Cys Arg
        35

<210> SEQ ID NO 113
<211> LENGTH: 38
<212> TYPE: PRT
<213> ORGANISM: Artificial Sequence
<220> FEATURE:
<223> OTHER INFORMATION: Synthetic: AgRp 5C

<400> SEQUENCE: 113

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Arg
            20                  25                  30

Arg Arg Cys Tyr Cys Arg
        35
```

```
<210> SEQ ID NO 114
<211> LENGTH: 38
<212> TYPE: PRT
<213> ORGANISM: Artificial Sequence
<220> FEATURE:
<223> OTHER INFORMATION: Synthetic: AgRp 5D

<400> SEQUENCE: 114

Gly Cys Val Arg Leu His Glu Ser Cys Leu Gly Gln Gln Val Pro Cys
1               5                   10                  15

Cys Asp Pro Ala Ala Thr Cys Tyr Cys Gln Gly Arg Gly Asp Gly Asp
                20                  25                  30

Val Lys Cys Tyr Cys Arg
        35

<210> SEQ ID NO 115
<211> LENGTH: 38
<212> TYPE: PRT
<213> ORGANISM: Artificial Sequence
<220> FEATURE:
<223> OTHER INFORMATION: Synthetic: AgRp 5E

<400> SEQUENCE: 115

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
                20                  25                  30

Leu Val Cys Tyr Cys Arg
        35

<210> SEQ ID NO 116
<211> LENGTH: 38
<212> TYPE: PRT
<213> ORGANISM: Artificial Sequence
<220> FEATURE:
<223> OTHER INFORMATION: Synthetic: AgRp 5F

<400> SEQUENCE: 116

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
                20                  25                  30

Ile Arg Cys Tyr Cys Arg
        35

<210> SEQ ID NO 117
<211> LENGTH: 38
<212> TYPE: PRT
<213> ORGANISM: Artificial Sequence
<220> FEATURE:
<223> OTHER INFORMATION: Synthetic: AgRp 5G

<400> SEQUENCE: 117

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
                20                  25                  30

Leu Val Cys Tyr Cys Arg
        35

<210> SEQ ID NO 118
```

```
<211> LENGTH: 38
<212> TYPE: PRT
<213> ORGANISM: Artificial Sequence
<220> FEATURE:
<223> OTHER INFORMATION: Synthetic: AgRp 5H

<400> SEQUENCE: 118

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Lys
            20                  25                  30

Met Lys Cys Tyr Cys Arg
        35

<210> SEQ ID NO 119
<211> LENGTH: 38
<212> TYPE: PRT
<213> ORGANISM: Artificial Sequence
<220> FEATURE:
<223> OTHER INFORMATION: Synthetic: AgRp 5I

<400> SEQUENCE: 119

Gly Cys Val Arg Leu His Glu Ser Cys Leu Gly Gln Gln Val Pro Cys
1               5                   10                  15

Cys Asp Pro Ala Ala Thr Cys Tyr Cys Ile Gly Arg Gly Asp Val Arg
            20                  25                  30

Arg Arg Cys Tyr Cys Arg
        35

<210> SEQ ID NO 120
<211> LENGTH: 38
<212> TYPE: PRT
<213> ORGANISM: Artificial Sequence
<220> FEATURE:
<223> OTHER INFORMATION: Synthetic: AgRp 5J

<400> SEQUENCE: 120

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Gly Arg
            20                  25                  30

Lys Lys Cys Tyr Cys Arg
        35

<210> SEQ ID NO 121
<211> LENGTH: 38
<212> TYPE: PRT
<213> ORGANISM: Artificial Sequence
<220> FEATURE:
<223> OTHER INFORMATION: Synthetic: AgRp 6B

<400> SEQUENCE: 121

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Arg Asp
            20                  25                  30

Met Lys Cys Tyr Cys Arg
        35

<210> SEQ ID NO 122
<211> LENGTH: 38
<212> TYPE: PRT
<213> ORGANISM: Artificial Sequence
```

```
<220> FEATURE:
<223> OTHER INFORMATION: Synthetic: AgRp 6C

<400> SEQUENCE: 122

Gly Cys Val Arg Leu His Glu Ser Cys Leu Gly Gln Gln Val Pro Cys
1               5                   10                  15

Cys Asp Pro Ala Ala Thr Cys Tyr Cys Thr Gly Arg Gly Asp Glu Lys
            20                  25                  30

Leu Arg Cys Tyr Cys Arg
        35

<210> SEQ ID NO 123
<211> LENGTH: 38
<212> TYPE: PRT
<213> ORGANISM: Artificial Sequence
<220> FEATURE:
<223> OTHER INFORMATION: Synthetic: AgRp 6E

<400> SEQUENCE: 123

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Asn
            20                  25                  30

Arg Arg Cys Tyr Cys Arg
        35

<210> SEQ ID NO 124
<211> LENGTH: 38
<212> TYPE: PRT
<213> ORGANISM: Artificial Sequence
<220> FEATURE:
<223> OTHER INFORMATION: Synthetic: AgRp 6F

<400> SEQUENCE: 124

Gly Cys Val Arg Leu His Glu Ser Cys Leu Gly Gln Gln Val Pro Cys
1               5                   10                  15

Cys Asp Pro Ala Ala Thr Cys Tyr Cys Glu Ser Arg Gly Asp Val Val
            20                  25                  30

Arg Lys Cys Tyr Cys Arg
        35

<210> SEQ ID NO 125
<211> LENGTH: 38
<212> TYPE: PRT
<213> ORGANISM: Artificial Sequence
<220> FEATURE:
<223> OTHER INFORMATION: Synthetic: AgRp 7C

<400> SEQUENCE: 125

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
            20                  25                  30

Leu Arg Cys Tyr Cys Arg
        35

<210> SEQ ID NO 126
<211> LENGTH: 51
<212> TYPE: PRT
<213> ORGANISM: Artificial Sequence
<220> FEATURE:
<223> OTHER INFORMATION: Synthetic: Linker
<220> FEATURE:
```

```
<221> NAME/KEY: misc_feature
<222> LOCATION: (7)..(51)
<223> OTHER INFORMATION: Any group of "Gly Gly Gly Gly Ser" may be
      present or absent

<400> SEQUENCE: 126

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
    50

<210> SEQ ID NO 127
<211> LENGTH: 16
<212> TYPE: PRT
<213> ORGANISM: Artificial Sequence
<220> FEATURE:
<223> OTHER INFORMATION: Synthetic: Linker

<400> SEQUENCE: 127

Ser Gly Gly Gly Gly Ser Gly Gly Gly Gly Ser Gly Gly Gly Gly Ser
1               5                   10                  15

<210> SEQ ID NO 128
<211> LENGTH: 30
<212> TYPE: PRT
<213> ORGANISM: Artificial Sequence
<220> FEATURE:
<223> OTHER INFORMATION: Synthetic: Linker
<220> FEATURE:
<221> NAME/KEY: misc_feature
<222> LOCATION: (6)..(30)
<223> OTHER INFORMATION: Any group of "Gly Gly Gly Gly Ser" may be
      present or absent

<400> SEQUENCE: 128

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 129
<211> LENGTH: 24
<212> TYPE: PRT
<213> ORGANISM: Artificial Sequence
<220> FEATURE:
<223> OTHER INFORMATION: Synthetic: Linker
<220> FEATURE:
<221> NAME/KEY: misc_feature
<222> LOCATION: (5)..(24)
<223> OTHER INFORMATION: Any group of "Gly Gly Gly Ser" may be present
      or absent

<400> SEQUENCE: 129

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 130
<211> LENGTH: 25
<212> TYPE: PRT
<213> ORGANISM: Artificial Sequence
```

```
<220> FEATURE:
<223> OTHER INFORMATION: Synthetic: lipophilic-CpG oligonucleotide
      conjugate
<220> FEATURE:
<221> NAME/KEY: MOD_RES
<222> LOCATION: (1)..(1)
<223> OTHER INFORMATION: Lipophilic compound
<220> FEATURE:
<221> NAME/KEY: misc_feature
<222> LOCATION: (2)..(5)
<223> OTHER INFORMATION: Any "g" may be present or absent

<400> SEQUENCE: 130

Gly Gly Gly Gly Gly Thr Cys Cys Ala Thr Gly Ala Cys Gly Thr Thr
1               5                   10                  15

Cys Cys Thr Gly Ala Cys Gly Thr Thr
            20                  25

<210> SEQ ID NO 131
<211> LENGTH: 294
<212> TYPE: PRT
<213> ORGANISM: Artificial Sequence
<220> FEATURE:
<223> OTHER INFORMATION: Synthetic: 2.5F- (K15S) mIgG2aFc    (Amino Acid
      Sequence with D265A mutation)

<400> SEQUENCE: 131

Met Arg Val Pro Ala Gln Leu Leu Gly Leu Leu Leu Leu Trp Leu Pro
1               5                   10                  15

Gly Ala Arg Cys Gly Cys Pro Arg Pro Arg Gly Asp Asn Pro Pro Leu
                20                  25                  30

Thr Cys Ser Gln Asp Ser Asp Cys Leu Ala Gly Cys Val Cys Gly Pro
            35                  40                  45

Asn Gly Phe Cys Gly Gly Arg Leu Glu Pro Arg Val Pro Ile Thr Gln
50                  55                  60

Asn Pro Cys Pro Pro Leu Lys Glu Cys Pro Pro Cys Ala Ala Pro Asp
65                  70                  75                  80

Leu Leu Gly Gly Pro Ser Val Phe Ile Phe Pro Pro Lys Ile Lys Asp
                85                  90                  95

Val Leu Met Ile Ser Leu Ser Pro Met Val Thr Cys Val Val Val Asp
            100                 105                 110

Val Ser Glu Asp Asp Pro Asp Val Gln Ile Ser Trp Phe Val Asn Asn
        115                 120                 125

Val Glu Val His Thr Ala Gln Thr Gln Thr His Arg Glu Asp Tyr Asn
130                 135                 140

Ser Thr Leu Arg Val Val Ser Ala Leu Pro Ile Gln His Gln Asp Trp
145                 150                 155                 160

Met Ser Gly Lys Glu Phe Lys Cys Lys Val Asn Asn Arg Ala Leu Pro
                165                 170                 175

Ser Pro Ile Glu Lys Thr Ile Ser Lys Pro Arg Gly Pro Val Arg Ala
            180                 185                 190

Pro Gln Val Tyr Val Leu Pro Pro Pro Ala Glu Glu Met Thr Lys Lys
        195                 200                 205

Glu Phe Ser Leu Thr Cys Met Ile Thr Gly Phe Leu Pro Ala Glu Ile
    210                 215                 220

Ala Val Asp Trp Thr Ser Asn Gly Arg Thr Glu Gln Asn Tyr Lys Asn
225                 230                 235                 240

Thr Ala Thr Val Leu Asp Ser Asp Gly Ser Tyr Phe Met Tyr Ser Lys
                245                 250                 255
```

Leu Arg Val Gln Lys Ser Thr Trp Glu Arg Gly Ser Leu Phe Ala Cys
            260                 265                 270

Ser Val Val His Glu Gly Leu His Asn His Leu Thr Thr Lys Thr Ile
        275                 280                 285

Ser Arg Ser Leu Gly Lys
    290

<210> SEQ ID NO 132
<211> LENGTH: 274
<212> TYPE: PRT
<213> ORGANISM: Artificial Sequence
<220> FEATURE:
<223> OTHER INFORMATION: Synthetic: Mature 2.5F- (K15S) mIgG2aFc
      (Amino Acid Sequence with D265A mutation)

<400> SEQUENCE: 132

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Gly Arg Leu Glu Pro Arg Val Pro Ile Thr Gln Asn Pro Cys Pro
        35                  40                  45

Pro Leu Lys Glu Cys Pro Pro Cys Ala Ala Pro Asp Leu Leu Gly Gly
    50                  55                  60

Pro Ser Val Phe Ile Phe Pro Pro Lys Ile Lys Asp Val Leu Met Ile
65                  70                  75                  80

Ser Leu Ser Pro Met Val Thr Cys Val Val Asp Val Ser Glu Asp
            85                  90                  95

Asp Pro Asp Val Gln Ile Ser Trp Phe Val Asn Asn Val Glu Val His
            100                 105                 110

Thr Ala Gln Thr Gln Thr His Arg Glu Asp Tyr Asn Ser Thr Leu Arg
            115                 120                 125

Val Val Ser Ala Leu Pro Ile Gln His Gln Asp Trp Met Ser Gly Lys
        130                 135                 140

Glu Phe Lys Cys Lys Val Asn Asn Arg Ala Leu Pro Ser Pro Ile Glu
145                 150                 155                 160

Lys Thr Ile Ser Lys Pro Arg Gly Pro Val Arg Ala Pro Gln Val Tyr
                165                 170                 175

Val Leu Pro Pro Pro Ala Glu Glu Met Thr Lys Lys Glu Phe Ser Leu
            180                 185                 190

Thr Cys Met Ile Thr Gly Phe Leu Pro Ala Glu Ile Ala Val Asp Trp
        195                 200                 205

Thr Ser Asn Gly Arg Thr Glu Gln Asn Tyr Lys Asn Thr Ala Thr Val
    210                 215                 220

Leu Asp Ser Asp Gly Ser Tyr Phe Met Tyr Ser Lys Leu Arg Val Gln
225                 230                 235                 240

Lys Ser Thr Trp Glu Arg Gly Ser Leu Phe Ala Cys Ser Val Val His
                245                 250                 255

Glu Gly Leu His Asn His Leu Thr Thr Lys Thr Ile Ser Arg Ser Leu
            260                 265                 270

Gly Lys

<210> SEQ ID NO 133
<211> LENGTH: 297
<212> TYPE: PRT
<213> ORGANISM: Artificial Sequence
<220> FEATURE:

<223> OTHER INFORMATION: Synthetic: 2.5F- (K15S) mIgG2aFc    (Amino Acid
      Sequence with LALA-PG mutation)

<400> SEQUENCE: 133

Met Asp Ala Met Lys Arg Gly Leu Cys Cys Val Leu Leu Leu Cys Gly
1               5                   10                  15

Ala Val Phe Val Ser Pro Ser Gly Cys Pro Arg Pro Arg Gly Asp Asn
            20                  25                  30

Pro Pro Leu Thr Cys Ser Gln Asp Ser Asp Cys Leu Ala Gly Cys Val
        35                  40                  45

Cys Gly Pro Asn Gly Phe Cys Gly Gly Arg Leu Glu Pro Arg Val Pro
    50                  55                  60

Ile Thr Gln Asn Pro Cys Pro Leu Lys Glu Cys Pro Pro Cys Ala
65                  70                  75                  80

Ala Pro Asp Ala Ala Gly Gly Pro Ser Val Phe Ile Phe Pro Pro Lys
                85                  90                  95

Ile Lys Asp Val Leu Met Ile Ser Leu Ser Pro Met Val Thr Cys Val
            100                 105                 110

Val Val Asp Val Ser Glu Asp Asp Pro Asp Val Gln Ile Ser Trp Phe
        115                 120                 125

Val Asn Asn Val Glu Val His Thr Ala Gln Thr Gln Thr His Arg Glu
    130                 135                 140

Asp Tyr Asn Ser Thr Leu Arg Val Val Ser Ala Leu Pro Ile Gln His
145                 150                 155                 160

Gln Asp Trp Met Ser Gly Lys Glu Phe Lys Cys Lys Val Asn Asn Arg
                165                 170                 175

Ala Leu Gly Ser Pro Ile Glu Lys Thr Ile Ser Lys Pro Arg Gly Pro
            180                 185                 190

Val Arg Ala Pro Gln Val Tyr Val Leu Pro Pro Ala Glu Glu Met
        195                 200                 205

Thr Lys Lys Glu Phe Ser Leu Thr Cys Met Ile Thr Gly Phe Leu Pro
    210                 215                 220

Ala Glu Ile Ala Val Asp Trp Thr Ser Asn Gly Arg Thr Glu Gln Asn
225                 230                 235                 240

Tyr Lys Asn Thr Ala Thr Val Leu Asp Ser Asp Gly Ser Tyr Phe Met
                245                 250                 255

Tyr Ser Lys Leu Arg Val Gln Lys Ser Thr Trp Glu Arg Gly Ser Leu
            260                 265                 270

Phe Ala Cys Ser Val Val His Glu Gly Leu His Asn His Leu Thr Thr
        275                 280                 285

Lys Thr Ile Ser Arg Ser Leu Gly Lys
    290                 295

<210> SEQ ID NO 134
<211> LENGTH: 274
<212> TYPE: PRT
<213> ORGANISM: Artificial Sequence
<220> FEATURE:
<223> OTHER INFORMATION: Synthetic: Mature 2.5F- (K15S) mIgG2aFc
      (Amino Acid Sequence with LALA-PG mutation)

<400> SEQUENCE: 134

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

-continued

```
Gly Gly Arg Leu Glu Pro Arg Val Pro Ile Thr Gln Asn Pro Cys Pro
            35                  40                  45
Pro Leu Lys Glu Cys Pro Pro Cys Ala Ala Pro Asp Ala Ala Gly Gly
 50                  55                  60
Pro Ser Val Phe Ile Phe Pro Pro Lys Ile Lys Asp Val Leu Met Ile
 65                  70                  75                  80
Ser Leu Ser Pro Met Val Thr Cys Val Val Val Asp Val Ser Glu Asp
                 85                  90                  95
Asp Pro Asp Val Gln Ile Ser Trp Phe Val Asn Asn Val Glu Val His
                100                 105                 110
Thr Ala Gln Thr Gln Thr His Arg Glu Asp Tyr Asn Ser Thr Leu Arg
            115                 120                 125
Val Val Ser Ala Leu Pro Ile Gln His Gln Asp Trp Met Ser Gly Lys
130                 135                 140
Glu Phe Lys Cys Lys Val Asn Asn Arg Ala Leu Gly Ser Pro Ile Glu
145                 150                 155                 160
Lys Thr Ile Ser Lys Pro Arg Gly Pro Val Arg Ala Pro Gln Val Tyr
                165                 170                 175
Val Leu Pro Pro Pro Ala Glu Glu Met Thr Lys Lys Glu Phe Ser Leu
                180                 185                 190
Thr Cys Met Ile Thr Gly Phe Leu Pro Ala Glu Ile Ala Val Asp Trp
            195                 200                 205
Thr Ser Asn Gly Arg Thr Glu Gln Asn Tyr Lys Asn Thr Ala Thr Val
210                 215                 220
Leu Asp Ser Asp Gly Ser Tyr Phe Met Tyr Ser Lys Leu Arg Val Gln
225                 230                 235                 240
Lys Ser Thr Trp Glu Arg Gly Ser Leu Phe Ala Cys Ser Val Val His
                245                 250                 255
Glu Gly Leu His Asn His Leu Thr Thr Lys Thr Ile Ser Arg Ser Leu
                260                 265                 270
Gly Lys

<210> SEQ ID NO 135
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: Human IgG1 Fc upper hinge

<400> SEQUENCE: 135

Glu Pro Lys Ser Cys
1               5

<210> SEQ ID NO 136
<211> LENGTH: 11
<212> TYPE: PRT
<213> ORGANISM: Artificial Sequence
<220> FEATURE:
<223> OTHER INFORMATION: Synthetic: Integrin binding loop
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid

<400> SEQUENCE: 136
```

Xaa Xaa Xaa Arg Gly Asp Xaa Xaa Xaa Xaa
1               5                   10

<210> SEQ ID NO 137
<211> LENGTH: 21
<212> TYPE: PRT
<213> ORGANISM: Artificial Sequence
<220> FEATURE:
<223> OTHER INFORMATION: Synthetic: Linker

<400> SEQUENCE: 137

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 138
<211> LENGTH: 12
<212> TYPE: DNA
<213> ORGANISM: Artificial Sequence
<220> FEATURE:
<223> OTHER INFORMATION: Synthetic: Lipid-linker
<220> FEATURE:
<221> NAME/KEY: modified_base
<222> LOCATION: (1)..(1)
<223> OTHER INFORMATION: lipophilic compound

<400> SEQUENCE: 138 gggggggtttt cg                                                          12

<210> SEQ ID NO 139
<211> LENGTH: 12
<212> TYPE: DNA
<213> ORGANISM: Artificial Sequence
<220> FEATURE:
<223> OTHER INFORMATION: Synthetic: Lipid-linker
<220> FEATURE:
<221> NAME/KEY: modified_base
<222> LOCATION: (1)..(1)
<223> OTHER INFORMATION: lipophilic compound

<400> SEQUENCE: 139
tttttttttt cg                                                           12

<210> SEQ ID NO 140
<211> LENGTH: 12
<212> TYPE: DNA
<213> ORGANISM: Artificial Sequence
<220> FEATURE:
<223> OTHER INFORMATION: Synthetic: Lipid-linker
<220> FEATURE:
<221> NAME/KEY: modified_base
<222> LOCATION: (1)..(1)
<223> OTHER INFORMATION: lipophilic compound

<400> SEQUENCE: 140
ggtttttttt cg                                                           12

<210> SEQ ID NO 141
<211> LENGTH: 12
<212> TYPE: DNA
<213> ORGANISM: Artificial Sequence
<220> FEATURE:
<223> OTHER INFORMATION: Synthetic: Lipid-linker
<220> FEATURE:
<221> NAME/KEY: modified_base
<222> LOCATION: (1)..(1)
<223> OTHER INFORMATION: lipophilic compound

```
<400> SEQUENCE: 141
ggggtttttt cg                                                           12

<210> SEQ ID NO 142
<211> LENGTH: 12
<212> TYPE: DNA
<213> ORGANISM: Artificial Sequence
<220> FEATURE:
<223> OTHER INFORMATION: Synthetic: Lipid-linker
<220> FEATURE:
<221> NAME/KEY: modified_base
<222> LOCATION: (1)..(1)
<223> OTHER INFORMATION: lipophilic compound

<400> SEQUENCE: 142
ggggggggtt cg                                                           12

<210> SEQ ID NO 143
<211> LENGTH: 12
<212> TYPE: DNA
<213> ORGANISM: Artificial Sequence
<220> FEATURE:
<223> OTHER INFORMATION: Synthetic: Lipid-linker
<220> FEATURE:
<221> NAME/KEY: modified_base
<222> LOCATION: (1)..(1)
<223> OTHER INFORMATION: lipophilic compound

<400> SEQUENCE: 143
gggggggggg cg                                                           12
```